US009034888B2

(12) United States Patent
Gaudreault et al.

(10) Patent No.: US 9,034,888 B2
(45) Date of Patent: May 19, 2015

(54) SUBSTITUTED 2-IMIDAZOLIDONES AND ANALOGS

(75) Inventors: René C. Gaudreault, St-Nicolas (CA); Sébastien Fortin, Saint-Etienne-de-Lauzon (CA)

(73) Assignee: Universite Laval, Quebec (CA)

( * ) Notice: Subject to any disclaimer, the term of this patent is extended or adjusted under 35 U.S.C. 154(b) by 0 days.

(21) Appl. No.: 13/579,534

(22) PCT Filed: Feb. 16, 2011

(86) PCT No.: PCT/CA2011/050095
§ 371 (c)(1), (2), (4) Date: Aug. 16, 2012

(87) PCT Pub. No.: WO2011/100840
PCT Pub. Date: Aug. 25, 2011

(65) Prior Publication Data

US 2012/0309777 A1 Dec. 6, 2012

Related U.S. Application Data

(60) Provisional application No. 61/305,248, filed on Feb. 17, 2010.

(51) Int. Cl.

| | |
|---|---|
| ***C07D 233/34*** | (2006.01) |
| ***C07D 239/10*** | (2006.01) |
| ***C07D 401/12*** | (2006.01) |
| ***C07D 403/12*** | (2006.01) |
| ***C07D 405/12*** | (2006.01) |

(52) U.S. Cl.
CPC ............ *C07D 233/34* (2013.01); *C07D 239/10* (2013.01); *C07D 401/12* (2013.01); *C07D 403/12* (2013.01); *C07D 405/12* (2013.01)

(58) Field of Classification Search
None
See application file for complete search history.

(56) References Cited

U.S. PATENT DOCUMENTS 5,541,197 A 7/1996 Fisher et al.

FOREIGN PATENT DOCUMENTS

| | | | |
|---|---|---|---|
| WO | 9932475 | A1 | 7/1999 |
| WO | 0102350 | A2 | 1/2001 |
| WO | 2005004810 | A2 | 1/2005 |
| WO | 2010/003127 | A2 | 1/2010 |

OTHER PUBLICATIONS

Freshney (Culture of Animal Cells, A Manual of Basic Technique, Alan R. Liss, Inc., 1983, New York, p4).*

Fortin, S., "Design, Synthesis, Biological Evaluation, and Structure-Activity Relationships of Substituted Phenyl 4-(2-Oxoimidazolidin-1-yl)-benzenesulfonates as New Tubulin Inhibitors Mimicking Combretastatin A-4", Journal of Medical Chemistry—ACS Publications; Feb. 16, 2011.

Gwaltney, S. L. et al., "Novel sulfonate analogues of combretastatin A-4—potent antimitotic agents," Bioorganic & Medicinal Chemistry Letters, Pergamon, Amsterdam, NL, vol. 11, No. 7, Apr. 9, 2001, pp. 871-874.

Supplementary European Search Report completed Jun. 27, 2014 for Application No. EP 11744232.

* cited by examiner

*Primary Examiner* — Kamal Saeed

(74) *Attorney, Agent, or Firm* — Sutherland Asbill & Brennan LLP

(57) ABSTRACT

Compounds of formula (I): wherein $R_1$, $R_2$, $R_3$, $R_4$, $R_7$, $R_6$, $R_7$, $R_8$, $R_9$, A, X and Y as defined herein are provided as useful for the treatment of cancer or for the manufacture of anti-cancer agents.

(I)

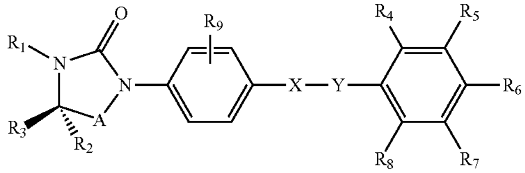

19 Claims, No Drawings

SUBSTITUTED 2-IMIDAZOLIDONES AND ANALOGS

CROSS-REFERENCE TO RELATED APPLICATION

This application is the national stage of International Application No. PCT/CA2011/050095, filed Feb. 16, 2011, which claims priority from U.S. provisional application 61/305,248 filed Feb. 17, 2010, the contents of which are entirely incorporated by reference.

FIELD OF THE INVENTION

The present invention relates to substituted 2-imidazolidones and analogs thereof. Particularly, the invention relates to processes for the preparation of these compounds. More particularly, these compounds are useful as anti-cancer agents. Still, the invention relates to the use of these compounds for the manufacture of anti-cancer agents and method of treating cancer with these compounds.

BACKGROUND OF THE INVENTION

Cancer is a disease that seriously jeopardizes the health of human beings. Around the globe, about 6 millions people die of cancer every year, with another 10 millions seriously affected by the disease. According to the estimate of the World Health Organization, in the 21st century, cancer will become the “number one killer” of mankind.

In the past several decades, many ways of treating cancer became available, mainly including surgery, radiotherapy, chemotherapy, hormonotherapy, gene therapy, and immunotherapy, among which surgery, radiotherapy and chemotherapy have become the major means. Chemotherapy refers to treating cancer with chemical medication. It is the moist rapidly expanding field in the diagnosis and treatment of cancer. A great number of new medicines aiming at different targets are ready for clinical application, and developments in research in mechanism of drug action and pharmacokinetics have made the clinical administration routes and means more fitting for killing tumor cells while protecting the normal tissues.

At present, pharmaceuticals for chemotherapy mainly includes: compounds that affects the biosynthesis of nucleic acid (e.g., 5-fluorouracil, amethopterin, cytarabine, hydroxyurea); compounds that directly destroys DNA and prevents its reproduction, e.g. alkylating agents; antineoplastic antibiotics (e.g., cisplatin and carboplatin); compounds that interferes with the transcription and prevents the synthesis of RNA (e.g., actinomycin D, adriamycin) and other transcription restraining antibiotics; compounds that affects the synthesis of protein (e.g., catharanthines, podophyllotoxins, asparaginase) hormones (e.g. adrenal cortical hormone, estrogen, androgen, tamoxifen, aminoglutethimide). The existing chemotherapies and radiotherapies that are commonly used in treating cancer may cause serious toxic and other side effects that are adverse to the human body. The property of interfering in the polymerization or depolymerization of microtubulin of many natural medicines is regarded as having antineoplastic activity. Historically, research focused on two classes of antimitotic agents. The first class includes compounds that bind reversibly to tubulin and prevent microtubule assembly (e.g., colchicine, vinblastine, combretastatin). The second class of antimicrotubule agents features molecules that prevent microtubule disassembly (e.g., taxotere, epothilone, discodermolide, eleutherobine).

Despite the utility of taxus and vinca alkaloids in the clinic, there are serious limitations to these therapies. On-target toxicity of these agents is associated with the notion that tubulin polymers play a critical role in the non-mitotic cytoskeletal functions in both proliferating and terminally differentiated cells. Microtubules are also essential for axonal transport in neurons. Peripheral neurotoxicity of Paclitaxel™, Docetaxel™ and Vincristine™ has been extensively studied. Although manageable and reversible for the majority of second-generation anti-mitotic drugs, this severe side effect may preclude repeated courses of therapy. Neuropathy continues to be an issue for novel agents in clinical development, for example Dolastatin-10. In addition, drug efflux pumps play a role in tumors developing resistance to the tubulin-binding drugs. For example, vinca alkaloids and taxanes are both substrates for the P-gp efflux pump encoded by the multidrug resistance mdr1 gene, resulting in decreased sensitivity to these compounds in vivo. Due to these limitations of the tubulin-binding antimitotic agents, there is ongoing need to identify new subsets of antimicrotubule agents that yield anti-mitotic effect with better specificity and more predictable pharmacology.

To that end, substituted 2-imidazolidones have been developed as a genuine new class of antimicrotubule agents.

SUMMARY OF THE INVENTION

In one aspect of the present invention, there is provided a compound of formula (I):

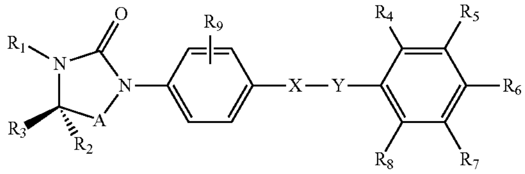

(I)

wherein:

$R_1$ is H or $C_{1-6}$ alkyl;

A is $(CH_2)_n$ wherein n is an integer from 1 to 3; or A is —CH— and is bound to adjacent —CH—$R_2$ by a double bond whereas $R_3$ is not present;

$R_2$ and $R_3$ is each independently selected from the group consisting of: H and $C_{1-6}$ alkyl;

X is O or NH when Y═$SO_2$; and X═$SO_2$ when Y is O or NH;

or X is —CH═CH— and Y is C═O;

or X is C═O, —S— or C═$CH_2$; and Y is absent;

or one of X or Y is N and the other is C and are so linked as to form an imidazole ring;

$R_5$, $R_6$ and $R_7$ is each independently selected from the group consisting of: H, OH, halogen, $C_{1-8}$ alkyl, $C_{4-6}$ cycloalkyl, $C_{2-6}$ alkenyl, $C_{1-6}$ alkoxy, O-alkylhalo, phenoxy, $C_{0-6}$ alkyl-CN, $C_{1-6}$ 2-ketyl, ω- and ω-1 $C_{1-6}$ alkanol, ω-$C_{1-6}$ alkyl carboxylate and corresponding $C_{1-3}$ esters, —$COOR_{10}$ wherein $R_{10}$ is selected from: H or $C_{1-3}$ alkyl; $NO_2$, —NH—C(O)—$C_{1-3}$ alkyl, and —N—($R_{11}$)($R_{12}$)

wherein $R_{11}$ and $R_{12}$ is each independently selected from the group consisting of: H and $C_{1-3}$ alkyl; or $R_5$ and $R_6$; or $R_6$ and $R_7$ are linked to each other and form a 4, 5 or 6-membered saturated or partially unsaturated ring optionally containing one or two N, O or S atoms thus forming a heterocycle, said ring or heterocycle optionally substituted with $C_{1-6}$ alkyl, OH, halogen, amines, $C_{1-4}$ alkyl-substituted amine, $C_{1-4}$ alkoxy; or $R_4$ and $R_8$ is each independently selected from the group consisting of: H, OH, halogen, $C_{1-6}$ alkyl, $C_{1-6}$ alkenyl, $C_{1-6}$ alkoxy, $C_{1-6}$ 2-ketyl, ω- and ω-1 $C_{1-6}$ alkanol, ω-$C_{1-6}$ alkyl carboxylate and corresponding $C_{1-3}$ esters, —$COOR_{10}$ wherein $R_{10}$ is selected from: H or $C_{1-3}$ alkyl, $NO_2$, and —N—$(R_{11})(R_{12})$ wherein $R_{11}$ and $R_{12}$ is each independently selected from the group consisting of: H and $C_{1-3}$ alkyl; and $R_9$ is H, OH, halogen, unbranched $C_{1-6}$ alkyl, branched $C_{1-4}$ alkyl, $C_{1-4}$ alkenyl, $C_{1-4}$ alkoxy, ω- and ω-1 $C_{1-4}$ alkanol, ω-$C_{1-4}$ alkyl carboxylate and corresponding $C_{1-3}$ esters, —$COOR_{10}$ wherein $R_{10}$ is as defined above, —NH—C(O)—$C_{1-3}$ alkyl, and —N—$(R_{11})(R_{12})$ wherein $R_{11}$ and $R_{12}$ are as defined above;

or a pharmaceutically acceptable salt thereof.

In a second aspect of the present invention, there is provided a compound of formula (Ia):

(Ia)

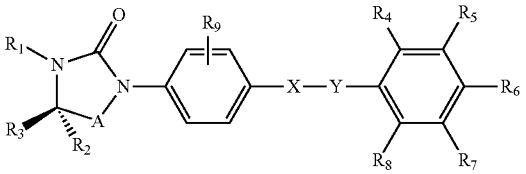

wherein:

$R_1$ is H or $C_{1-6}$ alkyl;

A is $(CH_2)_n$ wherein n is an integer from 1 to 3; or A is —CH— and is bound to adjacent —CH—$R_2$ by a double bond whereas $R_3$ is not present;

$R_2$ and $R_3$ is each independently selected from the group consisting of: H and $C_{1-6}$ alkyl;

X is O or NH when Y=$SO_2$; and X=$SO_2$ when Y is O or NH;

$R_5$, $R_6$ and $R_7$ is each independently selected from the group consisting of: H, OH, halogen, $C_{1-8}$ alkyl, $C_{4-6}$ cycloalkyl, $C_{2-6}$ alkenyl, $C_{1-6}$ alkoxy, phenoxy, $C_{0-6}$ alkyl-CN, $C_{1-6}$ 2-ketyl, ω and ω-1 $C_{1-6}$ alkanol, ω $C_{1-6}$ alkyl carboxy late and corresponding $C_{1-3}$ esters, —$COOR_{10}$ wherein $R_{10}$ is selected from: H or $C_{1-3}$ alkyl;

$NO_2$, —NH—C(O)—$C_{1-3}$ alkyl, and —N—$(R_{11})(R_{12})$ wherein $R_{11}$ and $R_{12}$ is each independently selected from the group consisting of: H and $C_{1-3}$ alkyl; or $R_5$ and $R_6$; or $R_6$ and $R_7$ are linked to each other and form a 4, 5 or 6-membered saturated or partially unsaturated ring optionally containing one or two N, O or S atoms thus forming a heterocycle, said ring or heterocycle optionally substituted with $C_{1-6}$ alkyl, OH, halogen, amines, $C_{1-4}$ alkyl-substituted amine, $C_{1-4}$ alkoxy; or $R_4$ and $R_8$ is each independently selected from the group consisting of: H, OH, halogen, $C_{1-6}$ alkyl, $C_{1-6}$ alkenyl, $C_{1-6}$ alkoxy, $C_{1-6}$ 2-ketyl, ω and ω-1 $C_{1-6}$ alkanol, ω $C_{1-6}$ alkyl carboxy late and corresponding $C_{1-3}$ esters, —$COOR_{10}$ wherein $R_{10}$ is selected from: H or $C_{1-3}$ alkyl, $NO_2$, and —N—$(R_{11})(R_{12})$ wherein $R_{11}$ and $R_{12}$ is each independently selected from the group consisting of: H and $C_{1-3}$ alkyl; and $R_9$ is H, OH, halogen, unbranched $C_{1-6}$ alkyl, branched $C_{1-4}$ alkyl, $C_{1-4}$ alkenyl, $C_{1-4}$ alkoxy, ω and ω-1 $C_{1-4}$ alkanol, ω $C_{1-4}$ alkyl carboxylate and corresponding $C_{1-3}$ esters, —$COOR_{10}$ wherein $R_{10}$ is as defined above, —NH—C(O)—$C_{1-3}$ alkyl, and —N—$(R_{11})(R_{12})$ wherein $R_{11}$ and $R_{12}$ are as defined above;

or a pharmaceutically acceptable salt thereof.

A third aspect of the present invention is directed to pharmaceutical compositions comprising at least one compound of Formula I or Ia, or a salt thereof, and one or more pharmaceutically-acceptable excipients.

A further aspect of the present invention is directed to a method of treating a condition that results from abnormal cell growth, cellular differentiation, tumor growth or invasion with one or more compounds of Formula I or Ia.

A further aspect of the invention is directed to a method of treating cancer in a human suffering therefrom, particularly wherein the cancer is a hormone-dependent cancer, gastrointestinal (GI) tract cancer, or skin cancer comprising administering a therapeutically effective amount of a compound of Formula I or Ia.

A further aspect of the invention is directed to the use of one or more compounds of formula I or Ia for the manufacture of medicament for the treatment of cancer in a human, particularly wherein the cancer is hormone-dependent cancer, GI tract cancer, or skin cancer.

A further aspect of the invention is directed to hindering or blocking cell cycle progression by contacting one or more cells with one or more compounds of Formula I or Ia.

A further aspect of the present invention is directed to a method of synthesizing compounds of Formula I or Ia by following one or more synthetic schemes as defined below.

The compounds of Formula I or Ia may also be solvated, especially hydrated. Hydration may occur during manufacturing of the compounds or compositions comprising the compounds, or the hydration may occur over time due to the hygroscopic nature of the compounds.

When any variable occurs more than one time in any constituent of Formula I or Ia, its definition on each occurrence is independent of its definition at every other occurrence. Also, combinations of substituents and/or variables are permissible only if such combinations result in stable compounds.

The invention disclosed herein is also meant to encompass the in vivo metabolic products of the disclosed compounds. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally in a detectable dose to an animal such as rat, mouse, guinea pig, monkey, or to human, allowing sufficient time for metabolism to occur and isolating its conversion products from the urine, blood or other biological samples.

The invention disclosed herein is also meant to encompass pro-drugs that, when administered in vivo, provide the compounds of formula (I) as metabolic products. Such products may result, for example, from the addition of phosphate, boronic acid or amino acid derivatives. Accordingly, the invention includes compounds of formula (I) wherein appropriate $R_4$, $R_5$, $R_6$, $R_7$ or $R_8$ is derivatized with a phosphate, a boronic acid or an amino acid, or a salt thereof.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

DETAILED DESCRIPTION OF THE INVENTION

Definitions

The term "$C_{1-n}$alkyl" such as "$C_{1-8}$alkyl" as employed herein by itself or as part of another group refers to both straight and branched chain radicals, and unless otherwise specified up to n carbons, such as for example $C_{1-8}$ alkyl; methyl, ethyl, propyl, isopropyl, butyl, s-butyl, t-butyl, isobutyl, pentyl, hexyl, isohexyl, heptl, 4,4-dimethylpentyl, octyl, and 2,2,4-trimethylpentyl.

The term "$C_{2-6}$alkenyl" is used herein to mean a straight or branched chain radical of 2-6 carbon atoms, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term $C_{1-6}$ 2-ketyl, is used herein to refer to any alkyl having a ketone group (=O).

The term "hydroxyalkyl" or "alkanol" as employed herein interchangeably refer to any of the above alkyl groups wherein one or more hydrogens thereof are substituted by one or more hydroxyl moieties. The terms ω and ω-1 used herein refer to the position of the hydroxyl group i.e. ultimate (at the end) and penultimate of the alkyl chain respectively.

The term "carboxyalkyl" or "alkyl carboxylate" as employed herein interchangeably refer to any of the above alkyl groups wherein one or more hydrogens thereof are substituted by one or more carboxylic acid moieties. The term w used herein refers to the position of the carboxy-late group i.e. ultimate (at the end of the alkyl chain).

The phrase "saturated or partially unsaturated ring" as employed herein, by itself or as part of another group, refers to a saturated or partially unsaturated ring system having 5 to ring atoms selected from carbon atoms and optionally having 1 or 2 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be optionally fused to a benzene ring.

The term "halogen" or "halo" as employed herein by itself or as part of another group refers to chlorine, bromine, fluorine or iodine.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The term "enantiomeric excess" refers to a mixture wherein one enantiomer is present in a greater concentration than its mirror image molecule.

As used herein, the term "GI tract cancer" or "gastrointestinal cancer" is meant to include the medical conditions which are characterized by presence of cancer cells in the esophagus, the stomach, the pancreas, the small intestine as well as in colon and rectum. Additionally, as used herein, the term "GI tract cancer" in meant to further include medical conditions which are characterized by presence of cancer cells in the pancreas, which like liver and gallbladder is an accessory organ of the GI tract.

DETAILED DESCRIPTION OF PARTICULAR EMBODIMENTS

Particularly, the invention provides a compound of formula (Ib):

(Ib)

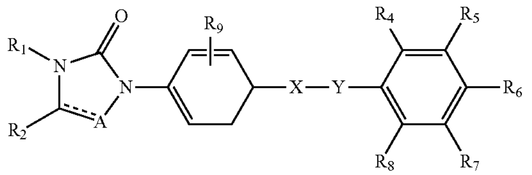

wherein:

$R_1$ is H or $C_{1-6}$ alkyl;

$R_2$ is H or $C_{1-4}$ alkyl;

A is $(CH_2)_n$ wherein n is an integer from 1 to 2;

X is O or NH when Y=$SO_2$; and X=$SO_2$ when Y is O or NH;

$R_5$, $R_6$ and $R_7$ is each independently selected from the group consisting of: H, OH, halogen, $C_{1-8}$ alkyl, $C_{3-6}$ cycloalkyl, $C_{2-6}$ alkenyl, $C_{1-6}$ alkoxy, phenoxy, $C_{0-6}$ alkyl-CN, $C_{1-6}$ 2-ketyl, ω and ω-1 $C_{1-6}$ alkanol, ω $C_{1-6}$ alkyl carboxylate and corresponding $C_{1-3}$ esters, $NO_2$, and —N—$(R_{11})(R_{12})$ wherein $R_{11}$ and $R_{12}$ is each independently selected from the group consisting of: H and $C_{1-3}$ alkyl; or $R_5$ and $R_6$; or $R_6$ and $R_7$ are linked to each other and form a 5- or 6-membered ring selected from the group consisting of:

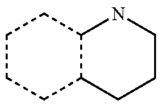,
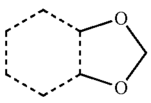,
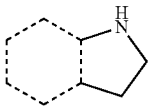 and
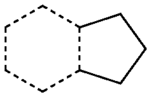

each optionally substituted with $C_{1-3}$ alkyl, OH, halogen, and amine;

$R_4$ and $R_8$ is each independently selected from the group consisting of: H, OH, halogen, $C_{1-3}$ alkyl, $C_{2-3}$ alkenyl, $C_{1-3}$ alkoxy, phenoxy, ω and ω-1 $C_{1-3}$ alkanol, $C_{1-3}$ 2-ketyl, ω $C_{1-3}$alkyl carboxylate and corresponding $C_{1-3}$ esters, $NO_2$, —$NH_2$, and —NH—C(O)—$C_{1-3}$ alkyl; and $R_9$ is H, OH, halogen, unbranched $C_{1-6}$ alkyl, branched $C_{1-4}$ alkyl, $C_{1-4}$ alkenyl, or $C_{1-4}$ alkoxy;

or a pharmaceutically acceptable salt thereof.

More particularly, the invention provides compounds of formula (Ic):

(Ic)

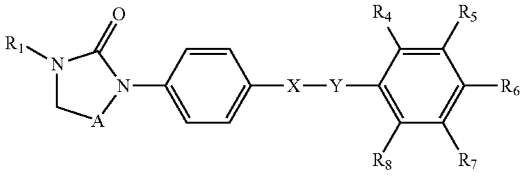

wherein:

$R_1$ is H or $C_{1-4}$alkyl;

A is $(CH_2)_n$ wherein n is an integer from 1 to 2;

X is O or NH when Y═$SO_2$; and X═$SO_2$ when Y is O or NH;

$R_5$, $R_6$ and $R_7$ is each independently selected from the group consisting of: H, OH, halogen, $C_{1-6}$ alkyl, $C_{2-6}$ alkenyl, $C_{1-6}$ alkoxy, phenoxy, $NO_2$, and —$NH_2$;

$R_4$ and $R_8$ is each independently selected from the group consisting of: H, halogen, $C_{1-3}$ alkyl, and $C_{1-3}$ alkoxy;

or a pharmaceutically acceptable salt thereof.

Most particularly, the invention provides compounds of formula (Id):

(Id)

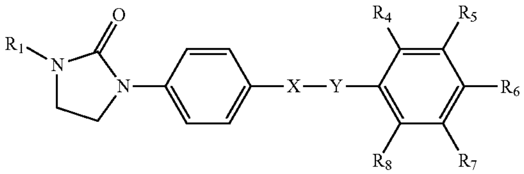

wherein:

$R_1$ is H or $C_{1-4}$ alkyl;

X is O or NH when Y═$SO_2$; and X═$SO_2$ when Y is O or NH;

$R_5$, $R_6$ and $R_7$ is each independently selected from the group consisting of H, halogen, $C_{1-4}$ alkyl, $C_{1-3}$ alkoxy, $NO_2$, and —$NH_2$;

$R_4$ and $R_8$ is each independently selected from the group consisting of H, halogen, $C_{1-3}$ alkyl, and $C_{1-3}$ alkoxy;

or a pharmaceutically acceptable salt thereof.

In connection with particular aspects of the invention, the compounds of any appropriate formula I, Ia, Ib, Ic or Id, and definitions herein are particularly defined wherein X is $SO_2$ and Y is O or NH; or X is O and Y is $SO_2$.

In connection with particular aspects of the invention, the compounds of any appropriate formulas I, Ia, Ib, Ic or Id, and definitions herein are particularly defined wherein $R_1$ is selected from group consisting of: H, Me, Et or Pr.

In connection with particular aspects of the invention, the compound of any appropriate formula I, Ia, Ib, Ic or Id, and definitions herein are defined wherein each of $R_2$ and $R_3$ is independently selected from group consisting of: H or Me.

In connection with particular aspects of the invention, the compound of any appropriate formula I, Ia, Ib, Ic or Id, and definitions herein are defined wherein each of $R_4$ and $R_8$ are independently selected from the group consisting of: H, Me, Et, Pr, F, Cl, I, OMe, and $NO_2$.

In connection with particular aspects of the invention, the compound of any appropriate formula I, Ia, Ib, Ic or Id, and definitions herein are particularly defined wherein each of $R_5$, $R_6$ and $R_7$ are independently selected from the group consisting of H, Me, Et, Pr, butyl, pentyl, hexyl, cyclohexyl, CH—CN, F, Cl, I, Br, OMe, OEt, OPr, Obutyl, Opentyl, Ohexyl, Ophenyl, $OCH(F)_2$, $NH_2$, $NO_2$, $N(Me)_2$, or $R_5$ and $R_6$; or $R_6$ and $R_7$ are linked to each other and form a 5- or 6-membered ring selected from the group consisting of:

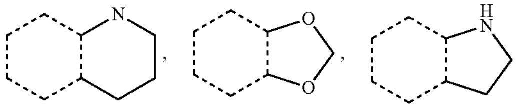

and

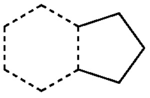

each being optionally substituted with Me.

In connection with particular aspects of the invention, the compound of any appropriate formula I, Ia, Ib, Ic or Id, and definitions herein are particularly defined wherein $R_9$ is selected from the group consisting of: H and Me.

The pharmaceutically-acceptable salts of the compounds of Formula I to Id (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, palmoate, pectinate, persulfate, 3-phenylpropionate, picrate, pivalate, propionate, succinate, sulfate, tartrate, thiocyanate, tosylate and undecanoate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; and aralkyl halides like benzyl and phenethyl bromides and others. Preferred acids for forming acid addition salts include HCl, acetic acid, trifluoroacetic acid and fumaric acid.

A further aspect of the present invention is directed to pharmaceutical compositions comprising at least one compound of Formula I to Id, or a salt thereof, and one or more pharmaceutically-acceptable excipients.

A further aspect of the present invention is directed to a method of treating a condition that results from abnormal cell growth, cellular differentiation, tumor growth or invasion with one or more compounds of Formula I to Id.

A further aspect of the invention is directed to a method of treating cancer in a human suffering therefrom, particularly wherein the cancer is a hormone-dependent cancer, gastrointestinal (GI) tract cancer, or skin cancer comprising administering a therapeutically effective amount of a compound of Formula I to Id.

A further aspect of the invention is directed to the use of one or more compounds of formula I to Id for the manufacture of medicament for the treatment of cancer in a human, particularly wherein the cancer is hormone-dependent cancer, GI tract cancer, or skin cancer.

A further aspect of the invention is directed to hindering or blocking cell cycle progression by contacting one or more cells with one or more compounds of Formula I to Id.

A further aspect of the present invention is directed to a method of synthesizing compounds of Formula I to Id by following one or more synthetic schemes as defined below.

The compounds of Formula I to Id may also be solvated, especially hydrated. Hydration may occur during manufacturing of the compounds or compositions comprising the compounds, or the hydration may occur over time due to the hygroscopic nature of the compounds.

When any variable occurs more than one time in any constituent of Formula I to Id, its definition on each occurrence is independent of its definition at every other occurrence. Also, combinations of substituents and/or variables are permissible only if such combinations result in stable compounds.

The invention disclosed herein is also meant to encompass the in vivo metabolic products of the disclosed compounds. Such products may result, for example, from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabeled compound of the invention, administering it parenterally in a detectable dose to an animal such as rat, mouse, guinea pig, monkey, or to human, allowing sufficient time for metabolism to occur and isolating its conversion products from the urine, blood or other biological samples.

Some of the compounds disclosed herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

Compositions and Methods of Use

Compositions of the present invention include pharmaceutical compositions comprising a compound of Formula I, Ia, Ib, Ic or Id wherein A, $R_1$, $R_2$, $R_3$, X, Y, $R_4$, $R_5$, $R_6$, $R_7$, $R_8$, and $R_9$, $R_{10}$ and $R_{11}$ and $R_{12}$ are defined herein, and one or more pharmaceutically acceptable excipients. Particular compositions of the present invention are pharmaceutical compositions comprising a compound selected from a preferred group of compounds of Formula Ia-Id as defined above, and one or more pharmaceutically acceptable excipients.

The pharmaceutical compositions of the invention can be administered to any animal that can experience the beneficial effects of the compounds of the invention. Foremost among such animals are mammals, particularly humans, although the invention is not intended to be so limited.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropyl methylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which can contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide ou metahydroxyde?, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferred to use the solid anionic surface-active agent in the form of a sodium salt.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., Meth. Cell Biol. 14:33 (1976)).

Compounds of the present invention are useful for treating, inhibiting or preventing abnormal cell growth, cellular differentiation, tumor growth and invasion. They are effective against a broad range of cancers such as GI tract, hormone-dependent or skin cancers. Particularly, GI tract cancer may include colorectal, stomach, liver, duodenal, esophagus, pancreas and gallbladder. Particularly, skin cancers may include basal cell cancer, squamous cell cancer and melanoma. These cancers and conditions are merely meant to be illustrative and are by no means meant to be a limiting or exhaustive list.

Particularly, hormone-dependent cancers may include ovarian, prostate, breast, uterin, cervical, and colon. These cancers and conditions are merely meant to be illustrative and are by no means meant to be a limiting or exhaustive list.

The compounds of the present invention may be administered in an effective amount within the dosage range of about 0.05 mg/kg to about 200 mg/kg, preferably from about 0.1 mg/kg to about 100 mg/kg body weight. The compounds are preferably administered in compositions in which the compound is present in a concentration of about 1 mg/mL to about 250 mg/mL (e.g., in a solution), or in an amount of about 1 mg to about 200 mg, preferably about 5 mg to about 100 mg (e.g., in one unit of a solid dosage form such as a tablet or capsule). When the composition is in the form of a tablet, the compound of the present invention may comprise about 1 to about 50% (wt/wt), preferably about 5 to about 25% (wt/wt) of the tablet. Compounds of the present invention may be administered in a single daily dose, or the total daily dosage may be administered in divided doses of two, three or four times daily.

The compounds and compositions according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Preparation of Compounds of Formula (I)

Scheme 1:
Part 1

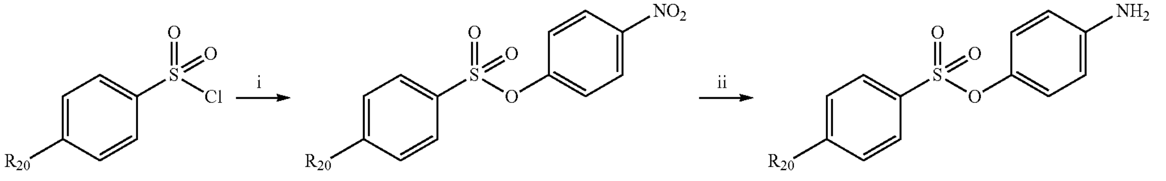

1a, b 2a, b

-continued

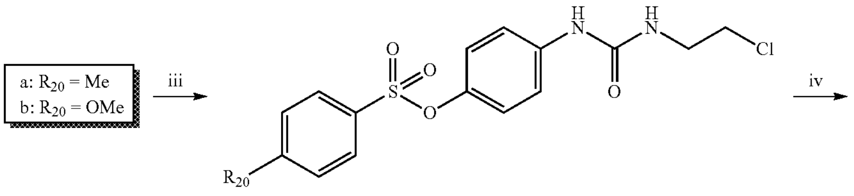

3a, b

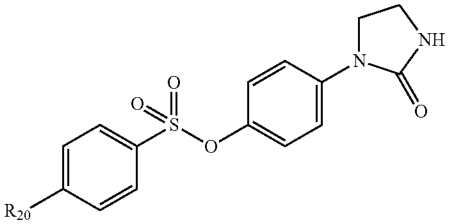

7: $R_{20}$ = 4-Me
8: $R_{20}$ = 4-OMe

Part 2

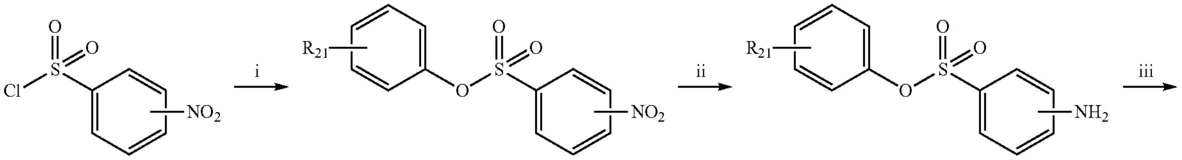

4a-k 5a-k

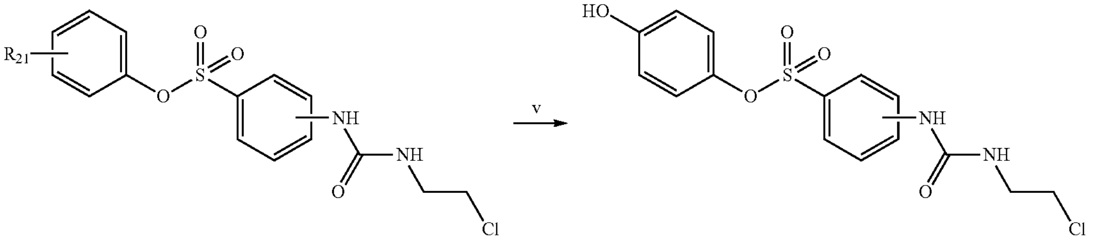

6a-k 6l, m

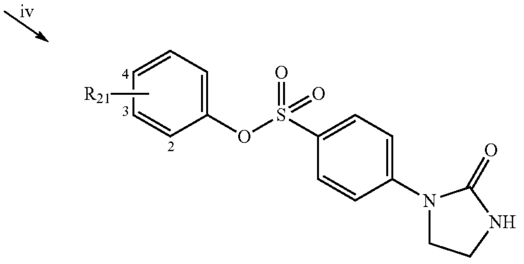

9: $R_{21}$ = 2-Me
10: $R_{21}$ = 3-Me
11: $R_{21}$ = 4-Me
12: $R_{21}$ = 4-OMe
13: $R_{21}$ = 4-NMe$_2$
14: $R_{21}$ = 4-OH a: m; $R_{21}$ = 4-OtBDMS
b: m; $R_{21}$ = 4-OMe
c: m; $R_{21}$ = 4-N(Me)$_2$
d: m; $R_{21}$ = 3,4,5-(OMe)$_3$
e: p; $R_{21}$ = 2-Me
f: p; $R_{21}$ = 3-Me
g: p; $R_{21}$ = 4-Me
h: p; $R_{21}$ = 4-OtBDMS
i: p; $R_{21}$ = 4-OMe
j: p; $R_{21}$ = 4-N(Me)$_2$
k: p; $R_{21}$ = 3,4,5-(OMe)$_3$
l: m; $R_{21}$ = 4-OH
m: p; $R_{21}$ = 4-OH

Reagents: (i) relevant phenol, TEA/DCM; (ii) $Na_2S_2O_4$/MeOH and $H_2O$, $SnCl_2$•$2H_2O$/EtOH or Fe, HCl/EtOH; (iii) 2-chloroethylisocyanate/DCM or 2-chloroethylisocyanate, DMAP/THF or 2-chloroethylisocyanate/microwave, THF; (iv) $Al_2O_3$•KF/$CH_3CN$; (v) TBAF 1M/THF.

Step i: Selected benzenesulfonyl chlorides or nitrobenzenesulfonyl chlorides (8.0 mmol) were dissolved in dry methylene chloride (20 mL) under nitrogen atmosphere. Relevant phenols or nitrophenols (8.0 mmol) were added dropwise to the solution followed by the slow addition of triethylamine (8.0 mmol). The mixture was stirred at room temperature for 24 h. The solvent was evaporated and the residue dissolved in ethyl acetate. The solution was washed with hydrochloric acid (1N), sodium hydroxide (1N), brine, dried over sodium sulfate, filtered, and evaporated to dryness.

Step ii: Method A: To a solution of the appropriate nitro compound 2a, b, 5b, c, d, h, i or k (2.0 mmol) in ethanol (40 mL) was added stannous chloride dihydrate (12.0 mmol) and the mixture was refluxed for 6 h. After cooling at room temperature, the solvent was evaporated, the residue was then taken up in 300 mL of sodium hydroxide (1N) and extracted with ether (200 mL). The combined organic extracts were washed with brine, dried over sodium sulfate and concentrated under reduced pressure.

Step ii: Method B: To a reflux solution of compound 5a (1.5 mmol) dissolved in 25 mL of methanol, sodium hydrosulfite (9.6 mmol) dissolved in 8 mL of water was added dropwise and the mixture was further refluxed for 4 h. After cooling at room temperature, the mixture was evaporated to remove methanol. Ethyl acetate (100 mL) and water (100 mL) were added and the mixture was extracted with ethyl acetate (100 mL). The organic portions were pooled, washed with brine, dried over sodium sulfate and concentrated under reduced pressure.

Step ii: Method C: The appropriate nitro compound 5e, f, g, or j (2.0 mmol) was dissolved in a mixture of ethanol and water (40 mL, 10:1). Powdered iron (8.0 mmol) and five drops of hydrochloric acid (12 M) were added. The mixture was refluxed overnight. After cooling at room temperature, the solvent was evaporated. Hydrochloric acid (1N) (100 mL) was added and the mixture was extracted with ethyl acetate (100 mL). The organic solutions were pooled, washed with brine, dried over sodium sulfate and concentrated under reduced pressure.

Step iii: Method D: 2-Chloroethylisocyanate (1.2 mmol) was added dropwise to a cold solution (ice bath) of the appropriate aniline 2a, b, 5a, b, c, e, g, h or i (1.0 mmol) in dry methylene chloride (10 mL) or dry tetrahydrofuran (20 mL) under dry nitrogen atmosphere. The ice bath was then removed and the reaction mixture was stirred at room temperature for 9 days. Afterward, the solvent was evaporated under reduced pressure and the crude compound was purified by flash chromatography.

Step iii: Method E: 2-Chloroethylisocyanate (1.2 mmol) and 4-dimethylaminopyridine was added dropwise to a solution of the appropriate aniline 5d or k (1.0 mmol) in dry tetrahydrofuran (10 mL) under nitrogen atmosphere. The reaction mixture was heated to reflux and stirred for 2 days. Afterward cooling to room temperature, the solvent was evaporated under reduced pressure and the crude compound was purified by flash chromatography.

Step iii: Method F: 2-Chloroethylisocyanate (1.2 mmol) was added dropwise the appropriate aniline 5f or j (1.0 mmol) in dry tetrahydrofuran (10 mL). The reaction mixture was stirred at 60 or 100° C. under microwave heating (100 W) for 15 to 20 minutes for aniline 5j and f, respectively.

Step iv: Method G: To a stirred solution of the appropriate N-phenyl-N'-(2-chloroethyl)urea derivative (0.4 mmol) in acetonitrile (10 mL) a mixture of aluminum oxide and potassium fluoride (6:4) (4.0 mmol) was added. The suspension was refluxed overnight. After cooling, the mixture was filtered, and the solvent evaporated under reduced pressure. The residue was purified by recrystallisation or flash chromatography on silica gel.

Step v; Compound 6a or h (0.1 mmol) was dissolved in dry tetrahydrofuran (5 mL). Tetrabutylammonium fluoride (1M) in dry tetrahydrofuran was added dropwise. The mixture was stirred at room temperature for 24 h. The solvent was evaporated and the residue dissolved with ethyl acetate (40 mL). The solution was washed with 40 mL hydrochloric acid (1N), brine, dried over sodium sulfate, filtered, and evaporated to dryness. The crude product was purified by flash chromatography (silica gel, methylene chloride to methylene chloride/ethyl acetate 85:15).

Scheme 2:

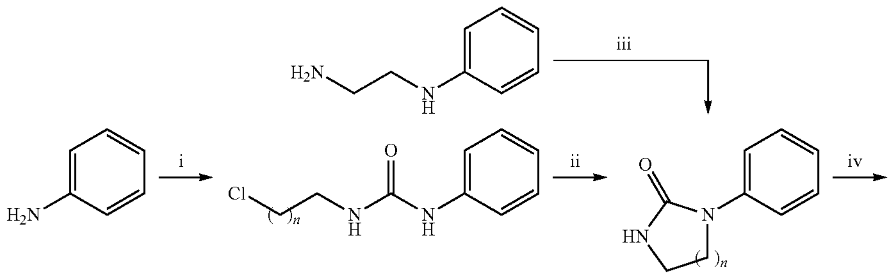

82: n = 1
83: n = 2

84: n = 1
85: n = 2

-continued

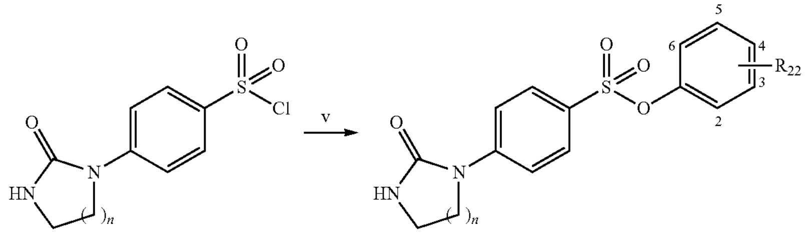

or

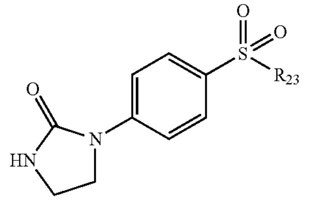

86: n = 1
87: n = 2

9-63 and 69-81

64-68

9: n = 1, $R_{22}$ = 2-Me
10: n = 1, $R_{22}$ = 3-Me
11: n = 1, $R_{22}$ = 4-Me
12: n = 1, $R_{22}$ = 4-OMe
13: n = 1, $R_{22}$ = 4-NMe$_2$
14: n = 1, $R_{22}$ = 4-OH
15: n = 1, $R_{22}$ = H
16: n = 1, $R_{22}$ = 2-Et
17: n = 1, $R_{22}$ = 2-Prop
18: n = 1, $R_{22}$ = 2-OMe
19: n = 1, $R_{22}$ = 2-OEt
20: n = 1, $R_{22}$ = 2-Cl
21: n = 1, $R_{22}$ = 2-F
22: n = 1, $R_{22}$ = 2-I
23: n = 1, $R_{22}$ = 2-NO$_2$
24: n = 1, $R_{22}$ = 2-Me, 3-Me
25: n = 1, $R_{22}$ = 2-Me, 4-Me
26: n = 1, $R_{22}$ = 2-Me, 5-Me
27: n = 1, $R_{22}$ = 2-Me, 4-Me, 5-Me
28: n = 1, $R_{22}$ = 2-Cl, 4-Cl, 5-Cl
29: n = 1, $R_{22}$ = 2-Cl, 4-Cl, 6-Cl
30: n = 1, $R_{22}$ = 2-F, 4-F
31: n = 1, $R_{22}$ = 2-F, 6-F
32: n = 1, $R_{22}$ = 2-F, 3-F, 4-F, 5-F, 6-F
33: n = 1, $R_{22}$ = 3-Prop
34: n = 1, $R_{22}$ = 3-OMe
35: n = 1, $R_{22}$ = 3-OEt
36: n = 1, $R_{22}$ = 3-Cl vii 37: n = 1, $R_{22}$ = 3-F
38: n = 1, $R_{22}$ = 3-I
vi
39: n = 1, $R_{22}$ = 3-NO$_2$
40: n = 1, $R_{22}$ = 3-NH$_2$
41: n = 1, $R_{22}$ = 3-Me, 5-Me
42: n = 1, $R_{22}$ = 3-Me, 4-Me, 5-Me
43: n = 1, $R_{22}$ = 3-OMe, 4-OMe
44: n = 1, $R_{22}$ = 3-OMe, 5-OMe
45: n = 1, $R_{22}$ = 3-OMe, 4-OMe, 5-OMe
46: n = 1, $R_{22}$ = 3-Cl, 5-Cl
47: n = 1, $R_{22}$ = 3-F, 4-F
48: n = 1, $R_{22}$ = 3-F, 5-F
vi
49: n = 1, $R_{22}$ = 3-F, 4-F, 5-F
50: n = 1, $R_{22}$ = 3-Me, 4-NO$_2$
51: n = 1, $R_{22}$ = 3-Me, 4-NH$_2$
52: n = 1, $R_{22}$ = 4-Et
53: n = 1, $R_{22}$ = 4-Prop
54: n = 1, $R_{22}$ = 4-secBut
55: n = 1, $R_{22}$ = 4-OEt
56: n = 1, $R_{22}$ = 4-OProp
57: n = 1, $R_{22}$ = 4-OBut
58: n = 1, $R_{22}$ = 4-OTBDMS
vi
59: n = 1, $R_{22}$ = 4-Cl
60: n = 1, $R_{22}$ = 4-F
61: n = 1, $R_{22}$ = 4-I
62: n = 1, $R_{22}$ = 4-NO$_2$
63: n = 1, $R_{22}$ = 4-NH$_2$

64: $R_{23}$ =

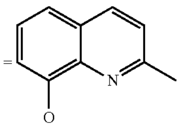

65: $R_{23}$ =

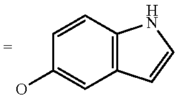

66: $R_{23}$ =

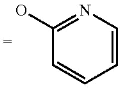

67: $R_{23}$ =

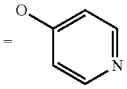

68: $R_{23}$ =

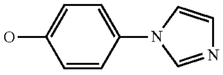

69: n = 2, $R_{22}$ = 2-Me
70: n = 2, $R_{22}$ = 2-Et
71: n = 2, $R_{22}$ = 2-Prop
72: n = 2, $R_{22}$ = 2-Me, 4-Me
73: n = 2, $R_{22}$ = 2-Cl, 4-Cl, 5-Cl
74: n = 2, $R_{22}$ = 2-Cl, 4-Cl, 5-Cl
75: n = 2, $R_{22}$ = 3-Me
76: n = 2, $R_{22}$ = 3-OMe
77: n = 2, $R_{22}$ = 3-F
78: n = 2, $R_{22}$ = 3-OME, 4-OMe, 5-OMe
79: n = 2, $R_{22}$ = 4-Me
80: n = 2, $R_{22}$ = 4-Cl
81: n = 2, $R_{22}$ = 4-F Reagents: (i) 2-chloroethylisocyanate or 3-chloropropylisocyanate, DCM; (ii) NaH, THF; (iii) triphosgene, TEA, THF; (iv) $ClSO_3H$, $CCl_4$; (v) relevant phenol, triethylamine, DCM; (vi) $H_2$, Pd/C 10%, EtOH and (vii) TBAF, THF.

Step i: 2-Chloroethylisocyanate or 3-chloropropylisocyanate (1.2 eq.) was added dropwise to a cold solution (ice bath) of the aniline (1.0 eq.) in dry methylene chloride (15 mL per g of aniline). The ice bath was then removed and the reaction mixture was stirred at room temperature for 24 h. After completion of the reaction, the solvent was evaporated under reduced pressure to give white solid, which was triturated twice with cold hexanes/ether 10:1.

Step ii: Sodium hydride (3 eq.) was added slowly to a cold solution of compound 82 or 83 (1 eq.) in tetrahydrofuran under dry nitrogen atmosphere. The ice bath was then removed after 30 min and the reaction mixture was stirred at room temperature for 5 h. The reaction was quenched at 0° C. with water and diluted with ethyl acetate. The organic layer was washed with water and brine, dried over sodium sulfate, filtered, and concentrated in vacuo to provide 84 or 85, which were used without further purification to afford white solids.

Step iii; Compound 84 was also synthesized using method described by Neville. Briefly, triphosgene (12.2 mmol) was dissolved in 40 mL of tetrahydrofuran and cooled at 0° C. To the resulting solution was added (36.7 mmol) of N-phenylethylenediamine dissolved in 65 mL of tetrahydrofuran and 7.7 mL of triethylamine over a period of 30 min. White solid immediately precipitated. The reaction was complete after 5 min. The reaction mixture was quenched with water and diluted with ethyl acetate. The organic layer was washed with water and brine, dried over sodium sulfate, filtered, and concentrated in vacuo. The residue was purified by flash chromatography (methylene chloride to methylene chloride/ethyl acetate 3:10) to afford a white solid.

Step iv: To 1.5 mL (23.1 mmol) of chlorosulfonic acid in 3 mL of carbon tetrachloride at 0° C. was added slowly (3.1 mmol) compound 84 or 85. The reaction was almost completed after 2 h at 0° C. The reaction mixture was poured slowly onto ice water, filtered to collect the solid. The white solid was dryed under vacuum.

Step v: 4-(2-oxoimidazolidin-1-yl)benzene-1-sulfonyl chloride or 4-(tetrahydro-2-oxopyrimidin-1(2H)-yl)benzene-1-sulfonyl chloride (8.00 mmol) was suspended in dry methylene chloride (10 mL) under nitrogen atmosphere. Appropriate phenol (8.00 mmol) and triethylamine (8.00 mmol) were successively added dropwise and the mixture was stirred at room temperature for 24 h. The mixture was evaporated and the residue dissolved with ethyl acetate (100 mL). The solution was washed with hydrochloric acid 1N (100 mL), sodium hydroxide 1N (100 mL), brine (100 mL), dried over sodium sulfate, filtered, and evaporated to dryness under vacuum. The residue was purified by flash chromatography on silica gel.

Step vi: A mixture of the appropriate nitro compound 39, 50 or 62 (1 eq.) dissolved in ethanol 99% (30 mL) was added dropwise Pd/C 10% (0.02 eq.). The nitro compound was reduced under hydrogen atmosphere (38 psi) overnight. The catalyst was removed by filtration and the filtrate was evaporated to dryness. The residue was purified by flash chromatography on silica gel to give compounds 40, 51 and 63.

Step vii: To a stirred solution of 58 (1 eq.) in tetrahydrofuran (10 mL) was added tetrabutylammoniumfluoride 1M in tetrahydrofuran (1.1 eq.). The mixture was stirred overnight then hydrochloric acid was added and extracted with 3× ethyl acetate, washed with brine, dried with sodium sulfate and the solvent was evaporated under reduced pressure to afford 14.

Scheme 3:

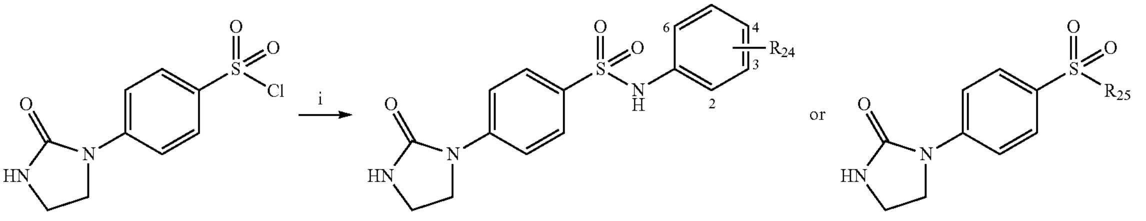

86 88-124 or 125-128

| | | |
|---|---|---|
| 88: $R_{24}$ = H | 104: $R_{24}$ = 3-F, 4-F | 121: $R_{24}$ = 3-F, 4-F |
| 89: $R_{24}$ = 2-Me | 105: $R_{24}$ = 3-OMe, 4-OMe | 121: $R_{24}$ = 3-OMe, 4-OMe |
| 90: $R_{24}$ = 2-Et | 106: $R_{24}$ = 3-OMe, 5-OMe | 122: $R_{24}$ = 3-OMe, 5-OMe |
| 91: $R_{24}$ = 2-OMe | 107: $R_{24}$ = 3-OMe, 4-OMe, 5-OMe | 123: $R_{24}$ = 3-OMe, 4-OMe, 5-OMe |
| 92: $R_{24}$ = 2-Me, 4-Me | 108: $R_{24}$ = 4-Me | 124: $R_{24}$ = 4-Me |
| 93: $R_{24}$ = 2-Me, 4-Me | 109: $R_{24}$ = 4-Et | |
| 94: $R_{24}$ = 2-Me, 5-Me | 110: $R_{24}$ = 4-But | |
| 95: $R_{24}$ = 3-Me | 111: $R_{24}$ = 4-secBut | 125: $R_{25}$ = 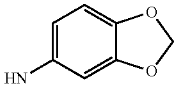 |
| 96: $R_{24}$ = 3-Et | 112: $R_{24}$ = 4-tBut | |
| 97: $R_{24}$ = 3-OMe | 113: $R_{24}$ = 4-Pent | |
| 98: $R_{24}$ = 3-OPh | 114: $R_{24}$ = 4-cHex | |
| 99: $R_{24}$ = 3-Br | 115: $R_{24}$ = 4-Hept | |
| 100: $R_{24}$ = 3-Cl | 116: $R_{24}$ = 4-OMe | 126: $R_{25}$ = 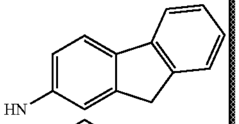 |
| 101: $R_{24}$ = 3-Me, 4-Me | 117: $R_{24}$ = 4-OBut | |
| 102: $R_{24}$ = 3-Me, 5-Me | 118: $R_{24}$ = 4-OHex | |
| 103: $R_{24}$ = 3-tBut, 5-tBut | 119: $R_{24}$ = 4-Br | |
| | | 127: $R_{25}$ = 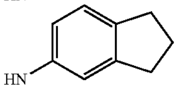 |
| | | 128: $R_{25}$ = 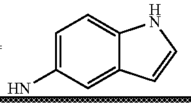 |

Reagents: (i) Relevant aniline, DMAP/$CH_3CN$.

Step i; Compound 86 (1.00 mmol) was suspended in dry acetonitrile (10 mL) under nitrogen atmosphere. Relevant aniline (1.00 mmol) and 4-dimethylaminopyridine (4.00 mmol) were successively added dropwise and the mixture was stirred at room temperature for 48 h. Ethyl acetate was added and the solution was washed with hydrochloric acid 1N, brine, dried over sodium sulfate, filtered, and evaporated to dryness under vacuum. The white solid was purified by flash chromatography on silica gel.

Scheme 4:

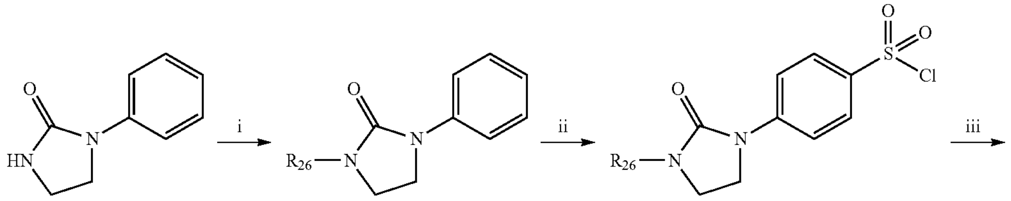

84

129: $R_{26}$ = Me
130: $R_{26}$ = Prop

131: $R_{26}$ = Me
132: $R_{26}$ = Prop

-continued

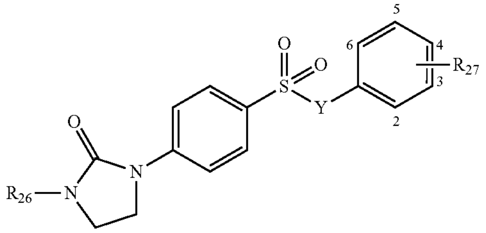

133-172

133: $R_{26}$ = Me; Y = O; $R_{27}$ = 2-Me
134: $R_{26}$ = Me; Y = O; $R_{27}$ = 2-Et
135: $R_{26}$ = Me; Y = O; $R_{27}$ = 2-Prop
136: $R_{26}$ = Me; Y = O; $R_{27}$ = 2-Me, 4-Me
137: $R_{26}$ = Me; Y = O; $R_{27}$ = 2-Cl, 4-Cl, 5-Cl
138: $R_{26}$ = Me; Y = O; $R_{27}$ = 2-Cl, 4-Cl, 6-Cl
139: $R_{26}$ = Me; Y = O; $R_{27}$ = 3-Me
140: $R_{26}$ = Me; Y = O; $R_{27}$ = 3-OMe
141: $R_{26}$ = Me; Y = O; $R_{27}$ = 3-F
142: $R_{26}$ = Me; Y = O; $R_{27}$ = 3-$NO_2$
143: $R_{26}$ = Me; Y = O; $R_{27}$ = 3-OMe, 4-OMe, 5-OMe
144: $R_{26}$ = Me; Y = O; $R_{27}$ = 4-Me
145: $R_{26}$ = Me; Y = O; $R_{27}$ = 4-OMe
146: $R_{26}$ = Me; Y = O; $R_{27}$ = 4-Cl
147: $R_{26}$ = Me; Y = O; $R_{27}$ = 4-F
148: $R_{26}$ = Prop; Y = O; $R_{27}$ = 2-Me
149: $R_{26}$ = Prop; Y = O; $R_{27}$ = 2-Me
150: $R_{26}$ = Prop; Y = O; $R_{27}$ = 2-Et
151: $R_{26}$ = Prop; Y = O; $R_{27}$ = 2-Prop
152: $R_{26}$ = Prop; Y = O; $R_{27}$ = 2-Me, 4-Me
153: $R_{26}$ = Prop; Y = O; $R_{27}$ = 2-Cl, 4-Cl, 5-Cl
154: $R_{26}$ = Prop; Y = O; $R_{27}$ = 2-Cl, 4-Cl, 6-Cl
155: $R_{26}$ = Prop; Y = O; $R_{27}$ = 3-Me
156: $R_{26}$ = Prop; Y = O; $R_{27}$ = 3-OMe
157: $R_{26}$ = Prop; Y = O; $R_{27}$ = 3-F
158: $R_{26}$ = Prop; Y = O; $R_{27}$ = 3-$NO_2$
159: $R_{26}$ = Prop; Y = O; $R_{27}$ = 3-OMe, 4-OMe
160: $R_{26}$ = Prop; Y = O; $R_{27}$ = 3-OMe, 5-OMe
161: $R_{26}$ = Prop; Y = O; $R_{27}$ = 3-OMe, 4-OMe, 5-OMe
162: $R_{26}$ = Prop; Y = O; $R_{27}$ = 4-Me
163: $R_{26}$ = Prop; Y = O; $R_{27}$ = 4-OMe
164: $R_{26}$ = Prop; Y = O; $R_{27}$ = 4-Cl
165: $R_{26}$ = Prop; Y = O; $R_{27}$ = 4-F
166: $R_{26}$ = Prop; Y = O; $R_{27}$ = H
167: $R_{26}$ = Prop; Y = O; $R_{27}$ = 2-Me, 4-Me
168: $R_{26}$ = Prop; Y = O; $R_{27}$ = 3-OMe
169: $R_{26}$ = Prop; Y = O; $R_{27}$ = 3-Me, 4-Me
170: $R_{26}$ = Prop; Y = O; $R_{27}$ = 3-OMe, 5-OMe
171: $R_{26}$ = Prop; Y = O; $R_{27}$ = 3-OMe, 4-OMe, 5-OMe
172: $R_{26}$ = Prop; Y = O; $R_{27}$ = 4-F Reagents: (i) NaH (60%), MeI or PropI/THF; (ii) $ClSO_3H/CCl_4$; (iii) relevant phenol, TEA/DCM or relevant aniline, DMAP/$CH_3CN$.

Step i: Sodium hydride 60% (33 mmol) was added slowly to a cold solution of 84 (30 mmol) in tetrahydrofuran under nitrogen atmosphere. The ice bath was then removed after 30 min and methyliodide or propyliodide (36 mmol) was then added slowly and the reaction mixture was stirred at room temperature for 20 h. The reaction was quenched at 0° C. and diluted with ethyl acetate. The organic layer was washed with water and brine, dried over sodium sulfate, filtered, and concentrated in vacuo. The residue was purified by flash chromatography (silica gel, methylene chloride to methylene chloride/ethyl acetate (85:15)).

Step ii: To chlorosulfonic acid (23.1 mmol) in carbontetrachloride (5 mL) at 0° C. was added slowly compounds 129 or 130 (3.1 mmol). The reaction was almost completed after 2 h at 0° C. The reaction mixture was poured into ice water slowly, then filtered to collect the solids formed. The solid was dried overnight under vacuum.

Step iii: Method H; Compound 131 or 132 (8.00 mmol) was suspended in dry-methylene chloride (10 mL) under nitrogen atmosphere. Relevant phenol (8.00 mmol) and triethylamine (8.00 mmol) were successively added dropwise and the mixture was stirred at room temperature for 24 h. The mixture was evaporated and dissolved with ethyl acetate. The solution was washed with hydrochloric acid 1N, sodium hydroxide 1N, brine, dried over sodium sulfate, filtered, and evaporated to dryness under vacuum. The white solid was purified by flash chromatography on silica gel.

Method I; Compound 132 (1.00 mmol) was suspended in dry acetonitrile (10 mL) under nitrogen atmosphere. Relevant aniline (1.00 mmol) and 4-dimethylaminopyridine (4.00 mmol) were successively added dropwise and the mixture was stirred at room temperature for 48 h. Ethyl acetate was added and the solution was washed with hydrochloric acid 1N, brine, dried over sodium sulfate, filtered, and evaporated to dryness under vacuum. The white solid was purified by flash chromatography on silica gel.

EXAMPLES OF SPECIFIC COMPOUNDS

Example 1

1a

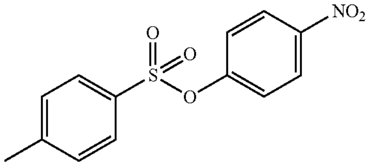

$C_{13}H_{11}NO_5S$
Exact Mass: 293,03579

4-Nitrophenyl 4-methylbenzenesulfonate (1a). Yield: 99%. mp: 89-90° C.; IR v: 1530 ($NO_2$), 1377 ($NO_2$) $cm^{-1}$; $^1H$ NMR ($CDCl_3$) δ: 8.15-8.13 (m, 2H, Ar), 7.69 (d, 2H, J=8.2 Hz, Ar), 7.32 (d, 2H, J=8.2 Hz, Ar), 7.17-7.14 (m, 2H, Ar), 2.42 (s, 3H, $CH_3$); $^{13}C$ NMR ($CDCl_3$) δ: 153.9, 146.3, 146.2, 131.7, 130.1, 128.4, 125.4, 123.2, 21.7.

Example 2

1b

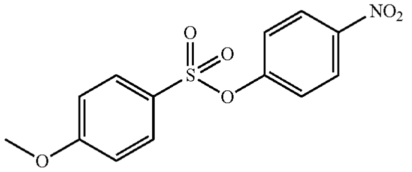

$C_{13}H_{11}NO_6S$
Exact Mass: 309.03071

4-Nitrophenyl 4-methoxybenzenesulfonate (1b). Yield: 84%. mp: 82-83° C.; IR v: 1593 ($NO_2$), 1347 ($NO_2$) $cm^{-1}$; $^1H$ NMR ($CDCl_3$) δ: 8.12 (d, 2H, J=9.1 Hz, Ar), 7.70 (d, 2H, J=9.0 Hz, Ar), 7.14 (d, 2H, J=9.1 Hz, Ar), 6.95 (d, 2H, J=9.0 Hz, Ar), 3.83 (s, 3H, $CH_3$); $^{13}C$ NMR ($CDCl_3$) δ: 164.6, 154.0, 146.1, 130.7, 125.7, 125.4, 123.3, 114.7, 55.8.

Example 3

2a

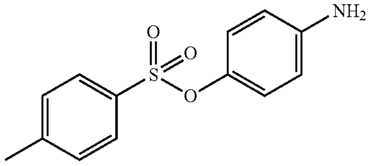

$C_{13}H_{13}NO_3S$
Exact Mass: 263.06161

4-Aminophenyl 4-methylbenzenesulfonate (2a). Method A. Yield: 87%. mp: 140-141° C.; IR v: 3369 ($NH_2$), 1505 ($NH_2$) $cm^{-1}$; $^1H$ NMR ($CDCl_3$) δ: 7.68 (d, 2H, J=8.2 Hz, Ar), 7.29 (d, 2H, J=8.2 Hz, Ar), 6.75-6.71 (m, 2H, Ar), 6.53-6.50 (m, 2H, Ar), 3.65 (s, 2H, $NH_2$), 2.44 (s, 3H, $CH_3$); $^{13}C$ NMR ($CDCl_3$) δ: 145.3, 141.7, 129.6, 128.6, 123.2, 115.4, 21.7.

Example 4

2b

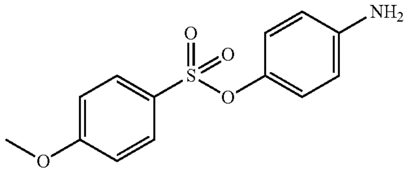

$C_{13}H_{13}NO_4S$
Exact Mass: 279.05653

4-Aminophenyl 4-methoxybenzenesulfonate (2b). Method A. Yield: 99%. mp: 110-112° C.; IR v: 3360 ($NH_2$), 1504 ($NH_2$) $cm^{-1}$; $^1H$ NMR ($CDCl_3$) δ: 7.72-7.68 (m, 2H, Ar), 6.96-6.92 (m, 2H, Ar), 6.72-6.70 (m, 2H, Ar), 6.52-6.49 (m, 2H, Ar), 3.86 (s, 3H, $CH_3$), 3.62 (s, 2H, NH); $^{13}C$ NMR ($CDCl_3$) δ: 164.0, 145.4, 141.7, 130.8, 126.8, 123.3, 115.3, 114.2, 55.7.

Example 5

3a

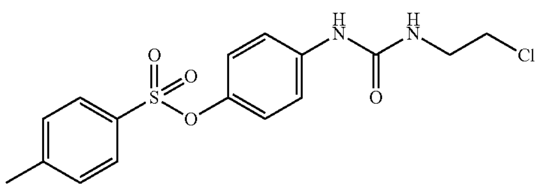

$C_{16}H_{17}ClN_2O_4S$
Exact Mass: 368,05976

4-[3-(2-Chloroethyl)ureido]phenyl 4-methylbenzenesulfonate (3a). Method D in methylene chloride. The crude product was crystallized with methylene chloride and filtered. Yield: 99%. mp: 149-150° C.; IR v: 3356 (NH), 1645 (C═O) $cm^{-1}$; $^1H$ NMR (DMSO-$d_6$) δ: 8.80 (s, 1H, NH), 7.71 (d, 2H, J=8.2 Hz, Ar), 7.47 (d, 2H, J=8.2 Hz, Ar), 7.37-7.34 (m, 2H, Ar), 6.88-6.85 (m, 2H, Ar), 6.44 (t, 1H, J=5.7 Hz, NH), 3.65 (t, 2H, J=6.) Hz, $CH_2$), 3.44-3.38 (min, 2H, $CH_2$), 2.43 (s, 3H, $CH_3$); $^{13}C$ NMR (DMSO-$d_6$) δ: 154.9, 145.7, 142.9, 139.4, 131.5, 130.2, 128.3, 122.4, 118.5, 44.3, 41.2, 21.2; MS (ESI) m/z: 369.0 $[M+H]^+$.

Example 6

3b

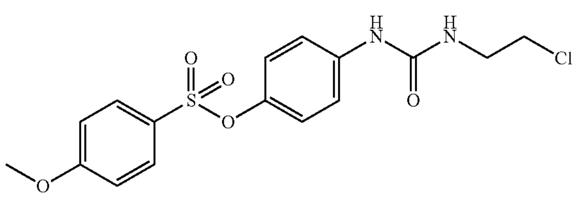

$C_{16}H_{17}ClN_2O_5S$
Exact Mass: 384,05467

4-[3-(2-Chloroethyl)ureido]phenyl 4-methoxybenzenesulfonate (3b). Method D in methylene chloride. The crude product was filtered off and recrystallized with methylene chloride/hexanes 50:50 and filtered. Yield: 97%. mp: 137-138° C.; IR v: 3323 (NH), 1645 (C═O) $cm^{-1}$; $^1H$ NMR (DMSO-$d_6$) δ: 8.80 (brs, 1H, NH), 7.76-7.73 (m, 2H, Ar), 7.36 (d, 2H, J=8.9 Hz, Ar), 7.17 (d, 2H, J=8.9 Hz, Ar), 6.87-6.84 (m, 2H, Ar), 6.44 (t, 1H, J=5.8 Hz, NH), 3.88 (s, 3H, $CH_3$), 3.65 (t, 2H, J=5.8 Hz, $CH_2$), 3.44-3.38 (m, 2H, $CH_2$); $^{13}C$ NMR ($CDCl_3$+MeOD) δ: 164.1, 155.8, 144.2, 138.4, 130.7, 126.3, 122.7, 119.3, 114.3, 55.6, 44.4, 41.6; MS (ESI) m/z: 384.9 $[M+H]^+$.

Example 7

4a

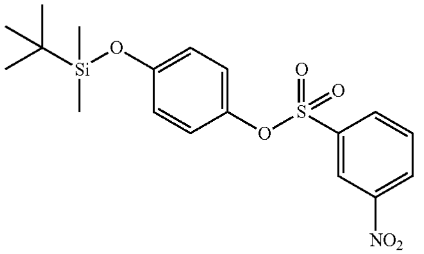

$C_{18}H_{23}NO_6SSi$
Exact Mass: 409,10153

4-(tert-Butyldimethylsilanyloxy)phenyl 3-nitrobenzenesulfonate (4a). Yield: 88%. IR v: 2932 (SiO), 1529 ($NO_2$), 1353 ($NO_2$) $cm^{-1}$; $^1H$ NMR ($CDCl_3$) δ: 8.59 (s, 1H, Ar), 8.51-8.48 (m, 1H, Ar), 8.12-8.10 (m, 1H, Ar), 7.79-7.74 (m, 1H, Ar), 6.83 (d, 2H, J=9.1 Hz, Ar), 6.72 (d, 2H, J=9.1 Hz, Ar), 0.92 (s, 9H, 3×$CH_3$), 0.14 (s, 6H, 2×$CH_3$); $^{13}C$ NMR ($CDCl_3$) δ: 155.0, 148.2, 143.1, 137.2, 134.0, 130.7, 128.7, 123.7, 123.1, 121.0, 25.6, 18.1, −4.6.

Example 8

4b

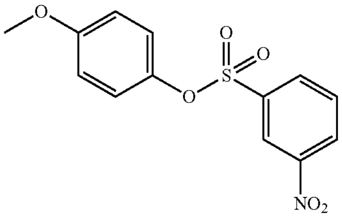

$C_{13}H_{11}NO_6S$
Exact Mass: 309,03071

4-Methoxyphenyl 3-nitrobenzenesulfonate (4b). Yield: 98%. mp: 84-85° C.; IR ν: 1502 ($NO_2$), 1379 ($NO_2$) $cm^{-1}$; $^1H$ NMR (DMSO-$d_6$) δ: 8.64-8.62 (m, 1H, Ar), 8.47-8.46 (m, 1H, Ar), 8.24-8.22 (m, 1H, Ar), 7.98-7.93 (m, 1H, Ar), 7.02-7.00 (m, 2H, Ar), 6.92-6.89 (m, 2H, Ar), 3.72 (s, 3H, $CH_3$); $^{13}C$ NMR (DMSO-$d_6$) δ: 158.3, 148.1, 142.1, 135.6, 134.2, 131.9, 129.5, 123.3, 123.0, 115.0, 55.5.

Example 9

4c

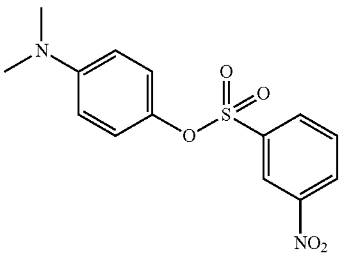

$C_{14}H_{14}N_2O_5S$
Exact Mass: 322,06234

4-(Dimethylamino)phenyl 3-nitrobenzenesulfonate (4c). The crude product was purified by flash chromatography (silica gel, hexanes to hexanes/ethyl acetate 85:15). Yield: 34%. mp: 142-143° C.; IR ν: 1528 ($NO_2$), 1371 ($NO_2$) $cm^{-1}$; $^1H$ NMR (DMSO-$d_6$) δ: 8.66-8.63 (m, 1H, Ar), 8.47-8.46 (m, 1H, Ar), 8.26-8.24 (m, 1H, Ar), 8.00-7.95 (m, 1H, Ar), 6.89-6.86 (m, 2H, Ar), 6.65-6.62 (m, 2H, Ar), 2.88 (s, 6H, 2×$CH_3$); $^{13}C$ NMR (DMSO-$d_6$) δ: 149.5, 148.1, 139.0, 136.0, 134.2, 131.9, 129.4, 122.9, 122.5, 112.5.

Example 10

4d

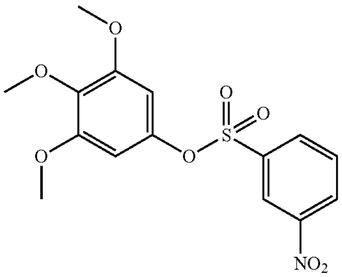

$C_{15}H_{15}NO_8S$
Exact Mass: 369,05184

3,4,5-Trimethoxyphenyl 3-nitrobenzenesulfonate (4d). The crude product was recrystallised from cold ether. Yield: 64%. mp: 123-125° C.; IR ν: 3094 (OMe), 1606 ($NO_2$) $cm^{-1}$; $^1H$ NMR (DMSO-$d_6$) δ: 8.66 (d, 1H, J=8.0 Hz, Ar), 8.53 (s, 1H, Ar), 8.31 (d, 1H, J=8.0 Hz, Ar), 8.01-7.96 (m, 1H, Ar), 6.42 (s, 2H, Ar), 3.65 (s, 6H, 2×$CH_3$), 3.63 (s, 3H, $CH_3$); $^{13}C$ NMR (DMSO-$d_6$) δ: 153.3, 148.2, 144.6, 135.5, 134.4, 131.8, 129.6, 123.2, 100.2, 56.2, 45.5.

Example 11

4e

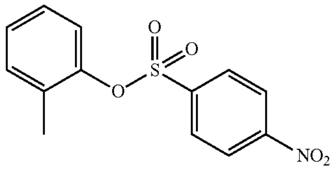

$C_{13}H_{11}NO_5S$
Exact Mass: 293,03579

2-Tolyl 4-nitrobenzenesulfonate (4e). Yield: 98%. mp: 84-85° C.; IR ν: 1533 ($NO_2$), 1191 (S═O) $cm^{-1}$; $^1H$ NMR ($CDCl_3$) δ: 8.35 (d, 2H, J=8.8 Hz, Ar), 8.06 (d, 2H, J=8.8 Hz, Ar), 7.19-7.10 (m, 3H, Ar), 6.96-6.93 (m, 1H, Ar), 2.09 (s, 3H, $CH_3$); $^{13}C$ NMR ($CDCl_3$) δ: 151.0, 148.0, 141.7, 132.0, 131.4, 129.8, 127.6, 127.3, 124.5, 121.9, 16.3.

Example 12

4f

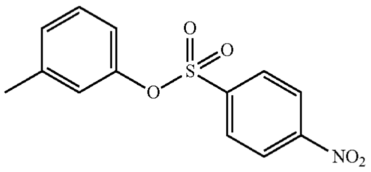

$C_{13}H_{11}NO_5S$
Exact Mass: 293,03579

3-Tolyl 4-nitrobenzenesulfonate (4f). Yield: 97%. mp: 94-95° C.; IR ν: 1533 ($NO_2$), 1351 ($NO_2$) $cm^{-1}$; $^1H$ NMR ($CDCl_3$) δ: 8.35 (d, 2H, J=8.8 Hz, Ar), 8.02 (d, 2H, J=8.8 Hz, Ar), 7.19-7.06 (m, 2H, Ar), 6.86 (s, 1H, Ar), 6.73-6.70 (m, 1H, Ar), 2.29 (s, 3H, $CH_3$); $^{13}C$ NMR ($CDCl_3$) δ: 151.0, 149.2, 141.1, 140.6, 129.9, 129.6, 128.5, 124.3, 122.7, 118.8, 21.2.

Example 13

4g

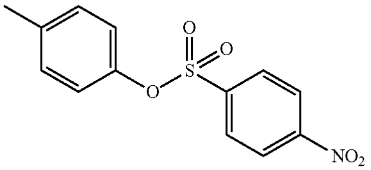

$C_{13}H_{11}NO_5S$
Exact Mass: 293,03579

4-Tolyl 4-nitrobenzenesulfonate (4g). Yield: 96%. mp: 94-95° C.; IR ν: 1520 ($NO_2$), 1199 (S═O) $cm^{-1}$; $^1H$ NMR ($CDCl_3$) δ: 8.35 (d, 2H, J=8.7 Hz, Ar), 8.01 (d, 2H, J=8.7 Hz, Ar), 7.09 (d, 2H, J=8.2 Hz, Ar), 6.85 (d, 2H, J=8.2 Hz, Ar), 2.30 (s, 3H, $CH_3$); $^{13}C$ NMR ($CDCl_3$) δ: 151.0, 147.1, 141.0, 137.8, 130.5, 129.9, 124.3, 121.8, 20.8.

Example 14

4h

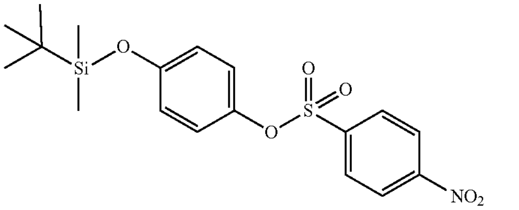

$C_{18}H_{23}NO_6SSi$
Exact Mass: 409,10153

4-(tert-Butyldimethylsilanyloxy)phenyl 4-nitrobenzenesulfonate (4h). Yield: 96%. mp: 94-95° C.; IR v: 1495 ($NO_2$), 1377 ($NO_2$) $cm^{-1}$; $^1H$ NMR ($CDCl_3$) δ: 8.33 (d, 2H, J=8.7 Hz, Ar), 7.98 (d, 2H, J=8.7 Hz, Ar), 6.84-6.70 (m, 4H, Ar), 0.92 (s, 9H, 3×$CH_3$), 0.15 (s, 6H, 2×$CH_3$); $^{13}C$ NMR ($CDCl_3$) δ: 154.9, 151.0, 143.1, 140.9, 130.0, 124.3, 123.1, 121.0, 25.6, 18.1, −4.5.

Example 15

4i

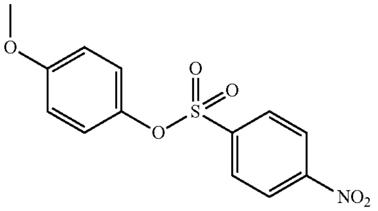

$C_{13}H_{11}NO_6S$
Exact Mass: 309,03071

4-Methoxyphenyl 4-nitrobenzenesulfonate (41). Yield: 89%. mp: 144-146° C.; IR v: 1540 ($NO_2$), 1378 ($NO_2$) $cm^{-1}$; $^1H$ NMR (DMSO-$d_6$) δ: 8.47 (d, 2H, J=8.7 Hz, Ar), 8.14 (d, 2H, J=8.7 Hz, Ar), 7.02-6.91 (m, 4H, Ar), 3.74 (s, 3H, $CH_3$); $^{13}C$ NMR (DMSO-$d_6$) δ: 158.3, 151.1, 142.1, 139.6, 130.1, 125.0, 123.2, 115.1, 55.6.

Example 16

4j

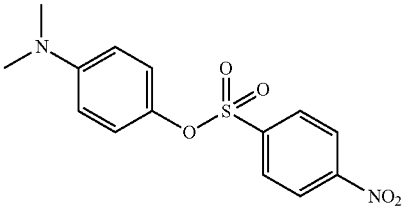

$C_{14}H_{14}N_2O_5S$
Exact Mass: 322,06234

4-(Dimethylamino)phenyl 4-nitrobenzenesulfonate (4j). The crude product was purified by flash chromatography (silica gel, hexanes/ethyl acetate 90:10 to hexanes/ethyl acetate 70:30). Yield: 41%. mp: 129-130° C.; IR v: 1513 ($NO_2$), 1187 (S═O) $cm^{-1}$; $^1H$ NMR (DMSO-$d_6$) δ: 8.47-8.44 (m, 2H, Ar), 8.14-8.11 (m, 2H, Ar), 6.86-6.83 (m, 2H, Ar), 6.64-6.61 (m, 2H, Ar), 2.87 (s, 6H, 2×$CH_3$); $^{13}C$ NMR (DMSO-$d_6$) δ: 149.4, 139.0, 130.1, 124.9, 122.4, 112.5, 40.1.

Example 17

4k

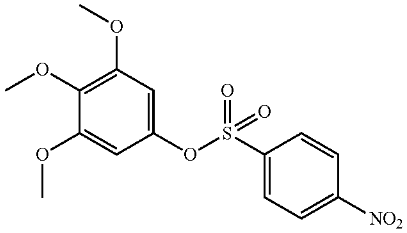

$C_{15}H_{15}NO_8S$
Exact Mass: 369,05184

3,4,5-Trimethoxyphenyl 4-nitrobenzenesulfonate (4k). The crude product was purified by recrystallisation from cold ether. Yield: 86%. mp: 182-185° C.; IR v: 3105 (OMe), 1606 ($NO_2$) $cm^{-1}$; $^1H$ NMR (DMSO-$d_6$) δ: 8.48 (d, 2H, J=7.0 Hz, Ar), 8.21 (d, 2H, J=7.0 Hz, Ar), 6.40 (s, 2H, Ar), 3.66 (s, 6H, 2×$CH_3$), 3.64 (s, 3H, $CH_3$); $^{13}C$ NMR (DMSO-de) δ: 153.3, 151.1, 144.6, 139.5, 130.3, 125.0, 100.0, 56.2, 45.4.

Example 18

5a

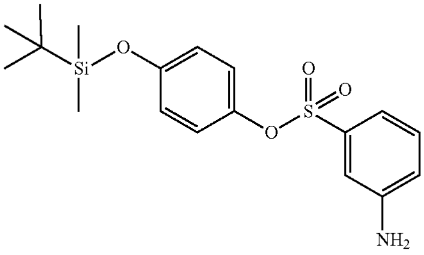

$C_{18}H_{25}NO_4SSi$
Exact Mass: 379,12736

4-(tert-Butyldimethylsilanyloxy)phenyl 3-aminobenzenesulfonate (5a). Method B. The crude product was purified by flash chromatography (silica gel, methylene chloride). Yield: 47%. IR v: 3384 ($NH_2$), 1496 ($NH_2$) $cm^{-1}$; $^1H$ NMR ($CDCl_3$) δ: 7.22-7.17 (m, 1H, Ar), 7.09-7.06 (m, 2H, Ar), 6.88-6.83 (m, 3H, Ar), 6.71-6.68 (m, 2H, Ar), 4.03 (s, 2H, $NH_2$), 0.95 (s, 9H, 3×$CH_3$), 0.15 (s, 6H, 2×$CH_3$); $^{13}C$ NMR ($CDCl_3$) δ: 154.5, 147.5, 143.7, 135.9, 129.9, 123.3, 120.7, 120.2, 117.8, 113.8, 25.6, 18.2, −4.5.

Example 19

5b

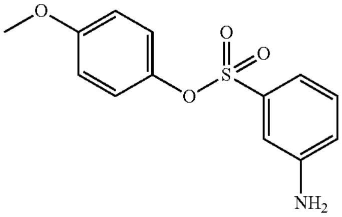

$C_{13}H_{13}NO_4S$
Exact Mass: 279,05653

4-Methoxyphenyl 3-aminobenzenesulfonate (5b). Method A. Yield: 99%. IR ν: 1501 (NH) $cm^{-1}$; $^{1}H$ NMR (DMSO-$d_6$) δ: 7.29-7.23 (m, 1H, Ar), 7.01 (s, 1H, Ar), 6.94-6.87 (m, 6H, Ar), 5.77 (s, 2H, $NH_2$), 3.73 (s, 3H, $CH_3$); $^{13}C$ NMR (DMSO-$d_6$) δ: 157.9, 149.8, 142.6, 134.9, 130.0, 123.1, 119.3, 114.8, 114.5, 112.0, 55.5.

Example 20

5c

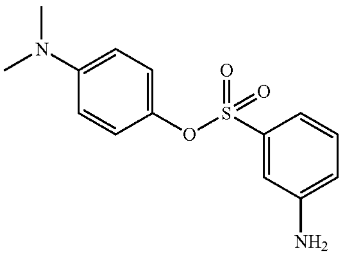

$C_{14}H_{16}N_2O_3S$
Exact Mass: 292,08816

4-(Dimethylamino)phenyl 3-aminobenzenesulfonate (5c). Method A. Yield: 93%. mp: 84-85° C.; IR ν: 3384 ($NH_2$), 1516 ($NH_2$) $cm^{-1}$; $^{1}H$ NMR ($CDCl_3$) δ: 7.24-7.18 (min, 1H Ar), 7.13-7.09 (min, 2H, Ar), 6.87-6.80 (min, 3H, Ar), 6.54-6.51 (min, 2H, Ar), 4.01 (s, 2H, $NH_2$), 2.88 (s, 6H, 2×$CH_3$); $^{13}C$ NMR ($CDCl_3$) δ: 149.4, 147.5, 140.2, 136.2, 129.9, 122.8, 120.1, 117.8, 113.8, 112.5, 40.6.

Example 21

5d

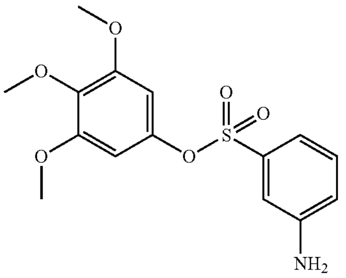

$C_{15}H_{17}NO_6S$
Exact Mass: 339,07766

3,4,5-Trimethoxyphenyl 3-aminobenzenesulfonate (5d). Method A. The crude product was purified by flash chromatography (silica gel, methylene chloride). Yield: 99%. mp: 121-124° C.; IR ν: 3472, 3380 ($NH_2$), 1608 ($NH_2$) $cm^{-1}$; $^{1}H$ NMR (DMSO-$d_6$) δ: 7.33-7.27 (m, 1H, Ar), 7.06-7.05 (m, 1H, Ar), 6.99-6.91 (m, 2H, Ar), 6.28 (s, 2H, Ar), 5.77 (brs, 2H, $NH_2$), 3.66 (s, 6H, 2×$CH_3$), 3.63 (s, 3H, $CH_3$); $^{13}C$ NMR (DMSO-$d_6$) δ: 153.0, 149.8, 145.1, 136.3, 134.9, 130.1, 119.3, 114.6, 112.3, 100.0, 60.1, 56.0.

Example 22

5e

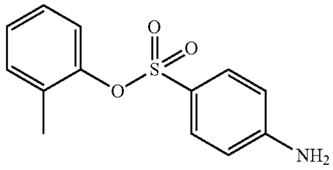

$C_{13}H_{13}NO_3S$
Exact Mass: 263,06161

2-Tolyl 4-aminobenzenesulfonate (5e). Method C. Yield: 88%. mp: 66-67° C.; IR ν: 3387 ($NH_2$), 1592 ($NH_2$) $cm^{-1}$; $^{1}H$ NMR ($CDCl_3$) δ: 7.55-7.53 (m, 2H, Ar), 7.13-7.10 (m, 3H, Ar), 7.04-7.00 (m, 1H, Ar), 6.62-6.60 (m, 2H, Ar), 4.41 (s, 2H, $NH_2$), 2.24 (s, 3H, $CH_3$); $^{13}C$ NMR ($CDCl_3$) δ: 152.4, 148.5, 131.8, 131.6, 130.6, 126.9, 122.7, 122.5, 113.9, 16.4.

Example 23

5f

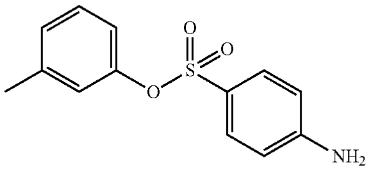

$C_{13}H_{13}NO_3S$
Exact Mass: 263,06161

3-Tolyl 4-aminobenzenesulfonate (5f). Method C. Yield: 92%. mp: 65-67° C.; IR ν: 3389 ($NH_2$), 1592 ($NH_2$) $cm^{-1}$; $^{1}H$ NMR ($CDCl_3$+MeOD) δ: 7.45-7.42 (m, 2H, Ar), 7.05-7.00 (m, 1H, Ar), 6.94-6.91 (m, 1H, Ar), 6.75 (s, 1H, Ar), 6.66-6.58 (m, 3H, Ar), 4.37 (s, 2H, $NH_2$), 2.15 (s, 3H, $CH_3$); $^{13}C$ NMR ($CDCl_3$+MeOD) δ: 152.2, 149.6, 139.9, 130.5, 129.2, 127.8, 123.0, 121.8, 119.2, 114.1, 21.0.

Example 24

5g

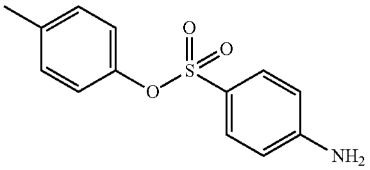

$C_{13}H_{13}NO_3S$
Exact Mass: 263,06161

4-Tolyl 4-aminobenzenesulfonate (5g). Method C. Yield: 92%. mp: 130-132° C.; IR ν: 3394 ($NH_2$), 1596 ($NH_2$) $cm^{-1}$; $^{1}H$ NMR ($CDCl_3$) δ: 7.52 (d, 2H, J=8.6 Hz, Ar), 7.05 (d, 2H, J=8.4 Hz, Ar), 6.85 (d, 2H, J=8.4 Hz, Ar), 6.61 (d, 2H, J=8.6 Hz, Ar), 4.36 (s, 2H, $NH_2$), 2.28 (s, 3H, $CH_3$); $^{13}C$ NMR ($CDCl_3$) δ: 152.1, 147.6, 136.8, 130.7, 130.0, 122.5, 122.2, 113.8, 20.9.

Example 25

5h

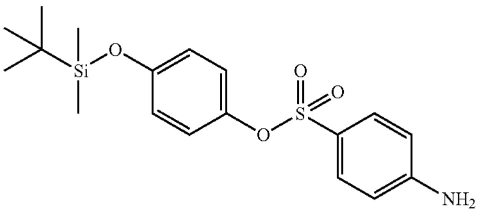

$C_{18}H_{25}NO_4SSi$
Exact Mass: 379,12736

4-(tert-Butyldimethylsilanyloxy)phenyl 4-aminobenzenesulfonate (5h). Method A. The crude product was purified by flash chromatography (silica gel, hexanes/ethyl acetate 90:10 to hexanes/ethyl acetate 70:30). Yield: 66%. IR ν: 1644 ($NH_2$)

$cm^{-1}$; $^{1}H$ NMR ($CDCl_3$) δ: 7.50 (d, 2H, J=8.7 Hz, Ar), 6.84-6.81 (min, 2H, Ar), 6.71-6.68 (min, 2H, Ar), 6.60 (d, 2H, J=8.7 Hz, Ar), 4.33 (s, 2H, $NH_2$), 0.95 (s, 9H, 3×$CH_3$), 0.19 (s, 6H, 2×$CH_3$); $^{13}C$ NMR ($CDCl_3$) δ: 154.3, 152.0, 143.8, 130.8, 123.5, 122.4, 120.6, 113.7, 25.6, 18.2, −4.5.

Example 26

5i

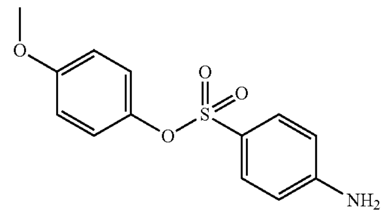

$C_{13}H_{13}NO_4S$
Exact Mass: 279, 05653

4-Methoxyphenyl 4-aminobenzenesulfonate (51). Method A. Yield: 97%. mp: 163-165° C.; IR ν: 1594 ($NH_2$) $cm^{-1}$; $^{1}H$ NMR (DMSO-$d_6$) δ: 7.38 (d, 2H, J=8.8 Hz, Ar), 6.89 (s, 4H, Ar), 6.62 (d, 2H, J=8.8 Hz, Ar), 6.37 (s, 2H, $NH_2$), 3.72 (s, 3H, $CH_3$); $^{13}C$ NMR (DMSO-$d_6$) δ: 157.7, 154.5, 142.8, 130.4, 123.3, 117.9, 114.6, 112.8, 55.5.

Example 27

5j

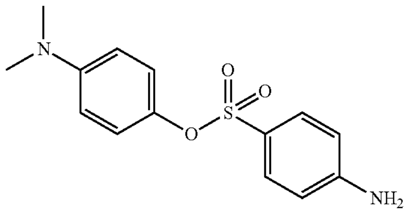

$C_{14}H_{16}N_2O_3S$
Exact Mass: 292, 08816

4-(Dimethylamino)phenyl 4-aminobenzenesulfonate (5j). Method C. Yield: 98%. mp: 192-194° C.; IR ν: 1593 ($NH_2$) $cm^{-1}$; $^{1}H$ NMR (acetone-$d_6$) δ: 7.46-7.43 (m, 2H, Ar), 6.82-6.73 (m, 4H, Ar), 6.63-6.60 (m, 2H, Ar), 5.76 (s, 2H, $NH_2$), 2.90 (s, 6H, 2×$CH_3$); $^{13}C$ NMR (acetone-$d_6$) δ: 154.8, 150.1, 141.3, 131.3, 123.6, 121.7, 113.8, 113.1, 40.5.

Example 28

5k

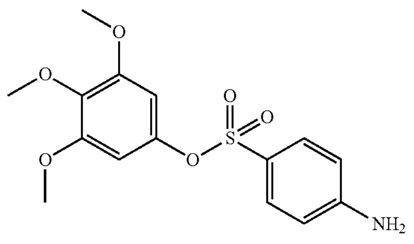

$C_{15}H_{17}NO_6S$
Exact Mass: 339, 07766

3,4,5-Trimethoxyphenyl 4-aminobenzenesulfonate (5k). Method A. The crude product was purified by flash chromatography (silica gel, methylene chloride). Yield: 56%, mp: 133-134° C.; IR ν: 3458 ($NH_2$) $cm^{-1}$; $^{1}H$ NMR (DMSO-$d_6$) δ: 7.46 (d, 2H, J=8.7 Hz, Ar), 6.66 (d, 2H, J=8.7 Hz, Ar), 6.40 (s, 2H, $NH_2$), 6.25 (s, 2H, Ar), 3.66 (s, 6H, 2×$CH_3$), 3.63 (s, 3H, $CH_3$); $^{13}C$ NMR (DMSO-$d_6$) δ: 154.8, 152.9, 145.3, 130.7, 117.8, 112.7, 112.6, 100.2, 60.1, 56.0.

Example 29

6a

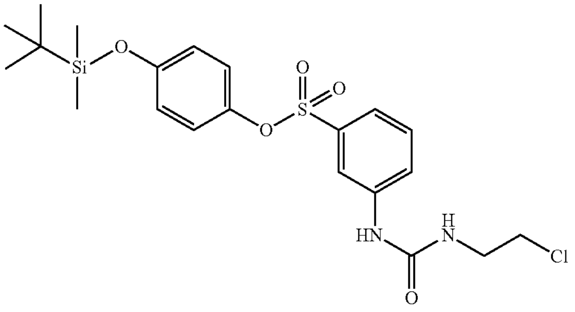

$C_{21}H_{29}ClN_2O_5SSi$
Exact Mass: 484, 1255

4-(tert-Butyldimethylsilanyloxy)phenyl 3-[3-(2-chloroethyl)ureido]benzenesulfonate (6a). Method D in methylene chloride. The crude product was purified by flash chromatography (silica gel, hexanes/ethyl acetate 75:25 to hexanes/ethyl acetate 60:40). Yield: 89%. IR ν: 3292 (NH), 1751 (C═O) $cm^{-1}$; $^{1}H$ NMR ($CDCl_3$) δ: 8.57 (br s, 1H, NH), 8.14 (br s, 1H, Ar), 7.5) (br s, 1H, Ar), 7.28-7.20 (m, 2H, Ar), 6.79 (d, 2H, J=8.9 Hz, Ar), 6.67 (d, 2H, J=8.9 Hz, Ar), 6.42 (br s, 1H, NH), 3.59 (s, 4H, 2×$CH_2$), 0.93 (s, 9H, 3×$CH_3$), 0.13 (s, 6H, 2×$CH_3$); $^{13}C$ NMR ($CDCl_3$) δ: 156.0, 154.6, 143.3, 140.5, 135.4, 129.6, 124.6, 123.2, 122.2, 120.8, 118.1, 44.0, 41.9, 25.6, 18.1, −4.5.

Example 30

6b

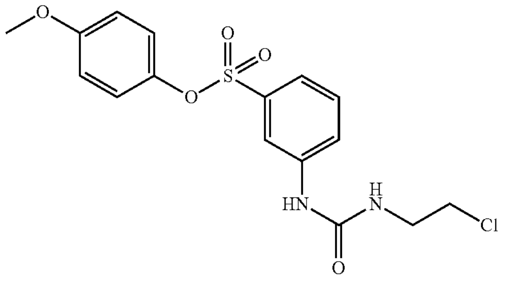

$C_{16}H_{17}ClN_2O_5S$
Exact Mass: 384, 05467

4-Methoxyphenyl 3-[3-(2-chloroethyl)ureido]benzenesulfonate (6b). Method D in methylene chloride. The crude product was purified by flash chromatography (silica gel, methylene chloride to methylene chloride/ethyl acetate 90:10). Yield: 85%; IR ν: 3315 (NH), 1662 (C═O) $cm^{-1}$; $^{1}H$ NMR ($CDCl_3$) δ: 8.32 (s, 1H, NH), 8.02 (s, 1H, Ar), 7.56-7.53 (min, 1H, Ar), 7.29-7.27 (m, 2H, Ar), 6.85-6.82 (m, 2H, Ar), 6.71-6.68 (m, 2H, Ar), 6.23 (brs, 1H, NH), 3.68 (s, 3H, $CH_3$), 3.58 (s, 4H, 2×$CH_2$); $^{13}C$ NMR ($CDCl_3$) δ: 158.3, 155.8, 142.8, 140.4, 135.5, 129.7, 124.6, 123.2, 122.2, 118.1, 114.6, 55.6, 44.1, 41.9; MS (ESI) m/z: 385.0 [M+H]$^+$.

Example 31

6c

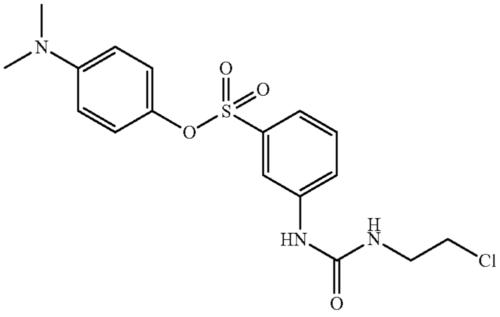

$C_{17}H_{20}ClN_3O_4S$
Exact Mass: 397, 0863

4-(Dimethylamino)phenyl 3-[3-(2-chloroethyl)ureido]benzenesulfonate (6c). Method D in methylene chloride. The crude product was purified by flash chromatography (silica gel, methylene chloride to methylene chloride/ethyl acetate 80:20). Yield: 76% mp: 134-135° C.; IR ν: 3300 (NH), 1653 (C═O) cm$^{-1}$; $^1$H NMR (acetone-$d_6$) δ: 8.59 (s, 1H, NH), 8.19-8.17 (m, 1H, Ar), 7.79-7.76 (m, 1H, Ar), 7.49-7.44 (m, 1H, Ar), 7.36-7.33 (m, 1H, Ar), 6.87-6.82 (m, 2H, Ar), 6.63-6.59 (m, 2H, Ar), 6.32 (t, 1H, J=5.0 Hz, NH), 3.69 (t, 2H, J=5.0 Hz, $CH_2$), 3.59-3.53 (m, 2H, $CH_2$), 2.89 (s, 6H, 2×$CH_3$); $^{13}$C NMR (acetone-$d_6$) δ: 155.6, 150.3, 142.3, 140.9, 137.0, 130.3, 123.9, 123.4, 121.9, 118.0, 113.2, 44.6, 42.5, 40.5; MS (ESI) m/z: 398.0 [M+H]$^+$.

Example 32

6d

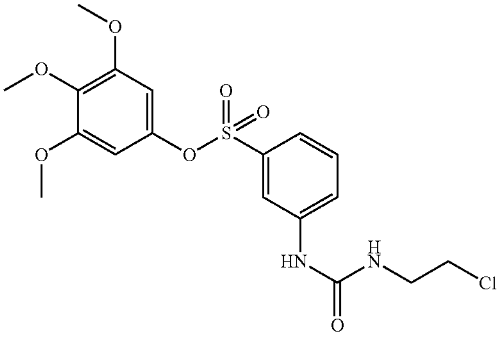

$C_{18}H_{21}ClN_2O_7S$
Exact Mass: 444, 0758

3,4,5-Trimethoxyphenyl 3-[3-(2-chloroethyl)ureido]benzenesulfonate (6d). Method E. The crude product was purified by flash chromatography (silica gel, methylene chloride to methylene chloride/ethyl acetate 75:25). Yield: 38%. IR ν: 1604 (C═O) cm$^{-1}$; $^1$H NMR (acetone-$d_6$) δ: 8.54 (brs, 1H, NH), 8.28 (s, 1H, Ar), 7.73 (d, 1H, J=8.0 Hz, Ar), 7.55-7.50 (m, 1H, Ar), 7.43 (d, 1H, J=8.0 Hz, Ar), 6.34-6.27 (m, 3H, Ar and NH), 3.77-3.65 (m, 11H, 3×$CH_3$ and $CH_2$), 3.59-3.53 (m, 2H, $CH_2$); $^{13}$C NMR (acetone-$d_6$) δ: 155.5, 154.4, 146.4, 142.4, 138.0, 136.6, 130.5, 124.1, 122.0, 118.3, 101.0, 60.5, 56.4, 44.2, 42.5; MS (ESI) m/z: 445.0 [M+H]$^+$.

Example 33

6e

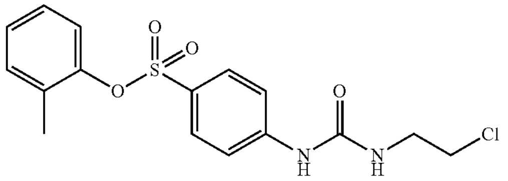

$C_{16}H_{17}ClN_2O_4S$
Exact Mass: 368, 05976

2-Tolyl 4-[3-(2-chloroethyl)ureido]benzenesulfonate (6e). Method D in methylene chloride. The crude product was purified by flash chromatography (silica gel, methylene chloride to methylene chloride/ethyl acetate 90:10). Yield: 57%. IR ν: 3369 (NH), 1592 (C═O) cm$^{-1}$; $^1$H NMR ($CDCl_3$) δ: 8.18 (brs, 1H, NH), 7.68 (d, 2H, J=8.8 Hz, Ar), 7.52 (d, 2H, J=8.8 Hz, Ar), 7.12-7.04 (m, 3H, Ar), 6.98-6.95 (m, 1H, Ar), 6.12 (t, 1H, J=4.8 Hz, NH), 3.58 (brs, 4H, 2×$CH_2$), 2.05 (s, 3H, $CH_3$); $^{13}$C NMR ($CDCl_3$) δ: 155.1, 148.1, 145.3, 131.8, 131.5, 129.8, 127.9, 127.3, 127.1, 122.2, 118.1, 44.2, 41.9, 16.3; MS (ESI) m/z: 368.9 [M+H]$^+$.

Example 34

6f

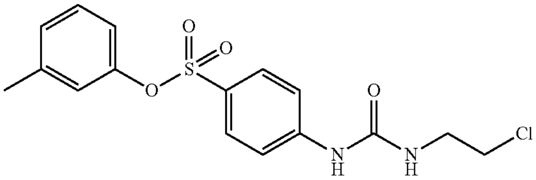

$C_{16}H_{17}ClN_2O_4S$
Exact Mass: 368, 05976

3-Tolyl 4-[3-(2-chloroethyl)ureido]benzenesulfonate (6f). Method F under microwave at 100° C. The crude product was purified by flash chromatography (silica gel, methylene chloride to methylene chloride/ethyl acetate 90:10). Yield: 29%. IR ν: 3348 (NH), 1594 (C═O) cm$^{-1}$; $^1$H NMR ($CDCl_3$) δ: 8.05 (s, 1H, NH), 7.67-7.64 (m, 2H, Ar), 7.54-7.51 (m, 2H, Ar), 7.13-7.00 (m, 2H, Ar), 6.84 (s, 1H, Ar), 6.70-6.67 (m, 1H, Ar), 6.06 (t, 1H, J=5.4 Hz, NH), 3.62-3.56 (m, 4H, 2×$CH_2$), 2.26 (s, 3H, $CH_3$); $^{13}$C NMR ($CDCl_3$) δ: 155.0, 149.4, 145.2, 140.2, 129.9, 129.3, 128.1, 127.3, 122.9, 119.0, 117.9, 44.3, 41.9, 21.2; MS (ESI) m/z: 368.9 [M+H]$^+$.

Example 35

6g

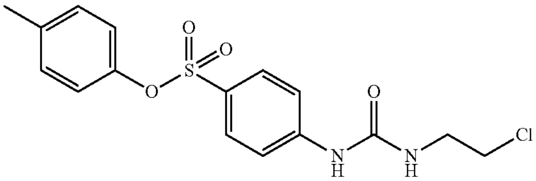

$C_{16}H_{17}ClN_2O_4S$
Exact Mass: 368, 05976

4-Tolyl 4-[3-(2-chloroethyl)ureido]benzenesulfonate (6g). Method D in dry methylene chloride. The crude product was purified by flash chromatography (silica gel, hexanes/ethyl acetate 80:20 to hexanes/ethyl acetate 60:40). Yield: 33%. IR v: 3369 (NH), 1539 (C═O) $cm^{-1}$; $^1H$ NMR ($CDCl_3$) δ: 8.17 (s, 1H, NH), 7.66-763 (m, 2H, Ar), 7.53-7.50 (m, 2H, Ar), 7.02 (d, 2H, J=8.4 Hz, Ar), 6.81 (d, 2H, J=8.4 Hz, Ar), 6.13 (brs, 1H, NH), 3.58 (brs, 4H, 2×$CH_2$), 2.25 (s, 3H, $CH_3$); $^{13}C$ NMR ($CDCl_3$) δ: 155.2, 147.2, 145.2, 137.3, 130.3, 129.9, 127.1, 122.0, 118.0, 44.2, 41.9, 20.9; MS (ESI) m/z: 368.9 $[M+H]^+$.

Example 36

6h

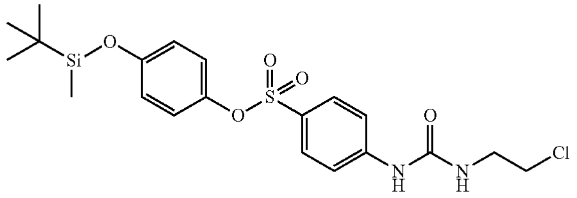

$C_{21}H_{29}ClN_2O_5SSi$
Exact Mass: 484, 1255

4-(tert-Butyldimethylsilanyloxy)phenyl 4-[3-(2-chloroethyl)ureido]benzenesulfonate (6h). Method D in methylene chloride. The crude product was purified by flash chromatography (silica gel, hexanes/ethyl acetate 90:10 to hexanes/ethyl acetate 60:40). Yield: 37%. IR v: 1670 (C═O) $cm^{-1}$; $^1H$ NMR ($CDCl_3$) δ: 8.20 (s, 1H, NH), 7.65-7.51 (m, 4H, Ar), 6.82-6.67 (m, 4H, Ar), 6.15 (t, 1H, J=5.0 Hz, NH), 3.60-3.54 (m, 4H, 2×$CH_2$), 0.93 (s, 9H, 3×$CH_3$), 0.15 (s, 6H, 2×$CH_3$); $^{13}C$ NMR ($CDCl_3$) δ: 155.0, 154.7, 145.3, 143.3, 129.9, 127.0, 123.3, 120.8, 118.0, 44.2, 41.9, 25.6, 18.1, −4.5.

Example 37

6i

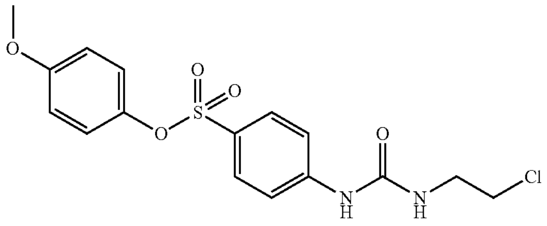

$C_{16}H_{17}ClN_2O_5S$
Exact Mass: 384, 05467

4-Methoxyphenyl 4-[3-(2-chloroethyl)ureido]benzenesulfonate (61). Method D in tetrahydrofuran. The crude product was purified by flash chromatography (silica gel, methylene chloride to methylene chloride/ethyl acetate 80:20). Yield: 46%. mp: 149-150° C.; IR v: 1500 (C═O) $cm^{-1}$; $^1H$ NMR ($CDCl_3$) δ: 7.92 (s, 1H, NH), 7.63 (d, 2H, J=8.8 Hz, Ar), 7.49 (d, 2H, J=8.8 Hz, Ar), 6.86-6.83 (m, 2H, Ar), 6.75-6.72 (m, 2H, Ar), 5.97 (t, 1H, J=5.2 Hz, NH), 3.72 (s, 3H, $CH_3$), 3.62-3.57 (m, 4H, 2×$CH_2$); $^{13}C$ NMR ($CDCl_3$) δ: 158.4, 154.9, 145.1, 142.8, 130.0, 127.1, 123.3, 118.0, 114.6, 55.6, 44.3, 42.0; MS (ESI) m/z: 385.0 $[M+H]^+$.

Example 38

6j

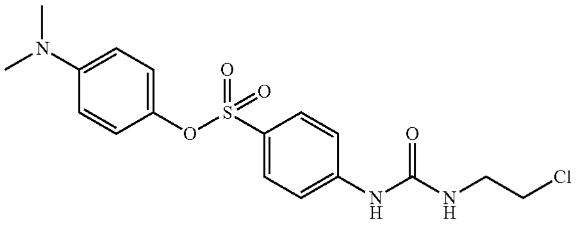

$C_{17}H_{20}ClN_3O_4S$
Exact Mass: 397, 0863

4-(Dimethylamino)phenyl 4-[3-(2-chloroethyl)ureido]benzenesulfonate (6j). Method F under microwave at 60° C. The crude product was purified by flash chromatography (silica gel, methylene chloride to methylene chloride/ethyl acetate 95:5). Yield: 22%. IR v: 3355 (NH), 1569 (C═O) $cm^{-1}$; $^1H$ NMR ($CDCl_3$) δ: 7.95 (s, 1H, NH), 7.64 (d, 2H, J=8.7 Hz, Ar), 7.50 (d, 2H, J=8.7 Hz, Ar), 6.77 (d, 2H, J=9.0 Hz, Ar), 6.49 (d, 2H, J=9.0 Hz, Ar), 5.98 (t, 1H, J=5.3 Hz, NH), 3.63-3.57 (m, 4H, 2×$CH_2$), 2.87 (s, 6H, 2×$CH_3$); $^{13}C$ NMR ($CDCl_3$) δ: 154.9, 149.4, 145.1, 139.9, 129.9, 127.4, 122.8, 117.9, 112.5, 44.3, 41.9, 40.5; MS (ESI) m/z: 397.9 $[M+H]^+$.

Example 39

6k

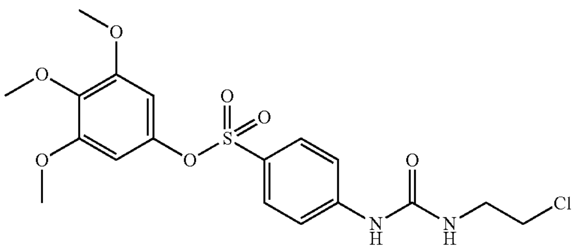

$C_{18}H_{21}ClN_2O_7S$
Exact Mass: 444, 0758

3,4,5-Trimethoxyphenyl 4-[3-(2-chloroethyl)ureido]benzenesulfonate (6k). Method E. The crude product was purified by flash chromatography (silica gel, methylene chloride to methylene chloride/ethyl acetate 75:25). Yield: 36%. mp: 153-154° C.; IR v: 3342 (NH), 1604 (C═O) $cm^{-1}$; $^1H$ NMR (acetone-$d_6$) δ: 8.70 (s, 1H, NH), 7.77-7.74 (m, 4H, Ar), 6.35 (t, 1H, J=5.0 Hz, NH), 6.29 (s, 2H, Ar), 3.73-3.67 (m, 11H, 3×$CH_3$ and $CH_2$), 3.60-3.54 (m, 2H, $CH_2$); $^{13}C$ NMR (acetone-$d_6$) δ: 155.2, 154.4, 147.1, 146.4, 137.9, 130.7, 127.5, 118.1, 101.0, 60.5, 56.4, 44.6, 42.5; MS (ESI) m/z: 445.0 $[M+H]^+$.

Example 40

61

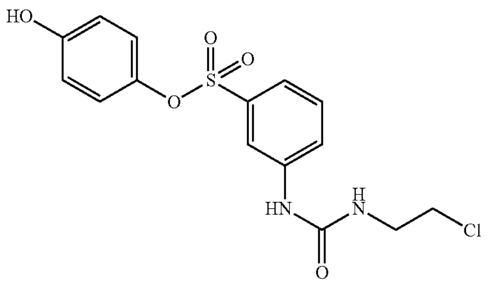

$C_{15}H_{15}ClN_2O_5S$
Exact Mass: 370, 03902

4-Hydroxyphenyl 3-[3-(2-chloroethyl)ureido]benzenesulfonate (61). Yield: 79%; IR ν: 3350 (NH), 1656 (C═O) $cm^{-1}$; $^1H$ NMR (acetone-$d_6$) δ: 8.80 (br s, 2H, NH and OH), 8.21 (brs, 1H, Ar), 7.77-7.71 (m, 1H, Ar), 7.46-7.43 (m, 1H, Ar), 7.35-7.33 (m, 1H, Ar), 6.87-6.76 (m, 4H, Ar), 6.45 (t, 1H, J=5.3 Hz, NH), 3.68 (t, 2H, J=5.3 Hz, $CH_2$), 3.58-3.52 (m, 2H, $CH_2$); $^{13}C$ NMR (acetone-$d_6$) δ: 157.1, 155.8, 143.1, 142.3, 136.7, 130.4, 124.1, 124.0, 121.9, 118.0, 116.7, 44.6, 42.5; MS (ESI) m/z: 371.0 $[M+H]^+$.

Example 41

6m

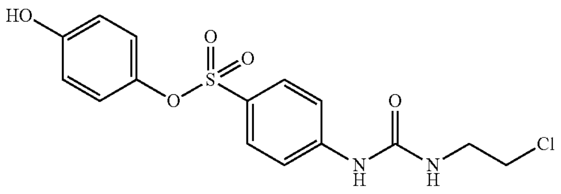

$C_{15}H_{15}ClN_2O_5S$
Exact Mass: 370,03902

4-Hydroxyphenyl 4-[3-(2-chloroethyl)ureido]benzenesulfonate (6m). Yield: 86%. IR ν: 3255 (NH), 1683 (C═O) $cm^{-1}$; $^1H$ NMR (acetone-$d_6$) δ: 8.86 (brs, 1H, NH), 7.73-7.64 (m, 4H, Ar), 6.87-6.75 (m, 4H, Ar), 6.47 (t, 1H, J=5.0 Hz, NH), 3.70 (t, 2H, J=5.0 Hz, $CH_2$), 3.60-3.54 (m, 2H, $CH_2$), 3.13 (s, 1H, OH); $^{13}C$ NMR (acetone-$d_6$) δ: 157.0, 155.3, 146.9, 143.2, 130.5, 127.6, 124.1, 118.1, 116.6, 44.5, 42.5; MS (ESI) m/z: 371.0 $[M+H]^+$.

Example 42

7

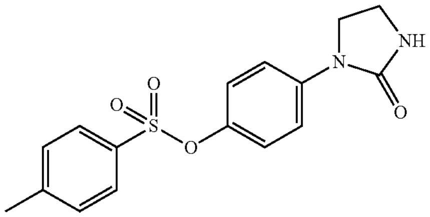

$C_{16}H_{16}N_2O_4S$
Exact Mass: 332,08308

4-(2-oxoimidazolidin-1-yl)phenyl 4-methylbenzenesulfonate (7). Flash chromatography (methylene chloride to methylene chloride/methanol (90:10)) and washed with acetone. Yield: 20%; White solid; m.p.: 149-150° C.; IR: 2877, 1683 $cm^{-1}$; $^1H$ NMR (DMSO-$d_6$) δ 7.75-7.72 (m, 2H, Ar), 7.55-7.47 (m, 4H, Ar), 7.07 (s, 1H, NH), 6.96-6.93 (m, 2H, Ar), 3.84-3.79 (m, 2H, $CH_2$), 3.42-3.36 (m, 2H, $CH_2$), 2.44 (s, 3H, $CH_3$); $^{13}C$ NMR (DMSO-$d_6$) δ 158.8, 145.7, 143.0, 139.8, 131.5, 130.2, 128.3, 122.2, 117.7, 44.4, 36.4, 21.2; HRMS (ES+) m/z found 333.0108; $C_{16}H_{16}N_2O_4S$ $(M^++H)$ requires 333.0909.

Example 43

8

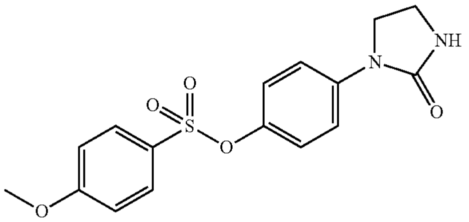

$C_{16}H_{16}N_2O_5S$
Exact Mass: 348,07799

4-(2-oxoimidazolidin-1-yl)phenyl 4-methoxybenzenesulfonate (8). Flash chromatography (methylene chloride to methylene chloride/ethyl acetate (70:30)). Yield: 33%; White solid; m.p.: 126-127° C.; IR: 3236, 1688 $cm^{-1}$; $^1H$ NMR ($CDCl_3$) δ 7.64-7.61 (m, 2H, Ar), 7.36-7.33 (m, 2H, Ar), 6.90-6.81 (m, 4H, Ar), 3.82-3.76 (m, 5H, $CH_2$ and $CH_3$), 3.48-3.43 (m, 2H, $CH_2$), 3.36 (s, 1H, NH); $^{13}C$ NMR ($CDCl_3$) δ 164.2, 159.9, 144.4, 138.9, 130.7, 126.3, 122.6, 118.4, 114.4, 55.7, 45.2, 37.2; HRMS (ES+) m/z found 348.9856; $C_{16}H_{16}N_2O_5S$ ($M^+$+H) requires 349.0858.

Example 44

9

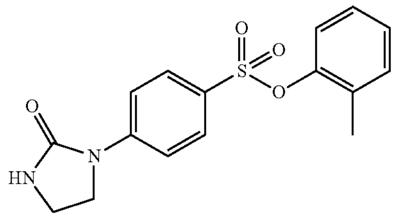

$C_{16}H_{16}N_2O_4S$
Exact Mass: 332,08308

2-Tolyl-4-(2-oxoimidazolidin-1-yl)benzenesulfonate (9). Method G: Recrystallization from methylene chloride/hexanes 1:20). Yield: 88%; Flash chromatography (methylene chloride to methylene chloride/ethyl acetate 8:2). Yield: 95%; White solid; mp: 166-167° C.; IR v: 3242, 1715 $cm^{-1}$; $^1H$ NMR (DMSO-$d_6$): δ 7.84-7.69 (m, 4H, Ar), 7.44 (s, 1H, NH), 7.31-7.20 (m, 3H, Ar), 7.00-6.96 (m, 1H, Ar), 3.96-3.91 (m, 2H, $CH_2$), 3.49-3.44 (m, 2H, $CH_2$), 2.04 (s, 3H, $CH_3$); $^{13}C$ NMR (DMSO-$d_6$): δ 158.2, 147.9, 146.2, 131.7, 131.0, 129.3, 127.3, 127.2, 126.0, 122.0, 116.4, 44.3, 36.3, 15.9; HRMS (ES+) m/z found 333.0889; $C_{16}H_{16}N_2O_4S$ ($M^+$+H) requires 333.0909.

Example 45

10

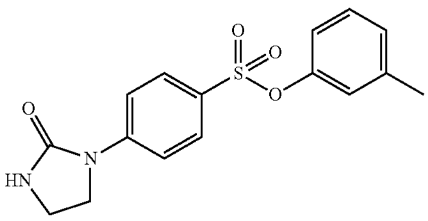

$C_{16}H_{16}N_2O_4S$
Exact Mass: 332,08308

3-Tolyl-4-(2-oxoimidazolidin-1-yl)benzenesulfonate (10). Method G: Flash chromatography (methylene chloride to methylene chloride/ethyl acetate 8:2). Yield: 56%; Flash chromatography (methylene chloride to methylene chloride/ethyl acetate 8:10). Yield: 97%; White solid; mp: 168-169° C.; IR v: 3217, 1704 $cm^{-1}$; $^1H$ NMR ($CDCl_3$): δ 7.78-7.68 (m, 4H, Ar), 7.16-7.10 (m, 1H, Ar), 7.04-7.02 (m, 1H, Ar), 6.88 (s, 1H, Ar), 6.73-6.70 (m, 1H, Ar), 5.40 (brs, 1H, NH), 4.00-3.95 (m, 2H, $CH_2$), 3.67-3.61 (m, 2H, $CH_2$), 2.29 (s, 3H, $CH_3$); $^{13}C$ NMR ($CDCl_3$): δ 159.2, 149.6, 145.3, 140.0, 129.6, 129.2, 127.9, 127.6, 122.9, 119.1, 116.6, 44.8, 37.1, 21.2; HRMS (ES+) m/z found 333.0354; $C_{16}H_{16}N_2O_4S$ ($M^+$+H) requires 333.0909.

Example 46

11

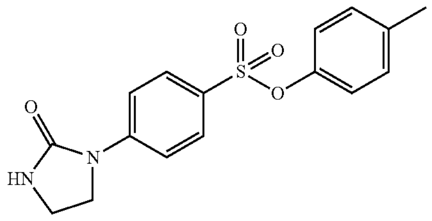

$C_{16}H_{16}N_2O_4S$
Exact Mass: 332,08308

4-Tolyl-4-(2-oxoimidazolidin-1-yl)benzenesulfonate (11). Method G: Recrystallization from methylene chloride/hexanes 1:20. Yield: 81%, Flash chromatography (methylene chloride to methylene chloride/ethyl acetate 8:2). Yield: 97%, White solid; mp: 192-193° C.; IR v: 3252, 1713 $cm^{-1}$; $^1H$ NMR (DMSO-$d_6$): δ 7.80-7.70 (m, 4H, Ar), 7.40 (s, 1H, NH), 7.15 (d, 2H, J=8.3 Hz, Ar), 6.87 (d, 2H, J=8.3 Hz, Ar), 3.93-3.87 (m, 2H, $CH_2$), 3.46-3.41 (m, 2H, $CH_2$), 2.25 (s, 3H, $CH_3$); $^{13}C$ NMR (DMSO-$d_6$): δ 163.4, 152.2, 151.3, 142.0, 135.5, 134.6, 130.5, 127.0, 121.5, 49.4, 41.5, 25.6; HRMS (ES+) m/z found 333.0380; $C_{16}H_{16}N_2O_4S$ ($M^+$+H) requires 333.0909.

Example 47

12

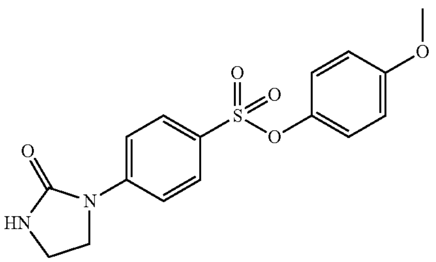 [SMILES: COc1ccc(OS(=O)(=O)c2ccc(N3CCNC3=O)cc2)cc1]

$C_{16}H_{16}N_2O_5S$
Exact Mass: 348,07799

4-Methoxyphenyl-4-(2-oxoimidazolidin-1-yl)benzenesulfonate (12). Method G: Flash chromatography (methylene chloride to methylene chloride/ethyl acetate 8:2). Yield: 62%; Flash chromatography (methylene chloride to methylene chloride/ethyl acetate 8:2). Yield: 75%; White solid; mp: 178-179° C.; IR v: 3244, 1709 $cm^{-1}$; $^1H$ NMR ($CDCl_3$ and MeOD): δ 7.68-7.60 (m, 4H, Ar), 6.82-6.79 (m, 2H, Ar), 6.72-6.69 (m, 2H, Ar), 3.94-3.89 (m, 2H, $CH_3$), 3.70 (s, 3H, $CH_3$), 3.58-3.53 (m, 2H, $CH_2$); $^{13}C$ NMR ($CDCl_3$ and MeOD): δ 159.1, 158.2, 145.3, 143.0, 129.6, 127.3, 123.3, 116.6, 114.5, 55.5, 44.8, 37.0; HRMS (ES+) m/z found 349.0623; $C_{16}H_{16}N_2O_5S$ ($M^+$+H) requires 349.0858.

Example 48

13

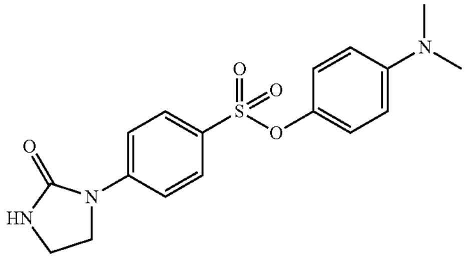

$C_{17}H_{19}N_3O_4S$
Exact Mass: 361,10963

4-(Dimethylamino)phenyl-4-(2-oxoimidazolidin-1-yl) benzenesulfonate (13). Method G: Flash chromatography (methylene chloride to methylene chloride/ethyl acetate 8:2). Yield: 53% Flash chromatography (methylene chloride to methylene chloride/ethyl acetate (8:2). Yield: 17%, White solid; mp: 206-207° C.; IR v: 2805, 1711 $cm^{-1}$; $^1H$ NMR ($CDCl_3$ and MeOD): δ 7.64-7.55 (m, 4H, Ar), 6.79 (d, 2H, J=9.1 Hz, Ar), 6.52 (d, 2H, J=9.1 Hz, Ar), 3.90-3.85 (m, 2H, $CH_2$), 3.54-3.48 (m, 3H, $CH_2$ and NH), 2.80 (s, 6H, 2×$CH_3$); $^{13}C$ NMR ($CDCl_3$ and MeOD): δ 158.9, 149.3, 145.0, 140.3, 129.7, 128.1, 122.9, 116.6, 112.6, 44.8, 40.6, 37.0; HRMS (ES+) m/z found 362.0071; $C_{17}H_{19}N_3O_4S$ ($M^+$+H) requires 362.1175.

Example 49

14

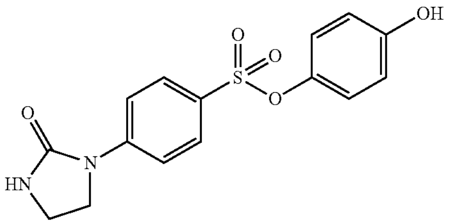

$C_{15}H_{14}N_2O_5S$
Exact Mass: 334,06234

4-Hydroxyphenyl-4-(2-oxoimidazolidin-1-yl)benzenesulfonate (14). Method G: Flash chromatography (methylene chloride/ethyl acetate/methanol 8:2:0 to 75:20:5). Yield: 35%; To a stirred solution of 58 (1 eq.) in tetrahydrofuran (10 mL) was added tetrabutylammoniumfluoride 1M in tetrahydrofuran (1.1 eq.). The mixture was stirred overnight then hydrochloric acid was added and extracted with 3× ethyl acetate, washed with brine, dried with sodium sulfate and the solvent was evaporated under reduced pressure to afford 14. Yield: 99%, White solid; mp: 241-242° C.; IR v: 3440, 1686 $cm^{-1}$; $^1H$ NMR (DMSO-$d_6$): δ 9.67 (s, 1H, OH), 7.81-7.69 (m, 4H, Ar), 7.41 (s, 1H, NH), 6.80-6.67 (m, 4H, Ar), 3.94-3.89 (m, 2H, $CH_2$), 3.48-3.42 (m, 2H, $CH_2$); $^{13}C$ NMR (DMSO-$d_6$): δ 158.2, 157.0, 146.0, 140.9, 129.4, 125.4, 123.0, 116.3, 116.0, 44.2, 36.3; HRMS (ES+) m/z found 334.9951; $C_{15}H_{14}N_2O_5S$ ($M^+$+H) requires 335.0702.

Example 50

15

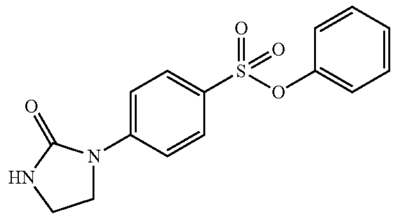

$C_{15}H_{14}N_2O_4S$
Exact Mass: 318,06743

Phenyl-4-(2-oxoimidazolidin-1-yl)benzenesulfonate (15). Flash chromatography (ethyl acetate to ethyl acetate/methanol 95:5). Yield: 75%; White solid; mp: 149-151° C.; IR v: 3262, 1713 $cm^{-1}$; $^1H$ NMR (DMSO-$d_6$): δ 7.82-7.73 (m, 4H, Ar), 7.41-7.29 (m, 4H, Ar or NH), 7.03 (s, 1H, Ar or NH), 7.01 (s, 1H, Ar or NH), 3.94-3.89 (m, 2H, $CH_2$), 3.48-3.43 (m, 2H, $CH_2$); $^{13}C$ NMR (DMSO-$d_6$): δ 158.2, 149.2, 146.1, 130.0, 129.4, 127.4, 125.3, 122.1, 116.3, 44.2, 36.3; HRMS (ES+) m/z found 319.0589; $C_{15}H_{14}N_2O_4S$ ($M^+$+H) requires 319.0753.

Example 51

16

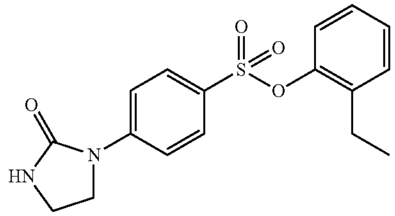

$C_{17}H_{18}N_2O_4S$
Exact Mass: 346,09873

2-Ethylphenyl-4-(2-oxoimidazolidin-1-yl)benzenesulfonate (16). Flash chromatography (methylene chloride to methylene chloride/ethyl acetate 8:2). Yield: 48%; White solid; mp: 163-164° C.; IR v: 3264, 1712 $cm^{-1}$; $^1H$ NMR ($CDCl_3$ and DMSO-$d_6$): δ 7.42-7.35 (m, 4H, Ar), 6.88-6.83 (m, 1H Ar), 6.75-6.73 (m, 1H, Ar), 6.52 (brs, 1H, NH), 6.46-6.41 (m, 2H, Ar), 3.64-3.59 (m, 2H, $CH_2$), 3.28-3.23 (m, 2H, $CH_2$), 2.25 (q, 2H, J=7.6 Hz, $CH_2$), 0.82 (t, 3H, J=7.6 Hz, $CH_3$); $^{13}C$ NMR ($CDCl_3$ and DMSO-$d_6$): δ 158.9, 148.0, 145.3, 137.3, 129.8, 129.5, 128.6, 127.1, 126.8, 122.1, 116.7, 44.9, 37.1, 22.8, 14.1; HRMS (ES+) m/z found 347.0495; $C_{17}H_{18}N_2O_4S$ ($M^+$+H) requires 347.1066.

Example 52

17

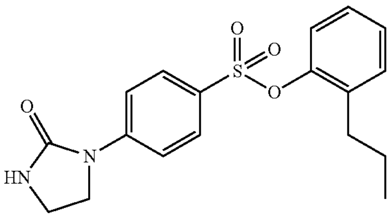

$C_{18}H_{20}N_2O_4S$
Exact Mass: 360,11438

2-Propylphenyl-4-(2-oxoimidazolidin-1-yl)benzene-sulfonate (17). Flash chromatography (methylene chloride to methylene chloride/ethyl acetate 8:2). Yield: 90% White solid; mp: 153-154° C.; IR v: 3235, 1714 $cm^{-1}$; $^1H$ NMR ($CDCl_3$ and DMSO-$d_6$): δ 7.38-7.35 (m, 4H, Ar), 6.83-6.72 (m, 3H, Ar), 6.63-6.61 (m, 1H, Ar), 6.56 (s, 1H, NH), 3.61-3.56 (m, 2H, $CH_2$), 3.24-3.19 (m, 2H, $CH_2$), 2.05 (t, 2H, J=7.7 Hz, $CH_2$), 1.20-1.07 (m, 2H, $CH_2$), 0.50 (t, 3H, J=7.3 Hz, $CH_3$); $^{13}C$ NMR ($CDCl_3$ and DMSO-$d_6$): δ 158.2, 147.6, 146.2, 135.1, 130.8, 129.2, 127.3, 127.2, 126.1, 121.8, 116.4, 44.3, 36.3, 31.2, 22.6, 13.8; HRMS (ES+) m/z found 361.0658; $C_{18}H_{20}N_2O_4S$ ($M^+$+H) requires 361.1222.

Example 53

18

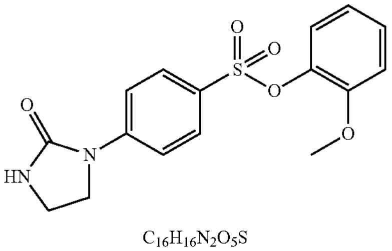

$C_{16}H_{16}N_2O_5S$
Exact Mass: 348,07799

2-Methoxyphenyl-4-(2-oxoimidazolidin-1-yl)benzene-sulfonate (18). Flash chromatography (ethyl acetate to ethyl acetate/methanol 95:5). Yield: 76%; White solid; mp: 183-185° C.; IR v: 3236, 1715 $cm^{-1}$; $^1H$ NMR (DMSO-$d_6$): δ 7.81-7.71 (m, 4H, Ar), 7.40 (s, 1H, NH), 7.29-7.24 (m, 1H, Ar), 7.08-7.05 (m, 2H, Ar), 6.96-6.91 (m, 1H, Ar), 3.95-3.90 (m, 2H, $CH_2$), 3.55 (s, 3H, $CH_3$), 3.49-3.44 (m, 2H, $CH_2$); $^{13}C$ NMR (DMSO-$d_6$): δ 158.3, 151.5, 146.0, 137.7, 129.4, 128.4, 126.2, 123.4, 120.6, 116.0, 113.4, 55.6, 44.3, 36.3; HRMS (ES+) m/z found 349.0858; $C_{16}H_{16}N_2O_5S$ ($M^+$+H) requires 348.9406.

Example 54

19

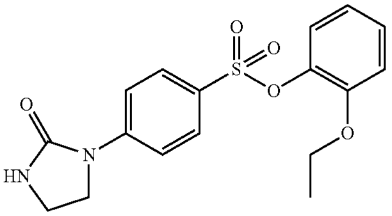

$C_{17}H_{18}N_2O_5S$
Exact Mass: 362,09364

2-Ethoxyphenyl-4-(2-oxoimidazolidin-1-yl)benzene-sulfonate (19). Flash chromatography (ethyl acetate to ethyl acetate/methanol 95:5). Yield: 64%; White solid; mp: 169-171° C.; IR v: 3236, 2907, 1713 $cm^{-1}$; $^1H$ NMR (DMSO-$d_6$): δ 7.81-7.70 (m, 4H, Ar), 7.40 (brs, 1H, NH), 7.27-7.22 (m, 1H, Ar), 7.14-7.12 (m, 1H, Ar), 7.05-7.02 (m, 1H, Ar), 6.96-6.91 (m, 1H, Ar), 3.94-3.89 (m, 2H, $CH_2$), 3.81 (q, 2H, J=7.0 Hz, $CH_2$), 3.46 (m, 2H, $CH_2$), 1.16 (t, 3H, J=7.0 Hz, $CH_3$); $^{13}C$ NMR (DMSO-$d_6$): δ 158.2, 150.7, 146.0, 137.7, 129.3, 128.3, 126.3, 123.6, 120.4, 116.1, 114.1, 63.8, 44.3, 36.3, 14.3; HRMS (ES+) m/z found 362.9793; $C_{17}H_{18}N_2O_5S$ ($M^+$+H) requires 363.1015.

Example 55

20

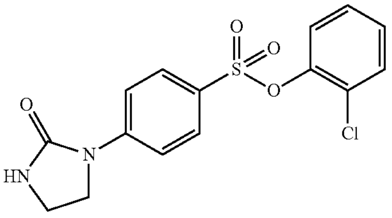

$C_{15}H_{13}ClN_2O_4S$
Exact Mass: 352,02846

2-Chlorophenyl-4-(2-oxoimidazolidin-1-yl)benzene-sulfonate (20). Flash chromatography (ethyl acetate to ethyl acetate/methanol 95:5). Yield: 86%; White solid; mp: 167-169° C.; IR v: 3255, 2909, 1709 $cm^{-1}$; $^1H$ NMR (DMSO-$d_6$): δ 7.85-7.78 (m, 4H, Ar), 7.58-7.54 (m, 1H, Ar), 7.43-7.33 (m, 3H, Ar and NH), 7.27-7.24 (m, 1H, Ar), 3.96-3.91 (m, 2H, $CH_2$), 3.49-3.43 (m, 2H, $CH_2$); $^{13}C$ NMR (DMSO-$d_6$): δ 158.2, 146.5, 145.0, 130.9, 129.6, 128.7, 126.5, 125.3, 123.9, 116.4, 44.3, 36.3; HRMS (ES+) m/z found 353.0363; $C_{15}H_{13}ClN_2O_4S$ ($M^+$+H) requires 353.0159.

Example 56

21

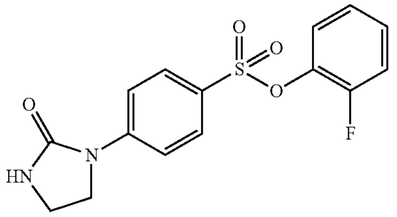

$C_{15}H_{13}FN_2O_4S$
Exact Mass: 336,05801

2-Fluorophenyl-4-(2-oxoimidazolidin-1-yl)benzene-sulfonate (21). Flash chromatography (ethyl acetate to ethyl acetate/methanol 95:5). Yield: 67%; White solid; mp: 164-166° C.; IR v: 3217, 2905, 1698 $cm^{-1}$; $^1$H NMR (DMSO-$d_6$): δ 7.85-7.76 (m, 4H, Ar), 7.45 (brs, 1H, NH), 7.38-7.33 (m, 2H, Ar), 7.26-7.14 (m, 2H, Ar), 3.96-3.91 (m, 2H, $CH_2$), 3.49-3.44 (m, 2H, $CH_2$); $^{13}$C NMR (DMSO-$d_6$): δ 158.2, 146.5, 129.5, 129.1, 129.0, 125.4, 125.3, 124.9, 124.6, 117.5, 117.2, 116.4, 44.3, 36.3; HRMS (ES+) m/z found 337.0649; $C_{15}H_{13}FN_2O_4S$ ($M^+$+H) requires 337.0658.

Example 57

22

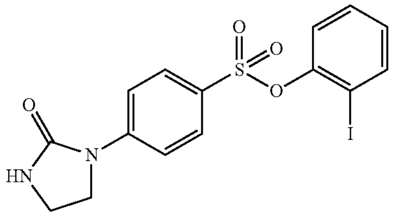

$C_{15}H_{13}IN_2O_4S$
Exact Mass: 443,96407

2-Iodophenyl-4-(2-oxoimidazolidin-1-yl)benzene-sulfonate (22). Flash chromatography (ethyl acetate to ethyl acetate/methanol 95:5). Yield: 73%; White solid; mp: 205-207° C.; IR v: 3226, 2913, 1703 $cm^{-1}$; $^1$H NMR (DMSO-$d_6$ and $CDCl_3$): δ 7.74-7.72 (m, 5H, Ar), 7.33-7.28 (m, 1H, Ar), 7.19-7.17 (m, 1H, Ar), 7.11 (brs, 1H, NH), 6.99-6.94 (m, 1H. Ar), 3.93-3.88 (m, 2H, $CH_2$), 3.53-3.48 (m, 2H, $CH_2$); $^{13}$C NMR (DMSO-$d_6$ and $CDCl_3$): δ 158.2, 149.5, 146.1, 139.7, 129.4, 129.3, 128.2, 126.1, 122.3, 116.0, 90.3, 44.2, 36.4; HRMS (ES+) m/z found 444.9523; $C_{15}H_{13}IN_2O_4S$ ($M^+$+H) requires 444.9719.

Example 58

23

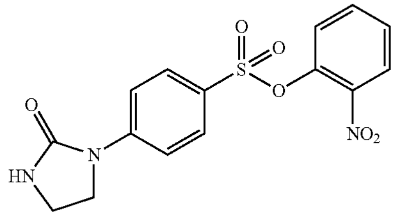

$C_{15}H_{13}N_3O_6S$
Exact Mass: 363,05251

2-Nitrophenyl-4-(2-oxoimidazolidin-1-yl)benzene-sulfonate (23). Flash chromatography (methylene chloride to methylene chloride/ethyl acetate 0:1). Yield: 83%; White solid; mp: 181-182° C.; IR v: 3423, 3113, 1710 $cm^{-1}$; $^1$H NMR ($CDCl_3$, MeOD and DMSO-$d_6$): δ 7.22-7.16 (m, 1H, Ar), 7.06-7.03 (m, 2H, Ar), 6.97-6.88 (m, 3H, Ar), 6.79-6.73 (m, 1H, Ar), 6.45-6.43 (m, 1H, Ar), 3.24-3.19 (m, 2H, $CH_2$), 8.82-2.77 (m, 2H, $CH_2$); $^{13}$C NMR ($CDCl_3$, MeOD and DMSO-$d_6$): δ 158.5, 146.7, 143.2, 141.1, 134.5, 129.5, 128.0, 125.8, 125.0, 124.9, 116.5, 44.5, 36.6; HRMS (ES+) m/z found 363.9450; $C_{15}H_{13}N_3O_6S$ ($M^+$+H) requires 364.0603.

Example 59

24

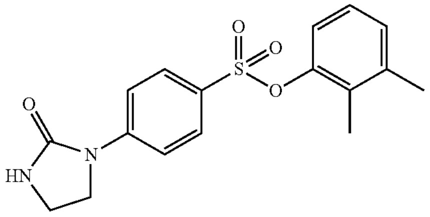

$C_{17}H_{18}N_2O_4S$
Exact Mass: 346,09873

2,3-Dimethylphenyl-4-(2-oxoimidazolidin-1-yl)benzene-sulfonate (24). Flash chromatography (ethyl acetate to ethyl acetate/methanol 95:5). Yield: 72%; White solid; mp: 190-192° C.; IR v: 3242, 3118, 1716 $cm^{-1}$; $^1$H NMR (DMSO-$d_6$ and $CDCl_3$): δ 7.75-7.65 (m, 4H, Ar), 7.17 (brs, 1H, NH), 7.02-6.94 (m, 2H, Ar), 6.74-6.72 (m, 1H, Ar), 3.93-3.89 (m, 2H, $CH_2$), 3.53-3.48 (m, 2H, $CH_2$), 2.19 (s, 3H, $CH_3$), 1.93 (s, 3H, $CH_3$); $^{13}$C NMR (DMSO-$d_6$ and $CDCl_3$): δ 158.3, 147.8, 145.8, 138.6, 129.7, 128.9, 128.0, 126.6, 125.7, 119.3, 116.0, 44.2, 36.5, 19.7, 12.4; HRMS (ES+) m/z found 347.1050; $C_{17}H_{18}N_2O_4S$ ($M^+$+H) requires 347.1066.

Example 60

25

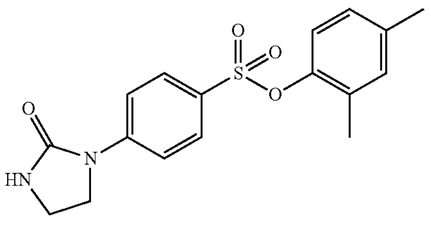 [SMILES: Cc1ccc(OS(=O)(=O)c2ccc(N3CCNC3=O)cc2)c(C)c1]

$C_{17}H_{18}N_2O_4S$
Exact Mass: 346,09873

2,4-Dimethylphenyl-4-(2-oxoimidazolidin-1-yl)benzenesulfonate (25). Flash chromatography (methylene chloride to methylene chloride/ethyl acetate 8:2). Yield: 98%; White solid; mp: 203-204° C.; IR v: 3228, 1714 $cm^{-1}$; $^1H$ NMR ($DMSO-d_6$): δ 7.84-7.74 (m, 4H, Ar), 7.44 (s, 1H, NH), 7.07-6.99 (m, 2H, Ar), 6.83-6.81 (m, 1H, Ar) 3.96-3.90 (m, 2H, $CH_2$), 3.49-3.43 (m, 2H, $CH_2$), 2.25 (s, 3H, $CH_3$), 1.98 (s, 3H, $CH_3$); $^{13}C$ NMR ($DMSO-d_6$): δ 158.2, 146.1, 145.7, 136.5, 132.1, 130.6, 129.3, 127.6, 126.0, 121.7, 116.4, 44.3, 36.3, 20.3, 15.8; HRMS (ES+) m/z found 347.0571; $C_{17}H_{18}N_2O_4S$ ($M^+$+H) requires 347.1066.

Example 61

26

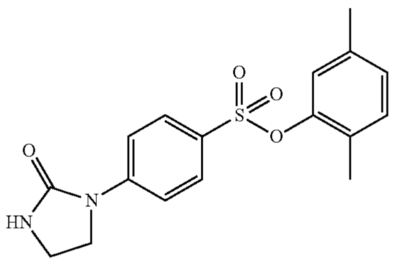

$C_{17}H_{18}N_2O_4S$
Exact Mass: 346,09873

2,5-Dimethylphenyl-4-(2-oxoimidazolidin-1-yl)benzenesulfonate (26). Flash chromatography (ethyl acetate to ethyl acetate/methanol 95:5). Yield: 76%; White solid; mp: 184-186° C.; IR v: 3241, 1710 $cm^{-1}$; $^1H$ NMR ($DMSO-d_6$): δ 7.84-7.76 (min, 4H, Ar), 7.41 (brs, 1H, NH), 7.15-7.13 (min, 1H, Ar), 7.05-7.02 (min, 1H, Ar), 6.86 (s, 1H, Ar), 3.95-3.90 (min, 2H, $CH_2$), 3.49-3.43 (min, 2H, $CH_2$), 2.24 (s, 3H, $CH_3$), 1.94 (s, 3H, $CH_2$); $^{13}C$ NMR ($DMSO-d_6$): δ 158.2, 147.6, 146.2, 136.8, 131.3, 129.2, 127.8, 127.6, 126.1, 122.5, 116.4, 44.3, 36.3, 20.4, 15.4; HRMS (ES+) m/z found 347.1055; $C_{17}H_{18}N_2O_4S$ ($M^+$+H) requires 347.1066.

Example 62

27

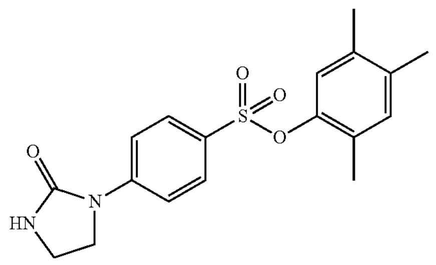

$C_{18}H_{20}N_2O_4S$
Exact Mass: 360,11438

2,4,5-Trimethylphenyl-4-(2-oxoimidazolidin-1-yl)benzenesulfonate (27). Flash chromatography (ethyl acetate to ethyl acetate/methanol 95:5). Yield: 69%; White solid; mp: 204-205° C.; IR v: 3232, 2917, 1710 $cm^{-1}$; $^1H$ NMR ($DMSO-d_6$ and $CDCl_3$): δ 7.74-7.64 (m, 4H, Ar), 7.16 (brs, 1H, NH), 6.86 (s, 1H, Ar), 6.71 (s, 1H, Ar), 3.93-3.88 (m, 2H, $CH_2$), 3.53-3.48 (m, 2H, $CH_2$), 2.13 (s, 3H, $CH_3$), 2.11 (s, 3H, $CH_3$), 1.88 (s, 3H, $CH_3$); $^{13}C$ NMR ($DMSO-d_6$ and $CDCl_3$): δ 158.3, 145.7, 145.6, 134.8, 134.8, 132.1, 128.9, 127.5, 126.8, 122.7, 116.0, 44.2, 36.5, 19.0, 18.7, 15.3; HRMS (ES+) m found 361.1190; $C_{15}H_{20}N_2O_4S$ ($M^+$+H) requires 361.1222.

Example 63

28

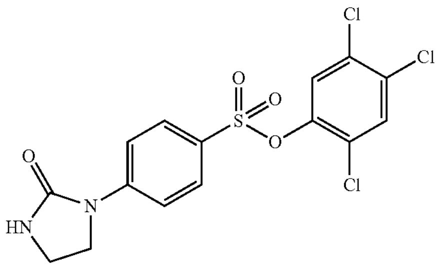

$C_{15}H_{11}Cl_3N_2O_4S$
Exact Mass: 419,95051

2,4,5-Trichlorophenyl-4-(2-oxoimidazolidin-1-yl)benzenesulfonate (28). Flash chromatography (methylene chloride to methylene chloride/ethyl acetate 8:2). Yield: 62%; White solid; mp: 186-187° C.; IR v: 3204, 1710 $cm^{-1}$; $^1H$ NMR ($DMSO-d_6$): δ 8.03 (s, 1H, Ar), 7.84-7.83 (m, 4H, Ar), 7.60 (s, 1H, Ar), 7.47 (brs, 1H, NH), 3.96-3.91 (m, 2H, $CH_2$), 3.49-3.44 (m, 2H, $CH_2$); $^{13}C$ NMR ($DMSO-d_6$): δ 158.1, 146.9, 144.0, 131.7, 130.9, 130.7, 129.8, 126.6, 125.7, 124.5, 116.5, 44.3, 36.3; HRMS (ES+) m/z found 420.8198; $C_{15}H_{11}Cl_3N_2O_4S$ ($M^+$+H) requires 420.9583.

Example 64

29

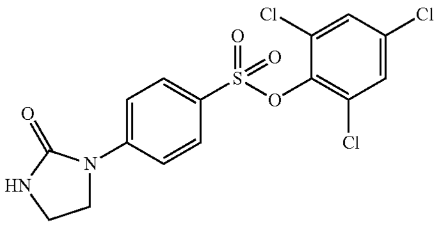

$C_{15}H_{11}Cl_3N_2O_4S$
Exact Mass: 419,95051

2,4,6-Trichlorophenyl-4-(2-oxoimidazolidin-1-yl)benzenesulfonate (29). Flash chromatography (methylene chloride to methylene chloride/ethyl acetate 7:3). Yield: 75%, White solid; mp: 254-255° C.; IR v: 3202, 1711 $cm^{-1}$; $^1H$ NMR ($CDCl_3$+MeOD): δ 7.92 (d, 2H, J=9.0 Hz, Ar), 7.73 (d, 2H, J=9.0 Hz, Ar), 7.33 (s, 2H, Ar), 4.01-3.96 (m, 2H, $CH_2$), 3.64-3.59 (m, 2H, $CH_2$); $^{13}C$ NMR ($CDCl_3$+MeOD): δ 159.9, 149.8, 145.7, 137.7, 130.9, 129.8, 129.1, 119.6, 116.7, 44.8, 36.9; HRMS (ES+) m/z found 420.9216; $C_{15}H_{11}Cl_3N_2O_4S$ ($M^+$+H) requires 420.9583.

Example 65

30

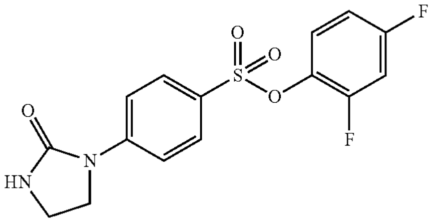

$C_{15}H_{12}F_2N_2O_4S$
Exact Mass: 354,04858

2,4-Difluorophenyl-4-(2-oxoimidazolidin-1-yl)benzenesulfonate (30). Flash chromatography (ethyl acetate to ethyl acetate/methanol 95:5). Yield: 85%; White solid; mp: 179-183° C.; IR v: 3236, 1722 $cm^{-1}$; $^1H$ NMR (DMSO-$d_6$ and $CDCl_3$): δ 7.73-7.64 (m, 4H, Ar), 7.09-6.80 (m, 3H, Ar), 5.06 (br s, 1H, NH), 3.93-3.88 (m, 2H, $CH_2$), 3.54-3.49 (m, 2H, $CH_2$); $^{13}C$ NMR (DMSO-$d_6$ and $CDCl_3$): δ 158.2, 146.1, 129.1, 126.3, 125.2, 125.0, 116.0, 115.8, 111.4, 111.4, 111.1, 111.1, 105.5, 105.2, 105.1, 104.8, 44.2, 36.4; HRMS (ES+) m/z found 355.0443; $C_{15}H_{12}F_2N_2O_4S$ ($M^+$+H) requires 355.0564.

Example 66

31

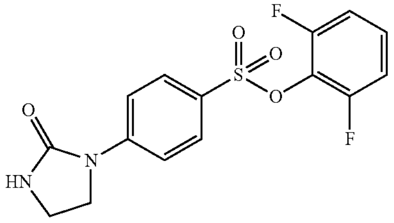

$C_{15}H_{12}F_2N_2O_4S$
Exact Mass: 354,04858

2,6-Difluorophenyl-4-(2-oxoimidazolidin-1-yl)benzenesulfonate (31). Flash chromatography (ethyl acetate to ethyl acetate/methanol 95:5). Yield: 81% White solid; mp: 187-189° C.; IR v: 3240, 1732 $cm^{-1}$; $^1H$ NMR (DMSO-$d_6$ and $CDCl_3$): δ 7.75 (s, 4H, Ar), 7.27-7.17 (m, 2H, Ar or NH), 7.00-6.95 (m, 2H, Ar or NH), 3.95-3.90 (m, 2H, $CH_2$), 3.54-3.49 (m, 2H, $CH_2$); $^{13}C$ NMR (DMSO-$d_6$ and $CDCl_3$): δ 158.2, 157.2, 157.1, 153.8, 153.8, 146.2, 129.1, 127.8, 127.7, 127.6, 125.7, 125.6, 116.1, 112.4, 112.4, 112.4, 112.2, 112.2, 112.1, 44.2, 36.4; HRMS (ES+) m/z found 354.9978; $C_{15}H_2F_2N_2O_4S$ ($M^+$+H) requires 355.0564.

Example 67

32

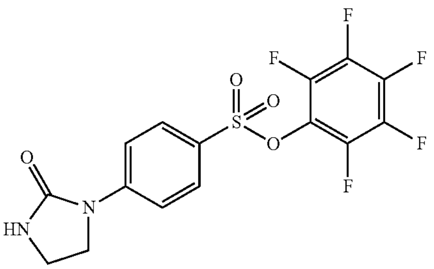

$C_{15}H_9F_5N_2O_4S$
Exact Mass: 408,02032

Perfluorophenyl-4-(2-oxoimidazolidin-1-yl)benzenesulfonate (32). Flash chromatography (methylene chloride to methylene chloride/ethyl acetate 8:2). Yield: 75%; White solid; mp: 217-218° C.; IR v: 3258, 1711 $cm^{-1}$; $^1H$ NMR (DMSO-$d_6$): δ 7.93-7.86 (m, 4H, Ar), 7.51 (brs, 1H, NH), 3.99-3.94 (m, 2H, $CH_2$), 3.50-3.45 (m, 2H, $CH_2$), $^{13}C$ NMR ($CDCl_3$ and MeOD): δ 164.2, 146.4, 146.3, 129.8, 116.9, 116.8, 44.8, 36.8; HRMS (ES+) m/z found 409.0188; $C_{15}H_9F_5N_2O_4S$ ($M^+$+H) requires 409.0282.

Example 68

33

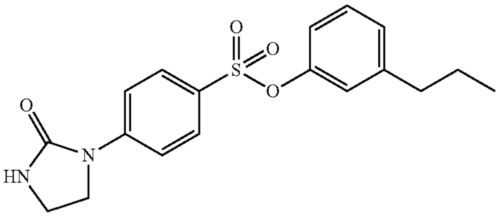

$C_{18}H_{20}N_2O_4S$
Exact Mass: 360,11438

3-Propylphenyl-4-(2-oxoimidazolidin-1-yl)benzene-sulfonate (33). Flash chromatography (ethyl acetate to ethyl acetate/methanol 95:5). Yield: 80%; White solid; mp: 144-145° C.; IR v: 3257, 2951, 1714 $cm^{-1}$; $^1H$ NMR (DMSO-$d_6$ and $CDCl_3$): δ 7.72-7.60 (m, 4H, Ar), 7.18-7.12 (m, 2H, Ar and NH), 7.02-7.00 (m, 1H, Hz, Ar), 6.73-6.68 (m, 2H, Ar), 3.91-3.86 (m, 2H, $CH_2$), 3.52-3.47 (m, 2H, $CH_2$), 2.46 (t, 2H, J=7.7 Hz, $CH_2$), 1.47 (m, 2H, $CH_2$), 0.79 (t, 3H, J=7.3 Hz, $CH_3$); $^{13}C$ NMR (DMSO-$d_6$ and $CDCl_3$): δ 158.2, 149.1, 145.7, 144.2, 129.0, 126.9, 125.9, 121.8, 119.1, 116.0, 44.2, 36.9, 36.4, 23.7, 13.2; HRMS (ES+) m/z found 361.1315; $C_{18}H_{20}N_2O_4S$ ($M^+$+H) requires 361.1222.

Example 69

34

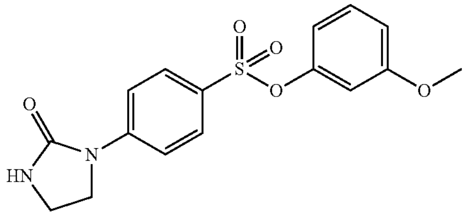

$C_{16}H_{16}N_2O_5S$
Exact Mass: 348,07799

3-Methoxyphenyl-4-(2-oxoimidazolidin-1-yl)benzene-sulfonate (34). Flash chromatography (methylene chloride to methylene chloride/ethyl acetate 8:2). Yield: 70%; White solid; mp: 139-140° C.; IR v: 3219, 1712 $cm^{-1}$; $^1H$ NMR ($CDCl_3$ and MeOD): δ 7.73-7.62 (m, 4H, Ar), 7.13-7.08 (m, 1H, Ar), 6.74-6.71 (m, 1H, Ar), 6.54-6.47 (m, 2H, Ar), 3.93-3.89 (m, 2H, $CH_2$), 3.68 (s, 3H, $CH_3$), 3.59-3.54 (m, 2H, $CH_2$), 2.6) (s, 1H, NH); $^{13}C$ NMR ($CDCl_3$ and MeOD): δ 160.4, 159.1, 150.5, 145.4, 129.9, 129.6, 127.5, 116.6, 114.3, 113.0, 108.3, 55.5, 44.8, 36.9; HRMS (ES+) m/z found 348.9994; $C_{16}H_{16}N_2O_5S$ ($M^+$+H) requires 349.0858.

Example 70

35

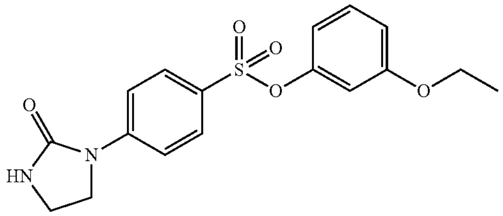

$C_{17}H_{18}N_2O_5S$
Exact Mass: 362,09364

3-Ethoxyphenyl-4-(2-oxoimidazolidin-1-yl)benzene-sulfonate (35). Flash chromatography (ethyl acetate to ethyl acetate/methanol 95:5). Yield: 81%; White solid; mp: 143-145° C.; IR v: 3255, 2898, 1713 $cm^{-1}$; $^1H$ NMR (DMSO-$d_6$ and $CDCl_3$): δ 7.79-7.63 (m, 4H, Ar), 7.16-7.09 (m, 2H, Ar and NH), 6.75-6.71 (m, 1H, Ar), 6.47-6.42 (m, 2H, Ar), 3.92-3.86 (m, 4H, 2×$CH_2$), 3.53-3.47 (m, 2H, $CH_2$), 1.30 (t, 3H, J=6.9 Hz, $CH_3$); $^{13}C$ NMR (DMSO-$d_6$ and $CDCl_3$): δ 159.3, 158.2, 150.0, 145.8, 129.6, 129.0, 125.9, 116.0, 113.6, 113.0, 108.4, 63.3, 44.2, 36.5, 14.3; HRMS (ES+) m/z found 363.0659; $C_{17}H_{18}N_2O_5S$ ($M^+$+H) requires 363.1015.

Example 71

36

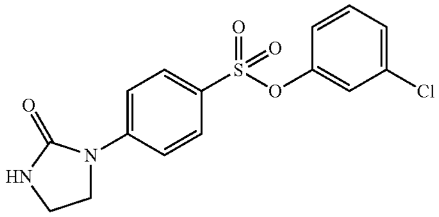

$C_{15}H_{13}ClN_2O_4S$
Exact Mass: 352,02846

3-Chlorophenyl-4-(2-oxoimidazolidin-1-yl)benzene-sulfonate (36). Flash chromatography (ethyl acetate to ethyl acetate/methanol 95:5). Yield: 77%; White solid; mp: 160-162° C.; IR v: 3223, 1707 $cm^{-1}$; $^1H$ NMR (DMSO-$d_6$): δ 7.85-7.77 (m, 4H, Ar), 7.46-7.42 (m, 3H, Ar), 7.20 (s, 1H, NH), 7.02-6.98 (m, 1H, Ar), 3.96-3.90 (m, 2H, $CH_2$), 3.49-3.44 (m, 2H, $CH_2$); $^{13}C$ NMR (DMSO-$d_6$): δ 158.2, 149.6, 146.4, 133.7, 131.4, 129.5, 127.6, 124.7, 122.5, 121.0, 116.4, 44.2, 36.3; HRMS (ES+) m/z found 353.0223; $C_{15}H_{13}ClN_2O_4S$ ($M^+$+H) requires 353.0363.

Example 72

37

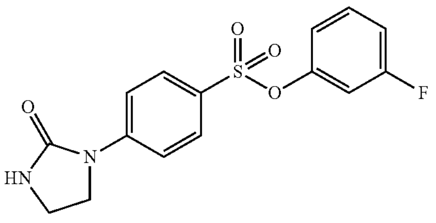

$C_{15}H_{13}FN_2O_4S$
Exact Mass: 336,05801

3-Fluorophenyl-4-(2-oxoimidazolidin-1-yl)benzenesulfonate (37). Flash chromatography (methylene chloride to methylene chloride/ethyl acetate 8:2). Yield: 56%; White solid; mp: 157-158° C.; IR v: 3243, 1712 $cm^{-1}$; $^1H$ NMR ($CDCl_3$ and MeOD): δ 7.68-7.58 (m, 4H, Ar), 7.21-7.13 (m, 1H, Ar), 6.91-6.85 (m, 1H, Ar), 6.71-6.66 (m, 2H, Ar), 3.91-3.86 (m, 2H, $CH_2$), 3.54-3.53 (m, 2H, $CH_2$); $^{13}C$ NMR ($CDCl_3$ and MeOD): δ 160.9, 159.1, 150.1, 145.6, 130.4, 129.5, 126.9, 118.1, 116.7, 114.2, 110.4, 44.8, 36.9; HRMS (ES+) m/z found 337.0745; $C_{15}H_{13}FN_2O_4S$ ($M^+$+H) requires 337.0658.

Example 73

38

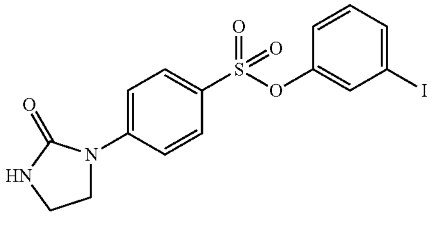

$C_{15}H_{13}IN_2O_4S$
Exact Mass: 443,96407

3-Iodophenyl-4-(2-oxoimidazolidin-1-yl)benzenesulfonate (38). Flash chromatography (ethyl acetate to ethyl acetate/methanol 95:5). Yield: 80% White solid; mp: 182-184° C.; IR v: 3250, 2906, 1711 $cm^{-1}$; $^1H$ NMR (DMSO-$d_6$ and $CDCl_3$): δ 7.76-7.64 (m, 4H, Ar), 7.57 (d, 1H, J=8.0 Hz, Ar), 7.34-7.32 (m, 1H, Ar), 7.25 (s, 1H, NH), 7.04 (t, 1H, J=8.0 Hz, Ar), 6.90-6.86 (m, 1H, Ar), 3.93-3.88 (m, 2H, $CH_2$), 3.52-3.47 (m, 2H, $CH_2$); $^{13}C$ NMR (DMSO-$d_6$ and $CDCl_3$): δ 158.2, 149.3, 146.1, 135.8, 131.0, 129.1, 125.2, 121.4, 116.1, 93.5, 44.2, 36.4; HRMS (ES+) m/z found 445.0218; $C_{15}H_3IN_2O_4S$ ($M^+$+H) requires 444.9719.

Example 74

39

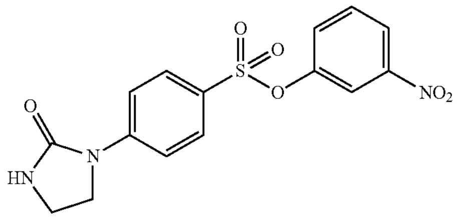

$C_{15}H_{13}N_3O_6S$
Exact Mass: 363,05251

3-Nitrophenyl-4-(2-oxoimidazolidin-1-yl)benzenesulfonate (39). Flash chromatography (methylene chloride to methylene chloride/ethyl acetate 8:2). Yield: 98%, White solid; mp: 152-153° C.; IR v: 3248, 1713 $cm^{-1}$; $^1H$ NMR ($CDCl_3$): δ 8.10-7.66 (m, 6H, Ar), 7.50-7.45 (m, 1H, Ar), 7.35-7.32 (m, 1H, Ar), 3.97-3.92 (m, 2H, $CH_2$), 3.63-3.57 (m, 2H, $CH_2$); $^{13}C$ NMR ($CDCl_3$): δ 159.0, 149.7, 146.0, 130.5, 129.7, 128.9, 128.4, 126.3, 122.0, 118.0, 116.8, 44.8, 36.9; HRMS (ES+) m/z found 364.0343; $C_{15}H_{13}N_3O_6S$ ($M^+$+H) requires 364.0603.

Example 75

40

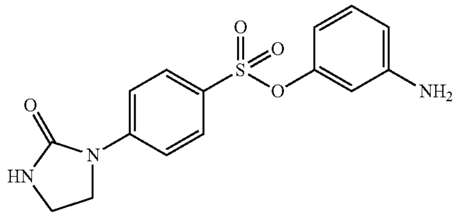

$C_{15}H_{15}N_3O_4S$
Exact Mass: 333,07833

3-Aminophenyl-4-(2-oxoimidazolidin-1-yl)benzenesulfonate (40). Flash chromatography (methylene chloride to methylene chloride/methanol 9:1). Yield: 32%; White solid; mp: 184-185° C.; IR v: 3233, 1709 $cm^{-1}$; $^1H$ NMR (acetone-$d_6$): δ 7.87-7.73 (m, 4H, Ar), 6.96 (t, 1H, J=8.1 Hz, Ar), 6.56-6.53 (m, 1H, Ar), 6.41-6.40 (m, 1H, Ar), 6.18-6.15 (m, 1H, Ar), 4.92 (s, 1H, NH), 4.04-4.00 (m, 2H, $CH_2$), 3.64-3.59 (m, 2H, $CH_2$); $^{13}C$ NMR (acetone-$d_6$): δ 159.2, 150.8, 147.0, 130.4, 130.2, 130.0, 117.0, 117.0, 113.5, 110.2, 108.4, 45.3, 37.4; HRMS (ES+) m/z found 334.0578; $C_{15}H_{15}N_3O_4S$ ($M^+$+H) requires 334.0862.

Example 76

41

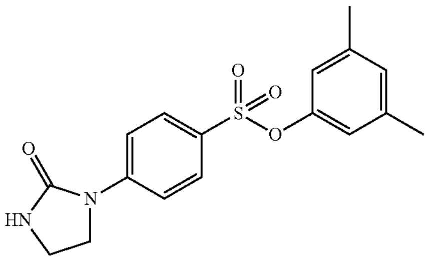

$C_{17}H_{18}N_2O_4S$
Exact Mass: 346,09873

3,5-Dimethylphenyl-4-(2-oxoimidazolidin-1-yl)benzenesulfonate (41). Flash chromatography (ethyl acetate to ethyl acetate/methanol 95:5). Yield: 75%, White solid; mp: 200-203° C.; IR v: 3230, 1711 $cm^{-1}$; $^1H$ NMR (DMSO-$d_6$): δ 7.83-7.75 (m, 4H, Ar), 7.41 (s, 1H, Ar or NH), 6.95 (s, 1H, Ar or NH), 6.65 (s, 2H, Ar or NH), 3.95-3.89 (m, 2H, $CH_2$), 3.48-3.43 (m, 2H, $CH_2$), 2.21 (s, 6H, 2×$CH_3$); $^{13}C$ NMR (DMSO-$d_6$): δ 158.2, 149.1, 146.1, 139.4, 129.3, 128.7, 125.6, 119.4, 116.3, 44.3, 36.3, 20.7; HRMS (ES+) m found 347.0825; $C_{17}H_{18}N_2O_4S$ ($M^+$+H) requires 347.1066.

Example 77

42

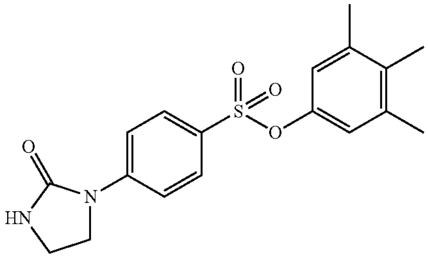

$C_{18}H_{20}N_2O_4S$
Exact Mass: 360,11438

3,4,5-Trimethylphenyl-4-(2-oxoimidazolidin-1-yl)benzenesulfonate (42). Flash chromatography (methylene chloride to methylene chloride/ethyl acetate 0:1 to ethyl acetate/methanol 95:5). Yield: 79%; White solid; mp: 211-212° C.; IR v: 3223, 2910, 1713 $cm^{-1}$; $^1H$ NMR (DMSO-$d_6$): δ 7.83-7.75 (m, 4H, Ar), 7.42 (s, 1H, NH), 6.67 (s, 2H, Ar), 3.95-3.90 (m, 2H, $CH_2$), 3.49-3.44 (m, 2H, $CH_2$), 2.17 (s, 6H, 2×$CH_3$), 2.07 (s, 3H, $CH_3$); $^{13}C$ NMR (DMSO-$d_6$): δ 158.3, 146.4, 146.0, 137.8, 134.0, 129.3, 125.8, 120.4, 116.3, 44.3, 36.3, 20.2, 14.7; HRMS (ES+) m/z found 361.1055; $C_{18}H_{20}N_2O_4S$ ($M^+$+H) requires 361.1178.

Example 78

43

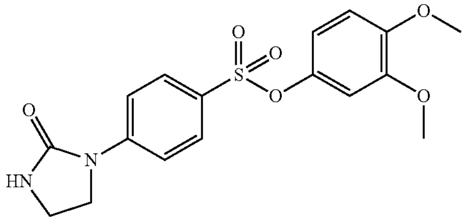

$C_{17}H_{18}N_2O_6S$
Exact Mass: 378,08856

3,4-Dimethoxyphenyl-4-(2-oxoimidazolidin-1-yl)benzenesulfonate (43). Flash chromatography (methylene chloride to methylene chloride/ethyl acetate 0:1). Yield: 70%; White solid; mp: 156-158° C.; IR v: 3235, 2969, 1710 $cm^{-1}$; $^1H$ NMR ($CDCl_3$ and MeOD): δ 7.66-7.58 (m, 4H, Ar), 6.63-6.60 (m, 1H, Ar), 6.48-6.47 (m, 1H, Ar), 6.38-6.34 (m, 1H, Ar), 3.90-3.85 (m, 2H, $CH_2$), 3.73 (s, 3H, $CH_3$), 3.66 (s, 3H, $CH_3$), 3.54-3.50 (m, 2H, $CH_2$), 3.32 (s, 1H, NH); $^{13}C$ NMR ($CDCl_3$ and MeOD): δ 159.1, 149.2, 147.8, 145.4, 143.1, 129.6, 127.2, 116.6, 113.8, 110.9, 106.5, 56.0, 56.0, 44.8, 36.9; HRMS (ES+) m/z found 378.9391; $C_{17}H_{18}N_2O_6S$ ($M^+$+H) requires 379.0964.

Example 79

44

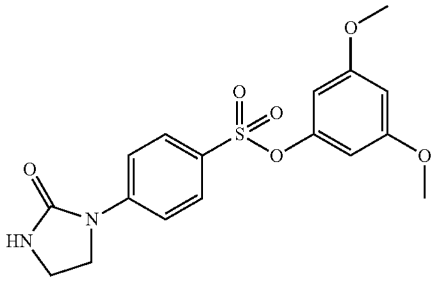

$C_{17}H_{18}N_2O_6S$
Exact Mass: 378,08856

3,5-Dimethoxyphenyl-4-(2-oxoimidazolidin-1-yl)benzenesulfonate (44). Flash chromatography (ethyl acetate to ethyl acetate/methanol 95:5). Yield: 71%, White solid; mp: 219-221° C.; IR v: 3235, 1711 $cm^{-1}$; $^1H$ NMR (DMSO-$d_6$): δ 7.85-7.78 (m, 4H, Ar), 7.43 (s, 1H, NH), 6.46-6.45 (m, 1H, Ar), 6.18-6.17 (m, 2H, Ar), 3.95-3.90 (m, 2H, $CH_2$), 3.68 (s, 6H, 2×$CH_3$), 3.49-3.44 (m, 2H, $CH_2$); $^{13}C$ NMR (DMSO-$d_6$): δ 160.8, 158.2, 150.6, 146.2, 129.5, 125.3, 116.4, 100.6, 99.0, 55.6, 44.3, 36.3; HRMS (ES+) m/z found 379.0741; $C_{17}H_{18}N_2O_6S$ ($M^+$+H) requires 379.0964.

Example 80

45

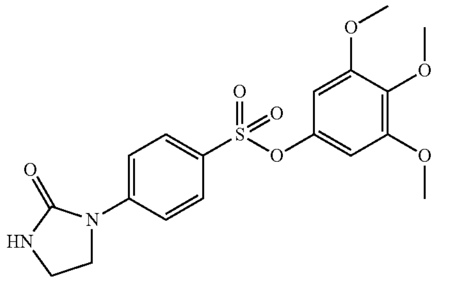

$C_{18}H_{20}N_2O_7S$
Exact Mass: 408,09912

3,4,5-Trimethoxyphenyl-4-(2-oxoimidazolidin-1-yl)benzenesulfonate (45). Flash chromatography (methylene chloride to methylene chloride/ethyl acetate 7:3). Yield: 31%; mp: 191-192° C.; IR v: 3201, 1706 $cm^{-1}$; $^1H$ NMR (DMSO-$d_6$): δ 7.86-7.80 (min, 4H, Ar), 7.42 (s, 1H, NH), 6.31 (s, 2H, Ar), 3.95-3.90 (m, 2H, $CH_2$), 3.65 (s, 6H, 2×$CH_3$), 3.63 (s, 3H, $CH_3$), 3.49-3.44 (m, 2H, $CH_2$); $^{13}C$ NMR (DMSO-$d_6$): δ 158.2, 153.1, 146.2, 145.1, 136.3, 129.6, 125.2, 116.4, 100.0, 60.1, 56.1, 44.3, 36.2; HRMS (ES+) m/z found 408.9720; $C_{18}H_{20}N_2O_7S$ ($M^+$+H) requires 409.1070.

Example 81

46

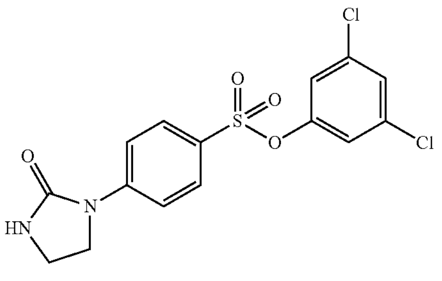

$C_{15}H_{12}Cl_2N_2O_4S$
Exact Mass: 385,98948

3,5-Dichlorophenyl-4-(2-oxoimidazolidin-1-yl)benzenesulfonate (46). Flash chromatography (ethyl acetate to ethyl acetate/methanol 95:5). Yield: 64%; White solid; mp: 179-181° C.; IR v: 3236, 1709 $cm^{-1}$; $^1H$ NMR (DMSO-$d_6$): δ 7.87-7.80 (m, 4H, Ar), 7.66 (m, 1H, Ar), 7.46 (s, 1H, NH), 7.21-7.20 (m, 2H, Ar), 3.97-3.91 (m, 2H, $CH_2$), 3.49-3.44 (m, 2H, $CH_2$); $^{13}C$ NMR (DMSO-$d_6$): δ 158.2, 149.7, 146.6, 134.7, 129.6, 127.6, 124.3, 121.7, 116.4, 44.2, 36.3; HRMS (ES+) m/z found 386.9923; $C_{15}H_{12}Cl_2N_2O_4S$ ($M^+$+H) requires 386.9973.

Example 82

47

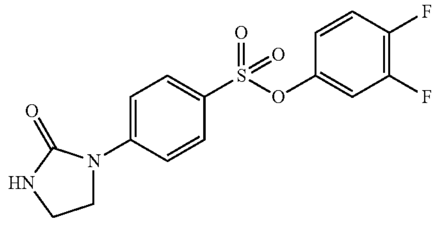

$C_{15}H_{12}F_2N_2O_4S$
Exact Mass: 354,04858

3,4-Difluorophenyl-4-(2-oxoimidazolidin-1-yl)benzenesulfonate (47). Flash chromatography (ethyl acetate to ethyl acetate/methanol 95:5). Yield: 78%; White solid; mp: 182-184° C.; IR v: 3230, 2918, 1716 $cm^{-1}$; $^1H$ NMR (DMSO-$d_6$ and $CDCl_3$): δ 7.77-7.51 (m, 5H, Ar and NH), 7.27-7.18 (m, 1H, Ar), 7.03-6.96 (m, 1H, Ar), 6.77-6.72 (m, 1H, Ar), 3.93-3.83 (m, 2H, $CH_2$), 3.51-3.43 (m, 2H, $CH_2$); $^{13}C$ NMR (DMSO-$d_6$ and $CDCl_3$): δ 158.8, 158.1, 146.2, 141.6, 138.9, 129.2, 126.2, 124.8, 118.8, 118.8, 118.7, 118.7, 117.7, 117.5, 116.2, 115.8, 112.4, 112.1, 44.5, 44.2, 36.6, 36.4; HRMS (ES+) m/z found 354.9966; $C_{15}H_{12}F_2N_2O_4S$ ($M^+$+H) requires 355.0564.

Example 83

48

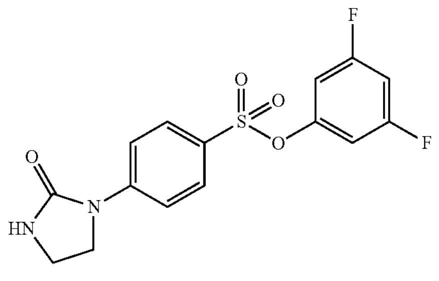

$C_{15}H_{12}F_2N_2O_4S$
Exact Mass: 354,04858

3,5-Difluorophenyl-4-(2-oxoimidazolidin-1-yl)benzenesulfonate (48). Flash chromatography (ethyl acetate to ethyl acetate/methanol 95:5). Yield: 90% White solid; mp: 172-174° C.; IR v: 3225, 1716 $cm^{-1}$; $^1H$ NMR (DMSO-$d_6$ and $CDCl_3$): δ 7.75-7.66 (m, 4H, Ar), 7.07 (s, 1H, NH), 6.81-6.74 (m, 1H, Ar), 6.59-6.55 (m, 2H, Ar), 3.93-3.87 (m, 2H, $CH_2$), 3.54-3.48 (m, 2H, $CH_2$); $^{13}C$ NMR (DMSO-$d_6$ and $CDCl_3$): δ 164.0, 163.8, 160.7, 160.5, 158.2, 150.2, 146.1, 129.1, 125.0, 116.1, 106.4, 106.3, 106.1, 106.0, 103.0, 102.7, 102.3, 44.2, 36.4; HRMS (ES+) m/z found 355.0141; $C_{15}H_{12}F_2N_2O_4S$ ($M^+$+H) requires 355.0564.

Example 84

49

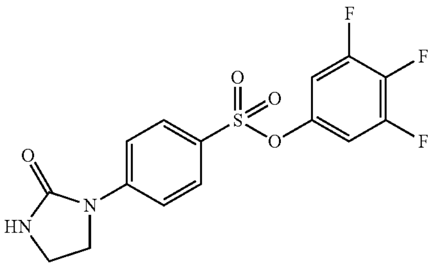

$C_{15}H_{11}F_3N_2O_4S$
Exact Mass: 372,03916

3,4,5-Trifluorophenyl-4-(2-oxoimidazolidin-1-yl)benzenesulfonate (49). Flash chromatography (ethyl acetate to ethyl acetate/methanol 95:5). Yield: 99%, White solid; mp: 178-180° C.; IR v: 3238, 2914, 1714 cm$^{-1}$; $^1$H NMR (DMSO-$d_6$ and $CDCl_3$): δ 7.78-7.67 (m, 4H, Ar), 7.24 (s, 1H, NH), 6.84-6.77 (m, 2H, Ar), 3.94-3.89 (m, 2H, $CH_2$), 3.53-3.48 (m, 2H, $CH_2$); $^{13}$C NMR (DMSO-$d_6$ and $CDCl_3$): δ 158.1, 152.0, 151.9, 151.9, 151.8, 148.7, 148.6, 148.5, 148.5, 146.4, 143.8, 143.8, 143.7, 140.3, 140.1, 139.9, 136.8, 129.2, 124.5, 116.2, 108.0, 107.9, 107.8, 107.7, 44.2, 36.4; HRMS (ES+) m/z found 372.9821; $C_{15}H_{11}F_3N_2O_4S$ ($M^+$+H) requires 373.0470.

Example 85

50

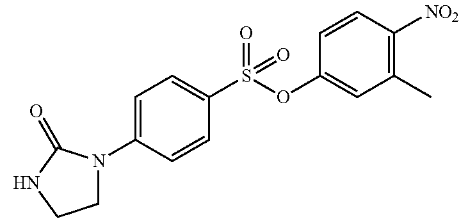

$C_{16}H_{15}N_3O_6S$
Exact Mass: 377,06816

3-Methyl-4-nitrophenyl-4-(2-oxoimidazolidin-1-yl)benzenesulfonate (50). Flash chromatography (methylene chloride to methylene chloride/ethyl acetate 8:2). Yield: 65%; White solid; mp: 215-216° C.; IR v: 3225, 1713 cm$^{-1}$; $^1$H NMR (DMSO-$d_6$): δ 8.03 (d, 1H, J=8.9 Hz, Ar), 7.85-7.81 (m, 4H, Ar), 7.45 (s, 1H, NH), 7.32-7.31 (m, 1H, Ar), 7.10-7.07 (m, 1H, Ar), 3.95-3.90 (m, 2H, $CH_2$), 3.48-3.43 (m, 2H, $CH_2$), 2.49 (s, 3H, $CH_3$); $^{13}$C NMR (DMSO-$d_6$): δ 158.2, 151.5, 147.3, 146.5, 135.7, 129.5, 126.7, 126.0, 124.7, 120.6, 116.5, 44.2, 36.3, 19.5; HRMS (ES+) m/z found 378.0916; $C_{16}H_{15}N_3O_6S$ ($M^+$+H) requires 378.0760.

Example 86

51

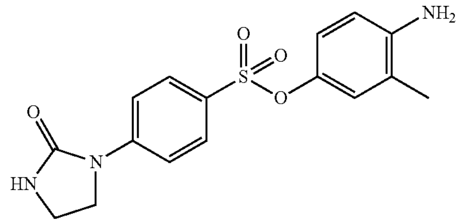

$C_{16}H_{17}N_3O_4S$
Exact Mass: 347,09398

4-Amino-3-methylphenyl-4-(2-oxoimidazolidin-1-yl)benzenesulfonate (51). Flash chromatography (methylene chloride to methylene chloride/methanol 9:1). Yield: 31%; yellow solid; mp: 160-162° C.; IR v: 3228, 1709 cm$^{-1}$; $^1$H NMR (acetone-$d_6$): δ 7.87-7.70 (m, 4H, Ar), 6.75-6.69 (m, 1H, Ar), 6.57-6.37 (m, 2H, Ar), 4.55 (s, 1H, NH), 4.06-4.00 (m, 2H, $CH_2$), 3.65-3.59 (m, 2H, $CH_2$), 1.29 (s, 3H, $CH_3$); $^{13}$C NMR (acetone-$d_6$): δ 159.1, 146.9, 146.0, 141.4, 130.1, 124.6, 124.5, 120.9, 120.7, 116.9, 114.8, 45.3, 37.4, 17.4; HRMS (ES+) m/z found 348.1060; $C_{16}H_{17}N_3O_4S$ ($M^+$+H) requires 348.1018.

Example 87

52

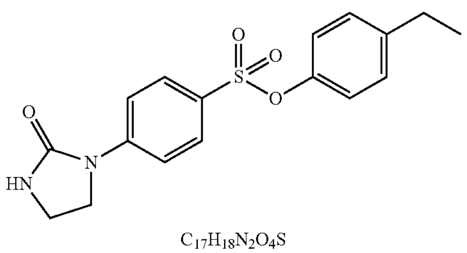

$C_{17}H_{18}N_2O_4S$
Exact Mass: 346,09873

4-Ethylphenyl-4-(2-oxoimidazolidin-1-yl)benzenesulfonate (52). Flash chromatography (ethyl acetate to ethyl acetate/methanol 95:5). Yield: 79%; White solid; mp: 155-157° C.; IR v: 3230, 1715 cm$^{-1}$; $^1$H NMR (DMSO-$d_6$): δ 7.83-7.74 (m, 4H, Ar), 7.42 (s, 1H, NH), 7.21 (d, 2H, J=8.4 Hz, Ar), 6.92 (d, 2H, J=8.4 Hz, Ar), 3.95-3.90 (m, 2H, $CH_2$), 3.49-3.43 (m, 2H, $CH_2$), 2.58 (q, 2H, J=7.5 Hz, $CH_2$), 1.15 (t, 3H, J=7.5 Hz, $CH_3$); $^{13}$C NMR (DMSO-$d_6$): δ 158.2, 147.2, 146.1, 142.9, 129.4, 129.2, 125.4, 121.9, 116.3, 44.2, 36.3, 27.5, 15.4; HRMS (ES+) m/z found 347.0906; $C_{17}H_{18}N_2O_4S$ ($M^+$+H) requires 347.1066.

Example 88

53

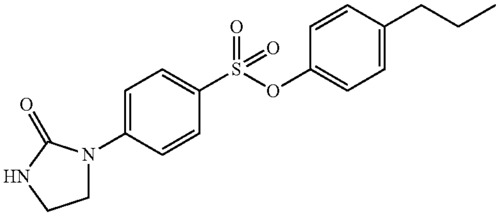

$C_{18}H_{20}N_2O_4S$
Exact Mass: 360,11438

4-Propylphenyl-4-(2-oxoimidazolidin-1-yl)benzenesulfonate (53). Flash chromatography (ethyl acetate to ethyl acetate/methanol 95:5). Yield: 78%, White solid; mp: 198-200° C.; IR v: 3208, 2955, 1712 $cm^{-1}$; $^1H$ NMR (DMSO-$d_6$ and $CDCl_3$): δ 7.68-7.60 (m, 4H, Ar), 7.02 (s, 1H, Ar or NH), 6.99 (s, 1H, Ar or NH), 6.79-6.76 (m, 3H, Ar), 3.91-3.86 (m, 2H, $CH_2$), 3.54-3.49 (m, 2H, $CH_2$), 2.47 (t, 2H, J=7.6 Hz, $CH_2$), 1.59-1.47 (m, 2H, $CH_2$), 0.84 (t, 3H, J=7.3 Hz, $CH_3$); $^{13}C$ NMR (DMSO-$d_6$ and $CDCl_3$): δ 158.3, 147.1, 145.4, 141.2, 129.0, 129.0, 126.3, 121.5, 116.0, 44.2, 36.8, 36.5, 23.8, 13.3; HRMS (ES+) m/z found 361.0652; $C_{18}H_{20}N_2O_4S$ ($M^+$+H) requires 361.1222.

Example 89

54

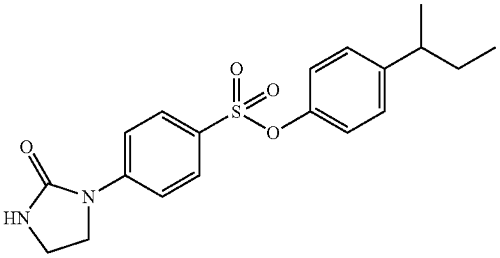

$C_{19}H_{22}N_2O_4S$
Exact Mass: 374,13003

4-sec-Butylphenyl-4-(2-oxoimidazolidin-1-yl)benzenesulfonate (54). Flash chromatography (methylene chloride to methylene chloride/ethyl acetate 8:2). Yield: 74% White solid; mp: 179-180° C.; IR v: 3245, 1711 $cm^{-1}$; $^1H$ NMR (acetone-$d_6$): δ 7.90-7.73 (m, 4H, Ar), 7.19 (d, 2H, J=8.6 Hz, Ar), 6.95 (d, 2H, J=8.6 Hz, Ar), 6.40 (brs, 1H, NH), 4.06-4.01 (m, 2H, $CH_2$), 3.65-3.60 (m, 2H, $CH_2$), 2.65-2.58 (m, 1H, $CH_2$), 1.58-1.23 (m, 2H, $CH_2$), 1.18 (d, 3H, J=6.9 Hz, $CH_3$), 0.77 (t, 3H, J=7.4 Hz, $CH_3$); $^{13}C$ NMR (acetone-$d_6$): δ 159.0, 147.6, 146.6, 145.3, 129.7, 128.1, 127.9, 122.1, 116.6, 44.9, 41.1, 37.1, 31.1, 21.7, 12.1; HRMS (ES+) m/z found 375.0776; $C_{19}H_{22}N_2O_4S$ ($M^+$+H) requires 375.1379.

Example 90

55

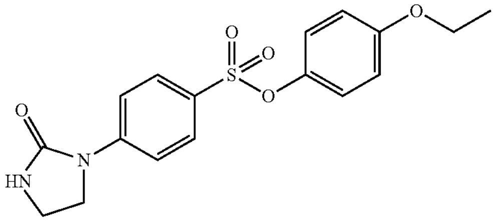

$C_{17}H_{18}N_2O_5S$
Exact Mass: 362,09364

4-Ethoxyphenyl-4-(2-oxoimidazolidin-1-yl)benzenesulfonate (55). Flash chromatography (ethyl acetate to ethyl acetate/methanol 95:5). Yield: 76%; White solid; mp: 185-187° C.; IR v: 3236, 2908, 1710 $cm^{-1}$; $^1H$ NMR (DMSO-$d_6$ and $CDCl_3$): δ 7.70-7.58 (m, 4H, Ar), 7.01 (s, 1H, NH), 6.79-6.75 (m, 2H, Ar), 6.72-6.68 (m, 2H, Ar), 3.95-3.86 (m, 4H, 2×$CH_2$), 3.53-3.48 (m, 2H, $CH_2$), 1.32 (t, 3H, J=7.0 Hz, $CH_3$); $^{13}C$ NMR (DMSO-$d_6$ and $CDCl_3$): δ 158.3, 157.1, 145.6, 142.4, 129.0, 125.9, 122.9, 115.9, 114.6, 63.3, 44.2, 36.5, 14.4; HRMS (ES+) m/z found 363.0692; $C_{17}H_{18}N_2O_5S$ ($M^+$+H) requires 363.1015.

Example 91

56

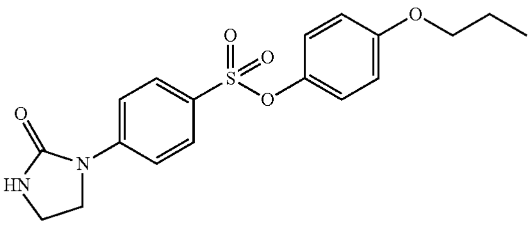

$C_{18}H_{20}N_2O_5S$
Exact Mass: 376,10929

4-Propoxyphenyl-4-(2-oxoimidazolidin-1-yl)benzenesulfonate (56). Flash chromatography (methylene chloride to methylene chloride/ethyl acetate 8:2). Yield: 56%; White solid; mp: 156-157° C.; IR v: 3226, 1711 $cm^{-1}$; $^1H$ NMR ($CDCl_3$): δ 7.74-7.65 (m, 4H, Ar), 6.87-6.83 (m, 2H, Ar), 6.76-6.72 (m, 2H, Ar), 5.73 (s, 1H, NH), 3.98-3.93 (m, 2H, $CH_2$), 3.84 (t, 2H, J=6.5 Hz, $CH_2$), 3.66-3.60 (m, 2H, $CH_2$), 1.80-1.71 (m, 2H, $CH_2$), 1.00 (t, 3H, J=7.4 Hz, $CH_3$); $^{13}C$ NMR ($CDCl_3$): δ 158.9, 157.8, 145.3, 142.9, 129.7, 127.6, 123.3, 116.6, 115.0, 69.9, 44.9, 37.1, 22.5, 10.5; HRMS (ES+) m/z found 377.0320; $C_{18}H_{20}N_2O_5S$ ($M^+$+H) requires 377.1171.

Example 92

57

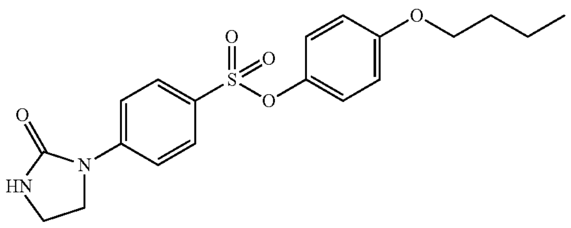

$C_{19}H_{22}N_2O_5S$
Exact Mass: 390,12494

4-Butoxyphenyl-4-(2-oxoimidazolidin-1-yl)benzenesulfonate (57). Flash chromatography (methylene chloride to methylene chloride/ethyl acetate 8:2). Yield: 58%; White solid; mp: 151-152° C.; IR v: 3218, 1696 $cm^{-1}$; $^1$H NMR ($CDCl_3$): δ 7.67-7.59 (m, 4H, Ar), 6.80-6.76 (m, 2H, Ar), 6.70-6.66 (m, 2H, Ar), 3.92-3.80 (m, 4H, 2×$CH_2$), 3.57-3.52 (m, 2H, $CH_2$), 3.10 (s, 1H, NH), 1.70-1.61 (m, 2H, $CH_2$), 1.45-1.35 (m, 2H, $CH_2$), 0.88 (t, 3H, J=7.4 Hz, $CH_3$); $^{13}$C NMR ($CDCl_3$): δ 159.2, 157.8, 145.3, 142.8, 129.6, 127.3, 123.2, 116.6, 115.0, 68.1, 44.8, 36.9, 31.1, 19.1, 13.7; HRMS (ES+) m/z found 391.0821; $C_{19}H_{22}N_2O_5S$ ($M^+$+H) requires 391.1328.

Example 93

58

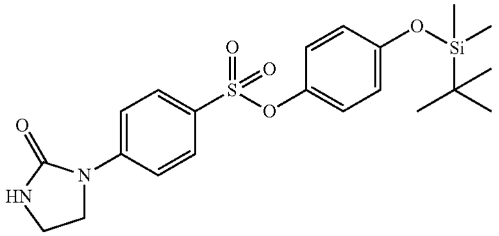

$C_{21}H_{28}N_2O_5SSi$
Exact Mass: 448,14882

4-(tert-Butyldimethylsilanyloxy)-4-(2-oxoimidazolidin-1-yl)benzenesulfonate (58). Flash chromatography (methylene chloride to methylene chloride/ethyl acetate 3:1). Yield: 53%; White solid; mp: 222-223° C.; IR v: 3227, 1716 $cm^{-1}$; $^1$H NMR ($CDCl_3$): δ 7.75-7.66 (m, 4H, Ar), 6.83-6.80 (m, 2H, Ar), 6.70-6.68 (m, 2H, Ar), 5.10 (s, 1H, NH), 4.00-3.95 (m, 2H, $CH_2$), 3.67-3.62 (m, 2H, $CH_2$), 0.95 (s, 9H, 3×$CH_3$), 0.16 (s, 6H, 2×$CH_3$); $^{13}$C NMR ($CDCl_3$): δ 158.6, 154.4, 145.2, 143.6, 129.8, 127.7, 123.4, 120.7, 116.6, 44.9, 37.1, 25.6, 18.2, −4.5; HRMS (ES+) m/z found 449.1721; $C_{21}H_{28}N_2O_5SSi$ ($M^+$+H) requires 449.1567.

Example 94

59

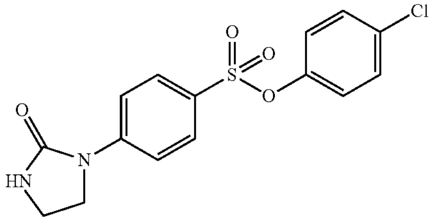

$C_{15}H_{13}ClN_2O_4S$
Exact Mass: 352,02846

4-Chlorophenyl-4-(2-oxoimidazolidin-1-yl)benzenesulfonate (59). Flash chromatography (methylene chloride to methylene chloride/ethyl acetate 8:2). Yield: 89%; White solid; mp: 179-180° C.; IR v: 3229, 1712 $cm^{-1}$; $^1$H NMR (DMSO-$d_6$): δ 7.84-7.75 (m, 4H, Ar), 7.51-7.46 (m, 3H, Ar and NH), 7.07-7.04 (m, 2H, Ar), 3.95-3.90 (m, 2H, $CH_2$), 3.49-3.44 (m, 2H, $CH_2$); $^{13}$C NMR (DMSO-$d_6$): δ 158.2, 131.7, 130.0, 129.5, 124.7, 124.1, 116.4, 115.6, 110.6, 44.2, 36.3; HRMS (ES+) m/z found 353.0836; $C_{15}H_{13}ClN_2O_4S$ ($M^+$+H) requires 353.0363.

Example 95

60

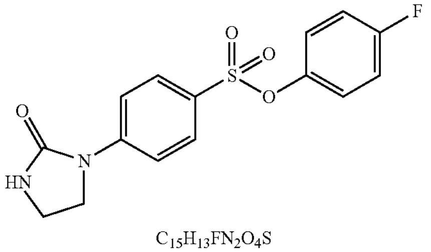

$C_{15}H_{13}FN_2O_4S$
Exact Mass: 336,05801

4-Fluorophenyl-4-(2-oxoimidazolidin-1-yl)benzenesulfonate (60). Flash chromatography (methylene chloride to methylene chloride/ethyl acetate 8:2). Yield: 33%; White solid; mp: 208-209° C.; IR v: 3227, 1714 $cm^{-1}$; $^1$H NMR ($CDCl_3$ and MeOD): δ 7.65-7.58 (m, 4H, Ar), 6.90-6.83 (m, 4H, Ar), 3.91-3.86 (m, 2H, $CH_2$), 3.55-3.49 (m, 2H, $CH_2$); $^{13}$C NMR ($CDCl_3$ and MeOD): δ 159.1, 145.5, 129.6, 126.8, 124.0, 123.9, 116.6, 116.4, 116.1, 44.8, 36.8; HRMS (ES+) m/z found 336.9669; $C_{15}H_{13}FN_2O_4S$ ($M^+$+H) requires 337.0658.

Example 96

61

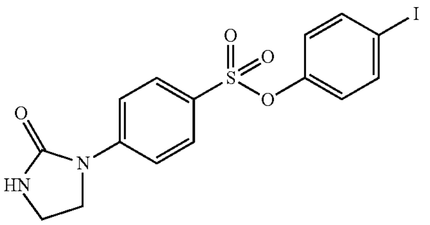

$C_{15}H_{13}IN_2O_4S$
Exact Mass: 443,96407

4-Iodophenyl-4-(2-oxoimidazolidin-1-yl)benzenesulfonate (61). Flash chromatography (ethyl acetate to ethyl acetate/methanol 95:5). Yield: 74%; White solid; mp: 202-204° C.; IR ν: 3203, 1710 $cm^{-1}$; $^1H$ NMR (DMSO-$d_6$ and $CDCl_3$): δ 7.73-7.70 (m, 2H, Ar), 7.64-7.55 (m, 4H, Ar), 7.13 (brs, 1H, NH), 6.71-6.68 (m, 2H, Ar), 3.92-3.87 (m, 2H, $CH_2$), 3.53-3.47 (m, 2H, $CH_2$); $^{13}C$ NMR (DMSO-$d_6$ and $CDCl_3$): δ 158.2, 149.0, 145.9, 138.3, 129.1, 125.4, 124.2, 116.1, 91.5, 44.2, 36.4; HRMS (ES+) m/z found 444.9747; $C_{15}H_{13}IN_2O_4S$ ($M^+$+H) requires 444.9719.

Example 97

62

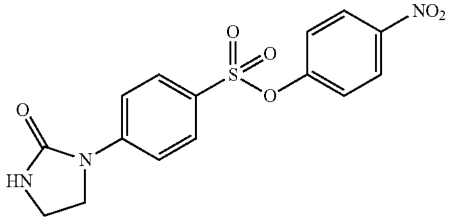

$C_{15}H_{13}N_3O_6S$
Exact Mass: 363,05251

4-Nitrophenyl-4-(2-oxoimidazolidin-1-yl)benzenesulfonate (62). Flash chromatography (methylene chloride to methylene chloride/ethyl acetate 7:3). Yield: 98%, White solid; mp: 195-196° C.; IR ν: 3267, 1704 $cm^{-1}$; $^1H$ NMR (DMSO-$d_6$): δ 8.29 (d, 2H, J=9.1 Hz, Ar), 7.83 (s, 4H, Ar), 7.46 (s, 1H, NH), 7.35 (d, 2H, J=9.1 Hz, Ar), 3.96-3.91 (m, 2H, $CH_2$), 3.49-3.44 (m, 2H, $CH_2$); $^{13}C$ NMR (DMSO-$d_6$): δ 158.2, 153.4, 146.6, 146.0, 129.6, 125.8, 124.5, 123.4, 116.5, 44.2, 36.3; HRMS (ES+) m/z found 363.9860; $C_{15}H_{13}N_3O_6S$ ($M^+$+H) requires 364.0603.

Example 98

63

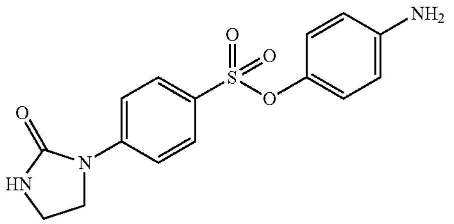

$C_{15}H_{15}N_3O_4S$
Exact Mass: 333,07833

4-Aminophenyl-4-(2-oxoimidazolidin-1-yl)benzenesulfonate (63). Flash chromatography (methylene chloride to methylene chloride/methanol 9:1). Yield: 46%; White solid; mp: 152-154° C.; IR ν: 3265, 1716 $cm^{-1}$; $^1H$ NMR (DMSO-$d_6$): δ 7.81-7.68 (m, 4H, Ar), 7.4) (s, 1H, Ar), 6.78-6.76 (m, 1H, Ar), 6.62 (d, 1H, J=8.7 Hz, Ar), 6.44 (d, 1H, J=8.7 Hz, Ar), 5.20 (s, 1H, NH), 3.95-3.90 (m, 2H, $CH_2$), 3.48-3.41 (m, 2H, $CH_2$); $^{13}C$ NMR (DMSO-$d_6$): δ 158.3, 145.9, 139.1, 129.4, 122.6, 122.3, 116.2, 114.0, 113.3, 44.3, 36.3; HRMS (ES+) m/z found 333.9906; $C_{15}H_{15}N_3O_4S$ ($M^+$+H) requires 334.0862.

Example 99

64

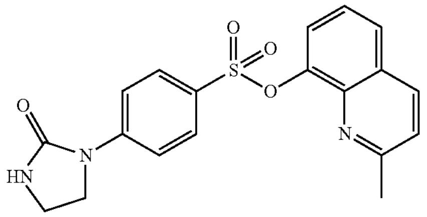

$C_{19}H_{17}N_3O_4S$
Exact Mass: 383,09398

2-Methylquinolin-8-yl-4-(2-oxoimidazolidin-1-yl)benzenesulfonate (64). Flash chromatography (methylene chloride to methylene chloride/methanol 9:1). Yield: 82%; mp: 234-235° C.; IR ν: 3255, 1724 $cm^{-1}$; $^1H$ NMR (DMSO-$d_6$): δ 8.25 (d, 1H, J=8.4 Hz, Ar), 7.91-7.87 (m, 1H, Ar), 7.82-7.69 (m, 4H, Ar), 7.58-7.51 (m, 2H, Ar), 7.41 (d, 1H, J=8.4 Hz, Ar), 7.36 (s, 1H, NH), 3.89-3.84 (m, 2H, $CH_2$), 3.47-3.41 (m, 2H, $CH_2$), 2.53 (s, 3H, $CH_3$); $^{13}C$ NMR (DMSO-$d_6$): δ 159.5, 158.2, 145.9, 144.3, 140.2, 136.0, 129.6, 127.7, 127.2, 126.4, 125.3, 123.0, 122.6, 115.8, 44.3, 36.3, 24.9; HRMS (ES+) m/z found 384.0133; $C_{19}H_{17}N_3O_4S$ ($M^+$+H) requires 384.1018.

Example 100

65

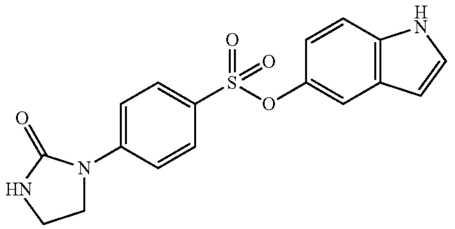

$C_{17}H_{15}N_3O_4S$
Exact Mass: 357,07833

1H-Indol-5-yl-4-(2-oxoimidazolidin-1-yl)benzenesulfonate (65). Flash chromatography (methylene chloride to methylene chloride/ethyl acetate 7:3). Yield: 82%; White solid; mp: 226-227° C.; IR v: 3417, 1712 $cm^{-1}$; $^1H$ NMR (DMSO-$d_6$): δ 11.28 (s, 1H, NH), 7.80-7.71 (m, 4H, Ar), 7.43-7.39 (m, 2H, Ar), 7.33-7.30 (m, 1H, Ar), 7.21-7.20 (m, 1H, Ar), 6.70-6.66 (m, 1H, Ar), 6.43 (brs, 1H, NH), 3.93-3.88 (m, 2H, $CH_2$), 3.47-3.42 (m, 2H, $CH_2$); $^{13}C$ NMR (DMSO-$d_6$): δ 158.3, 145.9, 142.5, 134.2, 129.3, 127.6, 127.4, 125.8, 116.3, 115.2, 112.9, 112.0, 101.7, 44.2, 36.3; HRMS (ES+) m/z found 358.0028; $C_{17}H_{15}N_3O_4S$ ($M^+$+H) requires 358.0862.

Example 101

66

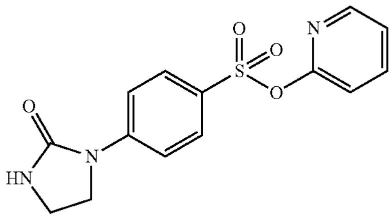

$C_{14}H_{13}N_3O_4S$
Exact Mass: 319,06268

Pyridin-2-yl-4-(2-oxoimidazolidin-1-yl)benzenesulfonate (66). Not washed with hydrochloric acid; Flash chromatography (methylene chloride to methylene chloride/ethyl acetate 0:1). Yield: 32%; White solid; mp: 153-155° C.; IR v: 3228, 3117, 1695 $cm^{-1}$; $^1H$ NMR (DMSO-$d_6$): δ 8.31-8.29 (m, 1H, Ar), 8.00-7.95 (m, 1H, Ar), 7.89-7.81 (111, 4H, Ar), 7.53-7.39 (m, 2H, NH and Ar), 7.20-7.17 (m, 1H, Ar), 3.96-3.91 (m, 2H, $CH_2$), 3.49-3.44 (m, 2H, $CH_2$); $^{13}C$ NMR (DMSO-$d_6$): δ 158.2, 156.4, 148.4, 146.1, 141.1, 129.4, 126.8, 123.4, 116.3, 115.8, 44.3, 36.3; HRMS (ES+) m/z found 320.0730; $C_{14}H_{13}N_3O_4S$ ($M^+$+H) requires 320.0705.

Example 102

67

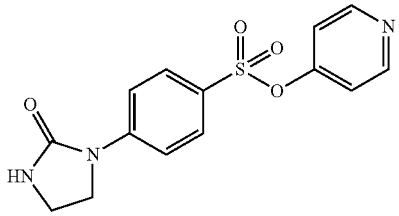

$C_{14}H_{13}N_3O_4S$
Exact Mass: 319,06268

Pyridin-4-yl-4-(2-oxoimidazolidin-1-yl)benzenesulfonate (67). Not washed with hydrochloric acid; Flash chromatography (methylene chloride to methylene chloride/methanol 9:1). Yield: 28%, White solid; mp: 188-192° C.; IR v: 3226, 3114, 1729 $cm^{-1}$; $^1H$ NMR (DMSO-$d_6$): δ 8.59 (d, 2H, J=7.0 Hz, Ar), 7.56-7.49 (m, 4H, Ar), 7.27 (d, 2H, J=7.0 Hz, Ar), 7.00 (s, 1H, NH), 3.88-3.83 (m, 2H, $CH_2$), 3.44-3.39 (m, 2H, $CH_2$); $^{13}C$ NMR (DMSO-$d_6$): δ 171.6, 158.9, 143.0, 141.4, 140.8, 126.0, 115.7, 114.0, 44.5, 36.5; HRMS (ES+) m/z found 320.0730; $C_{14}H_{13}N_3O_4S$ ($M^+$+H) requires 320.0705.

Example 103

68

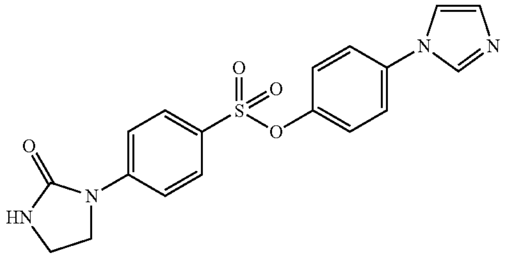

$C_{18}H_{16}N_4O_4S$
Exact Mass: 384,08923

4-(1H-Imidazol-1-yl)phenyl-4-(2-oxoimidazolidin-1-yl)benzenesulfonate (68). Flash chromatography (ethyl acetate to ethyl acetate/methanol 9:1). Yield: 74%; White solid; mp: 206-208° C.; IR v: 3220, 2910, 2811, 1713 $cm^{-1}$; $^1H$ NMR (DMSO-$d_6$): δ 8.26 (s, 1H, Ar), 7.86-7.78 (m, 4H, Ar), 7.74 (s, 1H, Ar), 7.71 (s, 1H, Ar), 7.68 (s, 1H, Ar), 7.43 (brs, 1H, NH), 7.19 (s, 1H, Ar), 7.16 (s, 1H, Ar), 7.11 (s, 1H, Ar), 3.95-3.90 (m, 2H, $CH_2$), 3.49-3.44 (m, 2H, $CH_2$); $^{13}C$ NMR (DMSO-$d_6$): δ 158.2, 147.3, 146.3, 135.7, 130.1, 129.5, 125.0, 123.6, 121.7, 118.1, 116.4, 44.3, 36.3; HRMS (ES+) m/z found 385.0567; $C_{18}H_{16}N_4O_4S$ ($M^+$+H) requires 385.0971.

Example 104

69

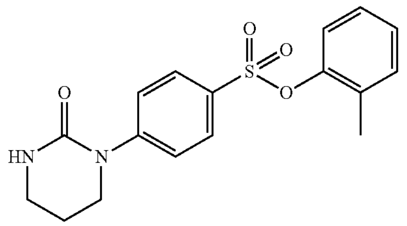

$C_{17}H_{18}N_2O_4S$
Exact Mass: 346,09873

2-Tolyl-4-[tetrahydro-2-oxopyrimidin-1(2H)-yl]benzenesulfonate (69). Flash chromatography (ethyl acetate to ethyl acetate/methanol 95:5). Yield: 58%; White solid; mp: 161-163° C.; IR ν: 3209, 2944, 1657 $cm^{-1}$; $^1$H NMR (DMSO-$d_6$): δ 7.81-7.65 (m, 4H, Ar), 7.32-7.22 (m, 3H, Ar and NH), 7.03-7.00 (m, 2H, Ar), 3.76-3.72 (m, 2H, $CH_2$), 3.27-3.23 (m, 2H, $CH_2$), 2.07 (s, 3H, $CH_3$), 2.03-1.98 (m, 2H, $CH_2$); $^{13}$C NMR (DMSO-$d_6$): δ 153.7, 149.7, 147.8, 131.8, 131.0, 128.3, 128.3, 127.4, 127.3, 123.5, 121.9, 47.1, 39.7, 22.0, 15.9; HRMS (ES+) m/z found 347.0853; $C_{17}H_{18}N_2O_4S$ ($M^+$+H) requires 347.1065.

Example 105

70

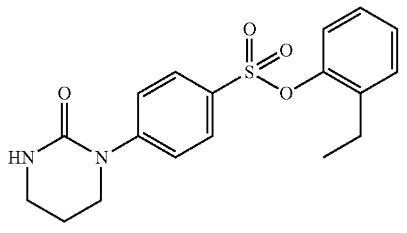

$C_{18}H_{20}N_2O_4S$
Exact Mass: 360,111438

2-Ethylphenyl-4-[tetrahydro-2-oxopyrimidin-1(2H)-yl] benzenesulfonate (70). Flash chromatography (ethyl acetate to ethyl acetate/methanol 95:5). Yield: 69%; White solid; mp: 142-144° C.; IR ν: 3209, 2976, 1655 $cm^{-1}$; $^1$H NMR (DMSO-$d_6$): δ 7.83-7.66 (m, 4H, Ar), 7.37-7.22 (m, 3H, Ar), 7.03-7.00 (m, 2H, Ar and NH), 3.74 (t, 2H, J=5.7 Hz, $CH_2$), 3.27-3.24 (m, 2H, $CH_2$), 2.49 (q, 2H, J=7.5 Hz, $CH_2$), 2.00 (quint, 2H, J=5.7 Hz, $CH_2$), 1.07 (t, 3H, J=7.5 Hz, $CH_3$); $^{13}$C NMR (DMSO-$d_6$): δ 153.7, 149.7, 147.3, 136.7, 130.2, 128.4, 128.2, 127.4, 127.3, 123.5, 121.7, 47.1, 39.7, 22.2, 22.0, 14.1; HRMS (ES+) m/z found 361.1032; $C_{18}H_{20}N_2O_4S$ ($M^+$+H) requires 361.1222.

Example 106

71

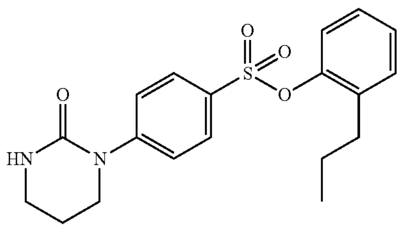

$C_{19}H_{22}N_2O_4S$
Exact Mass: 374,13003

2-Propylphenyl-4-[tetrahydro-2-oxopyrimidin-1(2H)-yl] benzenesulfonate (71). Flash chromatography (methylene chloride to methylene chloride/methanol 9:1). Yield: 98%; White solid; mp: 131-132° C.; IR ν: 3223, 1955, 1667 $cm^{-1}$; $^1$H NMR (DMSO-$d_6$): δ 7.81-7.65 (m, 4H, Ar), 7.33-7.21 (m, 3H, Ar and NH), 7.04-7.01 (m, 2H, Ar), 3.73 (t, 2H, J=5.6 Hz, $CH_2$), 3.26-3.23 (m, 2H, $CH_2$), 2.42-2.38 (m, 2H, $CH_2$), 1.98 (quint, 2H, J=5.6 Hz, $CH_2$) 1.48-1.41 (m, 2H, $CH_2$), 0.82 (t, 3H, J=7.3 Hz, $CH_3$); $^{13}$C NMR (DMSO-$d_6$): δ 153.7, 149.7, 147.6, 135.1, 130.8, 128.5, 128.2, 127.4, 127.3, 123.5, 121.8, 47.1, 39.7, 31.2, 22.6, 22.0, 13.8; HRMS (ES+) m/z found 375.1172; $C_{19}H_{22}N_2O_4S$ ($M^+$+H) requires 375.1378.

Example 107

72

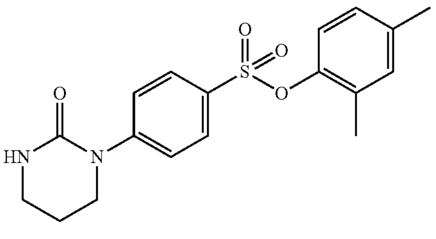

$C_{18}H_{20}N_2O_4S$
Exact Mass: 360,11438

2,4-Dimethylphenyl-4-[tetrahydro-2-oxopyrimidin-1 (2H)-yl]benzenesulfonate (72). Flash chromatography (ethyl acetate to ethyl acetate/methanol 95:5). Yield: 62%; White solid; mp: 161-163° C.; IR ν: 3228, 2949, 1684 $cm^{-1}$; $^1$H NMR (DMSO-$d_6$): δ 7.79-7.65 (m, 4H, Ar), 7.10 (s, 1H, NH), 7.03-7.02 (m, 2H, Ar), 6.88-6.86 (m, 1H, Ar), 3.74 (t, 2H, J=5.6 Hz, $CH_2$), 3.27-3.24 (m, 2H, $CH_2$), 2.27 (s, 3H, $CH_3$), 2.01-1.96 (m, 5H, $CH_2$ and $CH_3$); $^{13}$C NMR (DMSO-$d_6$): δ 153.7, 149.6, 145.7, 136.6, 132.2, 130.6, 128.4, 128.3, 127.7, 123.5, 121.7, 47.1, 39.7, 22.0, 20.3, 15.8; HRMS (ES+) m/z found 361.0231; $C_{18}H_{20}N_2O_4S$ ($M^+$+H) requires 361.1222.

Example 108

73

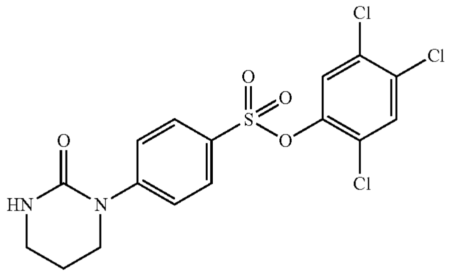

$C_{16}H_{13}Cl_3N_2O_4S$
Exact Mass: 433,96616

2,4,5-Trichlorophenyl-4-[tetrahydro-2-oxopyrimidin-1 (2H)-yl]benzenesulfonate (73). Flash chromatography (methylene chloride to methylene chloride/methanol 9:1). Yield: 88%, White solid; mp: 199-201° C.; IR ν: 3221, 3094, 1673 $cm^{-1}$; $^1H$ NMR (DMSO-$d_6$): δ 8.05 (s, 1H, NH or Ar), 7.85-7.66 (m, 4H, Ar), 7.61 (s, 1H, NH or Ar), 7.04 (brs, 1H, NH or Ar), 3.74 (t, 2H, J=5.6 Hz, $CH_2$), 3.26-3.23 (m, 2H, $CH_2$), 1.99 (quint, 2H, J=5.6 Hz, $CH_2$); $^{13}C$ NMR (DMSO-$d_6$): δ 153.6, 150.3, 143.9, 131.7, 131.0, 130.7, 128.8, 126.8, 126.6, 125.7, 123.4, 47.0, 39.7, 22.0, HRMS (ES+) m/z found 434.8303; $C_{16}H_{13}Cl_3N_2O_4S$ ($M^+$+H) requires 434.9740.

Example 109

74

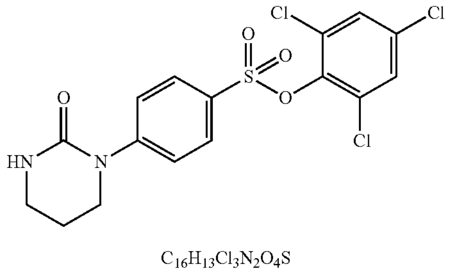

$C_{16}H_{13}Cl_3N_2O_4S$
Exact Mass: 433,96616

2,4,6-Trichlorophenyl-4-[tetrahydro-2-oxopyrimidin-1 (2H)-yl]benzenesulfonate (74). Flash chromatography (ethyl acetate to ethyl acetate/methanol 95:5). Yield: 68%; White solid; mp: 219-221° C.; IR ν: 3230, 3077, 1672 $cm^{-1}$; $^1H$ NMR (DMSO-$d_6$): δ 7.95-7.70 (m, 6H, Ar), 7.05 (s, 1H, NH), 3.77 (t, 2H, J=5.6 Hz, $CH_2$), 3.28-3.25 (m, 2H, $CH_2$), 2.04-1.96 (m, 2H, $CH_2$); $^{13}C$ NMR (DMSO-$d_6$): δ 153.7, 150.2, 141.7, 132.5, 130.1, 129.6, 128.7, 128.6, 123.4, 47.1, 39.7, 22.0; HRMS (ES+) m/z found 434.8474; $C_{16}H_{13}Cl_3N_2O_4S$ ($M^+$+H) requires 434.9740.

Example 110

75

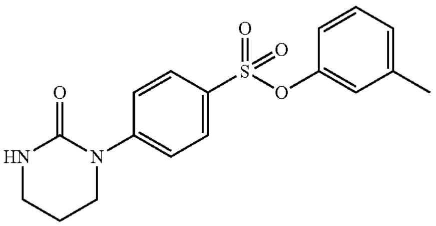

$C_{17}H_{18}N_2O_4S$
Exact Mass: 346,09873

3-Tolyl-4-[tetrahydro-2-oxopyrimidin-1(2H)-yl]benzenesulfonate (75). Flash chromatography (ethyl acetate to ethyl acetate/methanol 95:5). Yield: 57%; White solid; mp: 145-147° C.; IR ν: 3209, 1675 $cm^{-1}$; $^1H$ NMR (DMSO-$d_6$): δ 7.79-7.63 (m, 4H, Ar), 7.30-7.14 (m, 2H, Ar), 7.01 (brs, 1H, NH), 6.93 (s, 1H, Ar), 6.83-6.81 (m, 1H, Ar), 3.75-3.72 (m, 2H, $CH_2$), 3.27-3.24 (m, 2H, $CH_2$), 2.29 (s, 3H, $CH_3$), 2.01-1.97 (m, 2H, $CH_2$); $^{13}C$ NMR (DMSO-$d_6$): δ 153.7, 149.6, 149.1, 140.0, 129.7, 128.4, 128.0, 127.8, 123.4, 122.5, 118.8, 47.0, 39.7, 22.0, 20.8; HRMS (ES+) m/z found 347.0736; $C_{17}H_{18}N_2O_4S$ ($M^+$+H) requires 347.1065.

Example 111

76

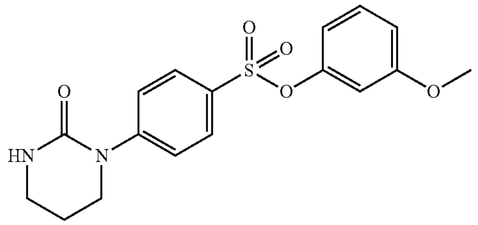

$C_{17}H_{18}N_2O_5S$
Exact Mass: 362,09364

3-Methoxyphenyl-4-[tetrahydro-2-oxopyrimidin-1(2H)-yl]benzenesulfonate (76). Flash chromatography (methylene chloride to methylene chloride/methanol 9:1). Yield: 72%; White solid; mp: 132-134° C.; IR ν: 3218, 3081, 1667 $cm^{-1}$; $^1H$ NMR (DMSO-$d_6$): δ 7.79-7.62 (m, 4H, Ar), 7.33-7.27 (m, 1H, Ar), 7.01 (brs, 1H, NH), 6.91-6.88 (m, 1H, Ar), 6.64-6.62 (m, 1H, Ar), 6.57-6.56 (m, 1H, Ar), 3.72 (t, 2H, J=5.8 Hz, $CH_2$), 3.68 (s, 3H, $CH_3$), 3.25-3.224 (m, 2H, $CH_2$), 1.99-1.96 (m, 2H, $CH_2$); $^{13}C$ NMR (DMSO-$d_6$): δ 160.1, 153.7, 150.0, 149.6, 130.5, 128.4, 127.6, 123.4, 113.9, 113.2, 107.9, 55.5, 47.0, 39.7, 22.0; HRMS (ES+) m/z found 363.0611; $C_{17}H_{18}N_2O_5S$ ($M^+$+H) requires 363.1014.

Example 112

77

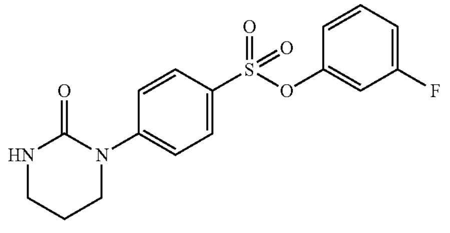

$C_{16}H_{15}FN_2O_4S$
Exact Mass: 350,07366

3-Fluorophenyl-4-[tetrahydro-2-oxopyrimidin-1(2H)-yl] benzenesulfonate (77). Flash chromatography (methylene chloride to methylene chloride/methanol 9:1). Yield: 74%; White solid; mp: 149-150° C.; IR v: 3209, 3076, 1670 $cm^{-1}$; $^1H$ NMR (DMSO-$d_6$): δ 7.80-7.63 (m, 4H, Ar), 7.54-7.42 (m, 1H, Ar), 7.25-7.19 (m, 1H, Ar), 7.05-7.01 (m, 1H, Ar), 6.94-6.91 (m, 1H, Ar), 3.74-3.60 (m, 2H, $CH_2$), 3.24 (t, 2H, J=5.7 Hz, $CH_2$), 1.97 (quint, 2H, J=5.7 Hz, $CH_2$); $^{13}C$ NMR (DMSO-$d_6$): δ 153.7, 149.8, 131.5, 131.3, 128.5, 127.1, 125.5, 123.9, 123.4, 118.3, 118.3, 114.7, 114.4, 110.3, 110.0, 47.0, 22.1, 22.0; HRMS (ES+) m/z found 351.0657; $C_{16}H_{15}FN_2O_4S$ ($M^+$+H) requires 351.0815.

Example 113

78

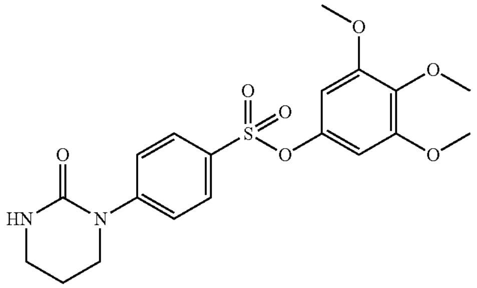

$C_{19}H_{22}N_2O_7S$
Exact Mass: 422,11477

3,4,5-Trimethoxyphenyl-4-[tetrahydro-2-oxopyrimidin-1(2H)-yl]benzenesulfonate (78). Flash chromatography (methylene chloride to methylene chloride/ethyl acetate 7:3). Yield: 75%; White solid; mp: 218-220° C.; IR v: 3430, 1697 $cm^{-1}$; $^1H$ NMR (DMSO-$d_6$): δ 7.81-7.62 (m, 4H, Ar), 7.00 (brs, 1H, NH), 6.28 (s, 2H, Ar), 3.72 (t, 2H, J=5.6 HZ, $CH_2$), 3.64 (s, 6H, 2×$CH_2$), 3.63 (s, 3H, $CH_3$), 3.28-3.23 (m, 2H, $CH_2$), 2.02-1.95 (m, 2H, $CH_2$); $^{13}C$ NMR (DMSO-$d_6$): δ 153.7, 153.1, 149.8, 145.0, 136.3, 128.7, 127.6, 123.7, 100.0, 60.1, 56.1, 47.1, 39.7, 22.0; HRMS (ES+) m/z found 423.1245; $C_{19}H_{22}N_2O_7S$ ($M^+$+H) requires 423.1226.

Example 114

79

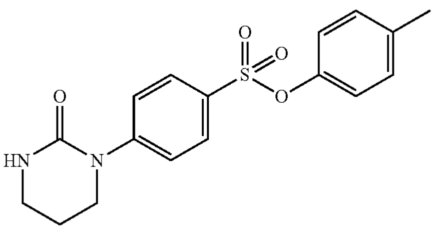

$C_{17}H_{18}N_2O_4S$
Exact Mass: 346,09873

4-Tolyl-4-[tetrahydro-2-oxopyrimidin-1(2H)-yl]benzene-sulfonate (79). Flash chromatography (ethyl acetate to ethyl acetate/methanol 95:5). Yield: 72%; White solid; mp: 204-205° C.; IR v: 3213, 3067, 1667 $cm^{-1}$; $^1H$ NMR (DMSO-$d_6$): δ 7.77-7.63 (m, 4H, Ar), 7.21-7.18 (m, 2H, Ar), 7.02 (brs, 1H, NH), 6.95-6.92 (m, 2H, Ar), 3.74-3.71 (m, 2H, $CH_2$), 3.28-3.23 (m, 2H, $CH_2$), 2.29 (s, 3H, $CH_3$), 2.02-1.95 (m, 2H, $CH_2$); $^{13}C$ NMR (DMSO-$d_6$): δ 153.7, 149.5, 147.0, 136.9, 130.4, 128.4, 127.7, 123.3, 121.8, 47.0, 39.7, 22.0, 20.4; HRMS (ES+) m/z found 347.1001; $C_{17}H_{18}N_2O_4S$ ($M^+$+H) requires 347.1065.

Example 115

80

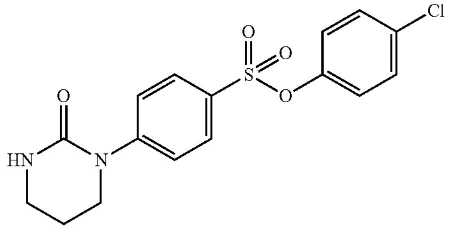

$C_{16}H_{15}ClN_2O_4S$
Exact Mass: 366,04411

4-Chlorophenyl-4-[tetrahydro-2-oxopyrimidin-1(2H)-yl] benzenesulfonate (80). Flash chromatography (ethyl acetate to ethyl acetate/methanol 95:5). Yield: 77%; White solid; mp: 190-192° C.; IR v: 3231, 3062, 1648 $cm^{-1}$; $^1H$ NMR (DMSO-$d_6$): δ 7.79-7.65 (m, 4H, Ar), 7.50-7.47 (m, 2H, Ar), 7.12-7.09 (m, 2H, Ar), 7.03 (brs, 1H, NH), 3.74 (t, 2H, J=5.4 Hz, $CH_2$), 3.27-3.24 (m, 2H, $CH_2$), 2.03-1.96 (m, 2H, $CH_2$); $^{13}C$ NMR (DMSO-$d_6$): δ 153.7, 149.8, 147.8, 131.8, 130.1, 128.5, 127.1, 124.0, 123.3, 47.0, 39.7, 22.0; HRMS (ES+) m/z found 367.0263; $C_{16}H_{15}ClN_2O_4S$ ($M^+$+H) requires 367.0519.

Example 116

81

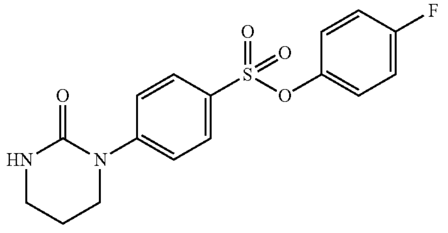

$C_{16}H_{15}FN_2O_4S$
Exact Mass: 350,07366

4-Fluorophenyl-4-[tetrahydro-2-oxopyrimidin-1(2H)-yl] benzenesulfonate (81). Flash chromatography (ethyl acetate to ethyl acetate/methanol 95:5). Yield: 80%; White solid; mp: 172-174° C.; IR v: 3224, 3088, 1666 $cm^{-1}$; $^1H$ NMR (DMSO-$d_6$): δ 7.78-7.64 (m, 4H, Ar), 7.29-7.23 (m, 2H, Ar), 7.13-7.09 (m, 2H, Ar), 7.03 (s, 1H, NH), 3.75-3.72 (m, 2H, $CH_2$), 3.28-3.23 (m, 2H, $CH_2$), 2.02-1.97 (m, 2H, $CH_2$); $^{13}C$ NMR (DMSO-$d_6$): δ 153.7, 149.7, 145.2, 145.2, 128.5, 127.2, 124.2, 124.1, 123.3, 116.9, 116.6, 47.0, 39.7, 22.0; HRMS (ES+) m/z found 351.0990; $C_{16}H_{15}FN_2O_4S$ ($M^+$+H) requires 351.0815.

Example 117

82

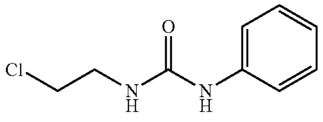

$C_9H_{11}ClN_2O$
Exact Mass: 198,05599

1-(2-Chloroethyl)-3-phenylurea (82). Yield: 99%; mp: 108-110° C.; IR v: 3304, 1637 $cm^{-1}$; $^1H$ NMR (DMSO-$d_6$): δ 8.69 (s, 1H, NH), 7.44-7.41 (m, 2H, Ar), 7.27-7.22 (min, 2H, Ar), 6.95-6.90 (m, 1H, Ar), 6.45 (t, 1H, J=5.1 Hz, NH), 3.68 (t, 2H, J=6.1 Hz, $CH_2$), 3.48-3.42 (m, 2H, $CH_2$); $^{13}C$ NMR ($CDCl_3$ and MeOD): δ 156.5, 138.9, 128.8, 122.7, 119.5, 44.0, 41.7.

Example 118

83

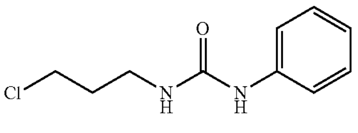

$C_{10}H_{13}ClN_2O$
Exact Mass: 212,07164

1-(3-Chloropropyl)-3-phenylurea (83). Yield: 93%; mp: 115-117° C.; IR v: 3329, 1633 $cm^{-1}$; $^1H$ NMR (DMSO-$d_6$): δ 8.45 (s, 1H, NH), 7.43-7.40 (m, 2H, Ar), 7.26-7.21 (m, 2H, Ar), 6.93-6.88 (m, 1H, Ar), 6.27 (t, 1H, J=5.6 Hz, NH), 3.68 (t, 2H, J=6.5 Hz, $CH_2$), 3.27-3.21 (m, 2H, $CH_2$), 1.90 (apparent quint, 2H, J=6.5 Hz, $CH_2$), $^{13}C$ NMR (DMSO-$d_6$): δ 155.3, 140.5, 128.6, 121.1, 117.7, 43.1, 36.6, 32.7.

Example 119

84

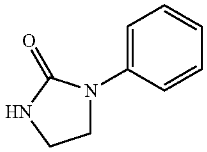

$C_9H_{10}N_2O$
Exact Mass: 162,07931

1-Phenylimidazolidin-2-one (84). Yield: 98%; Compound 84 was also synthesized using method described by Neville. Briefly, triphosgene (12.2 mmol) was dissolved in 40 mL of tetrahydrofuran and cooled at 0° C. To the resulting solution was added (36.7 mmol) of N-phenylethylenediamine dissolved in 65 mL of tetrahydrofuran and 7.7 mL of triethylamine over a period of 30 min. White solid immediately precipitated. The reaction was complete after 5 min. The reaction mixture was quenched with water and diluted with ethyl acetate. The organic layer was washed with water and brine, dried over sodium sulfate, filtered, and concentrated in vacuo. The residue was purified by flash chromatography (methylene chloride to methylene chloride/ethyl acetate 3:10) to afford a white solid. Yield: 80% mp: 154-156° C.; IR v: 3240, 1680 $cm^{-1}$; $^1H$ NMR (DMSO-$d_6$): δ 7.58-7.55 (m, 2H, Ar), 7.34-7.29 (m, 2H, Ar), 7.02-6.95 (m, 2H, Ar and NH), 3.88-3.83 (m, 2H, $CH_2$), 3.44-3.39 (m, 2H, $CH_2$); $^{13}C$ NMR ($CDCl_3$): δ 160.2, 140.2, 128.8, 122.7, 117.9, 45.3, 37.5.

Example 120

85

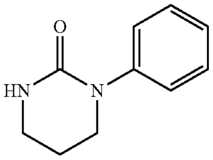

$C_{10}H_{12}N_2O$
Exact Mass: 176,09496

Tetrahydro-3-phenylpyrimidin-2(1H)-one (85). Yield: 95%, mp: 198-200° C.; IR v: 3216, 3060, 1643 $cm^{-1}$; $^1H$ NMR (DMSO-$d_6$): δ 7.32-7.28 (m, 4H, Ar), 7.14-7.10 (m, 1H, Ar), 6.58 (s, 1H, NH), 3.63 (t, 2H, J=5.7 Hz, $CH_2$), 3.27-3.22 (m, 2H, $CH_2$), 1.96 (apparent quint, 2H, J=5.7 Hz, $CH_2$); $^{13}C$ NMR (DMSO-$d_6$): δ 154.4, 144.4, 128.1, 125.1, 124.2, 48.0, 22.2.

Example 121

86

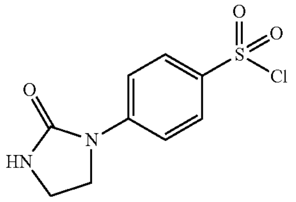

$C_9H_9ClN_2O_3S$
Exact Mass: 260,00224

4-(2-Oxoimidazolidin-1-yl)benzene-1-sulfonyl chloride (86). Yield: 56% mp: 257-259° C.; IR v: 3232, 1711 $cm^{-1}$; $^1H$ NMR (DMSO-$d_6$): δ 7.57-7.51 (m, 4H, Ar), 3.88-3.82 (m, 2H, $CH_2$), 3.44-3.38 (min, 2H, $CH_2$); $^{13}C$ NMR (DMSO-$d_6$): δ 158.9, 141.2, 140.5, 126.1, 115.8, 44.5, 36.5.

Example 122

87

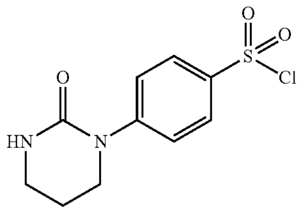

$C_{10}H_{11}ClN_2O_3S$
Exact Mass: 274,01789

4-(Tetrahydro-2-oxopyrimidin-1(2H)-yl)benzene-1-sulfonyl chloride (87). Yield: 32%; mp: 262-266° C.; IR v: 3093, 1667 $cm^{-1}$; $^1H$ NMR (DMSO-$d_6$): δ 7.56 (d, 2H, J=8.3 Hz, Ar), 7.28 (d, 2H, J=8.3 Hz, Ar), 3.66-3.61 (m, 2H, $CH_2$), 3.41-3.23 (m, 2H, $CH_2$), 2.03-1.92 (m, 2H, $CH_2$); $^{13}C$ NMR (DMSO-$d_6$): δ 154.6, 143.9, 143.8, 125.7, 124.4, 48.0, 21.7.

Example 123

88

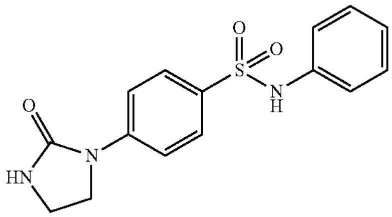

$C_{15}H_{15}N_3O_3S$
Exact Mass: 317,08341

N-Phenyl-4-(2-oxoimidazolidin-1-yl)benzenesulfonamide (88). Flash chromatography (methylene chloride to methylene chloride/ethyl acetate 0:1). Yield: 29%, White solid; mp: 262-264° C.; IR: 3434, 1686 $cm^{-1}$; $^1H$ NMR (DMSO-$d_6$ and $CDCl_3$) δ 7.63-7.53 (m, 4H, Ar), 7.11-7.02 (m, 4H, Ar), 6.95-6.88 (m, 1H, Ar), 3.82-3.78 (m, 2H, $CH_2$), 3.44-3.39 (m, 2H, $CH_2$); $^{13}C$ NMR (DMSO-$d_6$ and $CDCl_3$) δ 163.6, 149.2, 142.9, 136.7, 133.8, 132.7, 128.8, 125.2, 121.1, 49.4, 41.6; HRMS (ES+) m/z found 318.0634; $C_{15}H_{15}N_3O_3S$ ($M^+$+H) requires 318.0912.

Example 124

89

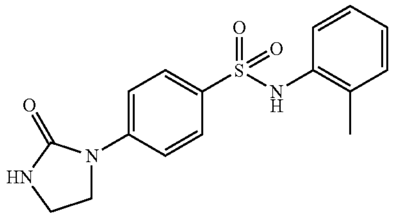

$C_{16}H_{17}N_3O_3S$
Exact Mass: 331,09906

N-2-Tolyl-4-(2-oxoimidazolidin-1-yl)benzenesulfonamide (89). Flash chromatography (methylene chloride to methylene chloride/ethyl acetate 0:1). Yield: 45%; White solid; mp: 209-210° C.; IR: 3234, 2920, 1694 $cm^{-1}$; $^1H$ NMR ($CDCl_3$, MeOD and DMSO-$d_6$) δ 7.21-7.15 (m, 4H, Ar), 6.67-6.60 (m, 4H, Ar), 3.52-3.47 (m, 2H, $CH_2$), 3.14-3.09 (m, 2H, $CH_2$), 1.62 (s, 3H, $CH_3$); $^{13}C$ NMR ($CDCl_3$, MeOD and DMSO-$d_6$) δ 158.8, 143.9, 134.6, 133.7, 132.5, 130.4, 127.5, 126.0, 126.0, 126.0, 116.1, 44.4, 36.5, 17.4; HRMS (ES+) m/z found 331.9980; $C_{16}H_{17}N_3O_3S$ ($M^+$+H) requires 332.1069.

Example 125

90

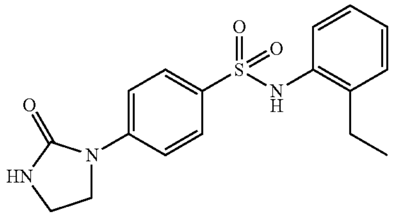

$C_{17}H_{19}N_3O_3S$
Exact Mass: 345,11471

N-(2-Ethylphenyl)-4-(2-oxoimidazolidin-1-yl)benzenesulfonamide (90). Flash chromatography (methylene chloride to methylene chloride/ethyl acetate 0:1). Yield: 40%; White solid; mp: 171-172° C.; IR: 3240, 2973, 1698 $cm^{-1}$; $^1H$ NMR ($CDCl_3$ and MeOD) δ 7.62-7.45 (m, 4H, Ar), 7.06-6.80 (m, 4H, Ar), 3.84-3.76 (m, 2H, $CH_2$), 3.50-3.45 (m, 2H, $CH_2$), 2.36 (q, 2H, J=7.5 Hz, $CH_2$), 0.95 (t, 3H, J=7.5 Hz, $CH_3$); $^{13}C$ NMR ($CDCl_3$ and MeOD) δ 159.4, 144.0, 138.7, 133.8, 132.5, 128.9, 128.1, 126.6, 126.4, 125.3, 116.6, 44.8, 36.9, 23.5, 14.1; HRMS (ES+) m/z found 346.0042; $C_{17}H_{19}N_3O_3S$ ($M^+$+H) requires 346.1225.

Example 126

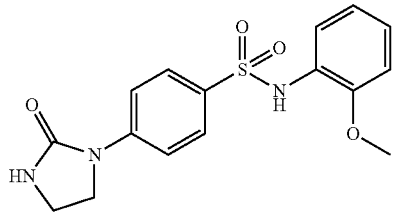

91

$C_{16}H_{17}N_3O_4S$
Exact Mass: 347,09398

N-(2-Methoxyphenyl)-4-(2-oxoimidazolidin-1-yl)benzenesulfonamide (91). Flash chromatography (methylene chloride to methylene chloride/ethyl acetate 0:1). Yield: 53%; White solid; mp: 209-211° C.; IR: 3279, 2906, 1697 $cm^{-1}$; $^1H$ NMR ($CDCl_3$, MeOD and DMSO-$d_6$) δ 7.08-7.01 (m, 4H, Ar), 6.78 (d, 1H, J=7.8 Hz, Ar), 6.46 (t, 1H, J=7.8 Hz, Ar), 6.29-6.19 (m, 2H, Ar), 3.34-3.28 (m, 5H, $CH_2$ and $CH_3$), 2.95-2.90 (m, 2H, $CH_2$); $^{13}C$ NMR ($CDCl_3$, MeOD and DMSO-$d_6$) δ 158.4, 150.6, 144.0, 131.5, 127.5, 125.5, 125.4, 122.5, 120.2, 115.7, 110.8, 55.2, 44.2, 36.3; HRMS (ES+) m/z found 347.9580; $C_{16}H_{17}N_3O_4S$ ($M^+$+H) requires 348.1018.

Example 127

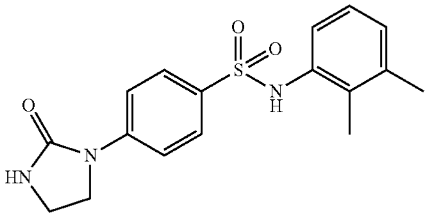

92

$C_{17}H_{19}N_3O_3S$
Exact Mass: 345,11471

N-(2,3-Dimethylphenyl)-4-(2-oxoimidazolidin-1-yl)benzenesulfonamide (92). Flash chromatography (methylene chloride to methylene chloride/ethyl acetate 0:1). Yield: 55%, White solid; mp: 231-232° C.; IR: 3257, 2902, 1703 $cm^{-1}$; $^1H$ NMR (DMSO-$d_6$ and $CDCl_3$) δ 8.87 (s, 1H, NH), 7.57-7.49 (min, 4H, Ar), 6.90-6.80 (min, 3H, Ar and NH), 6.74-6.71 (m, 1H, Ar), 3.86-3.81 (m, 2H, $CH_2$), 3.49-3.43 (m, 2H, $CH_2$), 2.12 (s, 3H, $CH_3$), 1.92 (s, 3H, $CH_3$); $^{13}C$ NMR (DMSO-$d_6$ and $CDCl_3$) δ 163.8, 149.0, 142.4, 139.7, 138.6, 137.7, 132.9, 132.7, 130.2, 129.6, 121.0, 49.5, 41.7, 25.4, 19.0, HRMS (ES+) m/z found 346.1540; $C_{17}H_{19}N_3O_3S$ ($M^+$+H) requires 346.1225.

Example 128

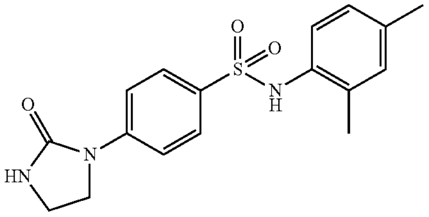

93

$C_{17}H_{19}N_3O_3S$
Exact Mass: 345,11471

N-(2,4-Dimethylphenyl)-4-(2-oxoimidazolidin-1-yl)benzenesulfonamide (93). Flash chromatography (methylene chloride to methylene chloride/ethyl acetate 0:1). Yield: 55%; White solid; mp: 238-239° C.; IR: 3463, 3283, 1704 $cm^{-1}$; $^1H$ NMR (DMSO-$d_6$) δ 8.86 (s, 1H, NH), 7.58-7.48 (m, 4H, Ar), 6.93 (s, 1H, NH), 6.82-6.74 (m, 3H, Ar), 3.87-3.81 (m, 2H, $CH_2$), 3.48-3.43 (m, 2H, $CH_2$), 2.16 (s, 3H, $CH_3$), 1.93 (s, 3H, $CH_3$); $^{13}C$ NMR (DMSO-$d_6$) δ 163.7, 149.1, 140.7, 139.2, 137.8, 137.3, 136.2, 132.6, 131.7, 121.0, 49.5, 41.7, 25.6, 22.7; HRMS (ES+) m/z found 345.9970; $C_{17}H_{19}N_3O_3S$ ($M^+$+H) requires 346.1225.

Example 129

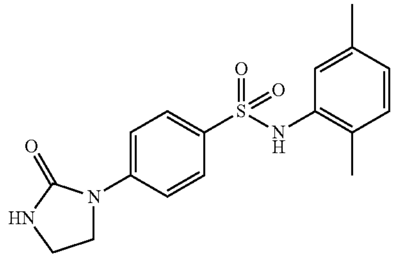

94

$C_{17}H_{19}N_3O_3S$
Exact Mass: 345,11471

N-(2,5-Dimethylphenyl)-4-(2-oxoimidazolidin-1-yl)benzenesulfonamide (94). Flash chromatography (methylene chloride to methylene chloride/ethyl acetate 0:1). Yield: 46%; White solid; mp: 213-215° C.; IR: 3274, 1695 $cm^{-1}$; $^1H$ NMR (DMSO-$d_6$ and $CDCl_3$) δ 9.05 (s, 1H, NH), 7.61-7.50 (m, 4H, Ar), 7.08 (s, 1H, NH), 6.90-6.79 (m, 3H, Ar), 3.87-3.82 (m, 2H, $CH_2$), 3.47-3.42 (m, 2H, $CH_2$), 2.15 (s, 3H, $CH_3$), 1.89 (s, 3H, $CH_3$); $^{13}C$ NMR (DMSO-$d_6$ and $CDCl_3$) δ 163.6, 149.2, 140.3, 139.9, 137.8, 135.7, 135.4, 132.6, 132.0, 131.8, 121.0, 49.5, 41.7, 25.7, 22.4; HRMS (ES+) m/z found 346.0067; $C_{17}H_{19}N_3O_3S$ ($M^+$+H) requires 346.1225.

Example 130

95

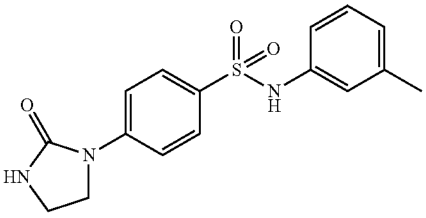

$C_{16}H_{17}N_3O_3S$
Exact Mass: 331,09906

N-3-Tolyl-4-(2-oxoimidazolidin-1-yl)benzenesulfonamide (95). Flash chromatography (methylene chloride to methylene chloride/ethyl acetate 0:1). Yield: 64%; White solid; mp: 188-190° C.; IR: 3419, 3077, 1697 $cm^{-1}$; $^1$H NMR ($DMSO-d_6$ and $CDCl_3$) δ 9.60 (s, 1H, NH), 7.63-7.52 (m, 4H, Ar), 6.97-6.92 (m, 1H, Ar), 6.84-6.82 (m, 2H, Ar or NH), 6.75-6.70 (m, 2H, Ar or NH), 3.83-3.77 (m, 2H, $CH_2$), 3.46-3.41 (m, 2H, $CH_2$), 2.15 (s, 3H, $CH_3$); $^{13}$C NMR ($DMSO-d_6$ and $CDCl_3$) δ 163.7, 149.0, 143.4, 142.7, 136.9, 133.5, 132.7, 129.6, 125.8, 122.2, 121.1, 49.5, 41.7, 26.2; HRMS (ES+) m/z found 332.1365; $C_{16}H_{17}N_3O_3S$ ($M^+$+H) requires 332.1069.

Example 131

96

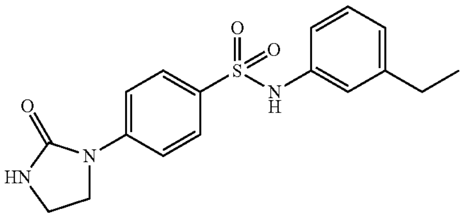

$C_{17}H_{19}N_3O_3S$
Exact Mass: 345,11471

N-(3-Ethylphenyl)-4-(2-oxoimidazolidin-1-yl)benzenesulfonamide (96). Flash chromatography (methylene chloride to methylene chloride/ethyl acetate 0:1 to ethyl acetate/methanol 95:5). Yield: 72%; White solid; mp: 188-190° C.; IR: 3400, 2961, 1697 $cm^{-1}$; $^1$H NMR ($DMSO-d_6$) δ 10.08 (s, 1H, NH), 7.69 (brs, 4H, Ar), 7.26 (brs, 1H, NH), 7.14-7.09 (m, 1H, Ar), 6.95-6.84 (m, 3H, Ar), 3.87-3.82 (m, 2H, $CH_2$), 3.43-3.38 (m, 2H, $CH_2$), 2.49 (q, 2H, J=7.5 Hz, $CH_2$), 1.09 (t, 3H, J=7.5 Hz, $CH_3$); $^{13}$C NMR ($DMSO-d_6$) δ 158.4, 144.7, 144.4, 138.0, 131.3, 129.0, 127.7, 123.3, 119.1, 117.1, 116.2, 44.2, 36.4, 28.1, 15.4; HRMS (ES+) m/z found 346.1010; $C_{17}H_{19}N_3O_3S$ ($M^+$+H) requires 346.1225.

Example 132

97

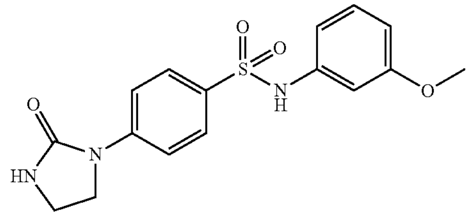

$C_{16}H_{17}N_3O_4S$
Exact Mass: 347,09398

N-(3-Methoxyphenyl)-4-(2-oxoimidazolidin-1-yl)benzenesulfonamide (97). Flash chromatography (ethyl acetate to ethyl acetate/methanol 95:5). Yield: 52%; White solid; mp: 179-181° C.; IR: 3428, 3084, 1700 $cm^{-1}$; $^1$H NMR ($DMSO-d_6$) δ 10.17 (brs, 1H, NH), 7.70 (brs, 4H, Ar), 7.26 (brs, 1H, NH), 7.14-7.09 (m, 1H, Ar), 6.68-6.67 (m, 2H, Ar), 6.60-6.56 (m, 1H, Ar), 3.88-3.83 (m, 2H, $CH_2$), 3.66 (s, 3H, $CH_3$), 3.43-3.38 (m, 2H, $CH_2$); $^{13}$C NMR ($DMSO-d_6$) δ 159.7, 158.4, 144.4, 139.3, 131.1, 130.0, 127.7, 116.2, 111.7, 108.8, 105.5, 55.0, 44.2, 36.4; HRMS (ES+) m/z found 348.0766; $C_{16}H_{17}N_3O_4S$ ($M^+$+H) requires 348.1018.

Example 133

98

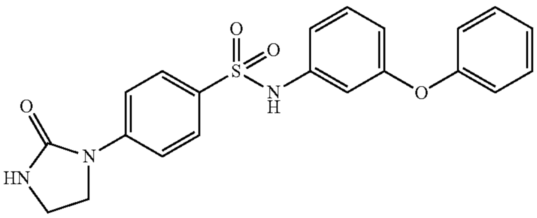

$C_{21}H_{19}N_3O_4S$
Exact Mass: 409,10963

N-(3-Phenoxyphenyl)-4-(2-Oxoimidazolidin-1-yl)benzenesulfonamide (98). Flash chromatography (methylene chloride to methylene chloride/ethyl acetate 0:1). Yield: 65%; White solid; mp: 208-211° C.; IR: 3389, 1696 $cm^{-1}$; $^1$H NMR ($DMSO-d_6$) δ 10.26 (brs, 1H, NH), 7.73-7.63 (m, 4H, Ar), 7.43-7.37 (m, 2H, Ar), 7.31 (brs, 1H, NH), 7.26-7.15 (m, 2H, Ar), 6.93-6.86 (m, 3H, Ar), 6.73-6.64 (m, 2H, Ar), 3.91-3.86 (m, 2H, $CH_2$), 3.47-3.41 (m, 2H, $CH_2$); $^{13}$C NMR ($DMSO-d_6$) δ 158.4, 157.3, 156.1, 144.6, 139.6, 130.8, 130.6, 130.1, 127.8, 123.8, 118.9, 116.3, 114.5, 113.7, 109.4, 44.3, 36.4; HRMS (ES+) m/z found 410.1010; $C_{21}H_{19}N_3O_4S$ ($M^+$+H) requires 410.1175.

Example 134

99

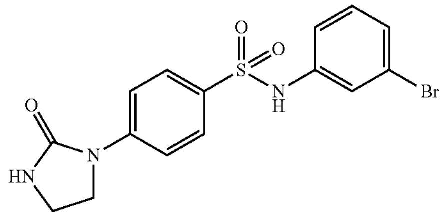

$C_{15}H_{14}BrN_3O_3S$
Exact Mass: 394,99392

N-(3-Bromophenyl)-4-(2-oxoimidazolidin-1-yl)benzenesulfonamide (99). Flash chromatography (methylene chloride to methylene chloride/ethyl acetate 0:1). Yield: 21%; White solid; mp: 184-185° C.; IR: 3388, 2860, 1692 $cm^{-1}$; $^1H$ NMR (DMSO-$d_6$ and $(CD_3)_2CO$) δ 7.74-7.65 (m, 4H, Ar), 7.34 (s, 1H, Ar), 7.18-7.09 (m, 3H, Ar), 3.92-3.87 (m, 2H, $CH_2$), 3.61 (s, 2H, NH), 3.52-3.46 (m, 2H, $CH_2$); $^{13}C$ NMR (DMSO-$d_6$ and $(CD_3)_2CO$) δ 159.0, 145.3, 140.4, 131.8, 131.0, 128.2, 126.7, 122.6, 122.4, 118.7, 116.6, 44.8, 37.0; HRMS (ES+) m/z found 395.9071; $C_{15}H_{14}BrN_3O_3S$ ($M^+$+H) requires 396.0018.

Example 135

100

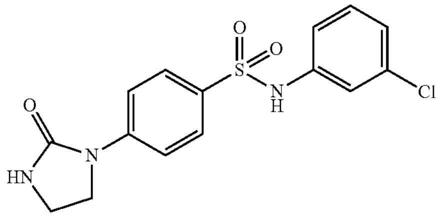

$C_{15}H_{14}ClN_3O_3S$
Exact Mass: 351,04444

N-(3-Chlorophenyl)-4-(2-oxoimidazolidin-1-yl)benzenesulfonamide (100). Flash chromatography (methylene chloride to methylene chloride/ethyl acetate 0:1). Yield: 30%; White solid; mp: 180-182° C.; IR: 3386, 1696 $cm^{-1}$; $^1H$ NMR ($CDCl_3$, MeOD and DMSO-$d_6$) δ 7.64-7.55 (m, 4H, Ar), 7.07-7.05 (m, 2H, Ar), 6.97-6.94 (m, 1H, Ar), 6.89-6.86 (m, 1H, Ar), 3.84-3.78 (m, 2H, $CH_2$), 3.45-3.40 (m, 2H, $CH_2$); $^{13}C$ NMR ($CDCl_3$, MeOD and DMSO-$d_6$) δ 153.3, 139.0, 133.9, 128.6, 125.9, 124.7, 122.3, 118.2, 114.1, 112.4, 110.9, 39.0, 31.2; HRMS (ES+) m/z found 352.0504; $C_{15}H_{14}ClN_3O_3S$ ($M^+$+H) requires 352.0523.

Example 136

101

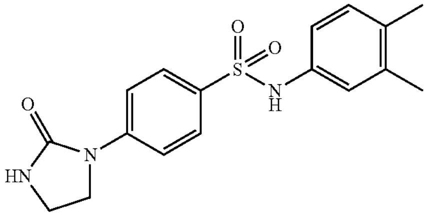

$C_{17}H_{19}N_3O_3S$
Exact Mass: 345,11471

N-(3,4-Dimethylphenyl)-4-(2-oxoimidazolidin-1-yl)benzenesulfonamide (101). Flash chromatography (ethyl acetate to ethyl acetate/methanol 95:5). Yield: 73%; White solid; mp: 206-208° C.; IR: 3413, 3256, 1700 $cm^{-1}$; $^1H$ NMR (DMSO-$d_6$) δ 9.92 (s, 1H, NH), 7.70-7.63 (m, 4H, Ar), 7.26 (s, 1H, NH), 6.97-6.94 (m, 1H, Ar), 6.88-6.87 (m, 1H, Ar), 6.83-6.80 (m, 1H, Ar), 3.88-3.83 (m, 2H, $CH_2$), 3.43-3.39 (m, 2H, $CH_2$), 2.11 (s, 3H, $CH_3$), 2.09 (s, 3H, $CH_3$); $^{13}C$ NMR (DMSO-$d_6$) δ 158.4, 144.3, 136.8, 135.6, 131.8, 131.4, 129.9, 127.7, 121.5, 117.6, 116.2, 44.2, 36.4, 19.6, 18.6; HRMS (ES+) m/z found 346.0768; $C_{17}H_{19}N_3O_3S$ ($M^+$+H) requires 346.1225.

Example 137

102

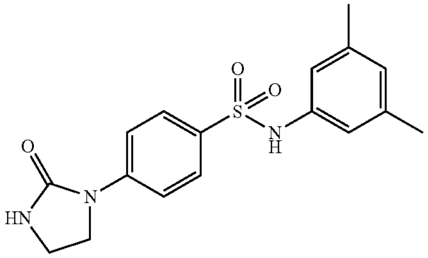

$C_{17}H_{19}N_3O_3S$
Exact Mass: 345,11471

N-(3,5-Dimethylphenyl)-4-(2-oxoimidazolidin-1-yl)benzenesulfonamide (102). Flash chromatography (methylene chloride to methylene chloride/ethyl acetate 0:1). Yield: 68%; White solid; mp: 216-218° C.; IR: 3406, 1699 $cm^{-1}$; $^1H$ NMR (DMSO-$d_6$ and $CDCl_3$) δ 9.66 (s, 1H, NH), 7.64-7.54 (m, 4H, Ar), 6.97 (s, 1H, NH), 6.66 (s, 2H, Ar), 6.54 (s, 1H, Ar), 3.84-3.79 (m, 2H, $CH_2$), 3.45-3.40 (m, 2H, $CH_2$), 2.11 (s, 6H, 2×$CH_2$); $^{13}C$ NMR (DMSO-$d_6$ and $CDCl_3$) δ 163.7, 149.2, 143.1, 142.8, 136.9, 132.7, 130.4, 122.7, 121.1, 49.4, 41.7, 26.1; HRMS (ES+) m/z found 346.0776; $C_{17}H_{19}N_3O_3S$ ($M^+$+H) requires 346.1225.

Example 138

103

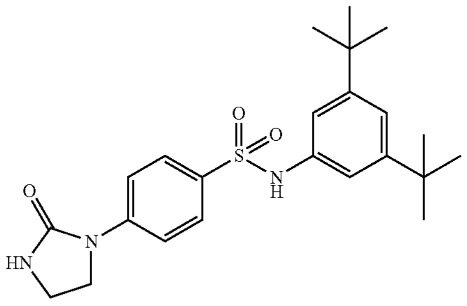

$C_{23}H_{31}N_3O_3S$
Exact Mass: 429,20861

N-(3,5-Di-tert-butylphenyl)-4-(2-oxoimidazolidin-1-yl) benzenesulfonamide (103). Flash chromatography (methylene chloride to methylene chloride/ethyl acetate 0:1 to ethyl acetate/methanol 95:5). Yield: 86%; White solid; mp: 276-278° C.; IR: 3400, 3107, 1703 $cm^{-1}$; $^1H$ NMR (DMSO-$d_6$) δ 9.95 (s, 1H, NH), 7.73-7.66 (m, 4H, Ar), 7.27 (brs, 1H, NH), 7.04 (s, 1H, Ar), 6.95-6.93 (m, 2H, Ar), 3.88-3.83 (m, 2H, $CH_2$), 3.45-3.40 (m, 2H, $CH_2$), 1.20 (s, 18H, 6×$CH_3$); $^{13}C$ NMR (DMSO-$d_6$) δ 158.4, 151.0, 144.4, 137.4, 131.4, 127.8, 117.3, 116.1, 114.3, 44.3, 36.3, 34.5, 31.1; HRMS (ES+) m/z found 430.2245; $C_{23}H_{31}N_3O_3S$ ($M^+$+H) requires 430.2164.

Example 139

104

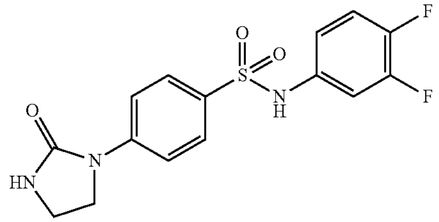

$C_{15}H_{13}N_3O_3S$
Exact Mass: 353,06457

N-(3,4-Difluorophenyl)-4-(2-oxoimidazolidin-1-yl)benzenesulfonamide (104). Flash chromatography (methylene chloride to methylene chloride/ethyl acetate 0:1). Yield: 37%; White solid; mp: 225-226° C.; IR: 3430, 3129, 1695 $cm^{-1}$; $^1H$ NMR ($CDCl_3$, MeOD and DMSO-$d_6$) δ 7.62-7.53 (m, 4H, Ar), 6.99-6.87 (m, 2H, Ar), 6.79-6.74 (m, 1H, Ar), 3.86-3.80 (m, 2H, $CH_2$), 3.48-3.43 (m, 2H, $CH_2$); $^{13}C$ NMR ($CDCl_3$, MeOD and DMSO-$d_6$) δ 158.7, 151.2, 151.0, 148.4, 148.2, 147.9, 147.7, 145.2, 145.0, 144.0, 134.2, 134.1, 134.1, 134.0, 130.9, 127.5, 117.0, 116.8, 116.5, 116.4, 116.4, 116.3, 116.1, 109.9, 109.6, 44.3, 36.4; HRMS (ES+) m/z found 354.0279; $C_{15}H_{13}F_2N_3O_3S$ ($M^+$+H) requires 354.0724.

Example 140

105

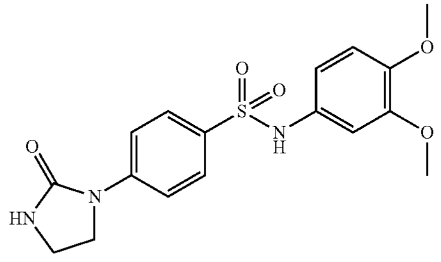

$C_{17}H_{19}N_3O_5S$
Exact Mass: 377,10454

N-(3,4-Dimethoxyphenyl)-4-(2-oxoimidazolidin-1-yl) benzenesulfonamide (105). Flash chromatography (methylene chloride to methylene chloride/ethyl acetate 0:1 to ethyl acetate/methanol 95:5). Yield: 59%, Brownish solid; mp: 215-216° C.; IR: 3357, 3111, 1701 $cm^{-1}$; $^1H$ NMR (DMSO-$d_6$) δ 9.80 (brs, 1H, NH), 7.71-7.63 (m, 4H, Ar), 7.27 (brs, 1H, NH), 6.81-6.78 (m, 1H, Ar), 6.73-6.72 (m, 1H, Ar), 6.58-6.54 (m, 1H, Ar), 3.90-3.84 (m, 2H, $CH_2$), 3.67 (s, 3H, $CH_3$), 3.66 (s, 3H, $CH_3$), 3.45-3.40 (m, 2H, $CH_2$); $^{13}C$ NMR (DMSO-$d_6$) δ 158.4, 148.8, 145.9, 144.3, 131.2, 131.0, 127.8, 116.1, 113.2, 112.1, 106.3, 55.6, 55.4, 44.3, 36.4; HRMS (ES+) m/z found 378.0635; $C_{17}H_{19}N_3O_5S$ ($M^+$+H) requires 378.1123.

Example 141

106

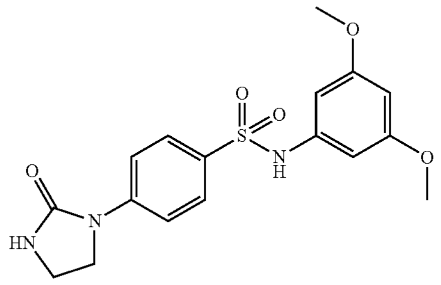

$C_{17}H_{19}N_3O_5S$
Exact Mass: 377,10454

N-(3,5-Dimethoxyphenyl)-4-(2-oxoimidazolidin-1-yl) benzenesulfonamide (106). Flash chromatography (methylene chloride to methylene chloride/ethyl acetate 0:1). Yield: 43%; White solid; mp: 200-201° C.; IR: 3434, 3178, 1702 $cm^{-1}$; $^1H$ NMR ($CDCl_3$, MeOD and DMSO-$d_6$) δ 7.67-7.56 (m, 4H, Ar), 6.25-6.24 (m, 2H, Ar), 6.01-6.00 (m, 1H, Ar), 3.83-3.78 (m, 2H, $CH_2$), 3.60 (s, 6H, 2×$CH_3$), 3.44-3.38 (m, 2H, $CH_2$); $^{13}C$ NMR ($CDCl_3$, MeOD and DMSO-$d_6$) δ 160.5, 158.3, 144.0, 139.3, 131.2, 127.5, 115.9, 97.5, 95.0, 54.6, 44.0, 36.2; HRMS (ES+) m/z found 378.0471; $C_{17}H_{19}N_3O_5S$ ($M^+$+H) requires 378.1124.

Example 142

107

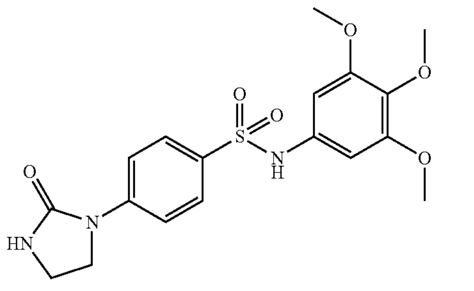

$C_{18}H_{21}N_3O_6S$
Exact Mass: 407,11511

N-(3,4,5-Trimethoxyphenyl)-4-(2-oxoimidazolidin-1-yl) benzenesulfonamide (107). Flash chromatography (ethyl acetate to ethyl acetate/methanol 95:5). Yield: 23%; White solid; mp: 233-235° C.; IR: 3416, 3120, 1704 $cm^{-1}$; $^1$H NMR (DMSO-$d_6$) δ 7.71 (s, 4H, Ar), 7.27 (s, 1H, NH), 6.4) (s, 2H, Ar), 3.89-3.84 (m, 2H, $CH_2$), 3.66 (s, 6H, 2×$CH_3$), 3.56 (s, 3H, $CH_3$), 3.44-3.39 (m, 2H, $CH_2$), 2.00 (s, 1H, NH); $^{13}$C NMR (DMSO-$d_6$) δ 158.4, 153.0, 144.5, 134.0, 133.9, 131.1, 127.9, 116.2, 97.6, 60.1, 55.8, 44.2, 36.4; HRMS (ES+) m/z found 408.0733; $C_{18}H_{21}N_3O_6S$ ($M^+$+H) requires 408.1229.

Example 143

108

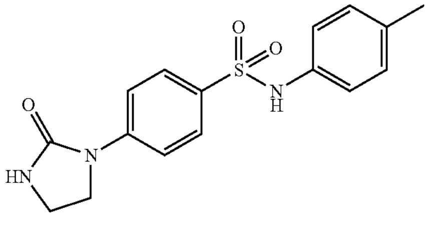

$C_{16}H_{17}N_3O_3S$
Exact Mass: 331,09906

N-4-Tolyl-4-(2-oxoimidazolidin-1-yl)benzenesulfonamide (108). Flash chromatography (methylene chloride to methylene chloride/ethyl acetate 0:1 to ethyl acetate/methanol 95:5). Yield: 83%; White solid; mp: 218-220° C.; IR: 3430, 1697 $cm^{-1}$; $^1$H NMR (DMSO-$d_6$) δ 9.97 (brs, 1H, NH), 7.70-7.63 (m, 4H, Ar), 7.26 (brs, 1H, NH), 7.04-6.96 (m, 4H, Ar), 3.88-3.82 (m, 2H, $CH_2$), 3.44-3.38 (m, 2H, $CH_2$), 2.19 (s, 3H, $CH_3$); $^{13}$C NMR (DMSO-$d_6$) δ 158.41, 144.31, 135.33, 133.12, 131.23, 129.54, 127.69, 120.44, 116.18, 44.24, 36.36, 20.31; HRMS (ES+) m/z found 332.1114; $C_{16}H_{17}N_3O_3S$ ($M^+$+H) requires 332.1069.

Example 144

109

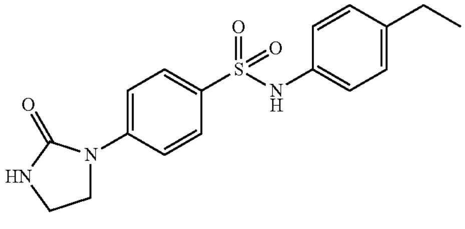

$C_{17}H_{19}N_3O_3S$
Exact Mass: 345,11471

N-(4-Ethylphenyl)-4-(2-oxoimidazolidin-1-yl)benzenesulfonamide (109). Flash chromatography (methylene chloride to methylene chloride/ethyl acetate 0:1 to ethyl acetate/methanol 95:5). Yield: 65%; White solid; mp: 195-196° C.; IR: 3250, 1695 $cm^{-1}$; $^1$H NMR ($CDCl_3$, MeOD and DMSO-$d_6$) δ 7.61-7.50 (m, 4H, Ar), 6.95-6.89 (m, 4H, Ar), 3.81-3.76 (m, 2H, Ar), 3.45-3.39 (m, 2H, $CH_2$), 2.44 (q, 2H, J=7.6 Hz, $CH_2$), 1.06 (t, 3H, J=7.6 Hz, $CH_3$); $^{13}$C NMR ($CDCl_3$, MeOD and DMSO-$d_6$) δ 158.7, 143.9, 139.9, 134.9, 131.8, 128.0, 127.7, 120.8, 116.1, 44.4, 36.5, 27.7, 15.2; HRMS (ES+) m/z found 346.0152; $C_{17}H_{19}N_3O_3S$ ($M^+$+H) requires 346.1225.

Example 145

110

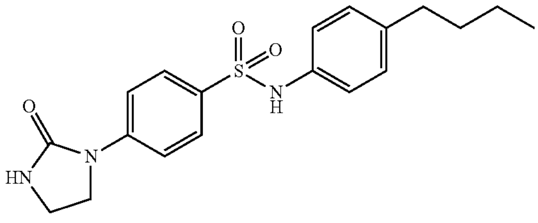

$C_{19}H_{23}N_3O_3S$
Exact Mass: 373,14601

N-(4-Butylphenyl)-4-(2-oxoimidazolidin-1-yl)benzenesulfonamide (110). Flash chromatography (methylene chloride to methylene chloride/ethyl acetate 0:1 to ethyl acetate/methanol 95:5). Yield: 81%; White solid; mp: 203-205° C.; IR: 3436, 2927, 1692 $cm^{-1}$; $^1$H NMR (DMSO-$d_6$) δ 10.00 (s, 1H, NH), 7.70-7.64 (m, 4H, Ar), 7.26 (s, 1H, NH), 7.06-6.98 (m, 4H, Ar), 3.89-3.83 (m, 2H, $CH_2$), 3.44-3.39 (m, 2H, $CH_3$), 2.49-2.44 (m, 2H, $CH_2$), 1.52-1.42 (m, 2H, $CH_2$), 1.31-1.19 (m, 2H, $CH_2$), 0.87 (t, 3H, J=7.3 Hz, $CH_2$); $^{13}$C NMR (DMSO-$d_6$) δ 158.4, 144.3, 138.0, 135.5, 131.4, 128.9, 127.7, 120.3, 116.2, 44.3, 36.4, 34.1, 33.1, 21.7, 13.8; HRMS (ES+) m/z found 374.1300; $C_{19}H_{23}N_3O_3S$ ($M^+$+H) requires 374.1538.

Example 146

111

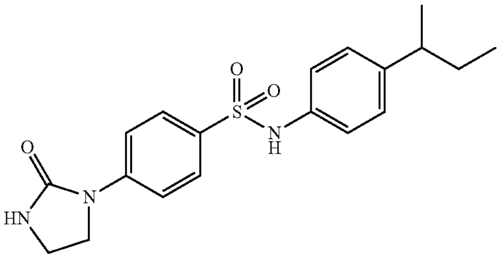

$C_{19}H_{23}N_3O_3S$
Exact Mass: 373, 14601

N-(4-sec-Butylphenyl)-4-(2-oxoimidazolidin-1-yl)benzenesulfonamide (111). Flash chromatography (ethyl acetate to ethyl acetate/methanol 95:5). Yield: 69%; White solid; mp: 157-159° C.; IR: 3436, 2960, 1690 $cm^{-1}$; $^1H$ NMR (DMSO-$d_6$) δ 10.01 (s, 1H, NH), 7.71-7.65 (m, 4H, Ar), 7.26 (s, 1H, NH), 7.06-6.98 (m, 4H, Ar), 3.88-3.83 (m, 2H, $CH_2$), 3.44-3.38 (m, 2H, $CH_2$), 2.49-2.44 (m, 1H, $CH_2$), 1.51-1.41 (m, 2H, $CH_2$), 1.11 (d, 3H, J=7.0 Hz, $CH_3$), 0.70 (t, 3H, J=7.3 Hz, $CH_3$); $^{13}C$ NMR (DMSO-$d_6$) δ 158.4, 144.3, 142.7, 135.6, 131.5, 127.7, 127.5, 120.2, 116.2, 44.2, 40.1, 36.4, 30.6, 21.5, 12.0; HRMS (ES+)$_m$ z found 374.1019; $C_{19}H_{23}N_3O_3S$ ($M^+$+H) requires 374.1538.

Example 147

112

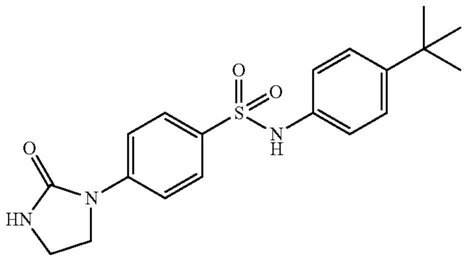

$C_{19}H_{23}N_3O_3S$
Exact Mass: 373, 14601

N-(4-tert-Butylphenyl)-4-(2-oxoimidazolidin-1-yl)benzenesulfonamide (112). Flash chromatography (methylene chloride to methylene chloride/ethyl acetate 0:1 to ethyl acetate/methanol 95:5). Yield: 84%; White solid; mp: 241-243° C.; IR: 3357, 3112, 1694 $cm^{-1}$; $^1H$ NMR (DMSO-$d_6$) δ 10.06 (s, 1H, NH), 7.70 (s, 4H, Ar), 7.26-7.23 (m, 3H, NH and Ar), 7.02-7.00 (m, 2H, Ar), 3.89-3.84 (m, 2H, $CH_2$), 3.44-3.39 (m, 2H, $CH_2$), 1.20 (s, 9H, 3×$CH_3$); $^{13}C$ NMR (DMSO-$d_6$) δ 158.4, 146.1, 144.3, 135.3, 131.6, 127.7, 125.8, 119.7, 116.3, 44.2, 36.4, 34.0, 31.1; HRMS (ES+) m/z found 374.0975; $C_{19}H_{23}N_3O_3S$ ($M^+$+H) requires 374.1538.

Example 148

113

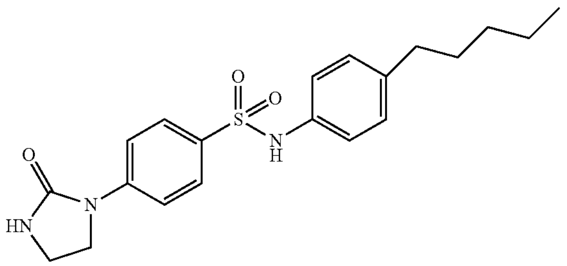

$C_{20}H_{25}N_3O_3S$
Exact Mass: 387, 16166

N-(4-Pentylphenyl)-4-(2-oxoimidazolidin-1-yl)benzenesulfonamide (113). Flash chromatography (methylene chloride to methylene chloride/ethyl acetate 0:1 to ethyl acetate/methanol 95:5). Yield: 82%; White solid; mp: 207-209° C.; IR: 3314, 2927, 1705 $cm^{-1}$; $^1H$ NMR (DMSO-$d_6$) δ 9.98 (brs, 1H, NH), 7.69-7.63 (m, 4H, Ar), 7.25 (brs, 1H, NH), 7.04-6.96 (m, 4H, Ar), 3.87-3.81 (m, 2H, $CH_2$), 3.43-3.37 (m, 2H, $CH_2$), 2.44 (t, 2H, J=7.5 Hz, $CH_2$), 1.52-1.45 (m, 2H, $CH_2$), 1.30-1.18 (m, 4H, 2×$CH_2$), 0.83 (t, 3H, J=6.8 Hz, $CH_3$); $^{13}C$ NMR (DMSO-$d_6$) δ 158.4, 144.3, 138.0, 135.5, 131.3, 128.8, 127.7, 120.3, 116.2, 44.2, 36.4, 34.4, 30.9, 30.5, 21.9, 13.9; HRMS (ES+) m/z found 388.1610; $C_{20}H_{25}N_3O_3S$ ($M^+$+H) requires 388.1695.

Example 149

114

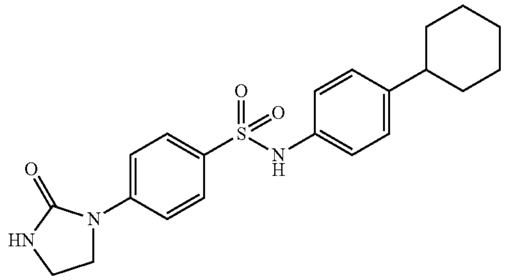

$C_{21}H_{25}N_3O_3S$
Exact Mass: 399, 16166

N-(4-Cyclohexylphenyl)-4-(2-oxoimidazolidin-1-yl)benzenesulfonamide (114). Flash chromatography (methylene chloride to methylene chloride/ethyl acetate 0:1 to ethyl acetate/methanol 95:5). Yield: 35%; White solid; mp: 256-257° C.; IR: 3287, 2927, 1708 $cm^{-1}$; $^1H$ NMR (DMSO-$d_6$) δ 10.04 (s, 1H, NH), 7.69 (s, 4H, Ar), 7.27 (s, 1H, NH), 7.09-6.98 (m, 4H, Ar), 3.89-3.84 (m, 2H, $CH_2$), 3.44-3.39 (m, 2H, $CH_2$), 2.42-2.35 (m, 1H, $CH_2$), 1.76-1.66 (m, 5H, 2.5×$CH_2$), 1.36-1.16 (m, 5H, 2.5×$CH_2$); $^{13}C$ NMR (DMSO-$d_6$) δ 158.4, 144.3, 143.2, 135.7, 131.5, 127.7, 127.2, 120.1, 116.2, 44.3, 43.0, 36.4, 33.9, 26.3, 25.6; HRMS (ES+) m/z found 400.1554; $C_{21}H_{25}N_3O_3S$ ($M^+$+H) requires 400.1695.

Example 150

115

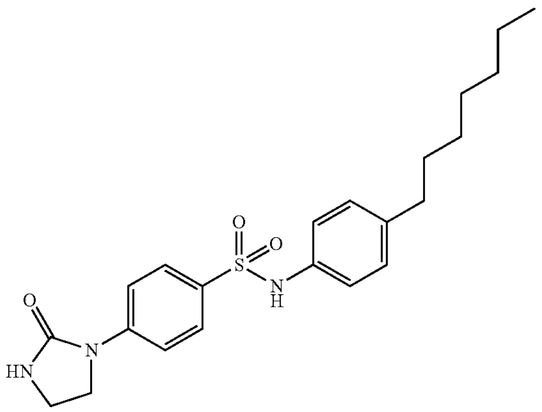

$C_{22}H_{29}N_3O_3S$
Exact Mass: 415, 19296

N-(4-Heptylphenyl)-4-(2-oxoimidazolidin-1-yl)benzenesulfonamide (115). Flash chromatography (methylene chloride to methylene chloride/ethyl acetate 0:1 to ethyl acetate/methanol 95:5). Yield: 90% White solid; mp: 188-190° C.; IR: 3250, 2924, 1710 $cm^{-1}$; $^1H$ NMR (DMSO-$d_6$) δ 9.99 (s, 1H, NH), 7.70-7.63 (m, 4H, Ar), 7.26 (s, 1H, NH), 7.05-6.97 (m, 4H, Ar), 3.88-3.83 (m, 2H, $CH_2$), 3.44-3.38 (m, 2H, $CH_2$), 2.45 (t, 2H, J=7.6 Hz, $CH_2$), 1.50-1.46 (m, 2H, $CH_2$), 1.28-1.19 (m, 8H, 4×$CH_2$), 0.85 (t, 3H, J=6.5 Hz, $CH_3$); $^{13}C$ NMR (DMSO-$d_6$) δ 158.4, 144.3, 138.0, 135.5, 131.3, 128.8, 127.7, 120.3, 116.2, 44.2, 36.4, 34.4, 31.2, 30.9, 28.6, 28.5, 22.1, 13.9; HRMS (ES+) m/z found 416.0854; $C_{22}H_{29}N_3O_3S$ ($M^+$+H) requires 416.2008.

Example 151

116

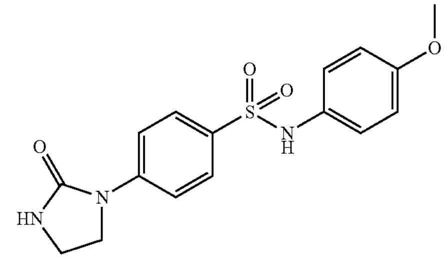

$C_{16}H_{17}N_3O_4S$
Exact Mass: 347, 09398

N-(4-Methoxyphenyl)-4-(2-oxoimidazolidin-1-yl)benzenesulfonamide (116). Flash chromatography (methylene chloride to methylene chloride/ethyl acetate 0:1). Yield: 68%; White solid; mp: 210-211° C.; IR: 3268, 3109, 1694 $cm^{-1}$; $^1H$ NMR ($CDCl_3$, MeOD and DMSO-$d_6$) δ 9.30 (s, 1H, NH), 7.56-7.49 (m, 4H, Ar), 6.93-6.90 (m, 2H, Ar), 6.75 (s, 1H, NH), 6.63-6.60 (m, 2H, Ar), 3.83-3.77 (m, 2H, $CH_2$), 3.62 (s, 3H, $CH_3$), 3.46-3.40 (m, 2H, $CH_2$); $^{13}C$ NMR ($CDCl_3$, MeOD and DMSO-$d_6$) δ 153.4, 151.4, 138.7, 126.3, 124.9, 122.5, 118.4, 110.7, 108.6, 49.7, 39.1, 31.3; HRMS (ES+) m/z found 347.9559; $C_{16}H_{17}N_3O_4S$ ($M^+$+H) requires 348.1018.

Example 152

117

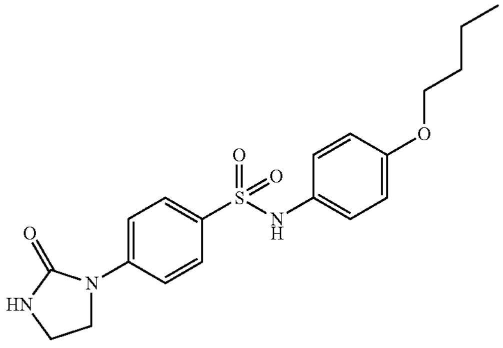

$C_{19}H_{23}N_3O_4S$
Exact Mass: 389, 14093

N-(4-Butoxyphenyl)-4-(2-oxoimidazolidin-1-yl)benzenesulfonamide (117). Flash chromatography (methylene chloride to methylene chloride/ethyl acetate 0:1 to ethyl acetate/methanol 95:5). Yield: 77%, White solid; mp: 223-225° C.; IR: 3270, 2954, 1693 $cm^{-1}$; $^1H$ NMR (DMSO-$d_6$) δ 9.77 (s, 1H, NH), 7.70-7.59 (m, 4H, Ar), 7.27 (s, 1H, NH), 6.99-6.96 (m, 2H, Ar), 6.81-6.78 (m, 2H, Ar), 3.89-3.85 (m, 4H, 2×$CH_2$), 3.45-3.40 (m, 2H, $CH_2$), 1.70-1.60 (m, 2H, $CH_2$), 1.47-1.35 (m, 2H, $CH_2$), 0.92 (t, 3H, J=7.4 Hz, $CH_3$); $^{13}C$ NMR (DMSO-$d_6$) δ 158.4, 155.9, 144.2, 131.2, 130.4, 127.7, 123.2, 116.1, 114.8, 67.2, 44.3, 36.4, 30.8, 18.7, 13.7; HRMS (ES+) m/z found 390.1243; $C_{19}H_{23}N_3O_4S$ ($M^+$+H) requires 390.1487.

Example 153

118

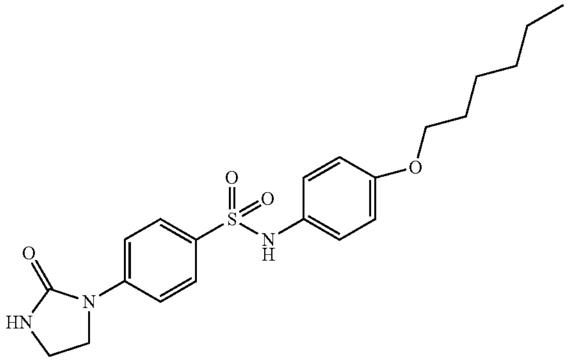

$C_{21}H_{27}N_3O_4S$
Exact Mass: 417, 17223

N-(4-Hexyloxyphenyl)-4-(2-oxoimidazolidin-1-yl)benzenesulfonamide (118). Flash chromatography (methylene chloride to methylene chloride/ethyl acetate 0:1). Yield: 41%; White solid; mp: 225-226° C.; IR: 3272, 2928, 1694 $cm^{-1}$; $^1H$ NMR (DMSO-$d_6$) δ 9.74 (s, 1H, NH), 7.67-7.56 (m, 4H, Ar), 7.24 (s, 1H, NH), 6.96-6.93 (min, 2H, Ar), 6.78-6.75 (m, 2H, Ar), 3.86-3.81 (m, 4H, 2×$CH_2$), 3.42-3.37 (m, 2H, $CH_2$), 1.68-1.58 (m, 2H, $CH_2$), 1.37-1.24 (m, 6H, 3×$CH_2$), 0.85 (t, 3H, J=6.6 Hz, $CH_3$); $^{13}C$ NMR (DMSO-$d_6$) δ 163.6, 161.1, 149.4, 136.4, 135.5, 132.9, 128.4, 121.3, 120.0, 72.7, 49.4, 41.6, 36.2, 33.9, 30.4, 27.3, 19.1; HRMS (ES+) m/z found 418.1668; $C_{21}H_{27}N_3O_4S$ ($M^+$+H) requires 418.1801.

Example 154

119

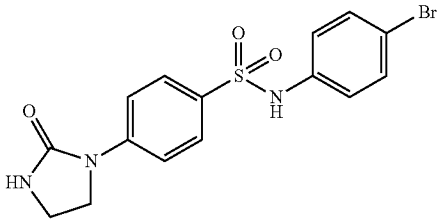

$C_{15}H_{14}BrN_3O_3S$
Exact Mass: 394, 99392

N-(4-Bromophenyl)-4-(2-oxoimidazolidin-1-yl)benzenesulfonamide (119). Flash chromatography (ethyl acetate to ethyl acetate/methanol 95:5). Yield: 57%, White solid; mp: 237-239° C.; IR: 3353, 3139, 1683 $cm^{-1}$; $^1H$ NMR (DMSO-$d_6$) δ 10.32 (s, 1H, NH), 7.72-7.66 (m, 4H, Ar), 7.42 (d, 2H, J=8.7 Hz, Ar), 7.28 (s, 1H, NH), 7.05 (d, 2H, J=8.7 Hz, Ar), 3.89-3.83 (min, 2H, $CH_3$), 3.44-3.38 (min, 2H, $CH_2$); $^{13}C$ NMR (DMSO-$d_6$) δ 158.4, 144.6, 137.5, 132.0, 130.7, 127.7, 121.7, 116.3, 115.9, 44.2, 36.4; HRMS (ES+) m/z found 395.7357; $C_{15}H_{14}BrN_3O_3S$ ($M^+$+H) requires 396.0018.

Example 155

120

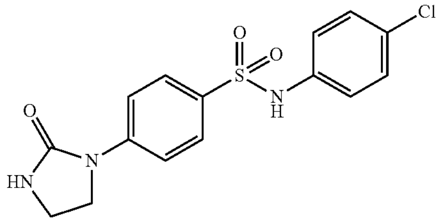

$C_{15}H_{14}ClN_3O_3S$
Exact Mass: 351, 04444

N-(4-Chlorophenyl)-4-(2-oxoimidazolidin-1-yl)benzenesulfonamide (120). Flash chromatography (ethyl acetate to ethyl acetate/methanol 95:5). Yield: 47%; White solid; mp: 234-236° C.; IR: 3267, 1696 $cm^{-1}$; $^1H$ NMR (DMSO-$d_6$) δ 10.31 (s, 1H, NH), 7.72-7.65 (m, 4H, Ar), 7.31-7.28 (m, 3H, NH and Ar), 7.11-7.09 (m, 2H, Ar), 3.89-3.83 (m, 2H, $CH_2$), 3.48-3.38 (m, 2H, $CH_2$); $^{13}C$ NMR (DMSO-$d_6$) δ 158.4, 144.6, 137.0, 130.8, 129.1, 127.9, 127.7, 121.4, 116.3, 44.2, 36.3; HRMS (ES+) m/z found 352.1068; $C_{15}H_{14}ClN_3O_3S$ ($M^+$+H) requires 352.0522.

Example 156

121

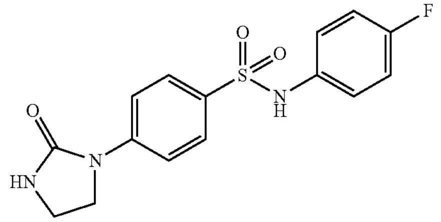

$C_{15}H_{14}FN_3O_3S$
Exact Mass: 335, 07399

N-(4-Fluorophenyl)-4-(2-oxoimidazolidin-1-yl)benzenesulfonamide (121). Flash chromatography (methylene chloride to methylene chloride/ethyl acetate 0:1). Yield: 68%; White solid; mp: 249-251° C.; IR: 3446, 3023, 1697 $cm^{-1}$; $^1H$ NMR ($CDCl_3$, MeOD and DMSO-$d_6$) δ 7.60-7.54 (m, 4H, Ar), 7.04-7.00 (m, 2H, Ar), 6.85-6.80 (m, 2H, Ar), 3.86-3.80 (m, 2H, $CH_2$), 3.47-3.42 (m, 2H, $CH_2$); $^{13}C$ NMR ($CDCl_3$, MeOD and DMSO-$d_6$) δ 160.8, 158.5, 157.6, 144.0, 133.6, 133.5, 131.1, 127.5, 122.8, 122.7, 116.0, 115.3, 115.0, 44.2, 36.4; HRMS (ES+) m/z found 335.9753; $C_{15}H_{14}FN_3O_3S$ ($M^+$+H) requires 336.0818.

Example 157

122

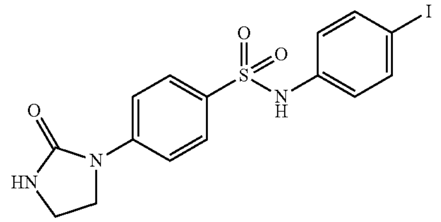

$C_{15}H_{14}IN_3O_3S$
Exact Mass: 442, 98006

N-(4-Iodophenyl)-4-(2-oxoimidazolidin-1-yl)benzenesulfonamide (122). Flash chromatography (ethyl acetate to ethyl acetate/methanol 95:5). Yield: 53%; White solid; mp: 266-267° C.; IR: 3353, 3134, 1684 $cm^{-1}$; $^1H$ NMR (DMSO-$d_6$) δ 10.31 (brs, 1H, NH), 7.72-7.66 (m, 4H, Ar), 7.56 (d, 2H, J=8.6 Hz, Ar), 7.28 (brs, 1H, NH), 6.92 (d, 2H, J=8.6 Hz, Ar), 3.89-3.83 (m, 2H, $CH_2$), 3.44-3.39 (m, 2H, $CH_2$); $^{13}C$ NMR (DMSO-$d_6$) δ 158.4, 144.6, 138.0, 137.8, 130.8, 127.7, 121.8, 116.3, 87.8, 44.2, 36.4; HRMS (ES+) m/z found 443.9131; $C_{15}H_{14}IN_3O_3S$ ($M^+$+H) requires 443.9879.

Example 158

123

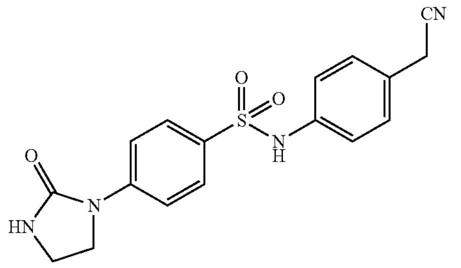

$C_{17}H_{16}N_4O_3S$
Exact Mass: 356, 09431

N-(4-Cyanomethylphenyl)-4-(2-oxoimidazolidin-1-yl) benzenesulfonamide (123). Flash chromatography (methylene chloride to methylene chloride/ethyl acetate 0:1 to ethyl acetate/methanol 95:5). Yield: 59%; Orange solid; mp: 204-206° C.; IR: 3298, 3136, 1699 $cm^{-1}$; $^1H$ NMR (DMSO-$d_6$) δ 10.25 (brs, 1H, NH), 7.74-7.70 (m, 4H, Ar), 7.27 (brs, 1H, NH), 7.23-7.11 (m, 4H, Ar), 3.92 (s, 2H, $CH_2$), 3.89-3.84 (m, 2H, $CH_2$), 3.44-3.39 (m, 2H, $CH_2$); $^{13}C$ NMR (DMSO-$d_6$) δ 158.4, 144.5, 137.5, 131.0, 128.9, 127.7, 126.5, 120.2, 119.2, 116.3, 44.2, 36.4, 21.7; HRMS (ES+) m/z found 357.0658; $C_{17}H_{16}N_4O_3S$ ($M^+$+H) requires 357.1021.

Example 159

124

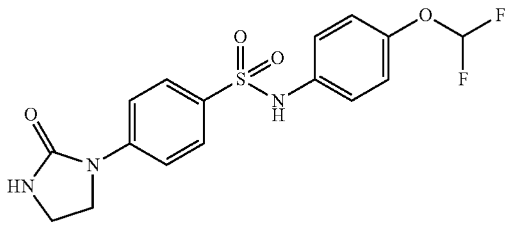

$C_{16}H_{15}F_2N_3O_4S$
Exact Mass: 383, 07513

N-(4-Difluoromethoxyphenyl)-4-(2-oxoimidazolidin-1-yl)benzenesulfonamide (124). Flash chromatography (methylene chloride to methylene chloride/ethyl acetate 0:1 to ethyl acetate/methanol 95:5). Yield: 81%; White solid; mp: 198-200° C.; IR: 3268, 3111, 1695 $cm^{-1}$; $^1H$ NMR (DMSO-$d_6$) δ 10.21 (brs, 1H, NH), 7.73-7.66 (m, 4H, Ar), 7.37 (s, 0.25H, $CHF_2$), 7.28 (brs, 1H, NH), 7.15-7.06 (m, 4.5H, Ar and $CHF_2$), 6.87 (s, 0.25H, $CHF_2$), 3.90-3.85 (m, 2H, $CH_2$), 3.45-3.40 (m, 2H, $CH_2$); $^{13}C$ NMR (DMSO-$d_6$) δ 158.4, 147.2, 144.5, 135.2, 131.0, 127.7, 121.7, 119.8, 116.4, 116.3, 44.2, 36.4; HRMS (ES+) m/z found 383.9433; $C_{16}H_{15}F_2N_3O_4S$ ($M^+$+H) requires 384.0829.

Example 160

125

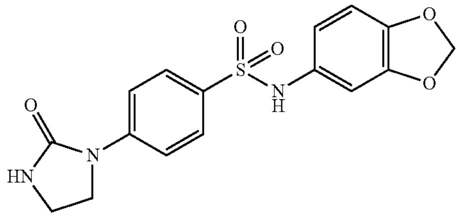

$C_{16}H_{15}N_3O_5S$
Exact Mass: 361, 07324

N-Benzo[1,3]dioxol-5-yl-4-(2-oxoimidazolidin-1-yl)benzenesulfonamide (125). Flash chromatography (methylene chloride to methylene chloride/ethyl acetate 0:1). Yield: 54%; White solid; mp: 219-220° C.; IR: 3223, 2969, 1694 $cm^{-1}$; $^1H$ NMR (DMSO-$d_6$) δ 9.86 (brs, 1H, NH), 7.72-7.62 (m, 4H, Ar), 7.28 (brs, 1H, NH), 6.78-6.76 (m, 1H, Ar), 6.67-6.66 (m, 1H, Ar), 6.51-6.48 (m, 1H, Ar), 5.97 (s, 2H, $CH_2$), 3.90-3.85 (m, 2H, $CH_2$), 3.45-3.40 (m, 2H, $CH_2$); $^{13}C$ NMR (DMSO-$d_6$) δ 158.4, 147.4, 144.4, 144.3, 131.8, 131.0, 127.7, 116.2, 114.5, 108.3, 103.2, 101.3, 44.3, 36.4; HRMS (ES+) m/z found 362.1037; $C_{16}H_{15}N_3O_5S$ ($M^+$+H) requires 362.0811.

Example 161

126

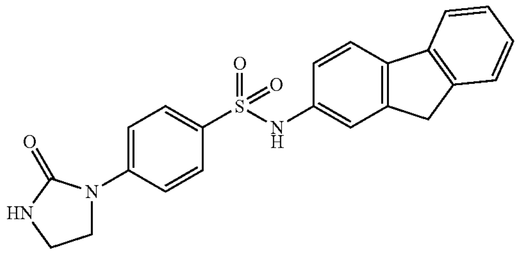

$C_{22}H_{19}N_3O_3S$
Exact Mass: 405,11471

N-(9H-Fluoren-2-yl)-4-(2-oxoimidazolidin-1-yl)benzenesulfonamide (126). Flash chromatography (methylene chloride to methylene chloride/ethyl acetate 0:1 to ethyl acetate/methanol 95:5). Yield: 38%; Orange solid; mp: 164-166° C.; IR: 3262, 1705 $cm^{-1}$; $^1H$ NMR (DMSO-$d_6$) δ 10.21 (brs, 1H, NH), 7.78-7.66 (m, 6H, Ar), 7.54-7.51 (m, 1H, Ar), 7.36-7.24 (m, 4H, Ar and NH), 7.14-7.11 (m, 1H, Ar), 3.84-3.80 (m, 4H, 2×$CH_2$), 3.41-3.37 (m, 2H, $CH_2$); $^{13}C$ NMR (DMSO-$d_6$) δ 158.4, 144.4, 144.1, 142.7, 140.6, 137.2, 136.9, 131.2, 127.7, 126.8, 126.4, 125.0, 120.5, 119.6, 118.9, 117.0, 116.2, 44.2, 36.4, 36.3; HRMS (ES+) m/z found 406.0688; $C_{22}H_{19}N_3O_3S$ ($M^+$+H) requires 406.1225.

Example 162

127

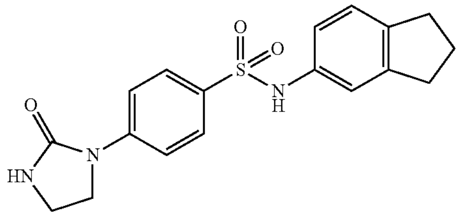

$C_{18}H_{19}N_3O_3S$
Exact Mass: 357,11471

N-Indan-5-yl-4-(2-oxoimidazolidin-1-yl)benzenesulfonamide (127). Flash chromatography (methylene chloride to methylene chloride/ethyl acetate 0:1 to ethyl acetate/methanol 95:5). Yield: 91%; White solid; mp: 228-230° C.; IR: 3251, 2964, 1694 $cm^{-1}$; $^1H$ NMR (DMSO-$d_6$) δ 9.97 (brs, 1H, NH), 7.71-7.65 (m, 4H, Ar), 7.27 (brs, 1H, NH), 7.07-7.04 (m, 1H, Ar), 6.98 (s, 1H, Ar), 6.87-6.84 (m, 1H, Ar), 3.89-3.84 (m, 2H, $CH_2$), 3.45-3.40 (m, 2H, $CH_2$), 2.78-2.72 (m, 4H, 2×$CH_2$), 2.00-1.90 (m, 2H, $CH_2$); $^{13}C$ NMR (DMSO-$d_6$) δ 158.4, 144.6, 144.3, 139.4, 136.1, 131.4, 127.7, 124.5, 118.4, 116.5, 116.2, 44.3, 36.4, 32.4, 31.6, 25.1; HRMS (ES+) m/z found 358.0985; $C_{18}H_{19}N_3O_3S$ ($M^+$+H) requires 358.1225.

Example 163

128

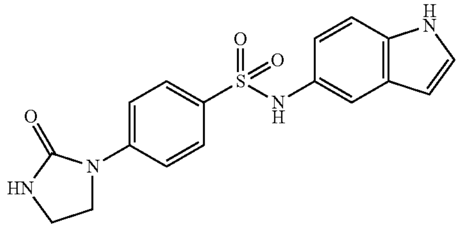

$C_{17}H_{16}N_4O_3S$
Exact Mass: 356,09431

N-(1H-Indol-5-yl)-4-(2-oxoimidazolidin-1-yl)benzenesulfonamide (128). Flash chromatography (methylene chloride to methylene chloride/ethyl acetate 0:1 to ethyl acetate/methanol 95:5). Yield: 82%; Reddish solid; mp: 239-241° C.; IR: 3372, 3252, 1960 $cm^{-1}$; $^1H$ NMR (DMSO-$d_6$) δ 11.04 (brs, 1H, NH), 9.68 (brs, 1H, NH), 7.67-7.59 (m, 4H, Ar), 7.31-7.30 (m, 1H, Ar), 7.25-7.22 (m, 3H, Ar), 6.86-6.83 (m, 1H, Ar), 6.34 (brs, 1H, NH), 3.86-3.81 (m, 2H, $CH_2$), 3.43-3.38 (m, 2H, $CH_2$); $^{13}C$ NMR (DMSO-$d_6$) δ 158.4, 144.1, 133.6, 131.6, 129.3, 127.7, 127.7, 126.2, 117.0, 116.0, 113.6, 111.5, 101.1, 44.2, 36.4; HRMS (ES+) m/z found 357.0972; $C_{17}H_{16}N_4O_3S$ ($M^+$+H) requires 357.1021.

Example 164

129

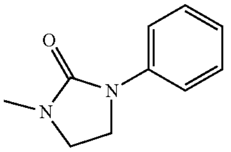

$C_{10}H_{12}N_2O$
Exact Mass: 176,09496

1-methyl-3-phenylimidazolidin-2-one (129). Yield: 73%; Yellow solid; mp: 96-97° C.; IR: 2926, 1687 $cm^{-1}$; $^1H$ NMR ($CDCl_3$) δ 7.53-7.50 (m, 2H, Ar), 7.31-7.26 (m, 2H, Ar), 7.01-6.96 (m, 1H, Ar), 3.70-3.65 (m, 2H, $CH_2$), 3.37-3.31 (m, 2H, $CH_2$), 2.80 (s, 3H, $CH_3$); $^{13}C$ NMR ($CDCl_3$) δ 158.0, 140.8, 128.7, 122.0, 117.0, 43.9, 42.1, 31.1.

Example 165

131

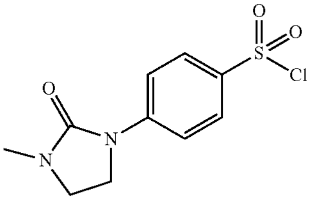

$C_{10}H_{11}ClN_2O_3S$
Exact Mass: 274,01789

4-(3-methyl-2-oxoimidazolidin-1-yl)benzene-1-sulfonyl chloride (131). Yield: 76%; White solid; mp: 147-149° C.; IR: 2905, 1702 $cm^{-1}$; $^1H$ NMR ($CDCl_3$) δ 7.98-7.95 (md, 2H, Ar), 7.81-7.78 (m, 2H, Ar), 3.91-3.86 (m, 2H, $CH_2$), 3.60-3.55 (m, 2H, $CH_2$), 2.95 (s, 3H, $CH_2$); $^{13}C$ NMR ($CDCl_3$) δ 156.9, 146.7, 136.4, 128.5, 116.4, 43.5, 42.0, 31.0.

Example 166

133

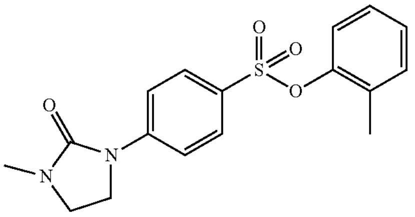

$C_{17}H_{18}N_2O_4S$
Exact Mass: 346,09873

4-(3-Methyl-2-oxoimidazolidin-1-yl)benzenesulfonic acid 2-tolyl ester (133). Method A: Flash chromatography (methylene chloride to methylene chloride/ethyl acetate (95:5)). Yield: 93%; White solid; mp: 157-158° C.; IR: 2928, 1701 $cm^{-1}$; $^1H$ NMR ($CDCl_3$) δ 7.74-7.66 (m, 4H, Ar), 7.12-7.07 (m, 3H, Ar), 6.98-6.95 (m, 1H, Ar), 3.82-3.77 (m, 2H, $CH_2$), 3.53-3.48 (m, 2H, $CH_2$), 2.89 (s, 3H, $CH_3$), 2.05 (s, 3H, $CH_3$); $^{13}C$ NMR ($CDCl_3$) δ 157.1, 148.4, 145.8, 131.6, 129.5, 127.7, 126.9, 126.9, 122.3, 116.1, 43.5, 42.0, 31.0, 16.3; HRMS (ES+) m/z found 347.0818; $C_{17}H_{19}N_2O_4S$ ($M^+$+H) requires 347.1066.

Example 167

134

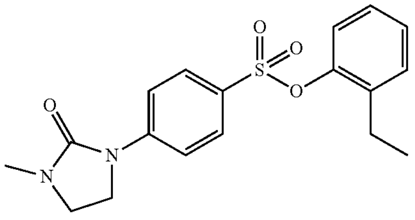

$C_{18}H_{20}N_2O_4S$
Exact Mass: 360,11438

4-(3-Methyl-2-oxoimidazolidin-1-yl)benzenesulfonic acid 2-ethylphenyl ester (134). Method A: Flash chromatography (methylene chloride to methylene chloride/ethyl acetate (95:5)). Yield: 92%; White solid; mp: 126-128° C.; IR: 2878, 1703 $cm^{-1}$; $^1H$ NMR ($CDCl_3$) δ 7.76-7.67 (m, 4H, Ar), 7.19-7.05 (m, 3H, Ar), 6.98-6.96 (m, 1H, Ar), 3.81-3.76 (m, 2H, $CH_2$), 3.52-3.47 (m, 2H, $CH_2$), 2.88 (s, 3H, $CH_3$), 2.48 (q, 2H, J=7.6 Hz, $CH_2$), 1.08 (t, 3H, J=7.6 Hz, $CH_3$); $^{13}C$ NMR ($CDCl_3$) δ 157.1, 147.9, 145.8, 137.3, 129.8, 129.5, 127.8, 127.1, 126.8, 122.1, 116.1, 43.5, 42.0, 31.0, 22.8, 14.1; HRMS (ES+) m/z found 361.1064; $C_{18}H_{21}N_2O_4S$ ($M^+$+H) requires 361.1222.

Example 168

135

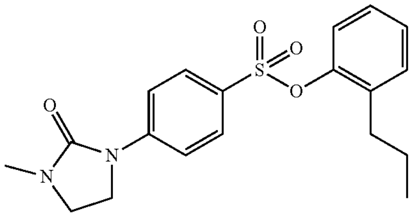

$C_{19}H_{22}N_2O_4S$
Exact Mass: 374,13003

4-(3-Methyl-2-oxoimidazolidin-1-yl)benzenesulfonic acid 2-propylphenyl ester (135). Method A: Flash chromatography (methylene chloride to methylene chloride/ethyl acetate (95:5)). Yield: 99%; White solid; mp: 103-105° C.; IR: 2960, 1703 $cm^{-1}$; $^1H$ NMR ($CDCl_3$) δ 7.78-7.68 (m, 4H, Ar), 7.17-7.06 (m, 3H, Ar), 7.01-6.98 (m, 1H, Ar), 3.83-3.78 (m, 2H, $CH_2$), 3.54-3.48 (m, 2H, $CH_2$), 2.90 (s, 3H, $CH_3$), 2.44-2.39 (m, 2H, $CH_2$), 1.56-1.44 (m, 2H, $CH_2$), 0.85 (t, 3H, J=7.4 Hz, $CH_2$); $^{13}C$ NMR ($CDCl_3$) δ 157.1, 148.2, 145.8, 135.8, 130.6, 129.5, 127.9, 126.9, 126.9, 122.1, 116.1, 43.5, 42.0, 31.8, 31.0, 23.0, 13.9; HRMS (ES+) m/z found 375.1224; $C_{19}H_{23}N_2O_4S$ ($M^+$+H) requires 375.1379.

Example 169

136

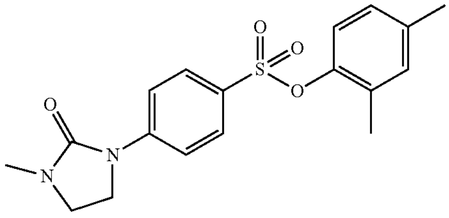

$C_{18}H_{20}N_2O_4S$
Exact Mass: 360,11438

4-(3-Methyl-2-oxoimidazolidin-1-yl)benzenesulfonic acid 2,4-dimethylphenyl ester (136). Method A: Flash chromatography (methylene chloride to methylene chloride/ethyl acetate (95:5)). Yield: 51%; White solid; mp: 159-161° C.; IR: 2899, 1706 $cm^{-1}$; $^1H$ NMR (DMSO-$d_6$) δ 7.72-7.64 (m, 4H, Ar), 6.90-6.79 (m, 3H, Ar), 3.81-3.76 (m, 2H, $CH_2$), 3.52-3.46 (m, 2H, $CH_2$), 2.87 (s, 3H, $CH_3$), 2.23 (s, 3H, $CH_3$), 1.99 (s, 3H, $CH_3$); $^{13}C$ NMR (DMSO-$d_6$) δ 157.1, 146.2, 145.8, 136.7, 132.2, 131.1, 129.5, 127.7, 127.4, 122.0, 116.1, 43.5, 42.0, 30.9, 20.8, 16.2; HRMS (ES+) m/z found 361.0505; $C_{18}H_{21}N_2O_4S$ ($M^+$+H) requires 361.1222.

Example 170

137

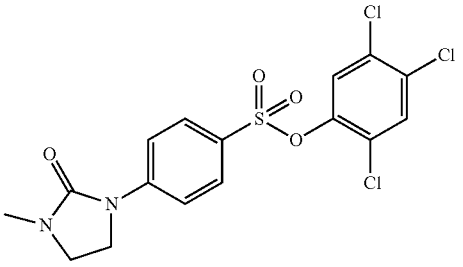

$C_{16}H_{13}Cl_3N_2O_4S$
Exact Mass: 433,96616

4-(3-Methyl-2-oxoimidazolidin-1-yl)benzenesulfonic acid 2,4,5-trichlorophenyl ester (137). Method A: Flash chromatography (methylene chloride to methylene chloride/ethyl acetate (95:5)). Yield: 84%; White solid; mp: 181-183° C.; IR: 2937, 1711 $cm^{-1}$; $^1H$ NMR ($CDCl_3$ and $CD_3OD$) δ 7.76-7.65 (m, 4H, Ar), 7.41-7.38 (m, 2H, Ar), 3.84-3.78 (m, 2H, $CH_2$), 3.53-3.48 (m, 2H, $CH_2$), 2.86 (s, 3H, $CH_3$); $^{13}C$ NMR ($CDCl_3$ and $CD_3OD$) δ 157.1, 146.3, 144.2, 131.6, 131.5, 131.3, 129.9, 126.8, 126.4, 125.7, 116.3, 43.5, 42.0, 30.8; HRMS (ES+) m/z found 434.7964; $C_{16}H_{14}Cl_3N_2O_4S$ ($M^+$+H) requires 434.9740.

Example 171

138

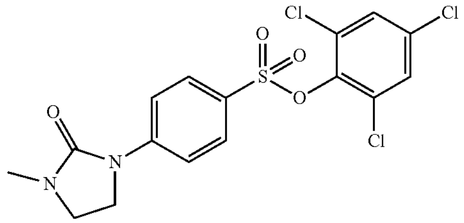

$C_{16}H_{13}Cl_3N_2O_4S$
Exact Mass: 433,96616

4-(3-Methyl-2-oxoimidazolidin-1-yl)benzenesulfonic acid 2,4,6-trichlorophenyl ester (138). Method A: Flash chromatography (methylene chloride to methylene chloride/ethyl acetate (95:5)). Yield: 73%; White solid; mp: 185-187° C.; IR: 3707, 1715 $cm^{-1}$; $^1H$ NMR ($CDCl_3$ and $CD_3OD$) δ 7.83-7.80 (m, 2H, Ar), 7.68-7.65 (m, 2H, Ar), 7.26 (s, 2H, Ar), 3.82-3.77 (m, 2H, $CH_2$), 3.51-3.46 (m, 2H, $CH_2$), 2.83 (s, 3H, $CH_3$); $^{13}C$ NMR ($CDCl_3$ and $CD_3OD$) δ 157.2, 146.1, 142.3, 132.7, 130.8, 129.7, 129.1, 128.3, 116.2, 43.5, 42.0, 30.8; HRMS (ES+) m/z found 434.8642; $C_{11}H_{14}Cl_3N_2O_4S$ ($M^+$+H) requires 434.9740.

Example 172

139

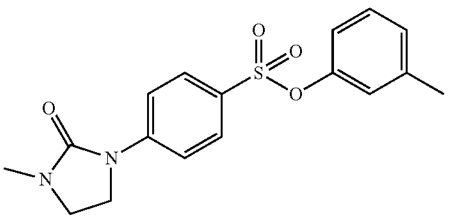

$C_{17}H_{18}N_2O_4S$
Exact Mass: 346,09873

4-(3-Methyl-2-oxoimidazolidin-1-yl)benzenesulfonic acid 3-tolyl ester (139). Method A: Flash chromatography (methylene chloride to methylene chloride/ethyl acetate (95:5)). Yield: 99%; White solid; mp: 123-125° C.; IR: 2926, 1694 $cm^{-1}$; $^1H$ NMR ($CDCl_3$) δ 7.71-7.64 (m, 4H, Ar), 7.12-6.99 (m, 2H, Ar), 6.82 (s, 1H, Ar), 6.69-6.67 (m, 1H, Ar), 3.80-3.75 (m, 2H, $CH_2$), 3.51-3.46 (m, 2H, $CH_2$), 2.87 (s, 3H, $CH_3$), 2.25 (s, 3H, $CH_3$); $^{13}C$ NMR ($CDCl_3$) δ 157.1, 149.6, 145.8, 140.0, 129.6, 129.2, 127.8, 127.1, 123.0, 119.1, 116.0, 43.5, 41.9, 31.0, 21.2; HRMS (ES+) m/z found 347.0814; $C_{17}H_{19}N_2O_4S$ ($M^+$+H) requires 347.1066.

Example 173

140

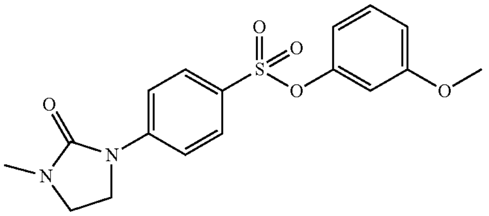

$C_{17}H_{18}N_2O_5S$
Exact Mass: 362,09364

4-(3-Methyl-2-oxoimidazolidin-1-yl)benzenesulfonic acid 3-methoxyphenyl ester (140). Method A: Flash chromatography (methylene chloride to methylene chloride/ethyl acetate (95:5)). Yield: 92%; White solid; mp: 111-113° C.; IR: 2897, 1713 $cm^{-1}$; $^1H$ NMR ($CDCl_3$) δ 7.71-7.63 (m, 4H, Ar), 7.13-7.08 (m, 1H, Ar), 6.75-6.71 (m, 1H, Ar), 6.54-6.48 (m, 2H, Ar), 3.78-3.74 (m, 2H, $CH_2$), 3.67 (s, 3H, $CH_3$), 3.51-3.45 (m, 2H, $CH_2$), 2.87 (s, 3H, $CH_3$); $^{13}C$ NMR ($CDCl_3$) δ 160.4, 157.0, 150.5, 145.9, 129.9, 129.6, 126.9, 116.1, 114.3, 112.9, 108.4, 55.5, 43.5, 41.9, 31.0; HRMS (ES+) m/z found 363.0738; $C_{17}H_{19}N_2O_5S$ ($M^+$+H) requires 363.1015.

Example 174

141

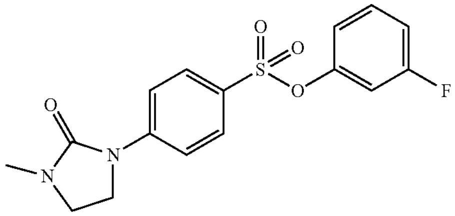

$C_{16}H_{15}FN_2O_4S$
Exact Mass: 350,07366

4-(3-Methyl-2-oxoimidazolidin-1-yl)benzenesulfonic acid 3-fluorophenyl ester (141). Method A: Flash chromatography (methylene chloride to methylene chloride/ethyl acetate (95:5)). Yield: 99%; White solid; mp: 175-177° C.; IR: 2902, 1697 $cm^{-1}$; $^1H$ NMR ($CDCl_3$ and $CD_3OD$) δ 7.65-7.58 (min, 4H, Ar), 7.18-7.11 (min, 1H Ar), 6.89-6.83 (min, 1H Ar), 6.68-6.64 (min, 2H, Ar), 3.79-3.74 (min, 2H, $CH_2$), 3.49-3.44 (min, 2H, $CH_2$), 2.81 (s, 3H, $CH_3$); $^{13}C$ NMR ($CDCl_3$ and $CD_3OD$) δ 164.2, 160.9, 157.3, 150.2, 150.0, 145.9, 130.4, 130.3, 129.6, 126.5, 118.1, 118.1, 116.2, 114.3, 114.1, 110.5, 110.2, 43.5, 42.0, 30.7; HRMS (ES+) m/z found 351.0753; $C_{11}H_{16}FN_2O_4S$ ($M^+$+H) requires 351.0815.

Example 175

142

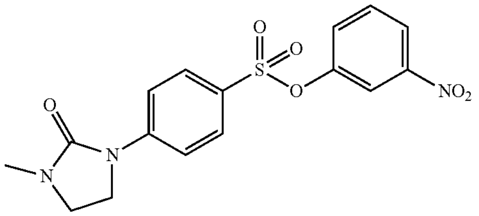

$C_{16}H_{15}N_3O_6S$
Exact Mass: 377,06816

4-(3-Methyl-2-oxoimidazolidin-1-yl)benzenesulfonic acid 3-nitrophenyl ester (142). Method A: Flash chromatography (methylene chloride to methylene chloride/ethyl acetate (95:5)). Yield: 82%; White solid; mp: 167-169° C.; IR: 2901, 1699 $cm^{-1}$; $^1H$ NMR ($CDCl_3$ and $CD_3OD$) δ 8.04-8.02 (min, 1H, Ar), 7.74-7.73 (min, 1H, Ar), 7.68-7.61 (min, 4H, Ar), 7.45-7.39 (m, 1H, Ar), 7.30-7.26 (m, 1H, Ar), 3.81-3.75 (m, 2H, $CH_2$), 3.51-3.45 (m, 2H, $CH_2$), 2.82 (s, 3H, $CH_2$); $^{13}C$ NMR ($CDCl_3$ and $CD_3OD$) δ 157.2, 149.7, 148.6, 146.2, 130.4, 129.6, 128.7, 125.9, 121.9, 117.9, 116.4, 43.4, 42.0, 30.7; HRMS (ES+) m/z found 378.0536; $C_{16}H_{16}N_3O_6S$ ($M^+$+H) requires 378.0760.

Example 176

143

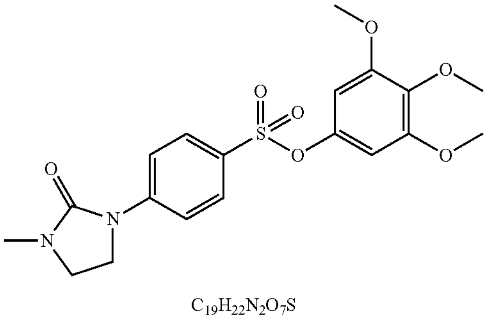

$C_{19}H_{22}N_2O_7S$
Exact Mass: 422.11477

4-(3-Methyl-2-oxoimidazolidin-1-yl)benzenesulfonic acid 3,4,5-trimethoxyphenyl ester (143). Method A: Flash chromatography (methylene chloride to methylene chloride/ethyl acetate (95:5)). Yield: 87%; White solid; mp: 160-162° C.; IR: 3107, 2938, 1712 $cm^{-1}$; $^1H$ NMR ($CDCl_3$) δ 7.74-7.66 (m, 4H, Ar), 6.18 (s, 2H, Ar), 3.81-3.76 (m, 2H, $CH_2$), 3.75 (s, 3H, $CH_3$), 3.67 (s, 6H, 2×$CH_3$), 3.53-3.47 (m, 2H, $CH_2$), 2.88 (s, 3H, $CH_3$); $^{13}C$ NMR ($CDCl_3$) δ 157.0, 153.3, 145.9, 145.5, 136.8, 129.8, 126.9, 116.1, 100.0, 60.9, 56.2, 43.5, 42.0, 31.0; HRMS (ES+) m/z found 423.0975; $C_{19}H_{23}N_2O_7S$ ($M^+$+H) requires 423.1226.

Example 177

144

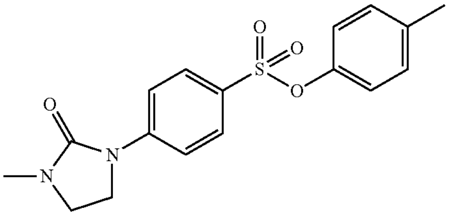

$C_{17}H_{18}N_2O_4S$
Exact Mass: 346.09873

4-(3-Methyl-2-oxoimidazolidin-1-yl)benzenesulfonic acid 4-tolyl ester (144). Method A: Flash chromatography (methylene chloride to methylene chloride/ethyl acetate (95:5)). Yield: 93%; White solid; mp: 155-157° C.; IR: 2896, 1709 $cm^{-1}$; $^1H$ NMR ($CDCl_3$) δ 7.65 (s, 4H, Ar), 7.00 (d, 2H, J=8.3 Hz, Ar), 6.79 (d, 2H, J=8.3 Hz, Ar), 3.78-3.73 (min, 2H, $CH_2$), 3.50-3.45 (m, 2H, $CH_2$), 2.86 (s, 3H, $CH_3$), 2.24 (s, 3H, $CH_3$); $^{13}C$ NMR ($CDCl_3$) δ 157.1, 147.5, 145.8, 136.9, 130.1, 129.6, 126.9, 122.1, 116.0, 43.5, 41.9, 30.9, 20.9; HRMS (ES+) m/z found 347.0903; $C_{17}H_{19}N_2O_4S$ ($M^+$+H) requires 347.1066.

Example 178

145

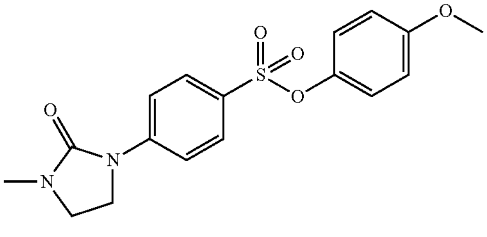

$C_{17}H_{18}N_2O_5S$
Exact Mass: 362.09364

4-(3-Methyl-2-oxoimidazolidin-1-yl)benzenesulfonic acid 4-methoxyphenyl ester (145). Method A: Flash chromatography (methylene chloride to methylene chloride/ethyl acetate (95:5)). Yield: 80%; White solid; mp: 183-185° C.; IR: 2919, 1706 $cm^{-1}$; $^1H$ NMR ($CDCl_3$) δ 7.69-7.62 (m, 4H, Ar), 6.84-6.80 (m, 2H, Ar), 6.74-6.70 (m, 2H, Ar), 3.84-3.78 (min, 2H, $CH_2$), 3.72 (s, 3H, $CH_3$), 3.54-3.48 (min, 2H, $CH_2$), 2.88 (s, 3H, $CH_3$); $^{13}C$ NMR ($CDCl_3$) δ 158.1, 157.3, 145.6, 143.1, 129.7, 127.0, 123.4, 116.1, 114.5, 55.5, 43.6, 42.0, 30.9; HRMS (ES+) m/z found 363.0640; $C_{17}H_{19}N_2O_5S$ ($M^+$+H) requires 363.1015.

Example 179

146

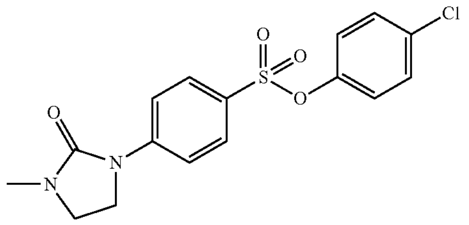

$C_{16}H_{15}ClN_2O_4S$
Exact Mass: 366.04411

4-(3-Methyl-2-oxoimidazolidin-1-yl)-benzenesulfonic acid 4-chlorophenyl ester (146). Method A: Flash chromatography (methylene chloride to methylene chloride/ethyl acetate (95:5)). Yield: 92%; White solid; mp: 165-168° C.; IR: 3106, 2901, 1705 $cm^{-1}$; $^1H$ NMR ($CDCl_3$ and $CD_3OD$) δ 7.64 (s, 4H, Ar), 7.19-7.15 (m, 2H, Ar), 6.86-6.83 (m, 2H, Ar), 3.80-3.75 (m, 2H, $CH_2$), 3.51-3.46 (m, 2H, $CH_2$), 2.85 (s, 3H, $CH_2$); $^{13}C$ NMR ($CDCl_3$ and $CD_3OD$) δ 157.2, 148.0, 145.9, 132.7, 129.7, 129.6, 126.4, 123.8, 116.2, 43.5, 42.0, 30.9; HRMS (ES+) m/z found 367.0227; $C_{16}H_{16}ClN_2O_4S$ ($M^+$+H) requires 367.0519.

Example 180

147

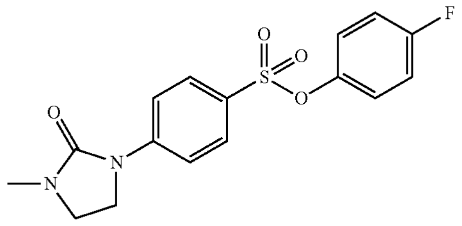

$C_{16}H_{15}FN_2O_4S$
Exact Mass: 350.07366

4-(3-Methyl-2-oxoimidazolidin-1-yl)benzenesulfonic acid 4-fluorophenyl ester (147). Method A: Flash chromatography (methylene chloride to methylene chloride/ethyl acetate (95:5)). Yield: 89%; White solid; mp: 170-172° C.; IR: 3106, 2918, 1702 $cm^{-1}$; $^1H$ NMR ($CDCl_3$) δ 7.63 (s, 4H, Ar), 6.92-6.87 (m, 4H, Ar), 3.81-3.76 (m, 2H, $CH_2$), 3.52-3.46 (m, 2H, $CH_2$), 2.85 (s, 3H, $CH_2$); $^{13}C$ NMR ($CDCl_3$) δ 162.6, 159.3, 157.2, 145.9, 145.4, 145.4, 129.6, 126.4, 124.1, 124.0, 116.4, 116.2, 116.1, 43.5, 42.0, 30.8; HRMS (ES+) m/z found 351.0803; $C_{16}H_{16}FN_2O_4S$ ($M^+$+H) requires 351.0815.

Example 181

Antiproliferative Activity on HT-29, M21 and MCF-7 Cells

Inhibition of tumor cell growth inhibition activity of 2-imidazolidones, derivatives, bioisosteres and isomers was evaluated on three human cell lines: breast carcinoma MCF-7, skin melanoma M21, and colon carcinoma HT-29 cells. Cell growth inhibition was assessed according to the NCI/NIH Developmental Therapeutics Program. The $GI_{50}$ is the concentration of the drug decreasing by 50% the proliferation of the tumor cells tested.

Tumor Cell Growth Inhibition Assay.

The growth inhibition potency of CEUs was assessed using the procedure described by the National Cancer Institute for its drug screening program. Ninety six-well microtiter plates were seeded with 100 μL of tumor cell lines in calf serum iron supplemented (Hyclone) medium. Plates were incubated at 37° C., 5% $CO_2$ for 24 h. Freshly solubilized drugs in DMSO were diluted in fresh medium and aliquots of 100 μL containing sequential dilution of drugs were added. Final drug concentrations ranged from 0.78 nM to 0.3 μM. DMSO concentration was maintained lower than 0.5% to avoid toxicity. Plates were incubated for 48 h. Assays were stopped by addition of cold trichloroacetic acid to the wells (10% final concentration), followed by incubation for 1 h at 4° C. Plates were washed five times with water. Sulforhodamine B solution (50 μL) at 0.1% (w/v) in 1% acetic acid was added to each well, and plates were incubated for 15 min at room temperature. After staining, unbound dye was removed by washing five times with 1% acetic acid. Bonded dye was solubilized with 10 mM Tris base, and the absorbance was read using a μQuant Universal Microplate Spectrophotometer (Biotek, Winooski, Vt.) at 585 ηm. A background OD from a control reference plate fixed on the day of treatment was subtracted from the OD obtained with the 48-h growth period. The growth inhibition percentage was calculated in reference to the control DMSO-treated cells for each drug concentration. The experiments were performed at least twice in triplicate. The $IG_{50}$ assay was considered valid when the variability among data for a given set of conditions, within the same experiment, was less than 10% with respect to the mean value.

All compounds presented in Table 1 were found to be active in at least one of the above-mentioned cell line assay with a $GI_{50}$ equal or below $10^{-4}$ M.

TABLE 1

| code # | Structure | Name |
|---|---|---|
| CEU-511 | 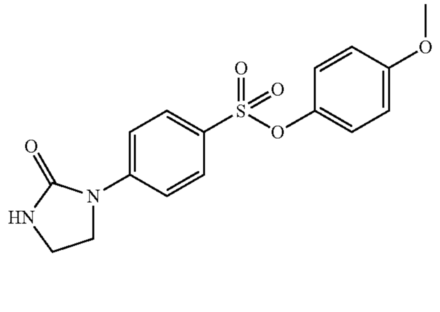 | 4-(2-Oxo-imidazolidin-1-yl)-benzenesulfonic acid 4-methoxy-phenyl ester |

TABLE 1-continued

| code # | Structure | Name |
|---|---|---|
| CEU-544 | 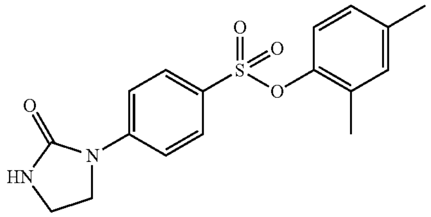 | 4-(2-Oxo-imidazolidin-1-yl)-benzenesulfonic acid 2,4-dimethyl-phenyl ester |
| CEU-560 | 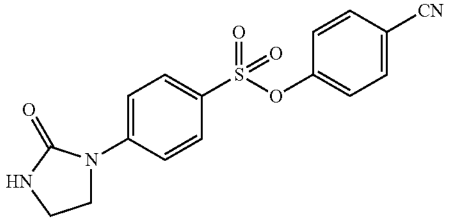 [SMILES: O=C1NCCN1c1ccc(S(=O)(=O)Oc2ccc(O)cc2)cc1] | 4-(2-Oxo-imidazolidin-1-yl)-benzenesulfonic acid 4-cyano-phenyl ester |
| CEU-567 | 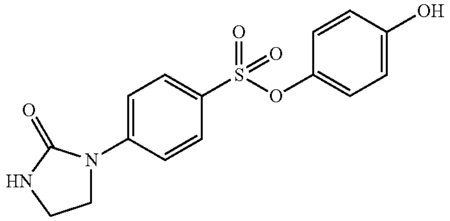 | 4-(2-Oxo-imidazolidin-1-yl)-benzenesulfonic acid 4-hydroxy-phenyl ester |
| CEU-572 | 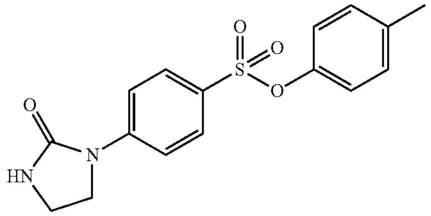 [SMILES: Cc1ccc(OS(=O)(=O)c2ccc(N3CCNC3=O)cc2)cc1] | 4-(2-Oxo-imidazolidin-1-yl)-benzenesulfonic acid p-tolyl ester |
| CEU-573 | 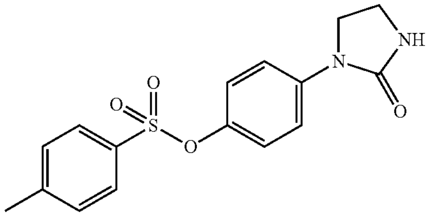 [SMILES: Cc1ccc(S(=O)(=O)Oc2ccc(N3CCNC3=O)cc2)cc1] | Toluene-4-sulfonic acid 4-(2-oxo-imidazolidin-1-yl)-phenyl ester |
| CEU-574 | 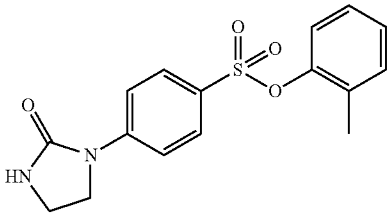 [SMILES: Cc1ccccc1OS(=O)(=O)c1ccc(N2CCNC2=O)cc1] | 4-(2-Oxo-imidazolidin-1-yl)-benzenesulfonic acid o-tolyl ester |
| CEU-577 | 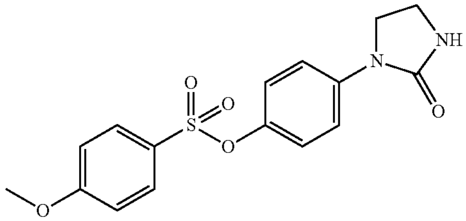 [SMILES: COc1ccc(S(=O)(=O)Oc2ccc(N3CCNC3=O)cc2)cc1] | 4-Methoxy-benzenesulfonic acid 4-(2-oxo-imidazolidin-1-yl)-phenyl ester |

TABLE 1-continued

| code # | Structure | Name |
|---|---|---|
| CEU-578 | 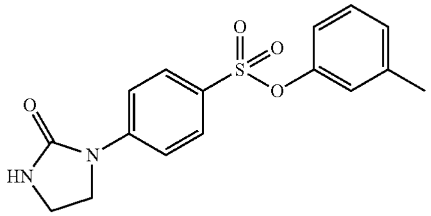 [SMILES: Cc1cccc(OS(=O)(=O)c2ccc(N3CCNC3=O)cc2)c1] | 4-(2-Oxo-imidazolidin-1-yl)-benzenesulfonic acid m-tolyl ester |
| CEU-579 | 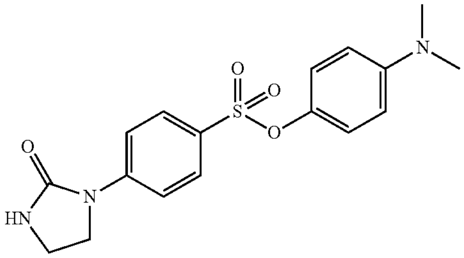 [SMILES: CN(C)c1ccc(OS(=O)(=O)c2ccc(N3CCNC3=O)cc2)cc1] | 4-(2-Oxo-imidazolidin-1-yl)-benzenesulfonic acid 4-dimethylamino-phenyl ester |
| CEU-582 | 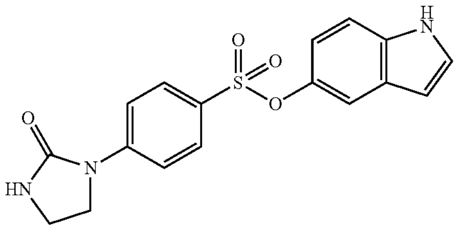 [SMILES: O=C1NCCN1c1ccc(S(=O)(=O)Oc2ccc3[nH]ccc3c2)cc1] | 4-(2-Oxo-imidazolidin-1-yl)-benzenesulfonic acid 1H-indol-5-yl ester |
| CEU-583 | 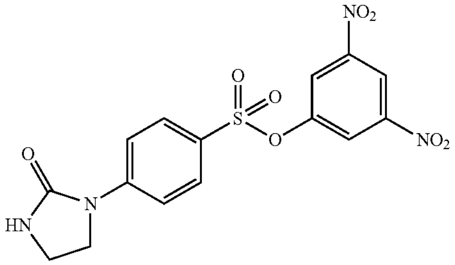 [SMILES: O=C1NCCN1c1ccc(S(=O)(=O)Oc2cc([N+](=O)[O-])cc([N+](=O)[O-])c2)cc1] | 4-(2-Oxo-imidazolidin-1-yl)-benzenesulfonic acid 2,4-dinitro-phenyl ester |
| CEU-602 | 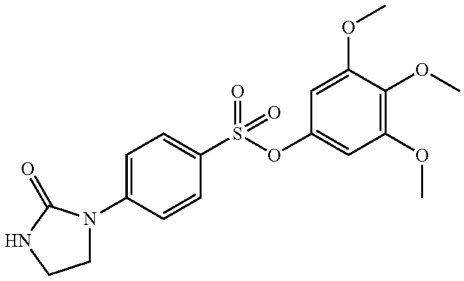 [SMILES: COc1cc(OS(=O)(=O)c2ccc(N3CCNC3=O)cc2)cc(OC)c1OC] | 4-(2-Oxo-imidazolidin-1-yl)-benzenesulfonic acid 3,4,5-trimethoxy-phenyl ester |
| CEU-603 | 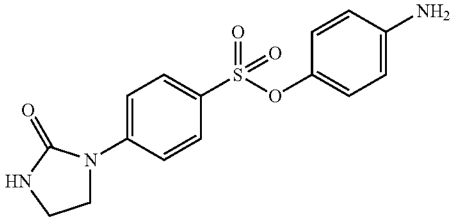 | 4-(2-Oxo-imidazolidin-1-yl)-benzenesulfonic acid 4-amino-phenyl ester |

TABLE 1-continued

| code # | Structure | Name |
|---|---|---|
| CEU-604 | 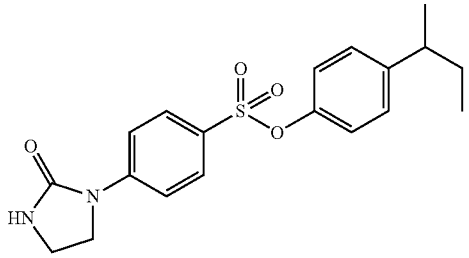 [SMILES: CCC(C)c1ccc(OS(=O)(=O)c2ccc(N3CCNC3=O)cc2)cc1] | 4-(2-Oxo-imidazolidin-1-yl)-benzenesulfonic acid 4-sec-butyl-phenyl ester |
| CEU-605 | 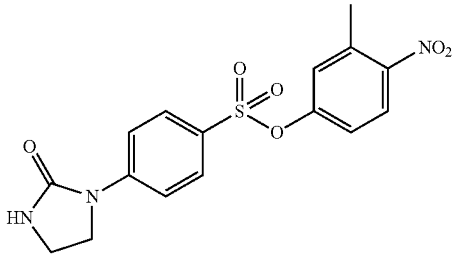 [SMILES: Cc1cc(OS(=O)(=O)c2ccc(N3CCNC3=O)cc2)ccc1[N+](=O)[O-]] | 4-(2-Oxo-imidazolidin-1-yl)-benzenesulfonic acid 3-methyl-4-nitro-phenyl ester |
| CEU-607 | 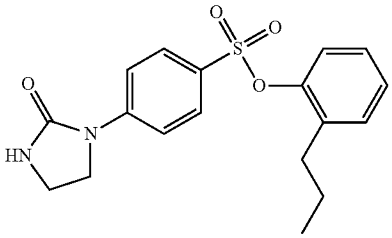 [SMILES: CCCc1ccccc1OS(=O)(=O)c1ccc(N2CCNC2=O)cc1] | 4-(2-Oxo-imidazolidin-1-yl)-benzenesulfonic acid 2-propyl-phenyl ester |
| CEU-608 | 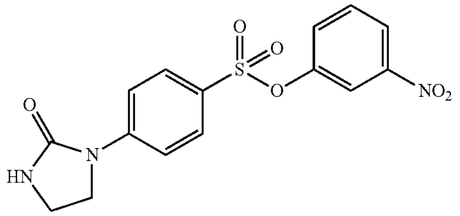 [SMILES: O=C1NCCN1c1ccc(S(=O)(=O)Oc2cccc([N+](=O)[O-])c2)cc1] | 4-(2-Oxo-imidazolidin-1-yl)-benzenesulfonic acid 3-nitro-phenyl ester |
| CEU-609 | 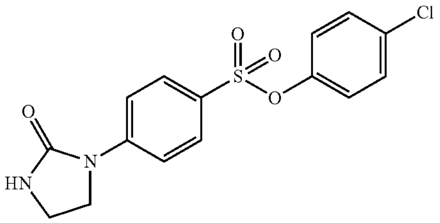 [SMILES: O=C1NCCN1c1ccc(S(=O)(=O)Oc2ccc(Cl)cc2)cc1] | 4-(2-Oxo-imidazolidin-1-yl)-benzenesulfonic acid 4-chloro-phenyl ester |
| CEU-620 | 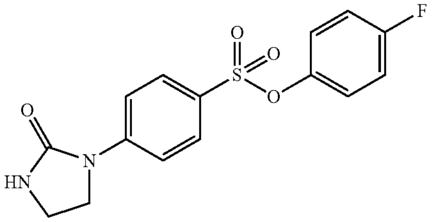 [SMILES: O=C1NCCN1c1ccc(S(=O)(=O)Oc2ccc(F)cc2)cc1] | 4-(2-Oxo-imidazolidin-1-yl)-benzenesulfonic acid 4-fluoro-phenyl ester |

TABLE 1-continued

| code # | Structure | Name |
|---|---|---|
| CEU-621 | 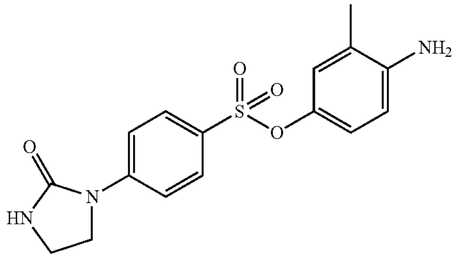 | 4-(2-Oxo-imidazolidin-1-yl)-benzenesulfonic acid 4-amino-3-methyl-phenyl ester |
| CEU-623 | 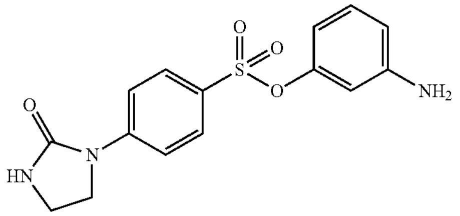 | 4-(2-Oxo-imidazolidin-1-yl)-benzenesulfonic acid 3-amino-phenyl ester |
| CEU-624 | 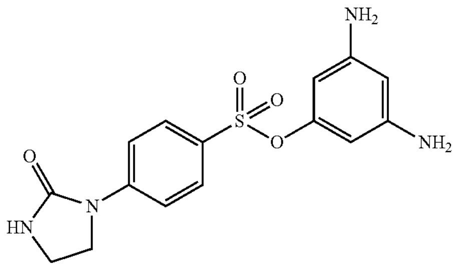 | 4-(2-Oxo-imidazolidin-1-yl)-benzenesulfonic acid 3,5-diamino-phenyl ester |
| CEU-625 | 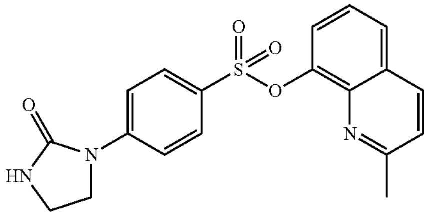 [SMILES: Cc1ccc2cccc(OS(=O)(=O)c3ccc(N4CCNC4=O)cc3)c2n1] | 4-(2-Oxo-imidazolidin-1-yl)-benzenesulfonic acid 2-methyl-quinolin-8-yl ester |
| CEU-626 | 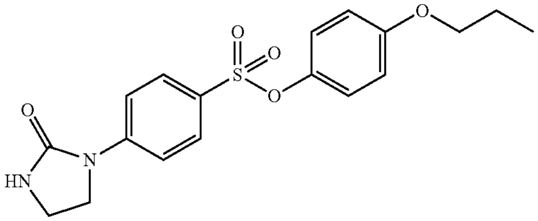 [SMILES: CCCOc1ccc(OS(=O)(=O)c2ccc(N3CCNC3=O)cc2)cc1] | 4-(2-Oxo-imidazolidin-1-yl)-benzenesulfonic acid 4-propoxy-phenyl ester |
| CEU-627 | 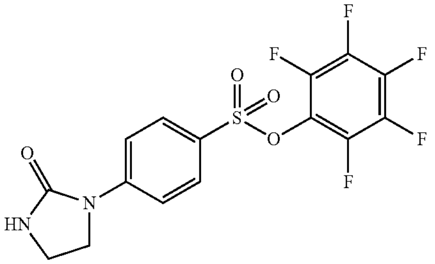 [SMILES: O=C1NCCN1c1ccc(S(=O)(=O)Oc2c(F)c(F)c(F)c(F)c2F)cc1] | 4-(2-Oxo-imidazolidin-1-yl)-benzenesulfonic acid pentafluorophenyl ester |

TABLE 1-continued

| code # | Structure | Name |
|---|---|---|
| CEU-628 | 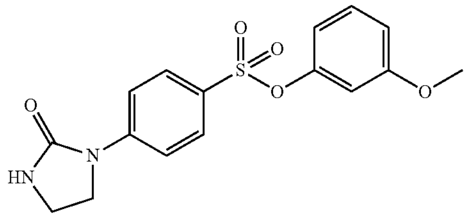 | 4-(2-Oxo-imidazolidin-1-yl)-benzenesulfonic acid 3-methoxy-phenyl ester |
| CEU-629 | 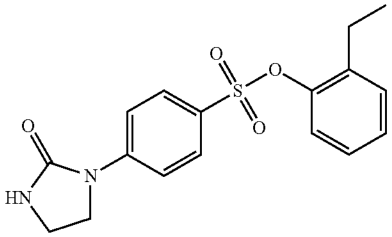 [SMILES: CCc1ccccc1OS(=O)(=O)c1ccc(N2CCNC2=O)cc1] | 4-(2-Oxo-imidazolidin-1-yl)-benzenesulfonic acid 2-ethyl-phenyl ester |
| CEU-630 | 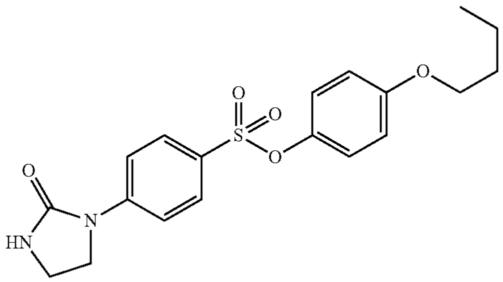 [SMILES: CCCCOc1ccc(OS(=O)(=O)c2ccc(N3CCNC3=O)cc2)cc1] | 4-(2-Oxo-imidazolidin-1-yl)-benzenesulfonic acid 4-butoxy-phenyl ester |
| CEU-631 | 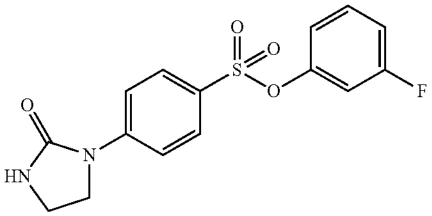 [SMILES: O=C1NCCN1c1ccc(S(=O)(=O)Oc2cccc(F)c2)cc1] | 4-(2-Oxo-imidazolidin-1-yl)-benzenesulfonic acid 3-fluoro-phenyl ester |
| CEU-632 | 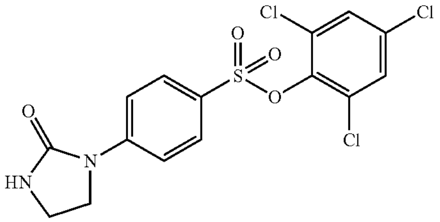 [SMILES: O=C1NCCN1c1ccc(S(=O)(=O)Oc2c(Cl)cc(Cl)cc2Cl)cc1] | 4-(2-Oxo-imidazolidin-1-yl)-benzenesulfonic acid 2,4,6-trichloro-phenyl ester |
| CEU-635 | 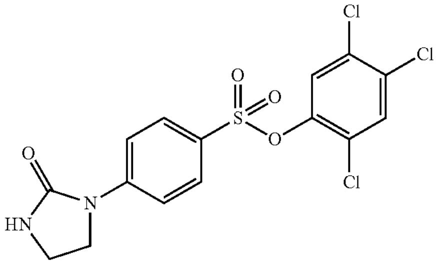 [SMILES: O=C1NCCN1c1ccc(S(=O)(=O)Oc2cc(Cl)c(Cl)cc2Cl)cc1] | 4-(2-Oxo-imidazolidin-1-yl)-benzenesulfonic acid 2,4,5-trichloro-phenyl ester |

TABLE 1-continued

| code # | Structure | Name |
| --- | --- | --- |
| CEU-636 | 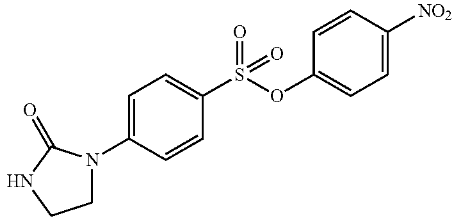 [SMILES: O=C1NCCN1c1ccc(S(=O)(=O)Oc2ccc([N+](=O)[O-])cc2)cc1] | 4-(2-Oxo-imidazolidin-1-yl)-benzenesulfonic acid 4-nitro-phenyl ester |
| CEU-638 | 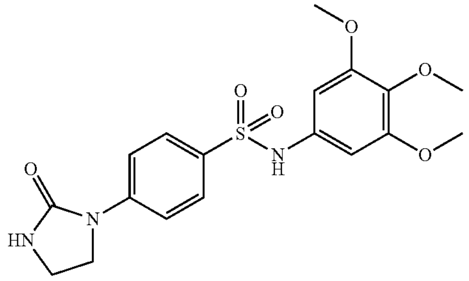 [SMILES: COc1cc(NS(=O)(=O)c2ccc(N3CCNC3=O)cc2)cc(OC)c1OC] | 4-(2-Oxo-imidazolidin-1-yl)-N-(3,4,5-trimethoxy-phenyl)-benzenesulfonamide |
| CEU-639 | 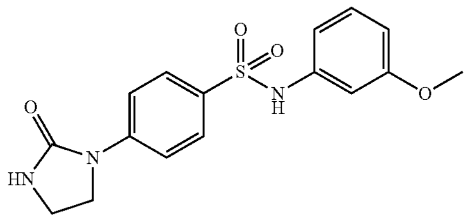 [SMILES: COc1cccc(NS(=O)(=O)c2ccc(N3CCNC3=O)cc2)c1] | N-(3-Methoxy-phenyl)-4-(2-oxo-imidazolidin-1-yl)-benzenesulfonamide |
| CEU-640 | 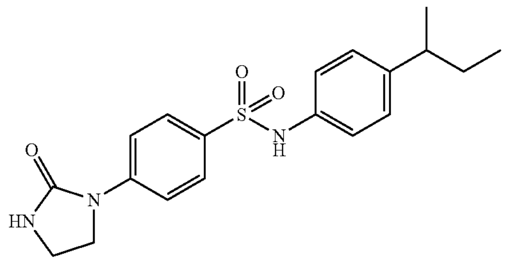 [SMILES: CCC(C)c1ccc(NS(=O)(=O)c2ccc(N3CCNC3=O)cc2)cc1] | N-(4-sec-Butyl-phenyl)-4-(2-oxo-imidazolidin-1-yl)-benzenesulfonamide |
| CEU-641 | 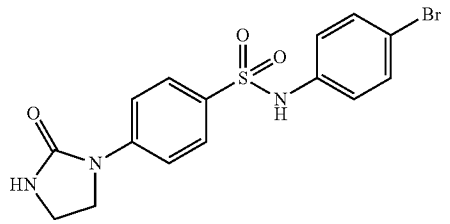 [SMILES: O=C1NCCN1c1ccc(S(=O)(=O)Nc2ccc(Br)cc2)cc1] | N-(4-Bromo-phenyl)-4-(2-oxo-imidazolidin-1-yl)-benzenesulfonamide |
| CEU-642 | 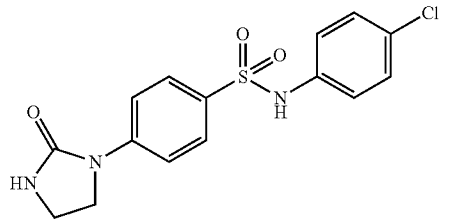 [SMILES: O=C1NCCN1c1ccc(S(=O)(=O)Nc2ccc(Cl)cc2)cc1] | N-(4-Chloro-phenyl)-4-(2-oxo-imidazolidin-1-yl)-benzenesulfonamide |

TABLE 1-continued

| code # | Structure | Name |
|---|---|---|
| CEU-643 | 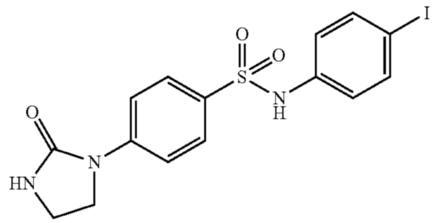 | N-(4-Iodo-phenyl)-4-(2-oxo-imidazolidin-1-yl)-benzenesulfonamide |
| CEU-644 | 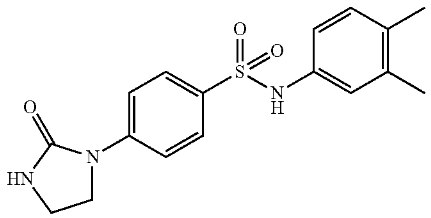 [SMILES: Cc1ccc(NS(=O)(=O)c2ccc(N3CCNC3=O)cc2)cc1C] | N-(3,4-Dimethyl-phenyl)-4-(2-oxo-imidazolidin-1-yl)-benzenesulfonamide |
| CEU-645 | 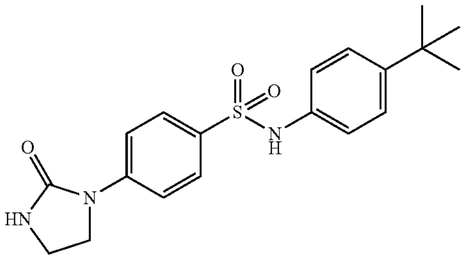 [SMILES: CC(C)(C)c1ccc(NS(=O)(=O)c2ccc(N3CCNC3=O)cc2)cc1] | N-(4-tert-Butyl-phenyl)-4-(2-oxo-imidazolidin-1-yl)-benzenesulfonamide |
| CEU-646 | 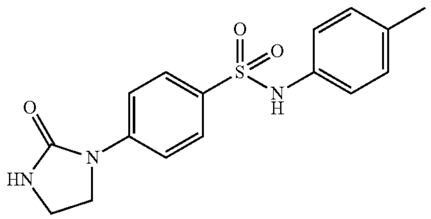 [SMILES: Cc1ccc(NS(=O)(=O)c2ccc(N3CCNC3=O)cc2)cc1] | N-(4-Heptyl-phenyl)-4-(2-oxo-imidazolidin-1-yl)-benzenesulfonamide |
| CEU-647 | 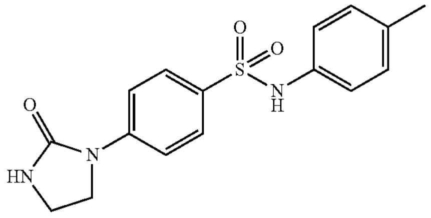 [SMILES: Cc1ccc(NS(=O)(=O)c2ccc(N3CCNC3=O)cc2)cc1] | 4-(2-Oxo-imidazolidin-1-yl)-N-p-tolyl-benzenesulfonamide |
| CEU-648 | 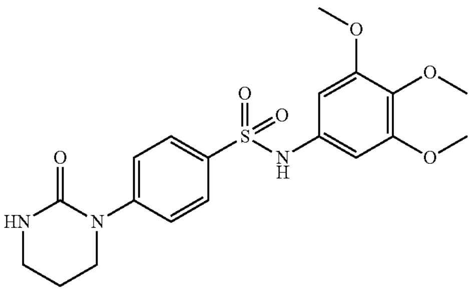 [SMILES: COc1cc(NS(=O)(=O)c2ccc(N3CCCNC3=O)cc2)cc(OC)c1OC] | 4-(2-Oxo-tetrahydro-pyrimidin-1-yl)-benzenesulfonic acid 3,4,5-trimethoxy-phenyl ester |

TABLE 1-continued

| code # | Structure | Name |
| --- | --- | --- |
| CEU-649 | 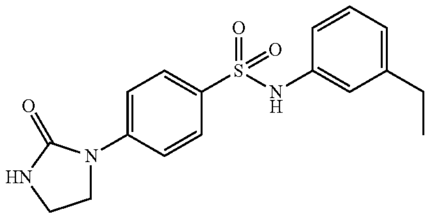 [SMILES: CCc1cccc(NS(=O)(=O)c2ccc(N3CCNC3=O)cc2)c1] | N-(3-Ethyl-phenyl)-4-(2-oxo-imidazolidin-1-yl)-benzenesulfonamide |
| CEU-652 | 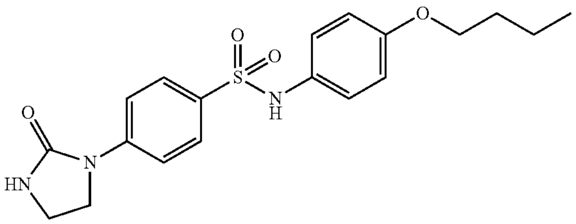 [SMILES: CCCCOc1ccc(NS(=O)(=O)c2ccc(N3CCNC3=O)cc2)cc1] | N-(4-Butoxy-phenyl)-4-(2-oxo-imidazolidin-1-yl)-benzenesulfonamide |
| CEU-653 | 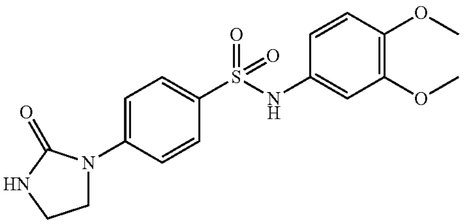 | N-(3,4-Dimethoxy-phenyl)-4-(2-oxo-imidazolidin-1-yl)-benzenesulfonamide |
| CEU-654 | 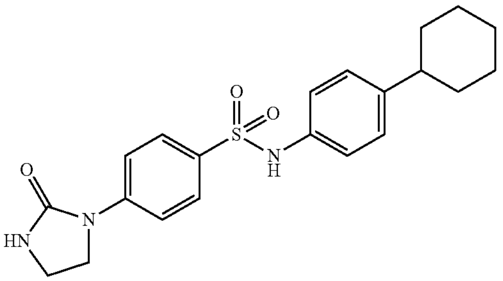 [SMILES: O=C1NCCN1c1ccc(S(=O)(=O)Nc2ccc(C3CCCCC3)cc2)cc1] | N-(4-Cyclohexyl-phenyl)-4-(2-oxo-imidazolidin-1-yl)-benzenesulfonamide |
| CEU-655 | 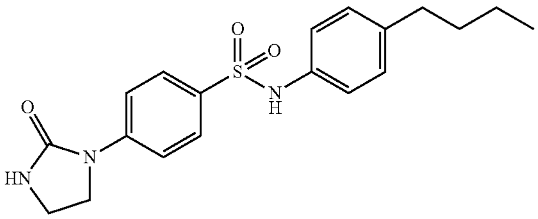 | N-(4-Butyl-phenyl)-4-(2-oxo-imidazolidin-1-yl)-benzenesulfonamide |
| CEU-656 | 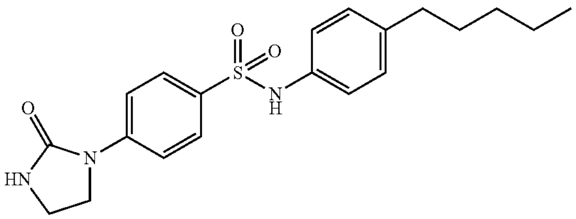 [SMILES: CCCCCc1ccc(NS(=O)(=O)c2ccc(N3CCNC3=O)cc2)cc1] | 4-(2-Oxo-imidazolidin-1-yl)-N-(4-pentyl-phenyl)-benzenesulfonamide |

TABLE 1-continued

| code # | Structure | Name |
|---|---|---|
| CEU-657 | 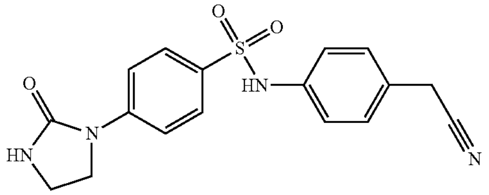 [SMILES: N#CCc1ccc(NS(=O)(=O)c2ccc(N3CCNC3=O)cc2)cc1] | N-(4-Cyanomethyl-phenyl)-4-(2-oxo-imidazolidin-1-yl)-benzenesulfonamide |
| CEU-659 | 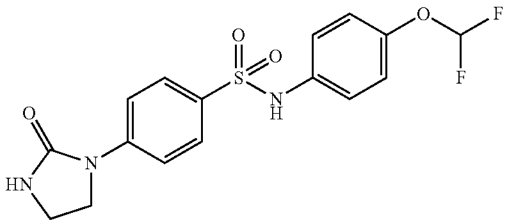 [SMILES: O=C1NCCN1c1ccc(S(=O)(=O)Nc2ccc(OC(F)F)cc2)cc1] | N-(4-Difluoromethoxy-phenyl)-4-(2-oxo-imidazolidin-1-yl)-benzenesulfonamide |
| CEU-660 | 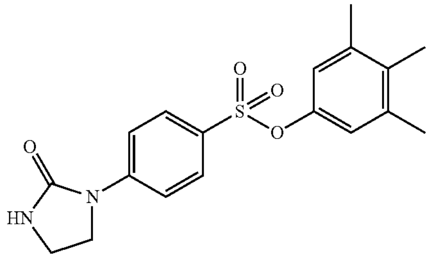 [SMILES: Cc1cc(OS(=O)(=O)c2ccc(N3CCNC3=O)cc2)cc(C)c1C] | 4-(2-Oxo-imidazolidin-1-yl)-benzenesulfonic acid 3,4,5-trimethyl-phenyl ester |
| CEU-661 | 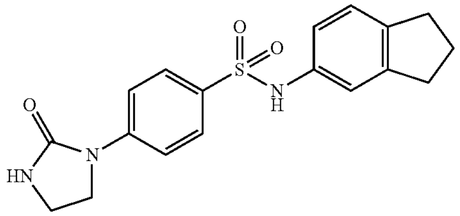 [SMILES: O=C1NCCN1c1ccc(S(=O)(=O)Nc2ccc3c(c2)CCC3)cc1] | N-Indan-5-yl-4-(2-oxo-imidazolidin-1-yl)-benzenesulfonamide |
| CEU-662 | 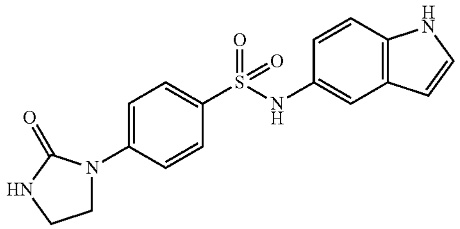 [SMILES: O=C1NCCN1c1ccc(S(=O)(=O)Nc2ccc3[nH]ccc3c2)cc1] | N-(1H-Indol-5-yl)-4-(2-oxo-imidazolidin-1-yl)-benzenesulfonamide |
| CEU-664 | 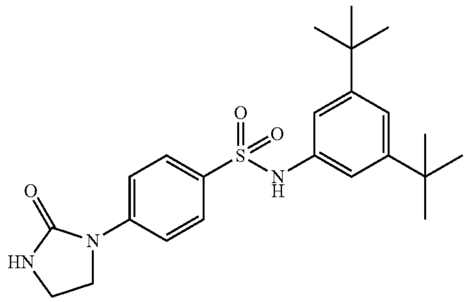 [SMILES: CC(C)(C)c1cc(NS(=O)(=O)c2ccc(N3CCNC3=O)cc2)cc(C(C)(C)C)c1] | N-(3,5-Di-tert-butyl-phenyl)-4-(2-oxo-imidazolidin-1-yl)-benzenesulfonamide |

TABLE 1-continued

| code # | Structure | Name |
| --- | --- | --- |
| CEU-665 | 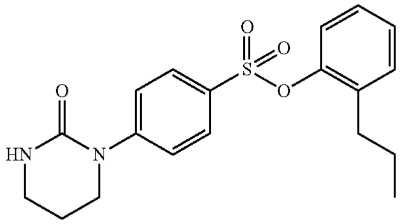 [SMILES: CCCc1ccccc1OS(=O)(=O)c1ccc(N2CCCNC2=O)cc1] | 4-(2-Oxo-tetrahydro-pyrimidin-1-yl)-benzenesulfonic acid 2-propyl-phenyl ester |
| CEU-666 | 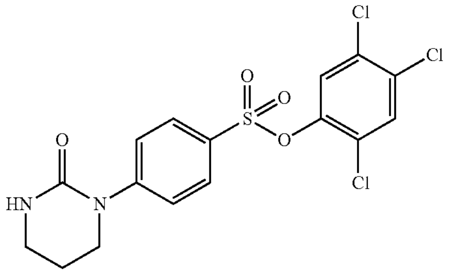 [SMILES: O=C1NCCCN1c1ccc(S(=O)(=O)Oc2cc(Cl)c(Cl)cc2Cl)cc1] | 4-(2-Oxo-tetrahydro-pyrimidin-1-yl)-benzenesulfonic acid 2,4,5-trichloro-phenyl ester |
| CEU-667 | 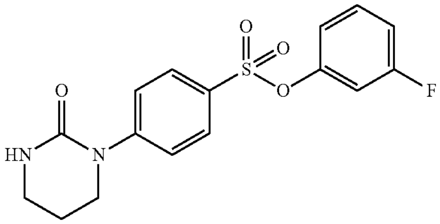 [SMILES: O=C1NCCCN1c1ccc(S(=O)(=O)Oc2cccc(F)c2)cc1] | 4-(2-Oxo-tetrahydro-pyrimidin-1-yl)-benzenesulfonic acid 3-fluoro-phenyl ester |
| CEU-668 | 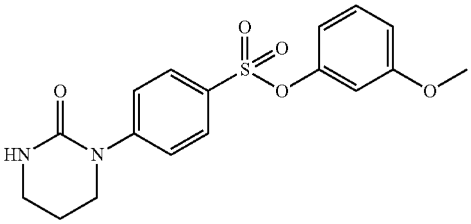 [SMILES: COc1cccc(OS(=O)(=O)c2ccc(N3CCCNC3=O)cc2)c1] | 4-(2-Oxo-tetrahydro-pyrimidin-1-yl)-benzenesulfonic acid 3-methoxy-phenyl ester |
| CEU-669 | 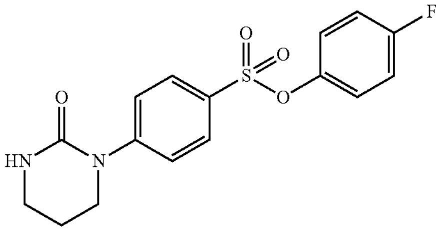 [SMILES: O=C1NCCCN1c1ccc(S(=O)(=O)Oc2ccc(F)cc2)cc1] | 4-(2-Oxo-tetrahydro-pyrimidin-1-yl)-benzenesulfonic acid 4-fluoro-phenyl ester |
| CEU-670 | 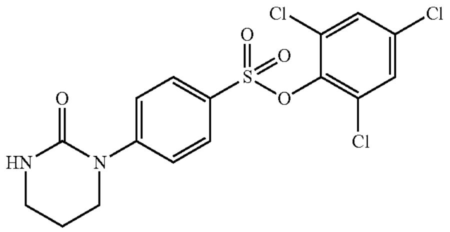 [SMILES: O=C1NCCCN1c1ccc(S(=O)(=O)Oc2c(Cl)cc(Cl)cc2Cl)cc1] | 4-(2-Oxo-tetrahydro-pyrimidin-1-yl)-benzenesulfonic acid 2,4,6-trichloro-phenyl ester |

TABLE 1-continued

| code # | Structure | Name |
| --- | --- | --- |
| CEU-671 | 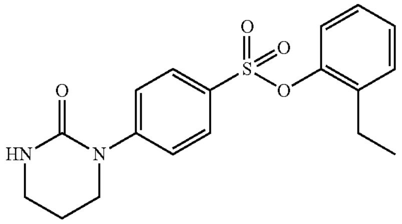 [SMILES: CCc1ccccc1OS(=O)(=O)c1ccc(N2CCCNC2=O)cc1] | 4-(2-Oxo-tetrahydro-pyrimidin-1-yl)-benzenesulfonic acid 2-ethyl-phenyl ester |
| CEU-672 | 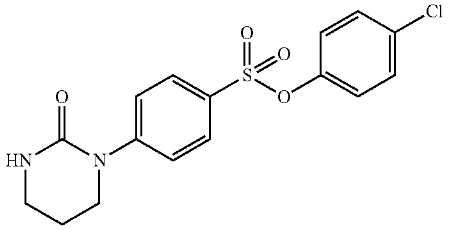 [SMILES: O=C1NCCCN1c1ccc(S(=O)(=O)Oc2ccc(Cl)cc2)cc1] | 4-(2-Oxo-tetrahydro-pyrimidin-1-yl)-benzenesulfonic acid 4-chloro-phenyl ester |
| CEU-673 | 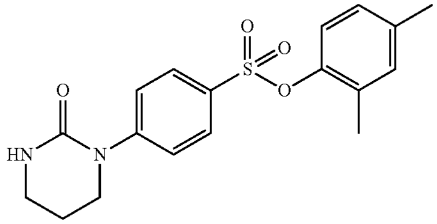 [SMILES: Cc1ccc(OS(=O)(=O)c2ccc(N3CCCNC3=O)cc2)c(C)c1] | 4-(2-Oxo-tetrahydro-pyrimidin-1-yl)-benzenesulfonic acid 2,4-dimethyl-phenyl ester |
| CEU-674 | 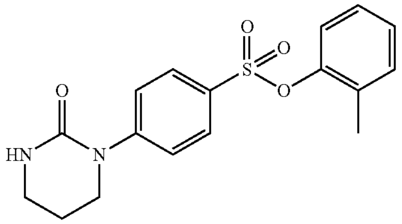 [SMILES: Cc1ccccc1OS(=O)(=O)c1ccc(N2CCCNC2=O)cc1] | 4-(2-Oxo-tetrahydro-pyrimidin-1-yl)-benzenesulfonic acid o-tolyl ester |
| CEU-675 | 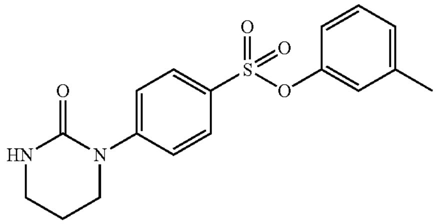 [SMILES: Cc1cccc(OS(=O)(=O)c2ccc(N3CCCNC3=O)cc2)c1] | 4-(2-Oxo-tetrahydro-pyrimidin-1-yl)-benzenesulfonic acid m-tolyl ester |
| CEU-676 | 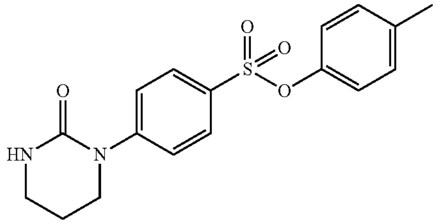 [SMILES: Cc1ccc(OS(=O)(=O)c2ccc(N3CCCNC3=O)cc2)cc1] | 4-(2-Oxo-tetrahydro-pyrimidin-1-yl)-benzenesulfonic acid p-tolyl ester |

TABLE 1-continued

| code # | Structure | Name |
| --- | --- | --- |
| CEU-681 | 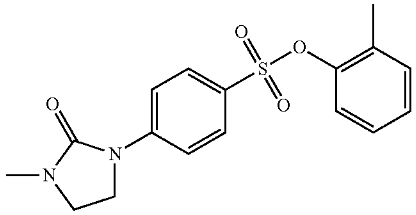 [SMILES: Cc1ccccc1OS(=O)(=O)c1ccc(N2CCN(C)C2=O)cc1] | 4-(3-Methyl-2-oxo-imidazolidin-1-yl)-benzenesulfonic acid o-tolyl ester |
| CEU-682 | 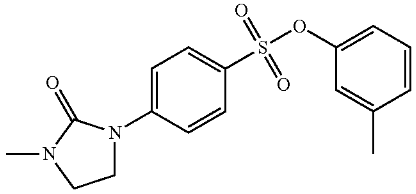 [SMILES: Cc1cccc(OS(=O)(=O)c2ccc(N3CCN(C)C3=O)cc2)c1] | 4-(3-Methyl-2-oxo-imidazolidin-1-yl)-benzenesulfonic acid m-tolyl ester |
| CEU-683 | 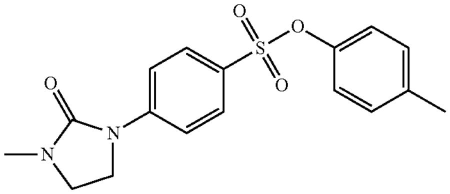 | 4-(3-Methyl-2-oxo-imidazolidin-1-yl)-benzenesulfonic acid p-tolyl ester |
| CEU-684 | 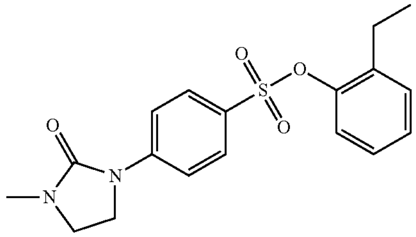 [SMILES: CCc1ccccc1OS(=O)(=O)c1ccc(N2CCN(C)C2=O)cc1] | 4-(3-Methyl-2-oxo-imidazolidin-1-yl)-benzenesulfonic acid 2-ethyl-phenyl ester |
| CEU-685 | 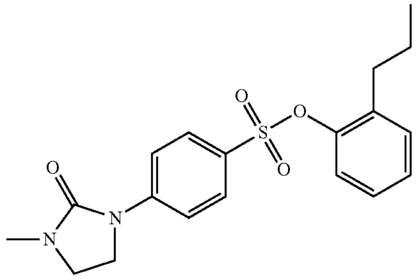 [SMILES: CCCc1ccccc1OS(=O)(=O)c1ccc(N2CCN(C)C2=O)cc1] | 4-(3-Methyl-2-oxo-imidazolidin-1-yl)-benzenesulfonic acid 2-propyl-phenyl ester |
| CEU-686 | 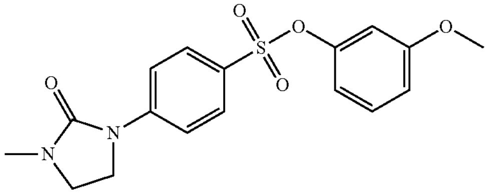 | 4-(3-Methyl-2-oxo-imidazolidin-1-yl)-benzenesulfonic acid 3-methoxy-phenyl ester |
| CEU-687 | 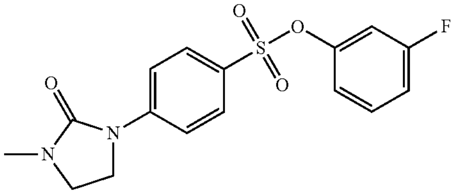 [SMILES: CN1CCN(c2ccc(S(=O)(=O)Oc3cccc(F)c3)cc2)C1=O] | 4-(3-Methyl-2-oxo-imidazolidin-1-yl)-benzenesulfonic acid 3-fluoro-phenyl ester |

TABLE 1-continued

| code # | Structure | Name |
|---|---|---|
| CEU-688 | 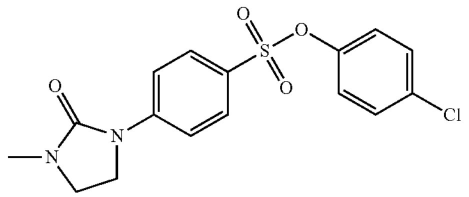 [SMILES: CN1CCN(c2ccc(S(=O)(=O)Oc3ccc(Cl)cc3)cc2)C1=O] | 4-(3-Methyl-2-oxo-imidazolidin-1-yl)-benzenesulfonic acid 4-chloro-phenyl ester |
| CEU-689 | 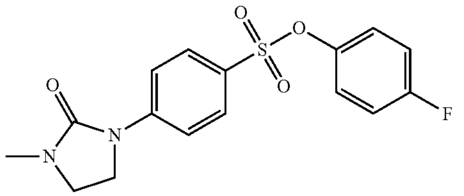 [SMILES: CN1CCN(c2ccc(S(=O)(=O)Oc3ccc(F)cc3)cc2)C1=O] | 4-(3-Methyl-2-oxo-imidazolidin-1-yl)-benzenesulfonic acid 4-fluoro-phenyl ester |
| CEU-690 | 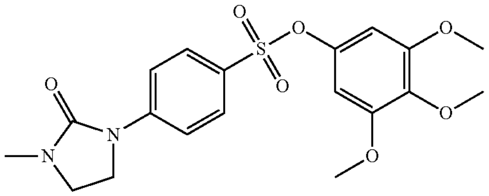 | 4-(3-Methyl-2-oxo-imidazolidin-1-yl)-benzenesulfonic acid 3,4,5-trimethoxy-phenyl ester |
| CEU-691 | 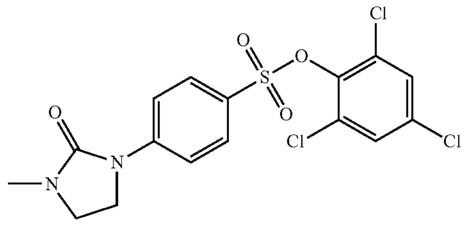 [SMILES: CN1CCN(c2ccc(S(=O)(=O)Oc3c(Cl)cc(Cl)cc3Cl)cc2)C1=O] | 4-(3-Methyl-2-oxo-imidazolidin-1-yl)-benzenesulfonic acid 2,4,6-trichloro-phenyl ester |
| CEU-692 | 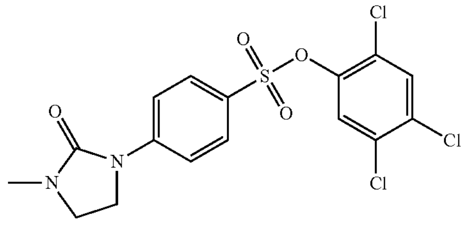 [SMILES: CN1CCN(c2ccc(S(=O)(=O)Oc3cc(Cl)c(Cl)cc3Cl)cc2)C1=O] | 4-(3-Methyl-2-oxo-imidazolidin-1-yl)-benzenesulfonic acid 2,4,5-trichloro-phenyl ester |
| CEU-693 | 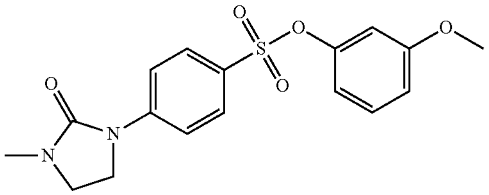 | 4-(3-Methyl-2-oxo-imidazolidin-1-yl)-benzenesulfonic acid 4-methoxy-phenyl ester |
| CEU-694 | 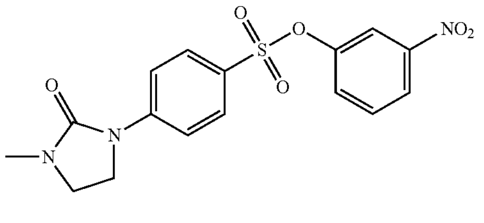 [SMILES: CN1CCN(c2ccc(S(=O)(=O)Oc3cccc([N+](=O)[O-])c3)cc2)C1=O] | 4-(3-Methyl-2-oxo-imidazolidin-1-yl)-benzenesulfonic acid 3-nitro-phenyl ester |

TABLE 1-continued

| code # | Structure | Name |
| --- | --- | --- |
| CEU-695 | 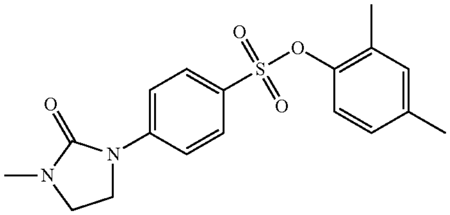 | 4-(3-Methyl-2-oxo-imidazolidin-1-yl)-benzenesulfonic acid 2,4-dimethyl-phenyl ester |
| CEU-696 | 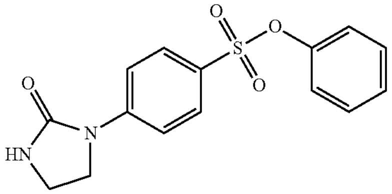 [SMILES: O=C1NCCN1c1ccc(S(=O)(=O)Oc2ccccc2)cc1] | 4-(2-Oxo-imidazolidin-1-yl)-benzenesulfonic acid phenyl ester |
| CEU-697 | 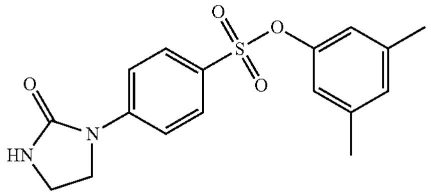 [SMILES: Cc1cc(C)cc(OS(=O)(=O)c2ccc(N3CCNC3=O)cc2)c1] | 4-(2-Oxo-imidazolidin-1-yl)-benzenesulfonic acid 3,5-dimethyl-phenyl ester |
| CEU-698 | 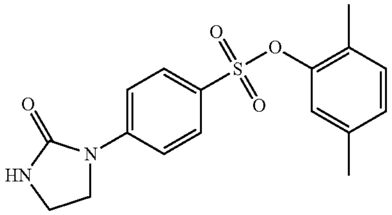 [SMILES: Cc1ccc(C)c(OS(=O)(=O)c2ccc(N3CCNC3=O)cc2)c1] | 4-(2-Oxo-imidazolidin-1-yl)-benzenesulfonic acid 2,5-dimethyl-phenyl ester |
| CEU-699 | 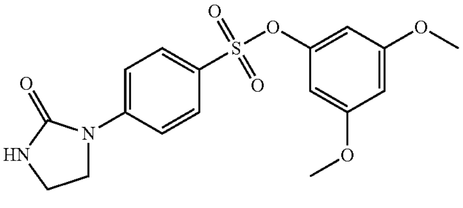 [SMILES: COc1cc(OC)cc(OS(=O)(=O)c2ccc(N3CCNC3=O)cc2)c1] | 4-(2-Oxo-imidazolidin-1-yl)-benzenesulfonic acid 3,5-dimethoxy-phenyl ester |
| CEU-700 | 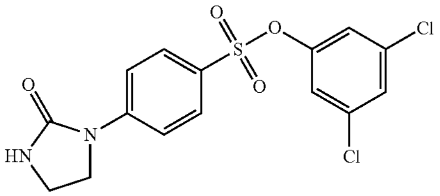 [SMILES: O=C1NCCN1c1ccc(S(=O)(=O)Oc2cc(Cl)cc(Cl)c2)cc1] | 4-(2-Oxo-imidazolidin-1-yl)-benzenesulfonic acid 3,5-dichloro-phenyl ester |
| CEU-704 | 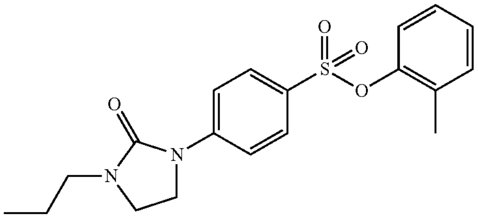 [SMILES: CCCN1CCN(c2ccc(S(=O)(=O)Oc3ccccc3C)cc2)C1=O] | 4-(2-Oxo-3-propyl-imidazolidin-1-yl)-benzenesulfonic acid o-tolyl ester |

TABLE 1-continued

| code # | Structure | Name |
| --- | --- | --- |
| CEU-705 | 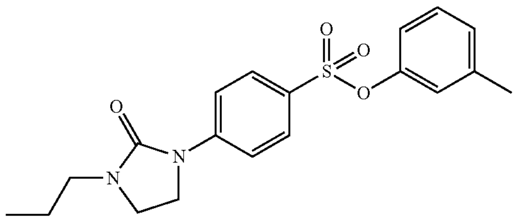 [SMILES: CCCN1CCN(c2ccc(S(=O)(=O)Oc3cccc(C)c3)cc2)C1=O] | 4-(2-Oxo-3-propyl-imidazolidin-1-yl)-benzenesulfonic acid m-tolyl ester |
| CEU-706 | 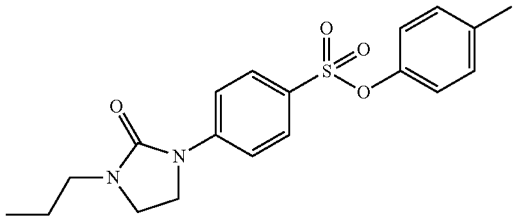 [SMILES: CCCN1CCN(c2ccc(S(=O)(=O)Oc3ccc(C)cc3)cc2)C1=O] | 4-(2-Oxo-3-propyl-imidazolidin-1-yl)-benzenesulfonic acid p-tolyl ester |
| CEU-707 | 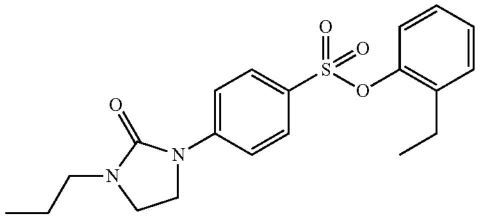 [SMILES: CCCN1CCN(c2ccc(S(=O)(=O)Oc3ccccc3CC)cc2)C1=O] | 4-(2-Oxo-3-propyl-imidazolidin-1-yl)-benzenesulfonic acid 2-ethyl-phenyl ester |
| CEU-708 | 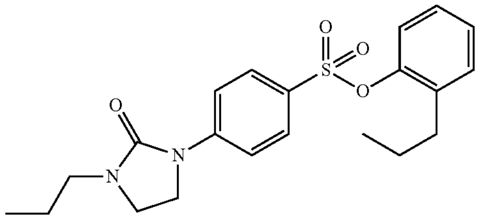 [SMILES: CCCc1ccccc1OS(=O)(=O)c1ccc(N2CCN(CCC)C2=O)cc1] | 4-(2-Oxo-3-propyl-imidazolidin-1-yl)-benzenesulfonic acid 2-propyl-phenyl ester |
| CEU-709 | 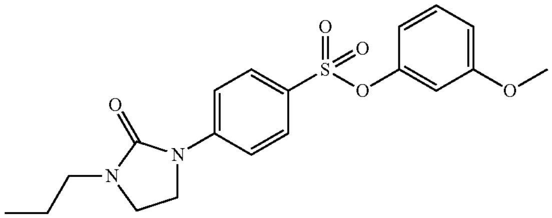 [SMILES: CCCN1CCN(c2ccc(S(=O)(=O)Oc3cccc(OC)c3)cc2)C1=O] | 4-(2-Oxo-3-propyl-imidazolidin-1-yl)-benzenesulfonic acid 3-methoxy-phenyl ester |
| CEU-710 | 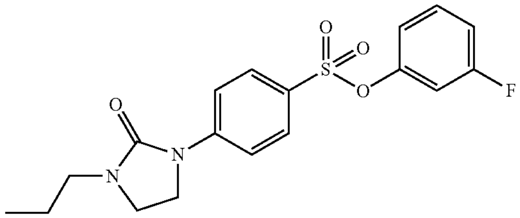 [SMILES: CCCN1CCN(c2ccc(S(=O)(=O)Oc3cccc(F)c3)cc2)C1=O] | 4-(2-Oxo-3-propyl-imidazolidin-1-yl)-benzenesulfonic acid 3-fluoro-phenyl ester |
| CEU-711 | 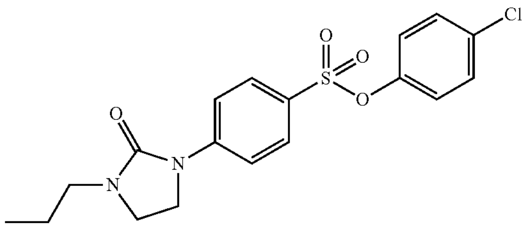 [SMILES: CCCN1CCN(c2ccc(S(=O)(=O)Oc3ccc(Cl)cc3)cc2)C1=O] | 4-(2-Oxo-3-propyl-imidazolidin-1-yl)-benzenesulfonic acid 4-chloro-phenyl ester |

TABLE 1-continued

| code # | Structure | Name |
|---|---|---|
| CEU-712 | 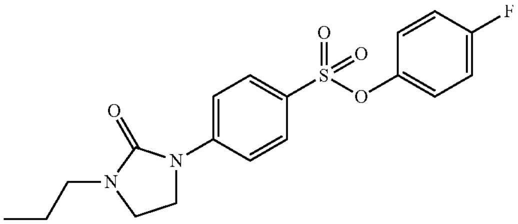 [SMILES: CCCN1CCN(c2ccc(S(=O)(=O)Oc3ccc(F)cc3)cc2)C1=O] | 4-(2-Oxo-3-propyl-imidazolidin-1-yl)-benzenesulfonic acid 4-fluoro-phenyl ester |
| CEU-713 | 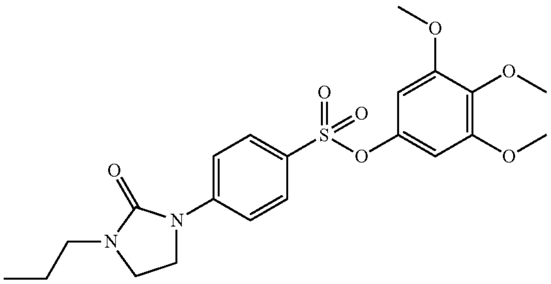 [SMILES: CCCN1CCN(c2ccc(S(=O)(=O)Oc3cc(OC)c(OC)c(OC)c3)cc2)C1=O] | 4-(2-Oxo-3-propyl-imidazolidin-1-yl)-benzenesulfonic acid 3,4,5-trimethoxy-phenyl ester |
| CEU-714 | 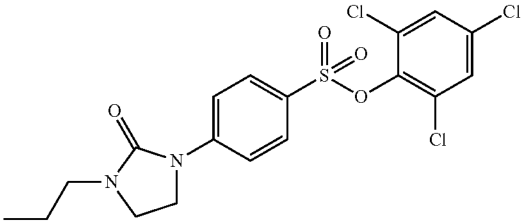 [SMILES: CCCN1CCN(c2ccc(S(=O)(=O)Oc3c(Cl)cc(Cl)cc3Cl)cc2)C1=O] | 4-(2-Oxo-3-propyl-imidazolidin-1-yl)-benzenesulfonic acid 2,4,6-trichloro-phenyl ester |
| CEU-715 | 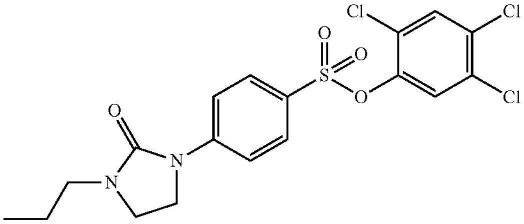 [SMILES: CCCN1CCN(c2ccc(S(=O)(=O)Oc3cc(Cl)c(Cl)cc3Cl)cc2)C1=O] | 4-(2-Oxo-3-propyl-imidazolidin-1-yl)-benzenesulfonic acid 2,4,5-trichloro-phenyl ester |
| CEU-716 | 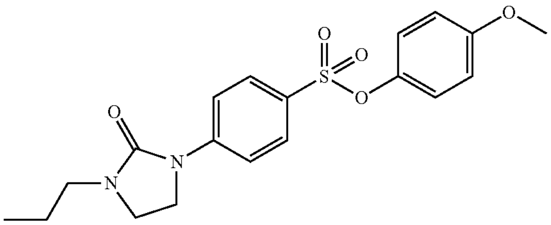 [SMILES: CCCN1CCN(c2ccc(S(=O)(=O)Oc3ccc(OC)cc3)cc2)C1=O] | 4-(2-Oxo-3-propyl-imidazolidin-1-yl)-benzenesulfonic acid 4-methoxy-phenyl ester |
| CEU-717 | 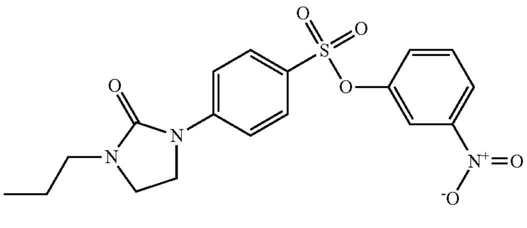 | 4-(2-Oxo-3-propyl-imidazolidin-1-yl)-benzenesulfonic acid 3-nitro-phenyl ester |

TABLE 1-continued

| code # | Structure | Name |
|---|---|---|
| CEU-718 | 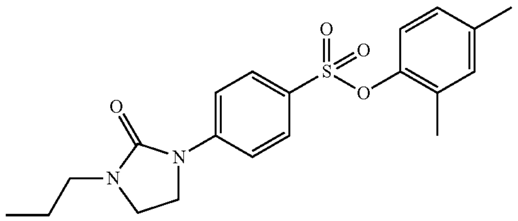 [SMILES: CCCN1CCN(c2ccc(S(=O)(=O)Oc3ccc(C)cc3C)cc2)C1=O] | 4-(2-Oxo-3-propyl-imidazolidin-1-yl)-benzenesulfonic acid 2,4-dimethyl-phenyl ester |
| CEU-719 | 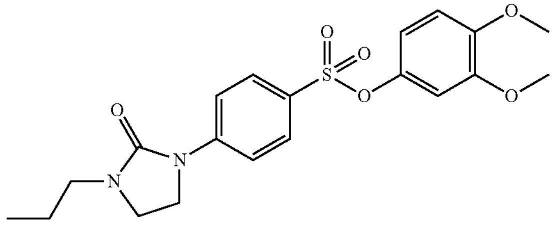 [SMILES: CCCN1CCN(c2ccc(S(=O)(=O)Oc3ccc(OC)c(OC)c3)cc2)C1=O] | 4-(2-Oxo-3-propyl-imidazolidin-1-yl)-benzenesulfonic acid 3,4-dimethoxy-phenyl ester |
| CEU-720 | 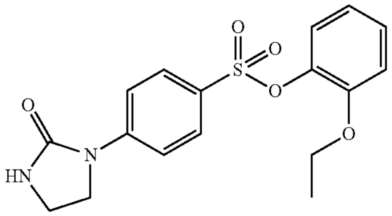 [SMILES: CCOc1ccccc1OS(=O)(=O)c1ccc(N2CCNC2=O)cc1] | 4-(2-Oxo-imidazolidin-1-yl)-benzenesulfonic acid 2-ethoxy-phenyl ester |
| CEU-721 | 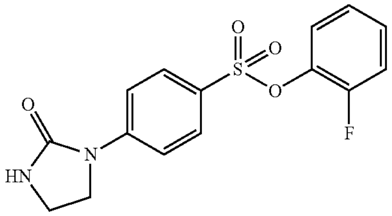 | 4-(2-Oxo-imidazolidin-1-yl)-benzenesulfonic acid 2-fluoro-phenyl ester |
| CEU-722 | 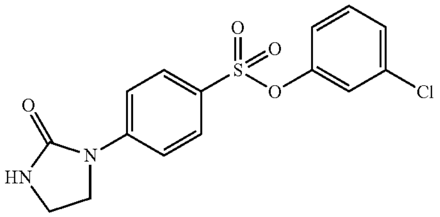 [SMILES: O=C1NCCN1c1ccc(S(=O)(=O)Oc2cccc(Cl)c2)cc1] | 4-(2-Oxo-imidazolidin-1-yl)-benzenesulfonic acid 3-chloro-phenyl ester |
| CEU-723 | 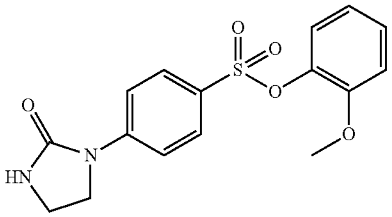 | 4-(2-Oxo-imidazolidin-1-yl)-benzenesulfonic acid 2-methoxy-phenyl ester |
| CEU-724 | 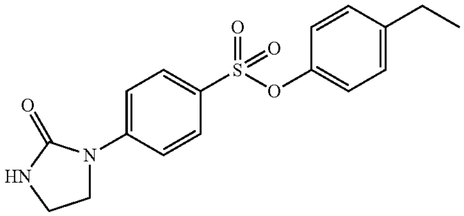 [SMILES: CCc1ccc(OS(=O)(=O)c2ccc(N3CCNC3=O)cc2)cc1] | 4-(2-Oxo-imidazolidin-1-yl)-benzenesulfonic acid 4-ethyl-phenyl ester |

TABLE 1-continued

| code # | Structure | Name |
| --- | --- | --- |
| CEU-725 | 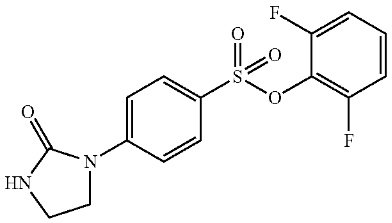 [SMILES: O=C1NCCN1c1ccc(S(=O)(=O)Oc2c(F)cccc2F)cc1] | 4-(2-Oxo-imidazolidin-1-yl)-benzenesulfonic acid 2,6-difluoro-phenyl ester |
| CEU-726 | 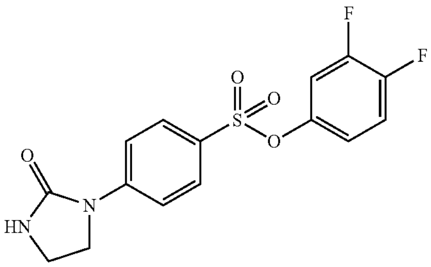 [SMILES: O=C1NCCN1c1ccc(S(=O)(=O)Oc2ccc(F)c(F)c2)cc1] | 4-(2-Oxo-imidazolidin-1-yl)-benzenesulfonic acid 3,4-difluoro-phenyl ester |
| CEU-727 | 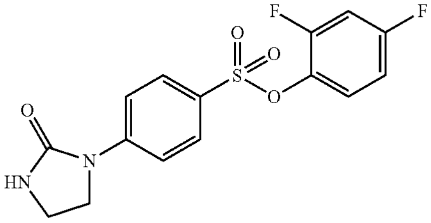 [SMILES: O=C1NCCN1c1ccc(S(=O)(=O)Oc2ccc(F)cc2F)cc1] | 4-(2-Oxo-imidazolidin-1-yl)-benzenesulfonic acid 2,4-difluoro-phenyl ester |
| CEU-728 | 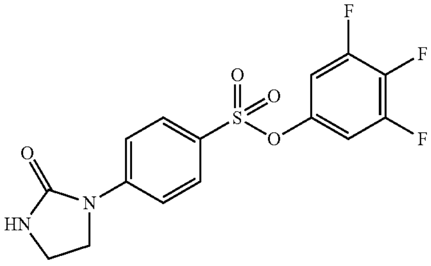 [SMILES: O=C1NCCN1c1ccc(S(=O)(=O)Oc2cc(F)c(F)c(F)c2)cc1] | 4-(2-Oxo-imidazolidin-1-yl)-benzenesulfonic acid 3,4,5-trifluoro-phenyl ester |
| CEU-729 | 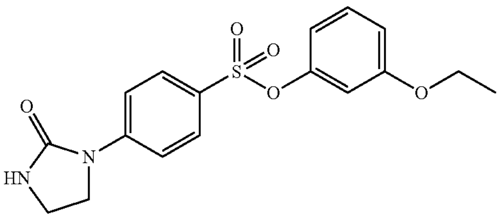 [SMILES: CCOc1cccc(OS(=O)(=O)c2ccc(N3CCNC3=O)cc2)c1] | 4-(2-Oxo-imidazolidin-1-yl)-benzenesulfonic acid 3-ethoxy-phenyl ester |
| CEU-730 | 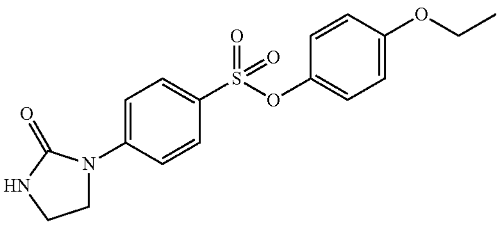 [SMILES: CCOc1ccc(OS(=O)(=O)c2ccc(N3CCNC3=O)cc2)cc1] | 4-(2-Oxo-imidazolidin-1-yl)-benzenesulfonic acid 4-ethoxy-phenyl ester |

TABLE 1-continued

| code # | Structure | Name |
|---|---|---|
| CEU-731 | 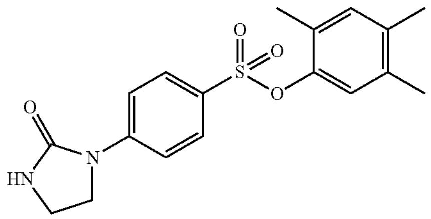 [SMILES: Cc1cc(C)c(OS(=O)(=O)c2ccc(N3CCNC3=O)cc2)cc1C] | 4-(2-Oxo-imidazolidin-1-yl)-benzenesulfonic acid 2,4,5-trimethyl-phenyl ester |
| CEU-732 | 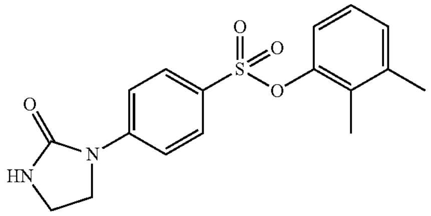 | 4-(2-Oxo-imidazolidin-1-yl)-benzenesulfonic acid 2,3-dimethyl-phenyl ester |
| CEU-733 | 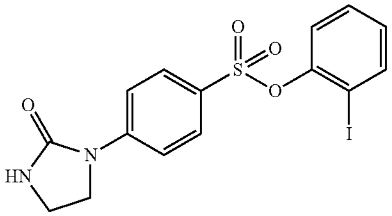 | 4-(2-Oxo-imidazolidin-1-yl)-benzenesulfonic acid 3-iodo-phenyl ester |
| CEU-734 | 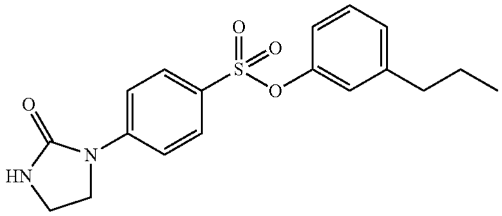 | 4-(2-Oxo-imidazolidin-1-yl)-benzenesulfonic acid 3-propyl-phenyl ester |
| CEU-735 | 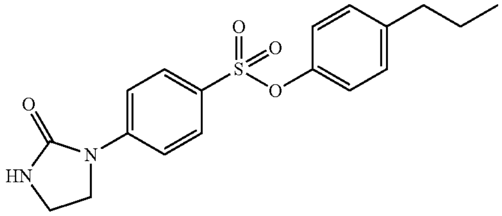 [SMILES: CCCc1ccc(OS(=O)(=O)c2ccc(N3CCNC3=O)cc2)cc1] | 4-(2-Oxo-imidazolidin-1-yl)-benzenesulfonic acid 4-propyl-phenyl ester |
| CEU-736 | 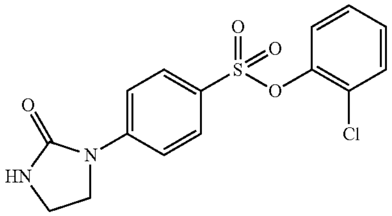 | 4-(2-Oxo-imidazolidin-1-yl)-benzenesulfonic acid 2-chloro-phenyl ester |
| CEU-737 | 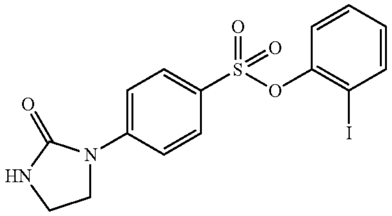 | 4-(2-Oxo-imidazolidin-1-yl)-benzenesulfonic acid 2-iodo-phenyl ester |

TABLE 1-continued

| code # | Structure | Name |
|---|---|---|
| CEU-738 | 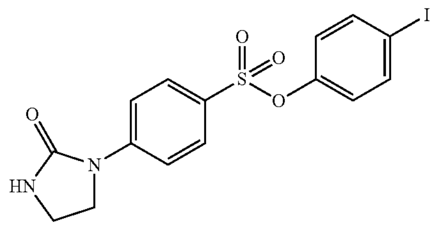 [SMILES: O=C1NCCN1c1ccc(S(=O)(=O)Oc2ccc(I)cc2)cc1] | 4-(2-Oxo-imidazolidin-1-yl)-benzenesulfonic acid 4-iodo-phenyl ester |
| CEU-739 | 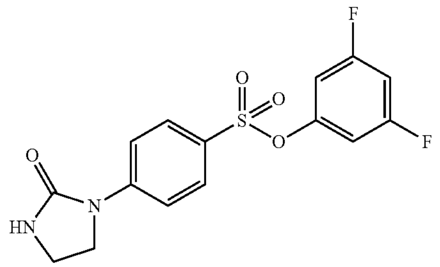 [SMILES: O=C1NCCN1c1ccc(S(=O)(=O)Oc2cc(F)cc(F)c2)cc1] | 4-(2-Oxo-imidazolidin-1-yl)-benzenesulfonic acid 3,5-difluoro-phenyl ester |
| CEU-740 | 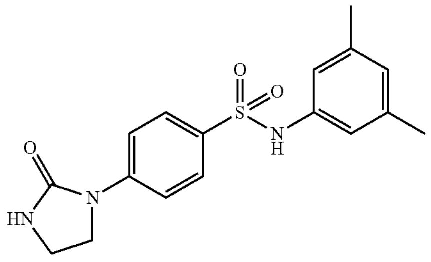 [SMILES: Cc1cc(C)cc(NS(=O)(=O)c2ccc(N3CCNC3=O)cc2)c1] | N-(3,5-Dimethyl-phenyl)-4-(2-oxo-imidazolidin-1-yl)-benzenesulfonamide |
| CEU-741 | 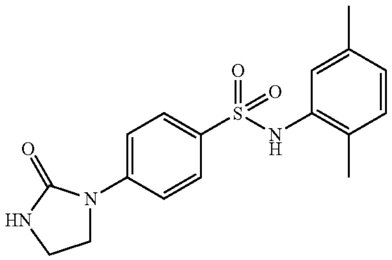 [SMILES: Cc1ccc(C)c(NS(=O)(=O)c2ccc(N3CCNC3=O)cc2)c1] | N-(2,5-Dimethyl-phenyl)-4-(2-oxo-imidazolidin-1-yl)-benzenesulfonamide |
| CEU-742 | 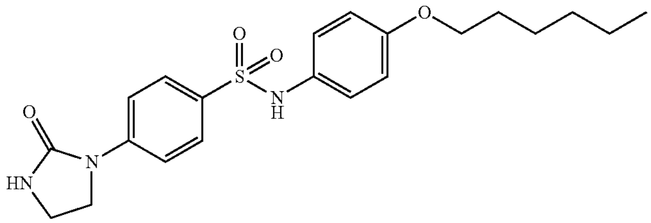 [SMILES: CCCCCCOc1ccc(NS(=O)(=O)c2ccc(N3CCNC3=O)cc2)cc1] | N-(4-Hexyloxy-phenyl)-4-(2-oxo-imidazolidin-1-yl)-benzenesulfonamide |
| CEU-743 | 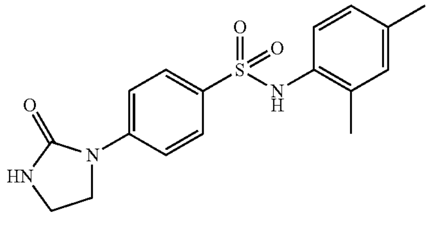 [SMILES: Cc1ccc(NS(=O)(=O)c2ccc(N3CCNC3=O)cc2)c(C)c1] | N-(2,4-Dimethyl-phenyl)-4-(2-oxo-imidazolidin-1-yl)-benzenesulfonamide |

TABLE 1-continued

| code # | Structure | Name |
|---|---|---|
| CEU-744 | 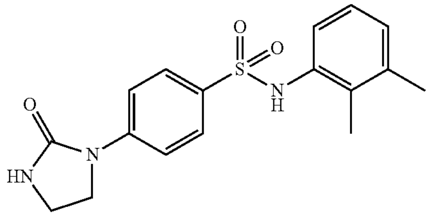 [SMILES: Cc1cccc(NS(=O)(=O)c2ccc(N3CCNC3=O)cc2)c1] | N-(2,3-Dimethyl-phenyl)-4-(2-oxo-imidazolidin-1-yl)-benzenesulfonamide |
| CEU-745 | 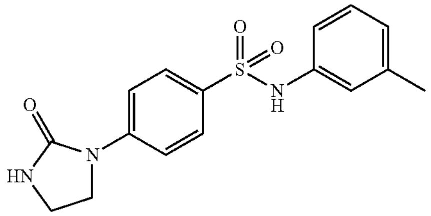 | 4-(2-Oxo-imidazolidin-1-yl)-N-m-tolyl-benzenesulfonamide |
| CEU-746 | 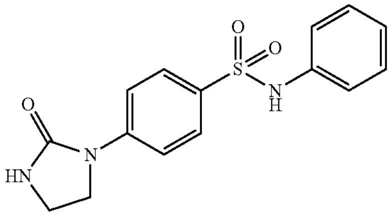 [SMILES: O=C1NCCN1c1ccc(S(=O)(=O)Nc2ccccc2)cc1] | 4-(2-Oxo-imidazolidin-1-yl)-N-phenyl-benzenesulfonamide |
| CEU-747 | 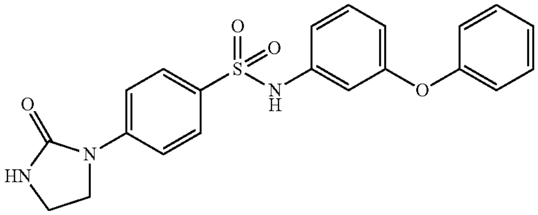 [SMILES: O=C1NCCN1c1ccc(S(=O)(=O)Nc2cccc(Oc3ccccc3)c2)cc1] | 4-(2-Oxo-imidazolidin-1-yl)-N-(3-phenoxy-phenyl)-benzenesulfonamide |
| CEU-748 | 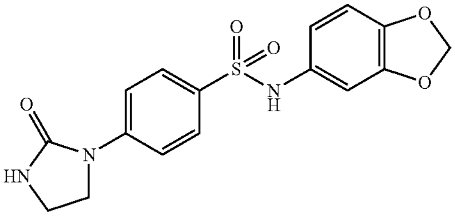 [SMILES: O=C1NCCN1c1ccc(S(=O)(=O)Nc2ccc3c(c2)OCO3)cc1] | N-Benzo[1,3]dioxol-5-yl-4-(2-oxo-imidazolidin-1-yl)-benzenesulfonamide |
| CEU-750 | 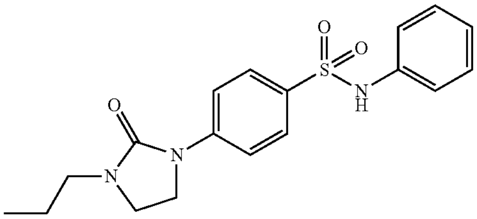 [SMILES: CCCN1CCN(c2ccc(S(=O)(=O)Nc3ccccc3)cc2)C1=O] | 4-(2-Oxo-3-propyl-imidazolidin-1-yl)-N-phenyl-benzenesulfonamide |
| CEU-751 | 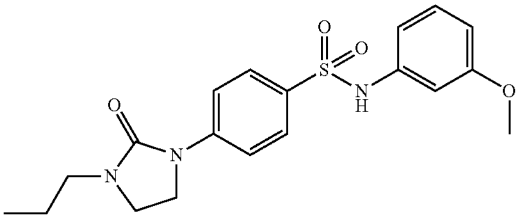 [SMILES: CCCN1CCN(c2ccc(S(=O)(=O)Nc3cccc(OC)c3)cc2)C1=O] | N-(3-Methoxy-phenyl)-4-(2-oxo-3-propyl-imidazolidin-1-yl)-benzenesulfonamide |

TABLE 1-continued

| code # | Structure | Name |
|---|---|---|
| CEU-752 | 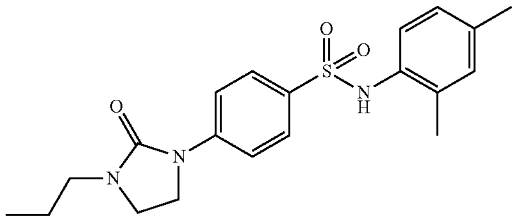 [SMILES: CCCN1CCN(c2ccc(S(=O)(=O)Nc3ccc(C)cc3C)cc2)C1=O] | N-(2,4-Dimethyl-phenyl)-4-(2-oxo-3-propyl-imidazolidin-1-yl)-benzenesulfonamide |
| CEU-753 | 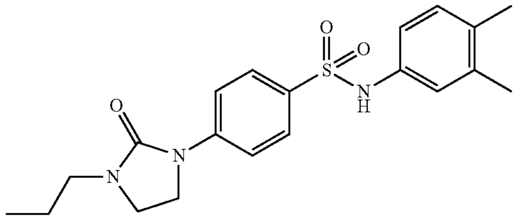 [SMILES: CCCN1CCN(c2ccc(S(=O)(=O)Nc3ccc(C)c(C)c3)cc2)C1=O] | N-(3,4-Dimethyl-phenyl)-4-(2-oxo-3-propyl-imidazolidin-1-yl)-benzenesulfonamide |
| CEU-754 | 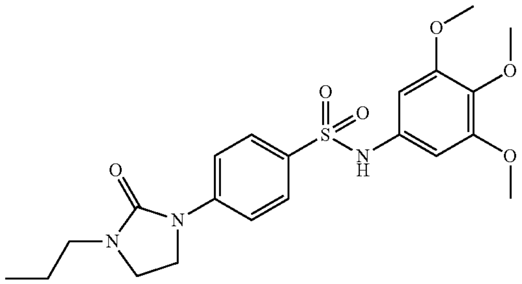 [SMILES: CCCN1CCN(c2ccc(S(=O)(=O)Nc3cc(OC)c(OC)c(OC)c3)cc2)C1=O] | 4-(2-Oxo-3-propyl-imidazolidin-1-yl)-N-(3,4,5-trimethoxy-phenyl)-benzenesulfonamide |
| CEU-755 | 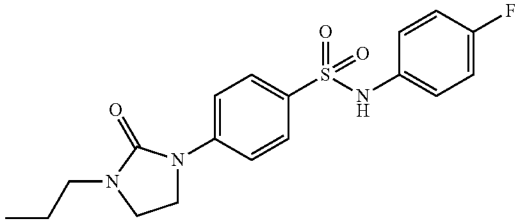 [SMILES: CCCN1CCN(c2ccc(S(=O)(=O)Nc3ccc(F)cc3)cc2)C1=O] | N-(4-Fluoro-phenyl)-4-(2-oxo-3-propyl-imidazolidin-1-yl)-benzenesulfonamide |
| CEU-756 | 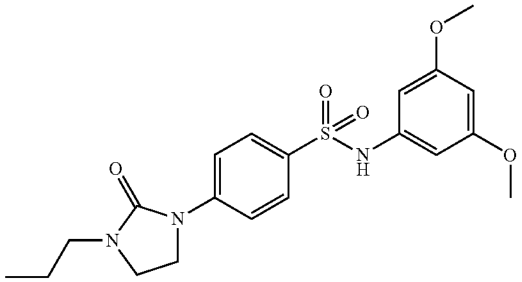 | N-(3,5-Dimethoxy-phenyl)-4-(2-oxo-3-propyl-imidazolidin-1-yl)-benzenesulfonamide |
| CEU-757 | 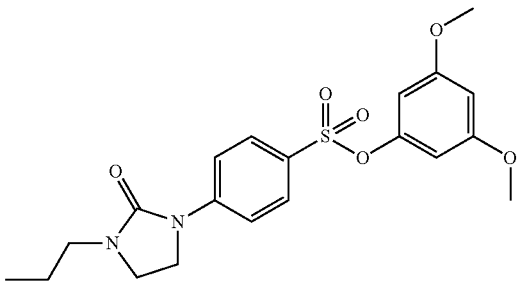 [SMILES: CCCN1CCN(c2ccc(S(=O)(=O)Oc3cc(OC)cc(OC)c3)cc2)C1=O] | 4-(2-Oxo-3-propyl-imidazolidin-1-yl)-benzenesulfonic acid 3,5-dimethoxy-phenyl ester |

TABLE 1-continued

| code # | Structure | Name |
|---|---|---|
| CEU-758 | 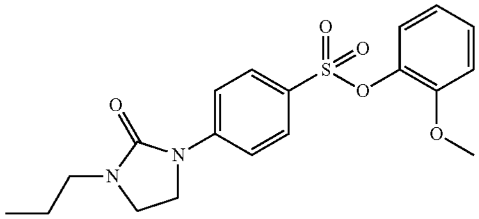 [SMILES: CCCN1CCN(c2ccc(S(=O)(=O)Oc3ccccc3OC)cc2)C1=O] | 4-(2-Oxo-3-propyl-imidazolidin-1-yl)-benzenesulfonic acid 2-methoxy-phenyl ester |
| CEU-759 | 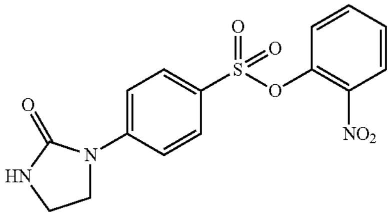 | 2-nitrophenyl 4-(2-oxoimidazolidin-1-yl)benzenesulfonate. |
| CEU-760 | 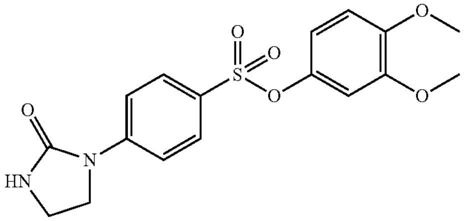 [SMILES: COc1ccc(OS(=O)(=O)c2ccc(N3CCNC3=O)cc2)cc1OC] | 4-(2-Oxo-imidazolidin-1-yl)-benzenesulfonic acid 3,4-dimethoxy-phenyl ester |
| CEU-761 | 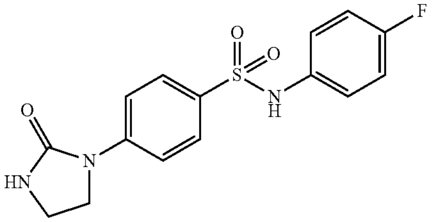 [SMILES: O=C1NCCN1c1ccc(S(=O)(=O)Nc2ccc(F)cc2)cc1] | N-(4-Fluoro-phenyl)-4-(2-oxo-imidazolidin-1-yl)-benzenesulfonamide |
| CEU-762 | 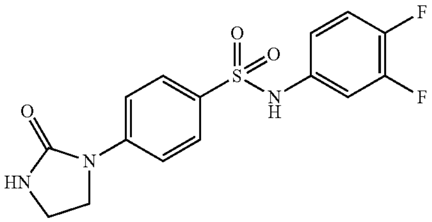 [SMILES: O=C1NCCN1c1ccc(S(=O)(=O)Nc2ccc(F)c(F)c2)cc1] | N-(3,4-Difluoro-phenyl)-4-(2-oxo-imidazolidin-1-yl)-benzenesulfonamide |
| CEU-763 | 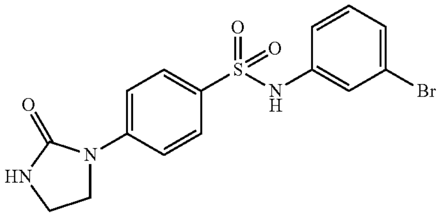 [SMILES: O=C1NCCN1c1ccc(S(=O)(=O)Nc2cccc(Br)c2)cc1] | N-(3-Bromo-phenyl)-4-(2-oxo-imidazolidin-1-yl)-benzenesulfonamide |
| CEU-764 | 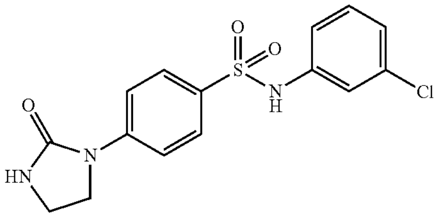 [SMILES: O=C1NCCN1c1ccc(S(=O)(=O)Nc2cccc(Cl)c2)cc1] | N-(3-Chloro-phenyl)-4-(2-oxo-imidazolidin-1-yl)-benzenesulfonamide |

TABLE 1-continued

| code # | Structure | Name |
|---|---|---|
| CEU-765 | 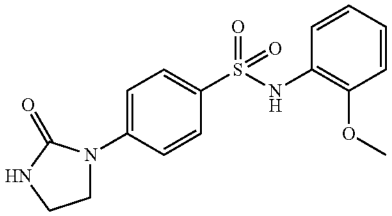 [SMILES: COc1ccccc1NS(=O)(=O)c1ccc(N2CCNC2=O)cc1] | N-(2-Methoxy-phenyl)-4-(2-oxo-imidazolidin-1-yl)-benzenesulfonamide |
| CEU-766 | 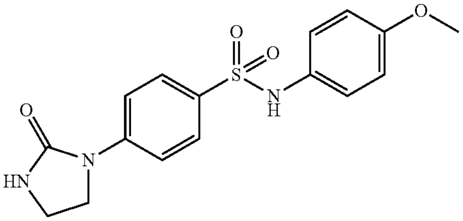 [SMILES: COc1ccc(NS(=O)(=O)c2ccc(N3CCNC3=O)cc2)cc1] | N-(4-Methoxy-phenyl)-4-(2-oxo-imidazolidin-1-yl)-benzenesulfonamide |
| CEU-767 | 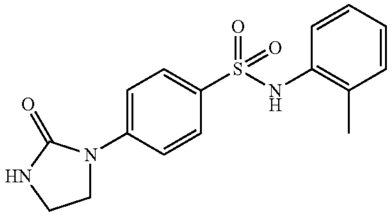 | 4-(2-Oxo-imidazolidin-1-yl)-N-o-tolyl-benzenesulfonamide |
| CEU-768 | 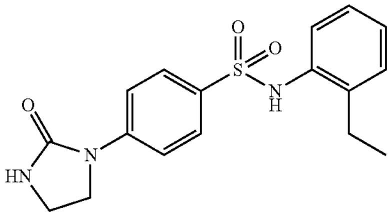 | N-(2-Ethyl-phenyl)-4-(2-oxo-imidazolidin-1-yl)-benzenesulfonamide |
| CEU-769 | 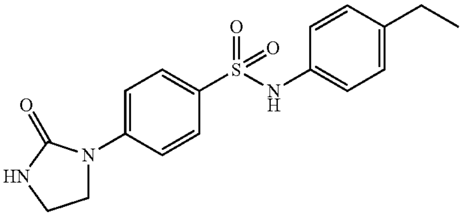 | N-(4-Ethyl-phenyl)-4-(2-oxo-imidazolidin-1-yl)-benzenesulfonamide |
| CEU-770 | 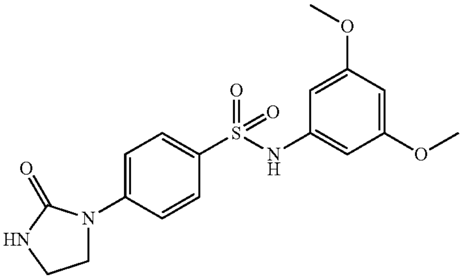 [SMILES: COc1cc(NS(=O)(=O)c2ccc(N3CCNC3=O)cc2)cc(OC)c1] | N-(3,5-Dimethoxy-phenyl)-4-(2-oxo-imidazolidin-1-yl)-benzenesulfonamide |

TABLE 1-continued

| code # | Structure | Name |
| --- | --- | --- |
| CEU-815 | 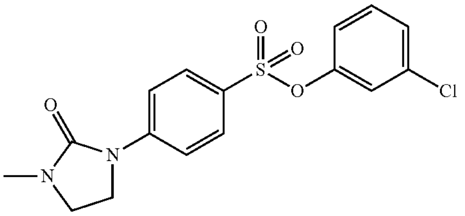 [SMILES: CN1CCN(c2ccc(S(=O)(=O)Oc3cccc(Cl)c3)cc2)C1=O] | 4-(3-Methyl-2-oxo-imidazolidin-1-yl)-benzenesulfonic acid 3-chloro-phenyl ester |
| CEU-816 | 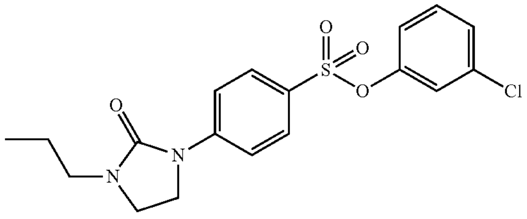 [SMILES: CCCN1CCN(c2ccc(S(=O)(=O)Oc3cccc(Cl)c3)cc2)C1=O] | 4-(2-Oxo-3-propyl-imidazolidin-1-yl)-benzenesulfonic acid 3-chloro-phenyl ester |

The invention claimed is:

1. A compound of formula (I):

(I)

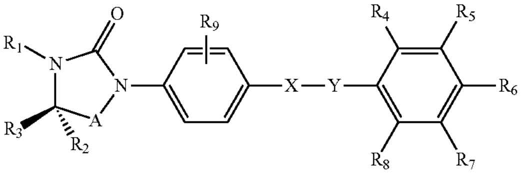

wherein:

$R_1$ is H or $C_{1-6}$ alkyl;

A is $(CH_2)n$ wherein n is an integer from 1 to 3; or A is —CH— and is bound to adjacent —CH—$R_2$ by a double bond whereas $R_3$ is not present;

$R_2$ and $R_3$ is each independently selected from the group consisting of: H and $C_{1-6}$ alkyl;

X is O or NH when Y=$SO_2$; and X=$SO_2$ when Y is O or NH;

$R_5$, $R_6$ and $R_7$ is each independently selected from the group consisting of: H, OH, halogen, $C_{1-8}$ alkyl, $C_{4-6}$ cycloalkyl, $C_{2-6}$ alkenyl, $C_{1-6}$ alkoxy, O-haloalkyl, phenoxy, $C_{0-6}$ alkyl-CN, $C_{1-6}$ 2-ketyl, ω- and ω-1 $C_{1-6}$ alkanol, ω-$C_{1-6}$ alkyl carboxylate and corresponding $C_{1-3}$ esters, —$COOR_{10}$ wherein $R_{10}$ is selected from: H or $C_{1-3}$ alkyl; $NO_2$, —NH—C(O)—$C_{1-3}$ alkyl, and —N—$(R_{11})(R_{12})$ wherein $R_{11}$ and $R_{12}$ is each independently selected from the group consisting of: H and $C_{1-3}$ alkyl; or $R_5$ and $R_6$; or $R_6$ and $R_7$ are linked to each other and for a 4, 5 or 6-membered saturated or partially unsaturated ring optionally containing one or two N, O or S atoms thus forming a heterocycle, said ring or heterocycle optionally substituted with $C_{1-6}$ alkyl, OH, halogen, amines, $C_{1-4}$ alkyl-substituted amine, $C_{1-4}$ alkoxy; or $R_4$ and $R_8$ is each independently selected from the group consisting of: H, OH, halogen, $C_{1-6}$ alkyl, $C_{1-6}$ alkenyl, $C_{1-6}$ alkoxy, $C_{1-6}$ 2-ketyl, ω- and ω-1 $C_{1-6}$ alkanol, ω-$C_{1-6}$ alkyl carboxylate and corresponding $C_{1-3}$ esters, —$COOR_{10}$ wherein $R_{10}$ is selected from: H or $C_{1-3}$ alkyl, $NO_2$, and —N—$(R_{11})(R_{12})$ wherein $R_{11}$ and $R_{12}$ is each independently selected from the group consisting of: H and $C_{1-3}$ alkyl; and $R_9$ is H, OH, halogen, unbranched $C_{1-6}$ alkyl, branched $C_{1-4}$ alkyl, $C_{1-4}$ alkenyl, $C_{1-4}$ alkoxy, ω- and ω-1 $C_{1-4}$ alkanol, ω-$C_{1-4}$ alkyl carboxylate and corresponding $C_{1-3}$ esters, —$COOR_{10}$ wherein $R_{10}$ is as defined above, —NH—C(O)—$C_{1-3}$ alkyl, and —N—$(R_{11})(R_{12})$ wherein $R_{11}$ and $R_{12}$ are as defined above;

or a pharmaceutically acceptable salt thereof.

2. The compound of claim 1, having formula (Ia):

(Ia)

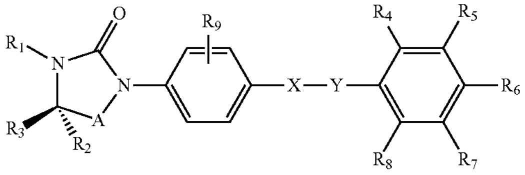

wherein:

$R_1$ is H or $C_{1-6}$ alkyl;

A is $(CH_2)_n$ wherein n is an integer from 1 to 3; or A is —CH— and is bound to adjacent —CH—$R_2$ by a double bond whereas $R_3$ is not present;

$R_2$ and $R_3$ is each independently selected from the group consisting of: H and $C_{1-6}$ alkyl;

X is O or NH when Y=$SO_2$; and X=$SO_2$ when Y is O or NH;

$R_5$, $R_6$ and $R_7$ is each independently selected from the group consisting of: H, OH, halogen, $C_{1-8}$ alkyl, $C_{4-6}$ cycloalkyl, $C_{2-6}$ alkenyl, $C_{1-6}$ alkoxy, phenoxy, $C_{0-6}$ alkyl-CN, $C_{1-6}$ 2-ketyl, ω and ω-1 $C_{1-6}$ alkanol, ω $C_{1-6}$ alkyl carboxylate and corresponding $C_{1-3}$ esters, —$COOR_{10}$ wherein $R_{10}$ is selected from: H or $C_{1-3}$ alkyl;

$NO_2$, —NH—C(O)—$C_{1-3}$ alkyl, and —N—$(R_{11})(R_{12})$ wherein $R_{11}$ and $R_{12}$ is each independently selected from the group consisting of: H and $C_{1-3}$ alkyl; or $R_5$ and $R_6$; or $R_6$ and $R_7$ are linked to each other and form a 4, 5 or 6-membered saturated or partially unsaturated ring optionally containing one or two N, O or S atoms thus forming a heterocycle, said ring or heterocycle optionally substituted with $C_{1-6}$ alkyl, OH, halogen, amines, $C_{1-4}$ alkyl-substituted amine, $C_{1-4}$ alkoxy; or $R_4$ and $R_8$ is each independently selected from the group consisting of: H, OH, halogen, $C_{1-6}$ alkyl, $C_{1-6}$ alkenyl, $C_{1-6}$ alkoxy, $C_{1-6}$ 2-ketyl, ω and ω-1 $C_{1-6}$ alkanol, ω $C_{1-6}$ alkyl carboxylate and corresponding $C_{1-3}$ esters, —$COOR_{10}$ wherein $R_{10}$ is selected from: H or $C_{1-3}$ alkyl, $NO_2$, and —N—$(R_{11})(R_{12})$ wherein $R_{11}$ and $R_{12}$ is each independently selected from the group consisting of: H and $C_{1-3}$ alkyl; and $R_9$ is H, OH, halogen, unbranched $C_{1-6}$ alkyl, branched $C_{1-4}$ alkyl, $C_{1-4}$alkenyl, $C_{1-4}$ alkoxy, ω and ω-1 $C_{1-4}$ alkanol, ω $C_{1-4}$ alkyl carboxylate and corresponding $C_{1-3}$ esters, —$COOR_{10}$ wherein $R_{10}$ is as defined above, —NH—C(O)—$C_{1-3}$ alkyl, and —N—$(R_{11})(R_{12})$ wherein $R_{11}$ and $R_{12}$ are as defined above;

or a pharmaceutically acceptable salt thereof.

3. The compound of claim 1, having formula (Ib):

(Ib)

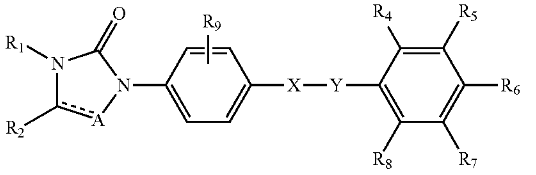

wherein:

$R_1$ is H or $C_{1-6}$ alkyl;

$R_2$ is H or $C_{1-4}$ alkyl;

A is $(CH_2)_n$ wherein n is an integer from 1 to 2;

X is O or NH when Y═$SO_2$; and X═$SO_2$ when Y is O or NH;

$R_5$, $R_6$ and $R_7$ is each independently selected from the group consisting of: H, OH, halogen, $C_{1-8}$ alkyl, $C_{3-6}$ cycloalkyl, $C_{2-6}$ alkenyl, $C_{1-6}$ alkoxy, phenoxy, $C_{0-6}$ alkyl-CN, $C_{1-6}$ 2-ketyl, ω and ω-1 $C_{1-6}$ alkanol, ω $C_{1-6}$ alkyl carboxylate and corresponding $C_{1-3}$ esters, $NO_2$, and —N—$(R_{11})(R_{12})$ wherein $R_{11}$ and $R_{12}$ is each independently selected from the group consisting of H and $C_{1-3}$alkyl; or $R_5$ and $R_6$; or $R_6$ and $R_7$ are linked to each other and form a 5-membered ring selected from:

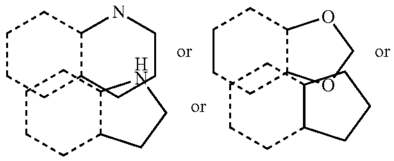

or or or each optionally substituted with $C_{1-3}$ alkyl, OH, halogen, and amine;

$R_4$ and $R_8$ is each independently selected from the group consisting of: H, OH, halogen, $C_{1-3}$ alkyl, $C_{2-3}$ alkenyl, $C_{1-3}$ alkoxy, phenoxy, ω and ω-1 $C_{1-3}$ alkanol, $C_{1-3}$2-ketyl, ω $C_{1-3}$alkyl carboxylate and corresponding $C_{1-3}$ esters, $NO_2$, —$NH_2$, and —NH—C(O)—$C_{1-3}$ alkyl; and $R_9$ is H, OH, halogen, unbranched $C_{1-6}$ alkyl, branched $C_{1-4}$ alkyl, $C_{1-4}$alkenyl, $C_{1-4}$ alkoxy;

or a pharmaceutically acceptable salt thereof.

4. The compound of claim 1, having formula (Ic):

(Ic)

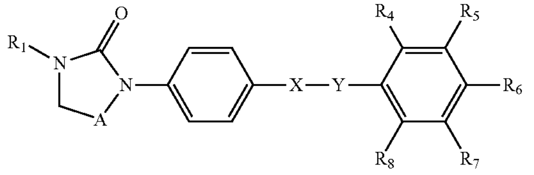

wherein:

$R_1$ is H or $C_{1-4}$alkyl;

A is $(CH_2)_n$ wherein n is an integer from 1 to 2;

X is O or NH when Y═$SO_2$; and X═$SO_2$ when Y is O or NH;

$R_5$, $R_6$, and $R_7$ is each independently selected from the group consisting of: H, OH, halogen, $C_{1-6}$ alkyl, $C_{2-6}$ alkenyl, $C_{1-6}$ alkoxy, phenoxy, $NO_2$, and —$NH_2$;

$R_4$ and $R_8$ is each independently selected from the group consisting of: H, halogen, $C_{1-3}$ alkyl, and $C_{1-3}$ alkoxy;

or a pharmaceutically acceptable salt thereof.

5. The compound of claim 1, having formula (Id):

(Id)

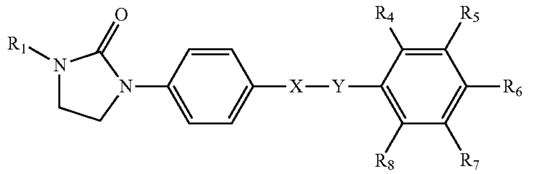

wherein:

$R_1$ is H or $C_{1-4}$ alkyl;

X is O or NH when Y═$SO_2$; and X═$SO_2$ when Y is O or NH;

$R_5$, $R_6$ and $R_7$ is each independently selected from the group consisting of: H, halogen, $C_{1-4}$ alkyl, $C_{1-3}$ alkoxy, $NO_2$, and —$NH_2$;

$R_4$ and $R_8$ is each independently selected from the group consisting of: H, halogen, $C_{1-3}$ alkyl, and $C_{1-3}$ alkoxy;

or a pharmaceutically acceptable salt thereof.

6. The compound of claim 1, wherein X is $SO_2$ and Y is O or NH; or X is O and Y is $SO_2$.

7. The compound of claim 1, wherein $R_1$ is selected from group consisting of: H, Me, Et or Pr.

8. The compound of claim 1, wherein each of $R_2$ and $R_3$ is independently selected from group consisting of: H or Me.

9. The compound of claim 1, wherein each of $R_4$ and $R_8$ are independently selected from the group consisting of: H, Me, Et, Pr, F, Cl, I, OMe, and $NO_2$.

10. The compound of claim 1, wherein each of $R_5$, $R_6$ and $R_7$ are independently selected from the group consisting of: H, Me, Et, Pr, butyl, pentyl, hexyl, cyclohexyl, CH—CN, F, Cl, I, Br, OMe, OEt, OPr, Obutyl, Opentyl, Ohexyl, Ophenyl, $OCH(F)_2$, $NH_2$, $NO_2$, $N(Me)_2$, or $R_5$ and $R_6$; or $R_6$ and $R_7$ are linked to each other and form a 5- or 6-membered ring selected from the group consisting of:

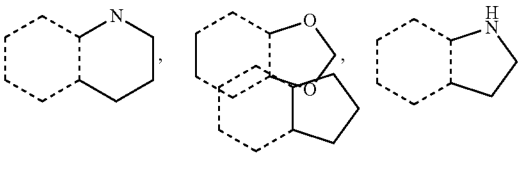

, , and each being optionally substituted with Me.

11. The compound of claim 1, wherein $R_9$ is selected from the group consisting of: H and Me.

12. The compound of claim 1, selected from the group consisting of:
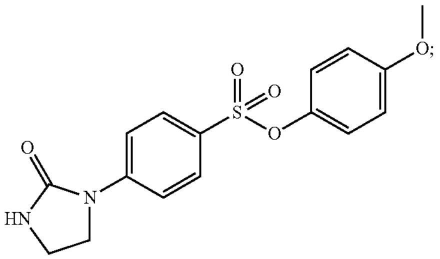
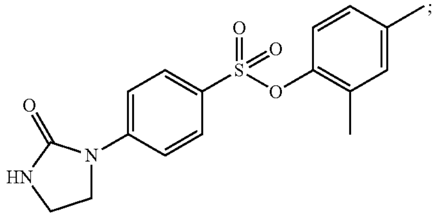
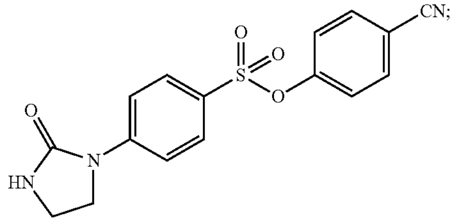
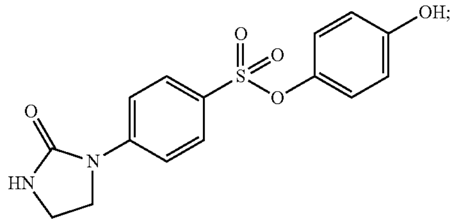
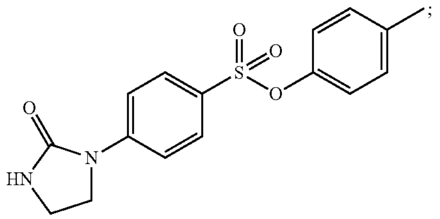
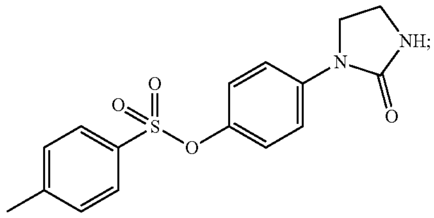
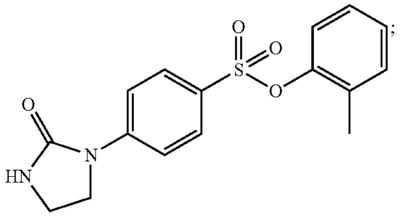
-continued
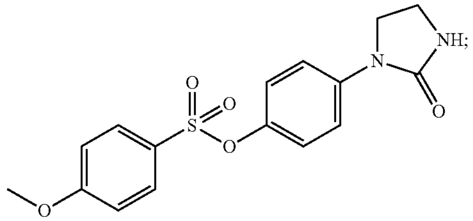
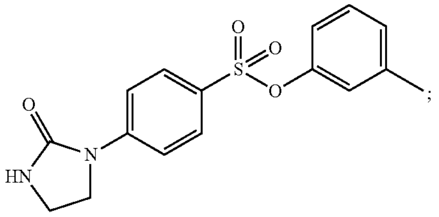
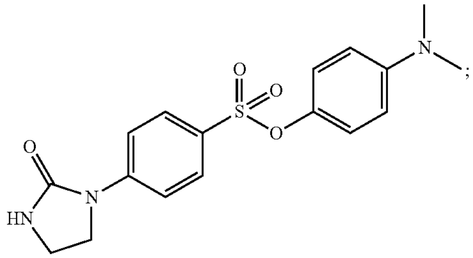
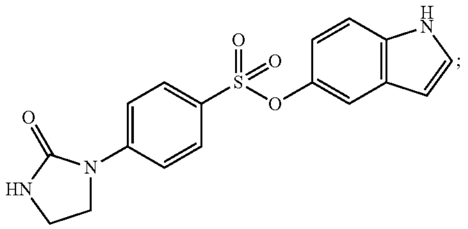
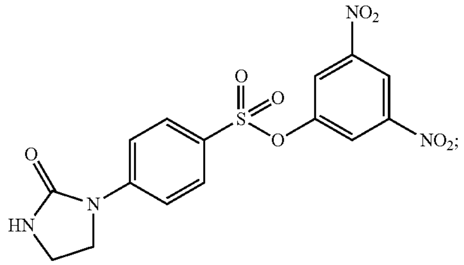
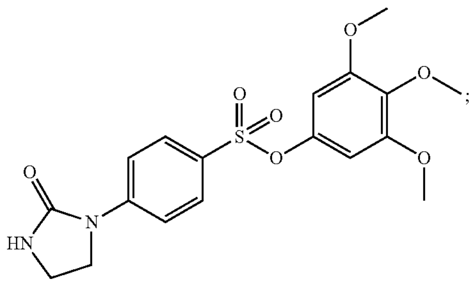
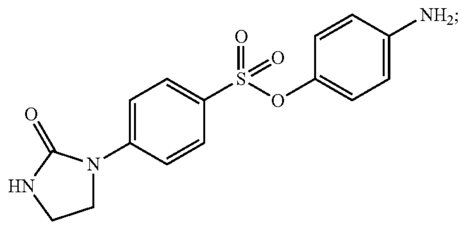

-continued
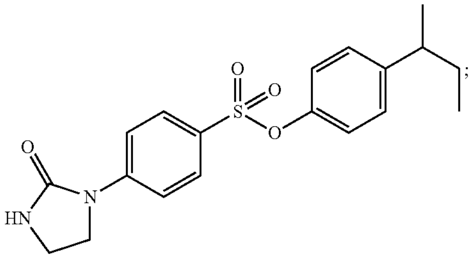
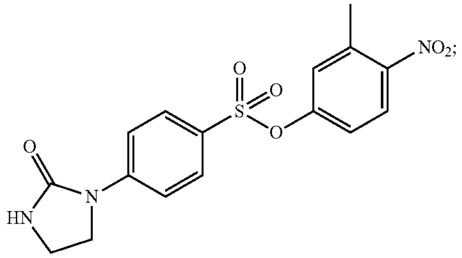
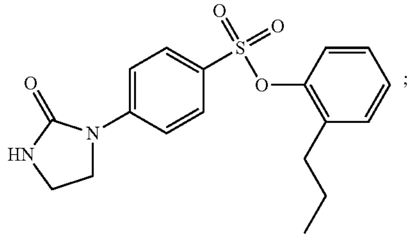
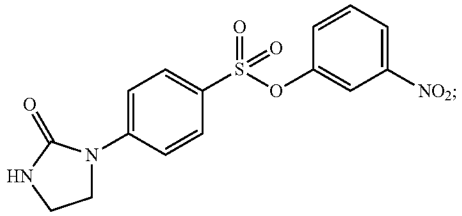
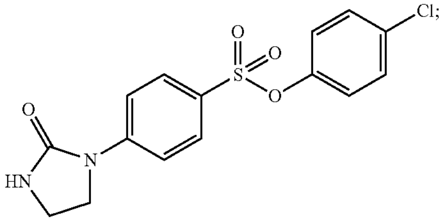
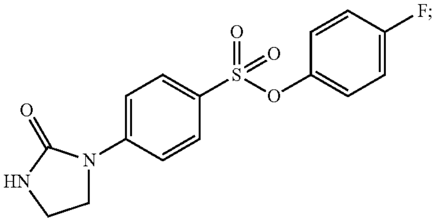
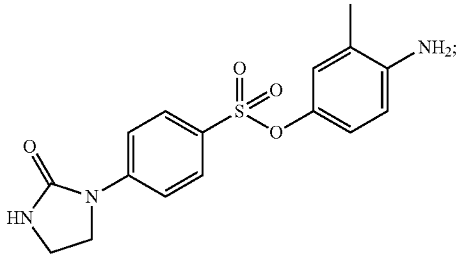
-continued
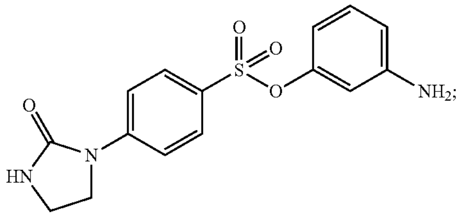
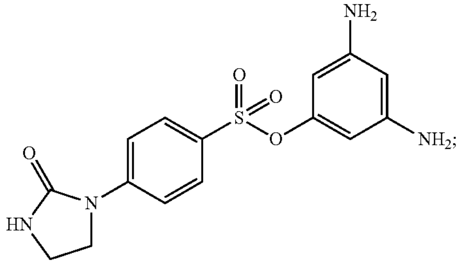
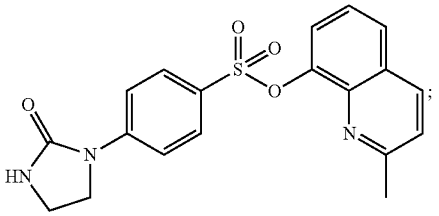
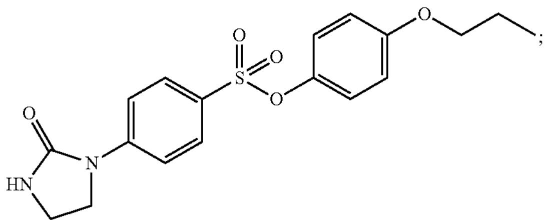
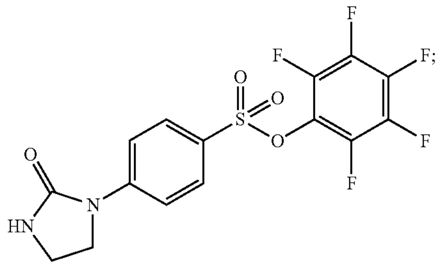
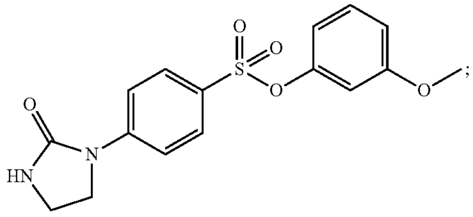
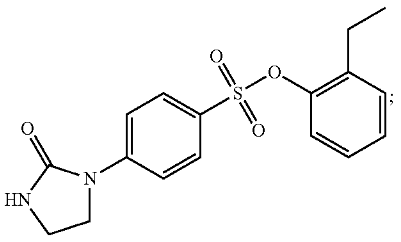

-continued
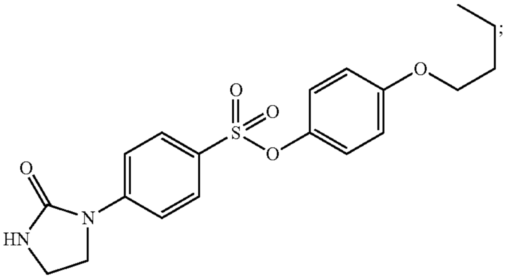
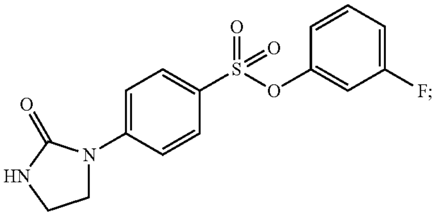
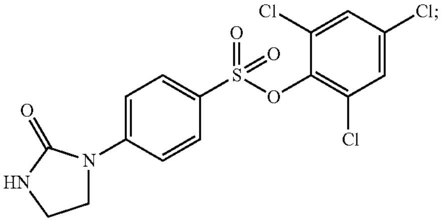
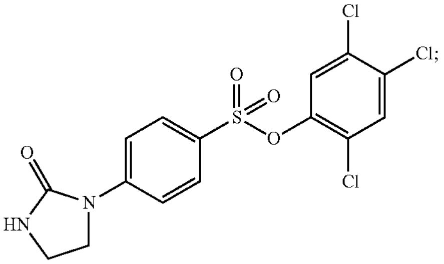
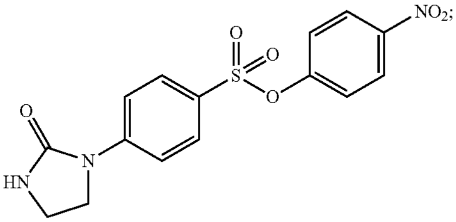
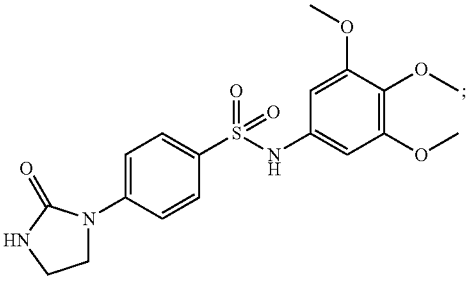
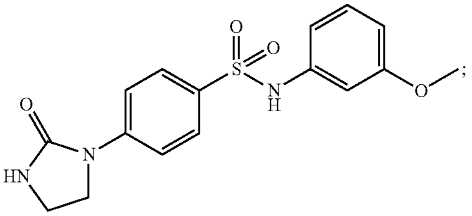
-continued
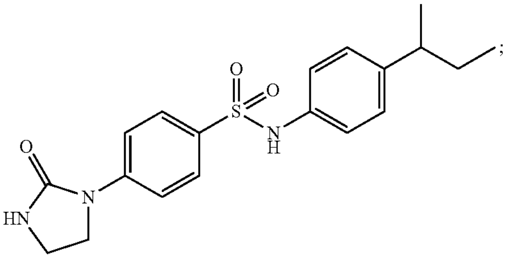
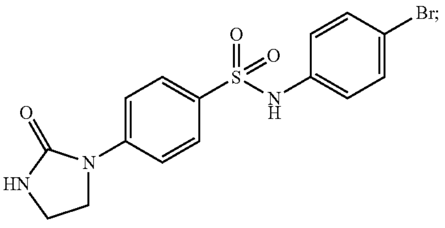
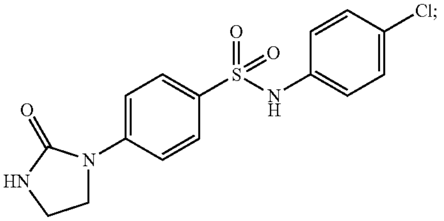
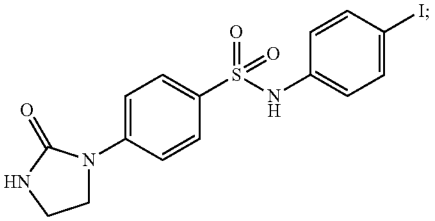
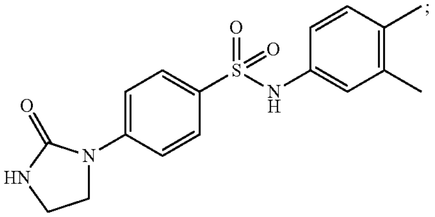
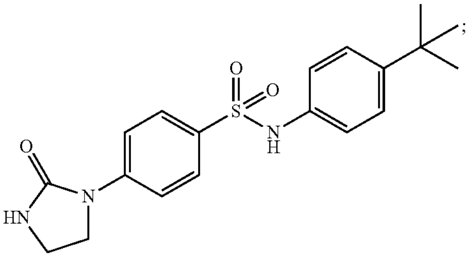
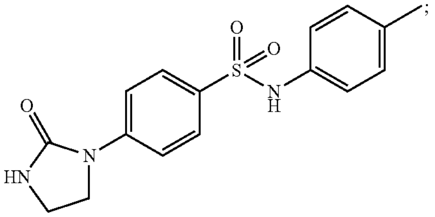

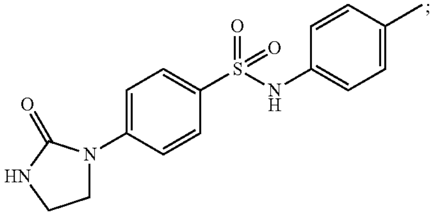
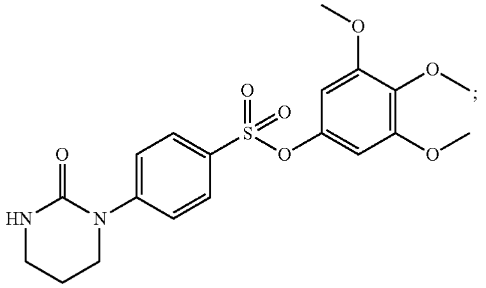
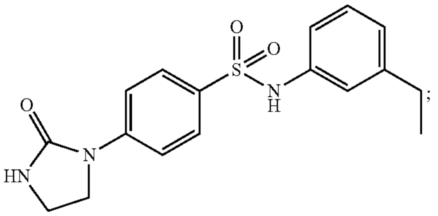
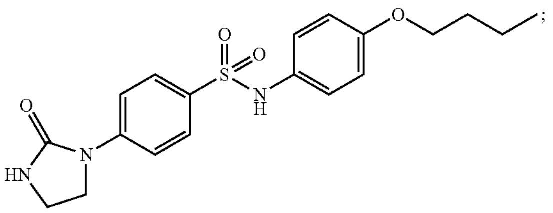
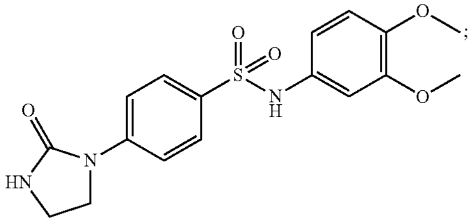
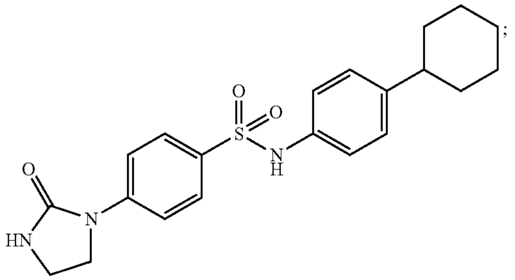
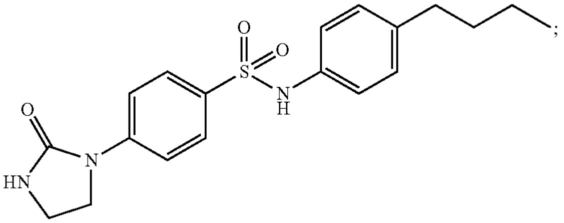
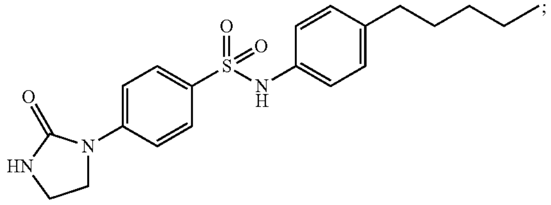
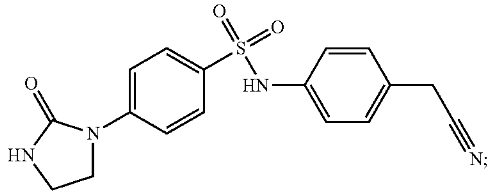
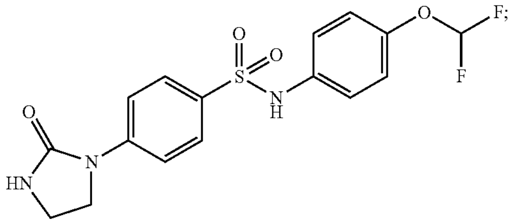
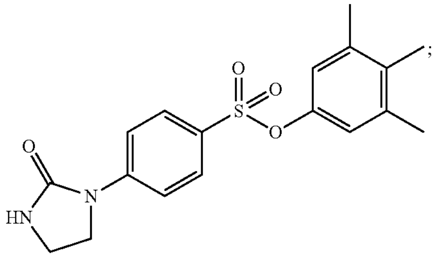
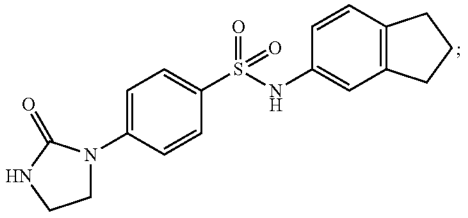
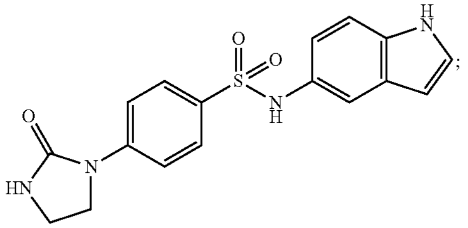
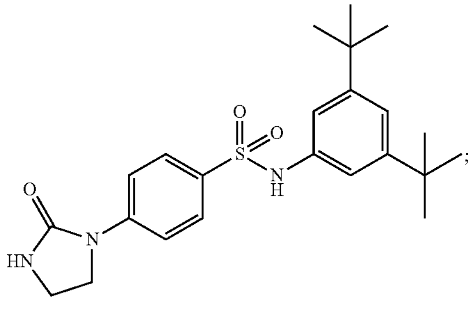

-continued
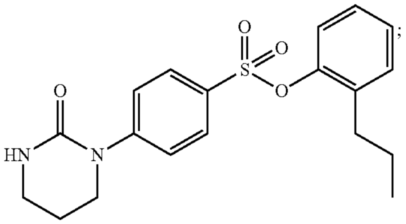
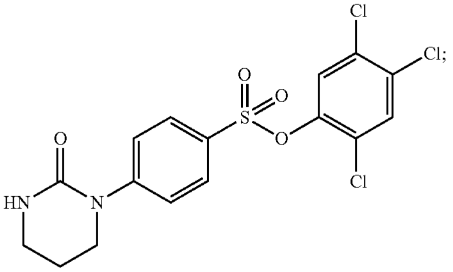
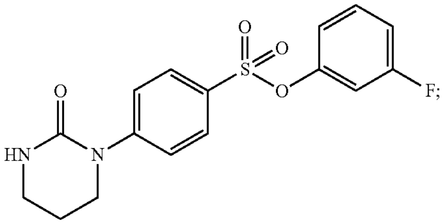
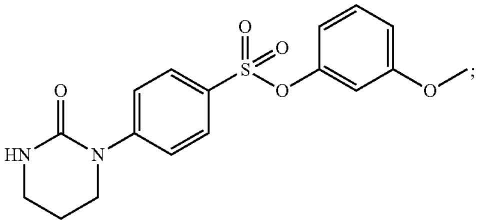
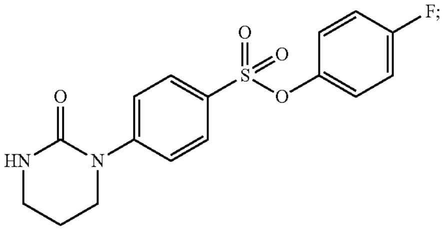
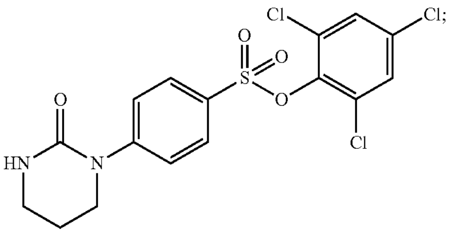
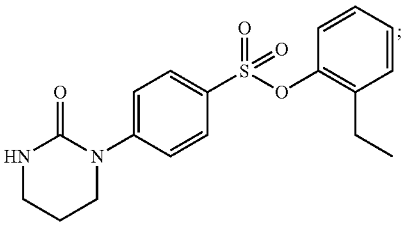
-continued
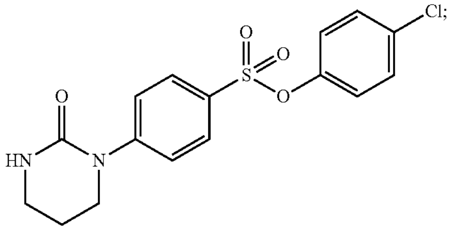
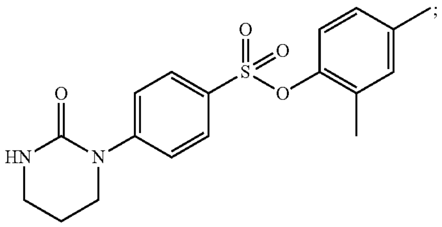
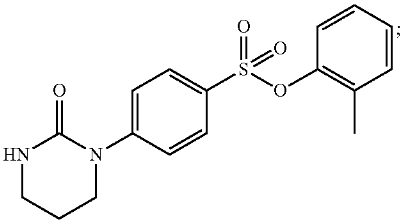
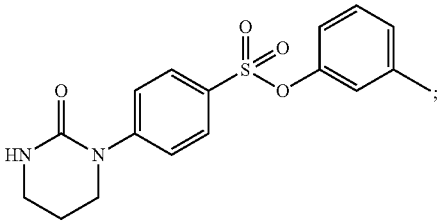
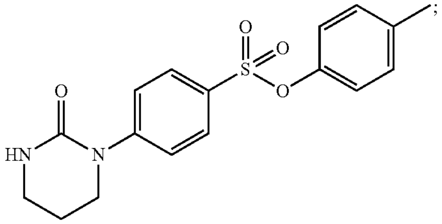
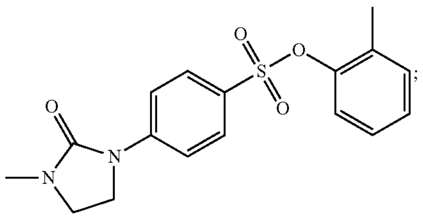
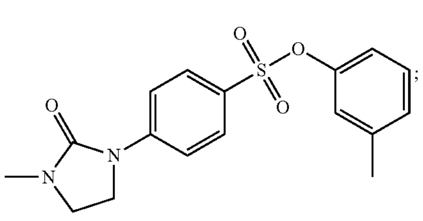

-continued
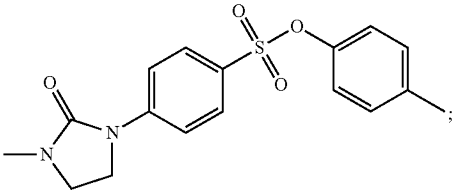
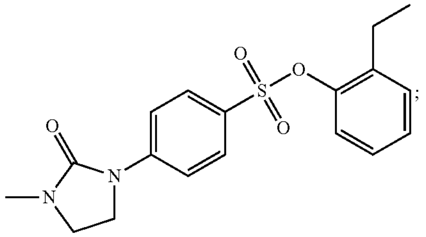
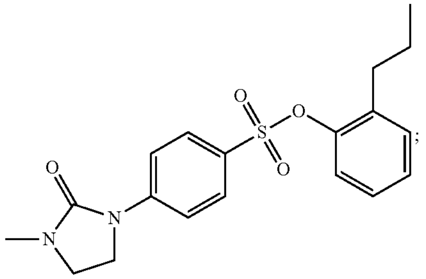
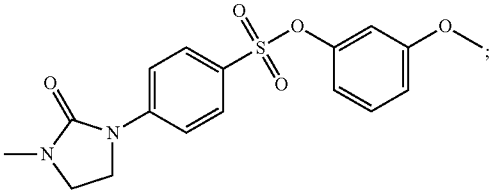
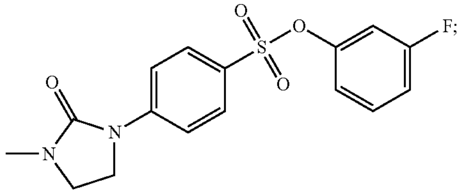
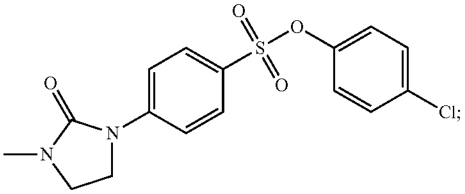
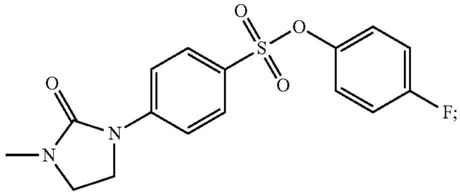
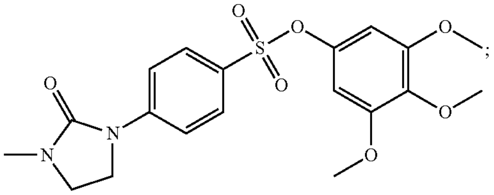
-continued
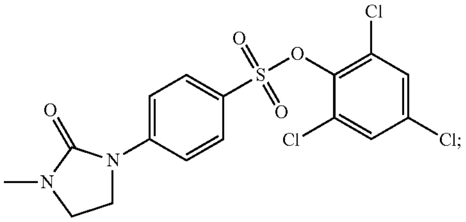
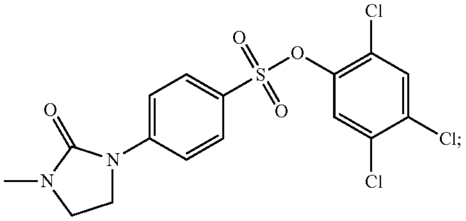
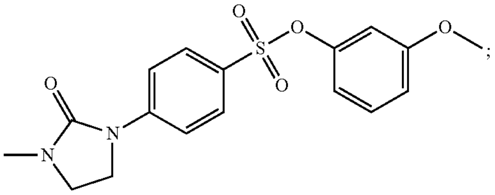
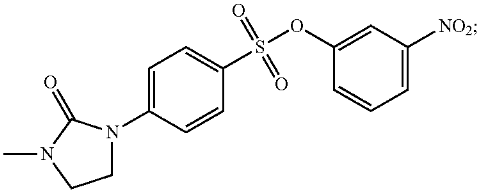
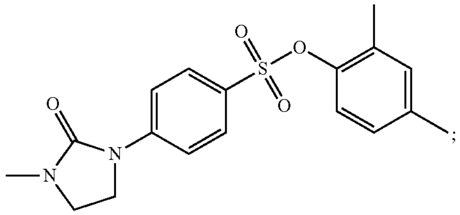
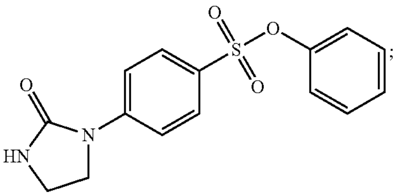
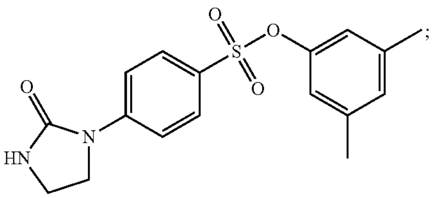
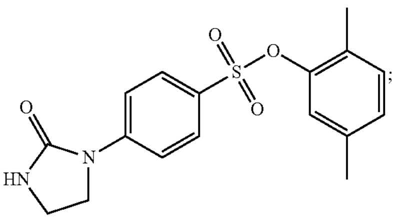

-continued
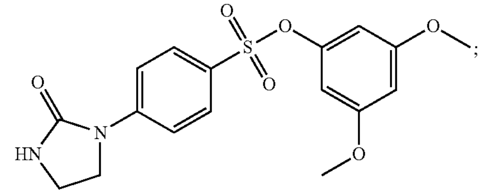
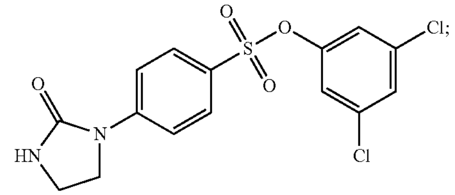
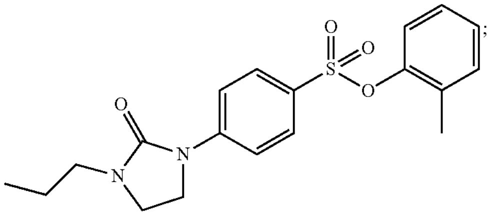
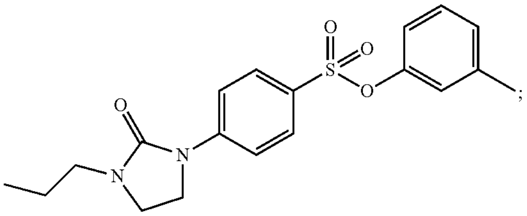
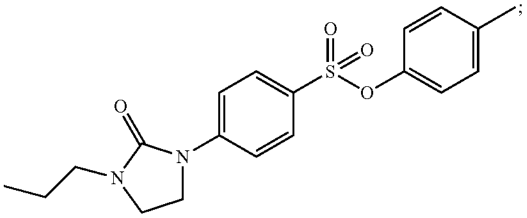
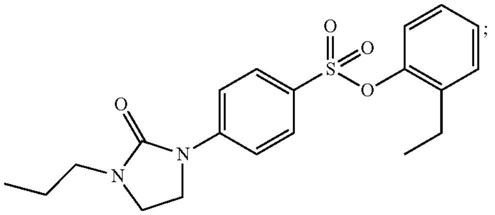
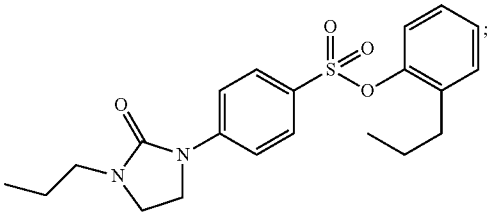
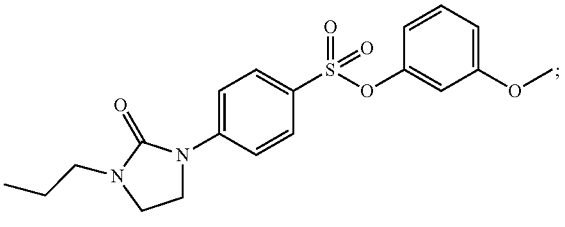
-continued
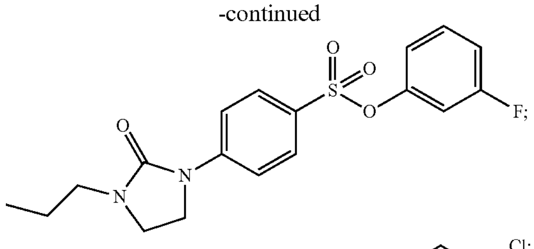
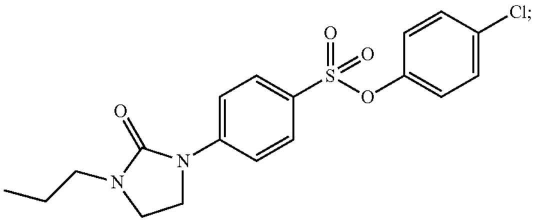
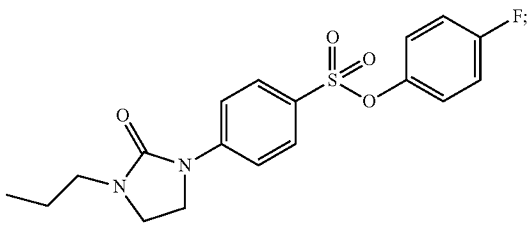
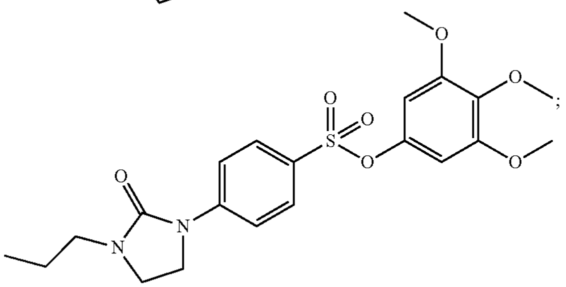
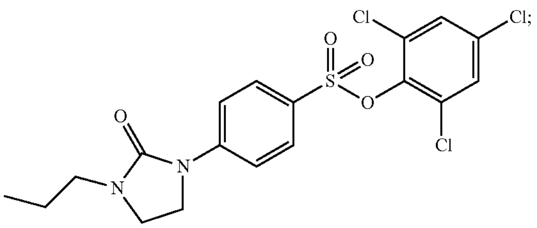
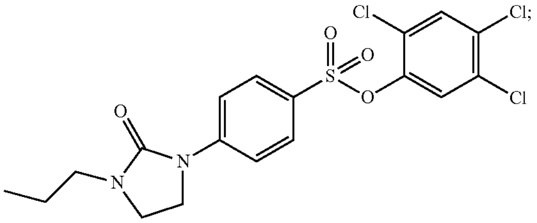
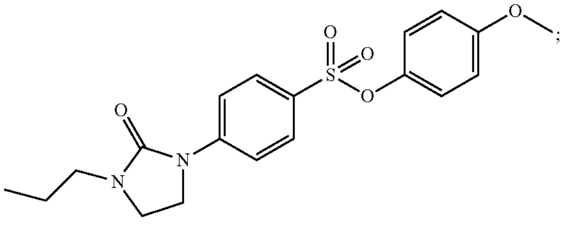

-continued
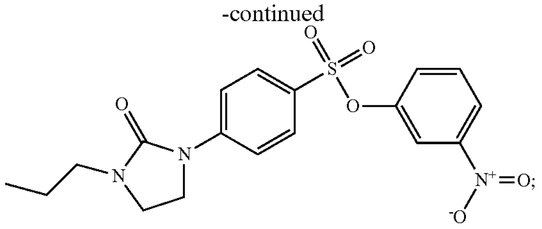
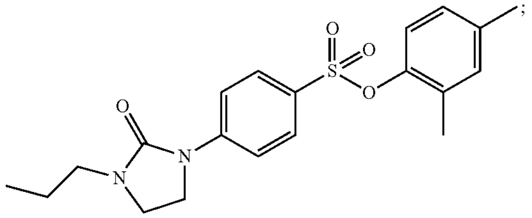
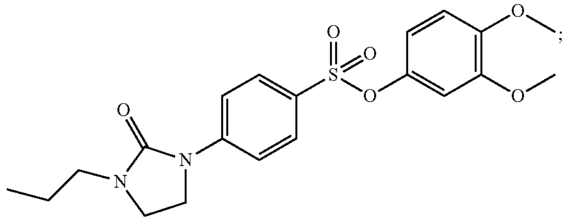
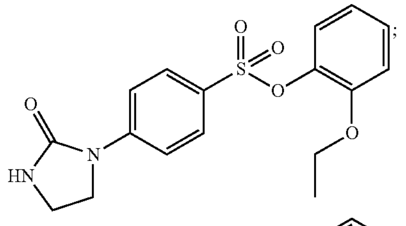
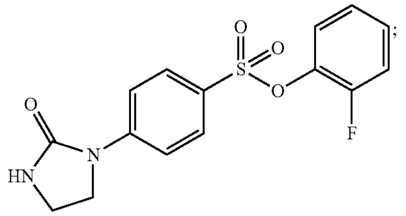
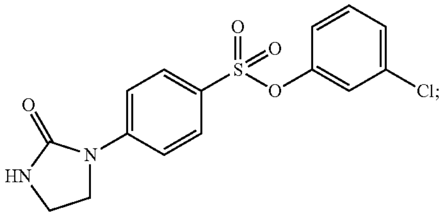
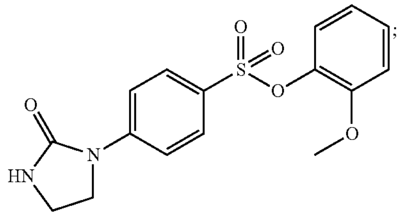
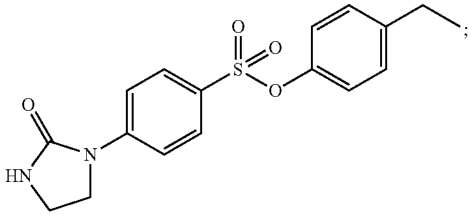
-continued
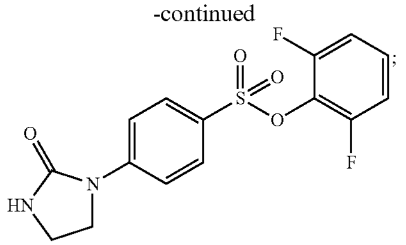
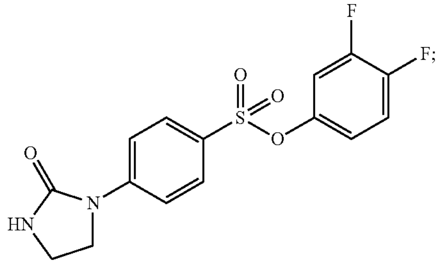
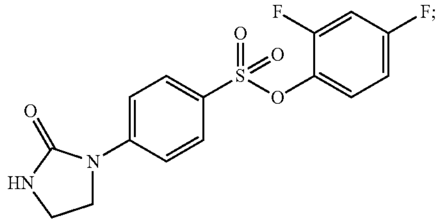
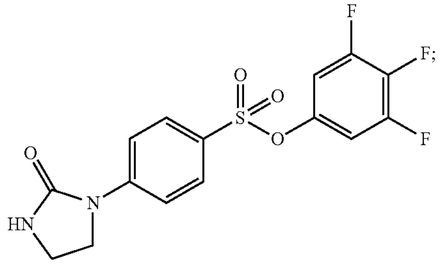
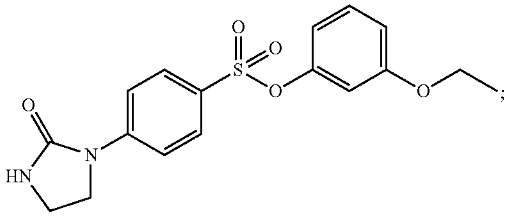
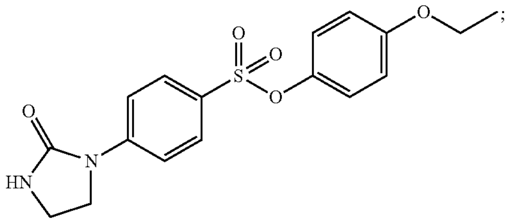
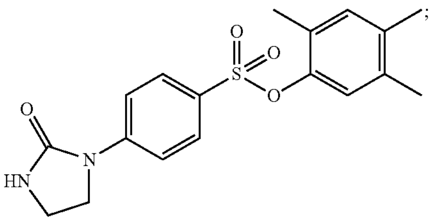

-continued
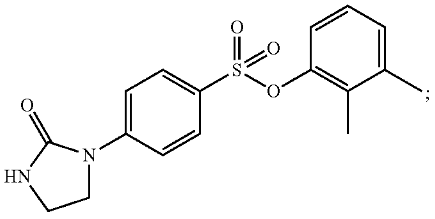
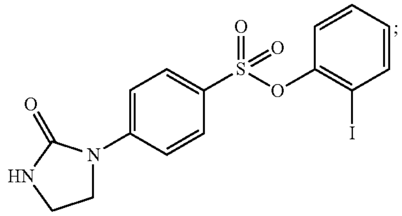
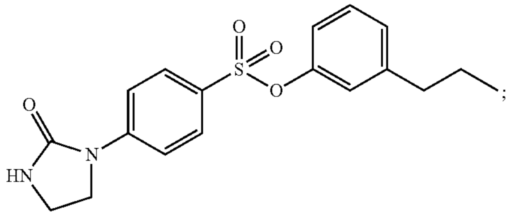
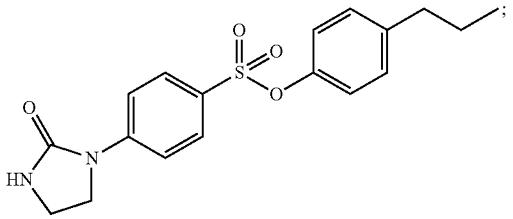
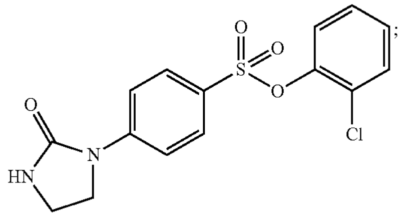
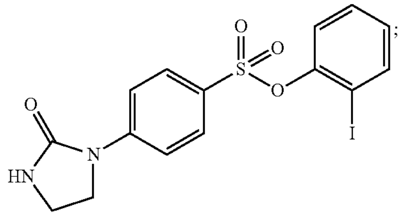
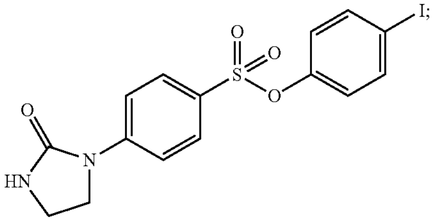
-continued
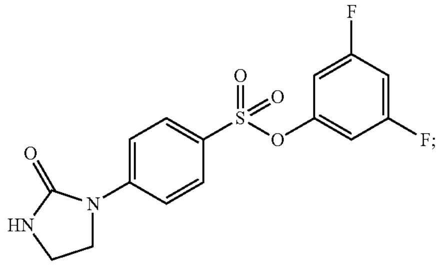
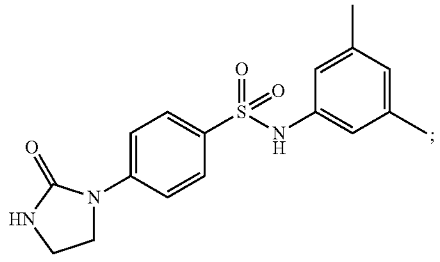
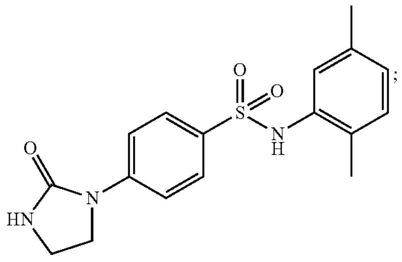
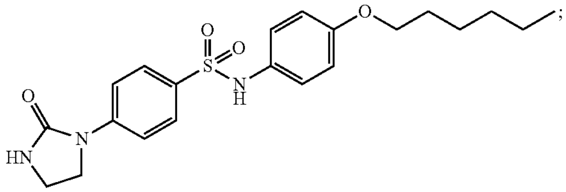
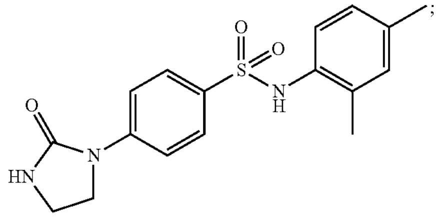
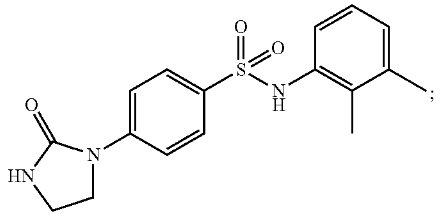
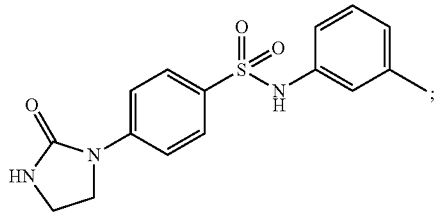

-continued
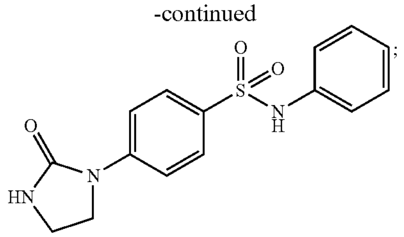
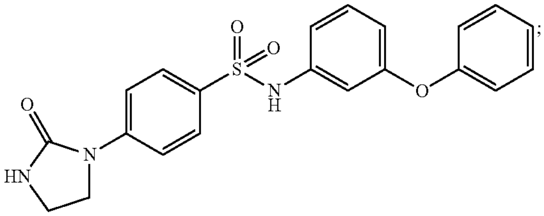
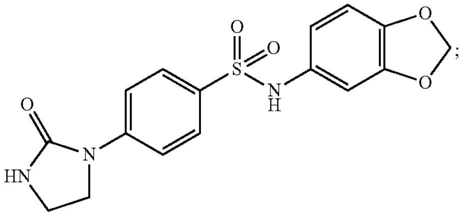
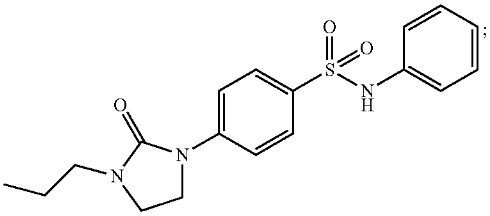
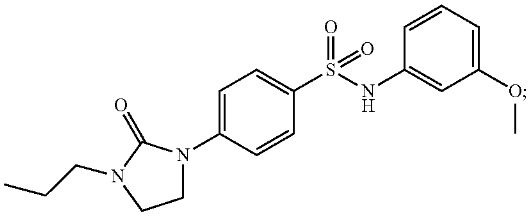
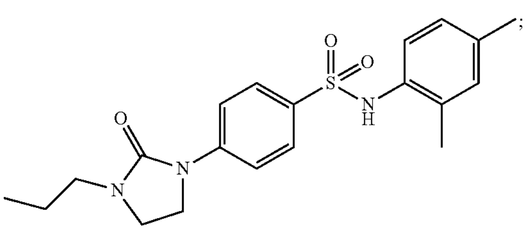
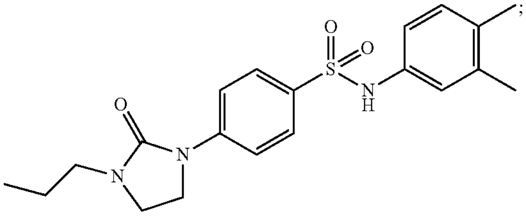
-continued
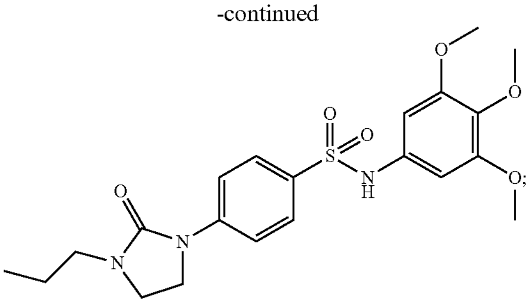
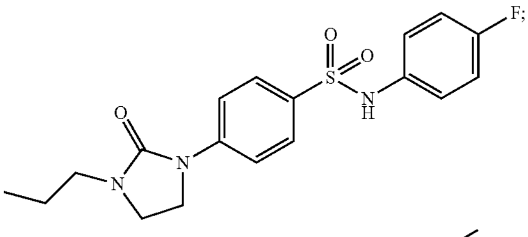
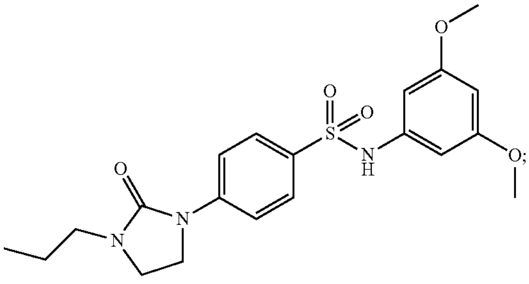
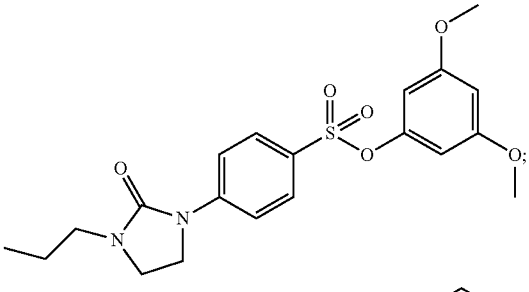
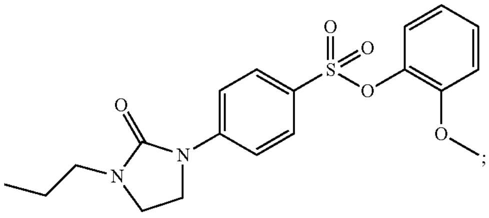
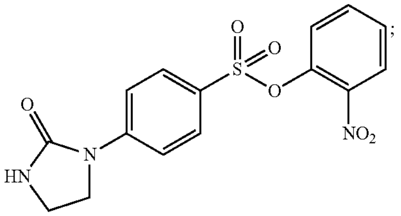
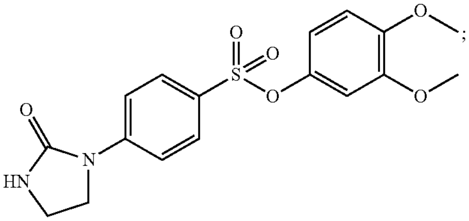

-continued

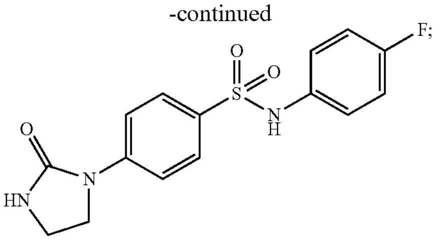

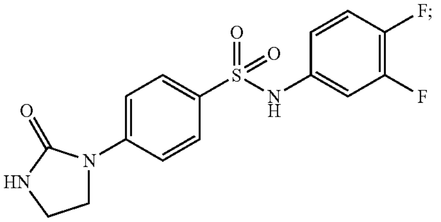

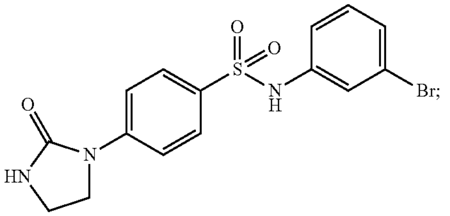

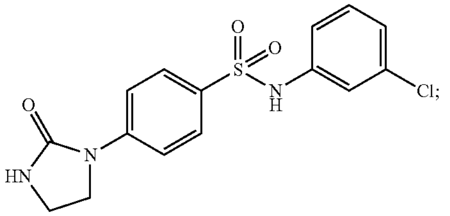

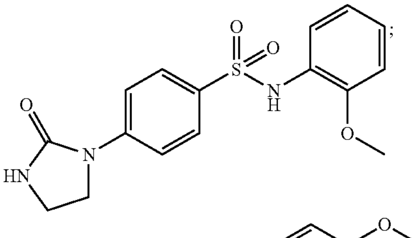

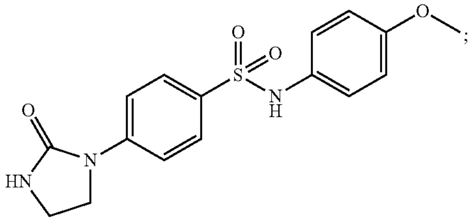

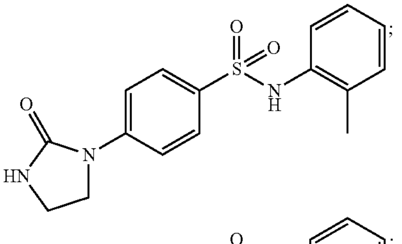

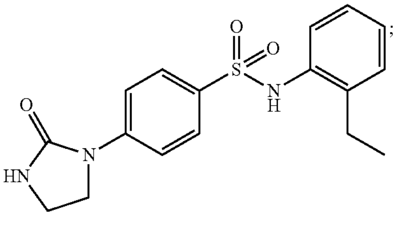

-continued

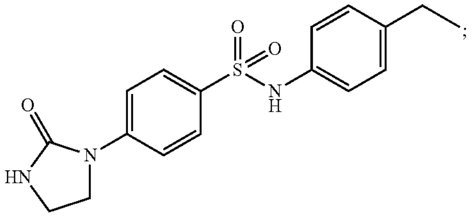

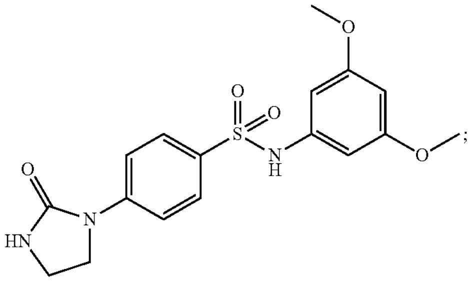

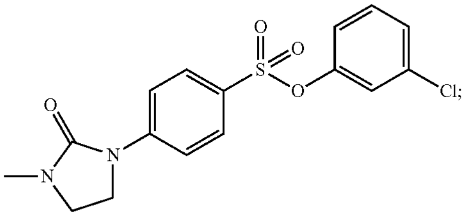

and

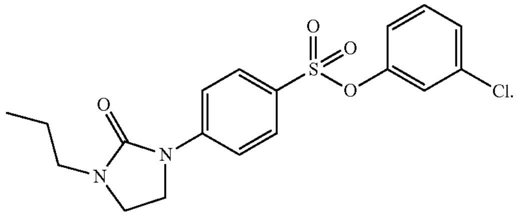

13. A pharmaceutical composition comprising at least one compound of claim 1, in admixture with at least one pharmaceutically-acceptable excipient.

14. A method of treating cancer, said method comprising administering a therapeutically effective amount of a composition of claim 13, to a patient suffering from said cancer, wherein the cancer is a hormone-dependent cancer, gastrointestinal (GI) tract cancer, or skin cancer.

15. A method of synthesizing a compound of Formula I wherein X is O, Y is $SO_2$, and $R_{20}$ corresponds to $R_5$, $R_6$ or $R_7$ as defined in claim 1, comprising the steps of:

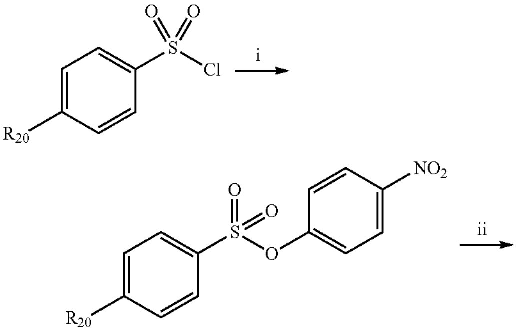

-continued

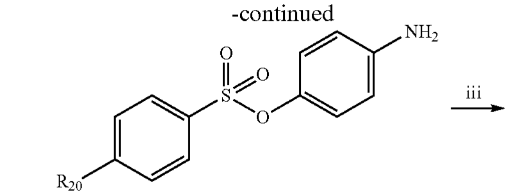

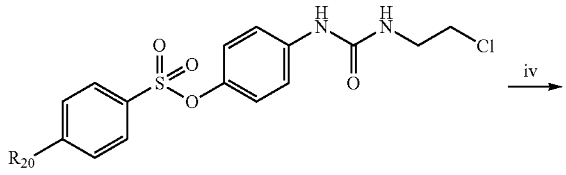

-continued

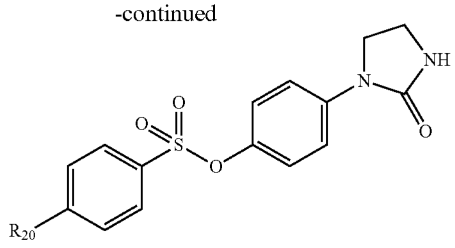

i) nucleophilic addition of (nitro-)benzenesulfonylchloride derivatives and relevant phenol or nitrophenol;

ii) reduction of nitro moiety to yield aniline;

iii) nucleophilic addition of aniline to 2-chloroethylisocyanate to yield N-phenyl-N'-(2-chloroethyl)urea; and iv) cyclization of 2-chloroethylurea moiety to yield 2-imidazolidone.

16. A method of synthesizing a compound of Formula I wherein X is $SO_2$, Y is O, and $R_{21}$ corresponds to $R_4$, $R_5$ or $R_6$ as defined in claim 1, comprising the steps of:

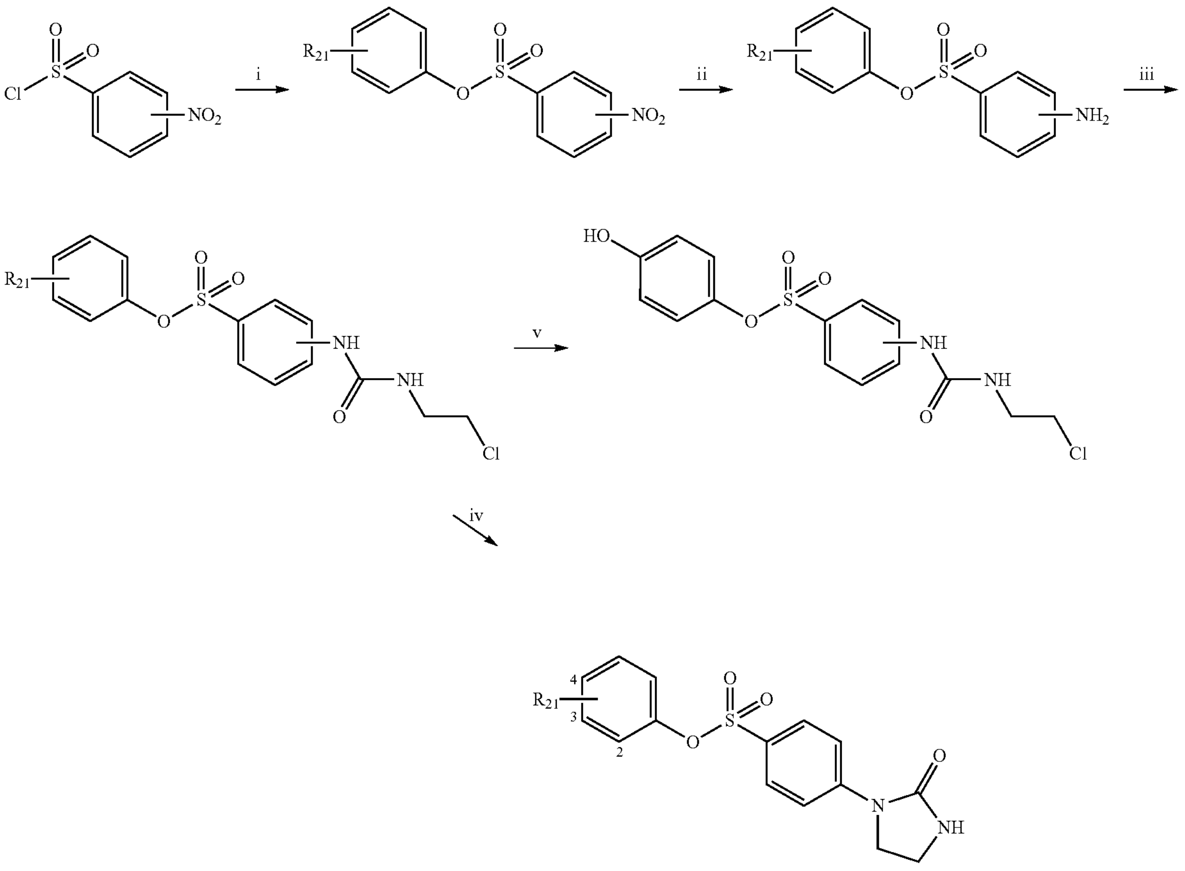

i) nucleophilic addition of (nitro-)benzenesulfonylchloride derivatives and relevant phenol or nitrophenol;

ii) reduction of nitro moiety to yield aniline;

iii) nucleophilic addition of aniline to 2-chloroalkylisocyanate;

iv) cyclization of 2-chloroalkylurea moiety to yield 2-imidazolidone; and v) deprotection of tBDMS to corresponding phenol.

17. A method of synthesizing a compound of Formula I, wherein X is $SO_2$, Y is O and $R_{22}$ and $R_{23}$ correspond to $R_4$, $R_5$, $R_6$, $R_7$ or $R_8$ as defined in claim 1, comprising the steps of:

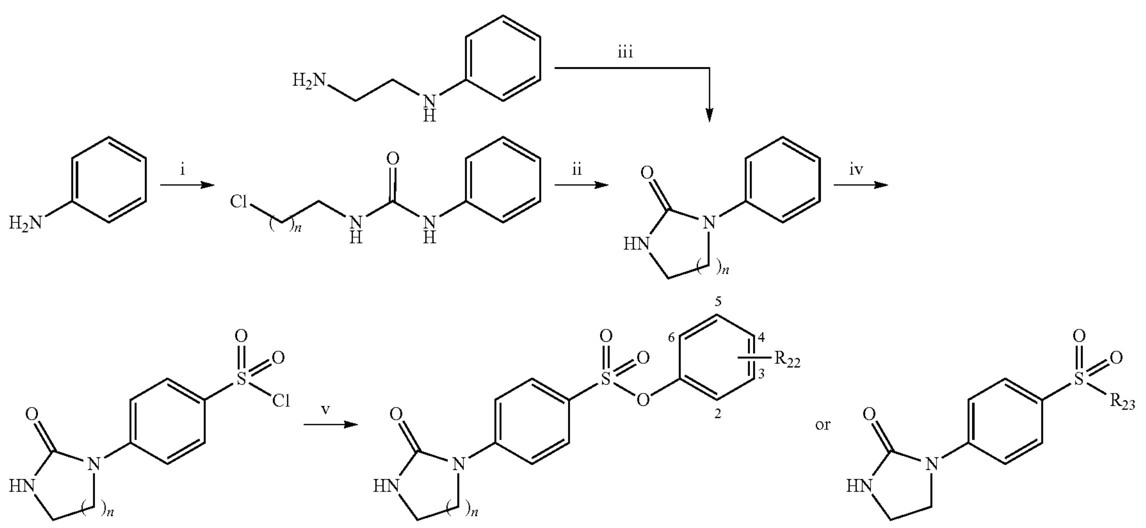

or i) nucleophilic addition of aniline to 2-chloroalkylisocyanate to yield chloroalkylurea;

ii) cyclization of chloroalkylurea to 2-imidazolidone; or optionally, instead of steps i) and ii);

iii) double nucleophilic addition of n-(2 aminoalkylamine)benzeneamine to yield 2-imidazolidone;

iv) chlorosulfonation of phenyl moiety; and v) nucleophilic addition of phenol derivative to sulfonylchloride derivative.

18. A method of synthesizing a compound of Formula I, wherein X is $SO_2$, Y is NH, and $R_{24}$ and $R_{25}$ correspond to $R_4$, $R_5$, $R_6$, $R_7$ or $R_8$ as defined in claim 1, comprising the steps of:

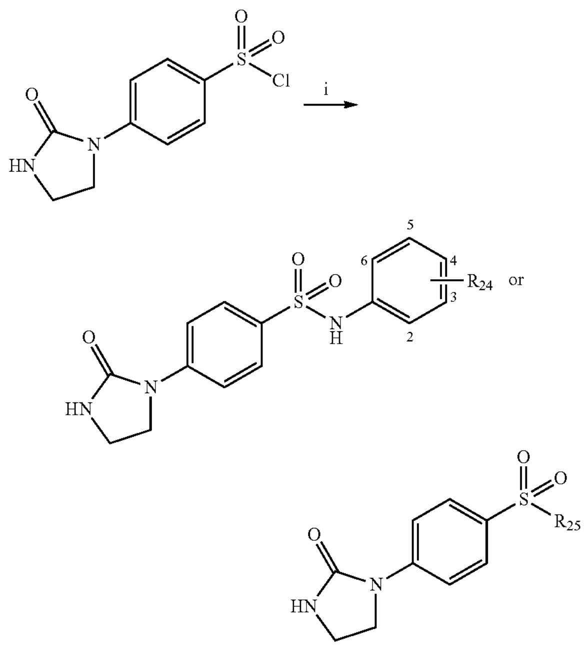

or i) nucleophilic addition of aniline to sulfonylchloride derivative.

19. A method of synthesizing a compound of Formula I wherein X is $SO_2$, Y is O or NH, and $R_{26}$ corresponds to $R_1$ and $R_{27}$ corresponds to $R_4$, $R_5$, $R_6$, $R_7$ or $R_8$ as defined in claim 1, comprising the steps of:

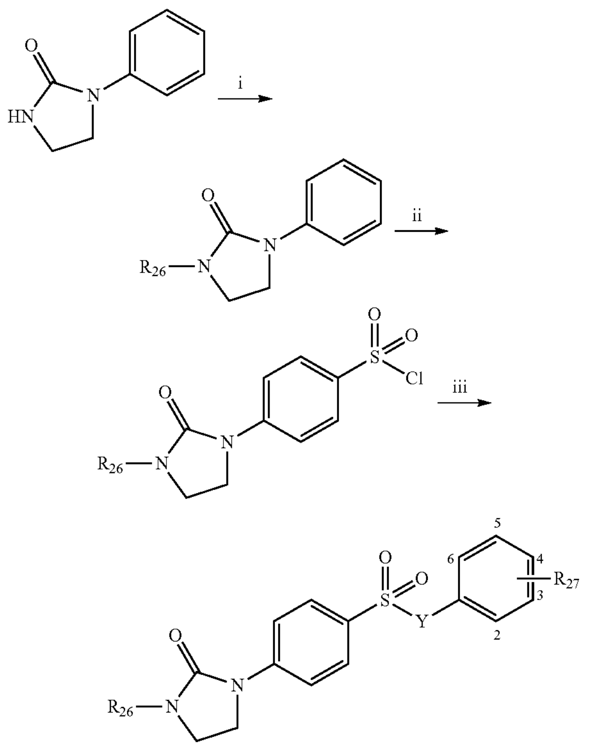

i) nucleophilic addition of alkylhalide to 2-imidazolidone;

ii) chlorosulfonation; and iii) nucleophilic addition of phenol or aniline derivative to sulfonylchloride derivative.

* * * * *